(12) United States Patent
Gentz et al.

(10) Patent No.: US 7,364,865 B2
(45) Date of Patent: Apr. 29, 2008

(54) ANTIBODIES TO MYELOID PROGENITOR INHIBITORY FACTOR-1 (MPIF-1)

(75) Inventors: Reiner L. Gentz, Gauting (DE); Brent L. Kreider, Bedford, MA (US); Jun Zhang, San Diego, CA (US); Michael Antonaccio, New Hope, PA (US); Donna Mendrick, Mount Airy, MD (US); Pablo Jimenez, Chatham, NJ (US); Vikram Patel, Germantown, MD (US); Craig A. Rosen, Laytonsville, MD (US); Mark D. Adams, Cleveland Heights, OH (US); Haodong Li, Gaithersburg, MD (US); Steven M. Ruben, Brookeville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 11/381,977

(22) Filed: May 5, 2006

(65) Prior Publication Data

US 2006/0228359 A1 Oct. 12, 2006

Related U.S. Application Data

(60) Division of application No. 10/626,530, filed on Jul. 25, 2003, now Pat. No. 7,041,460, which is a division of application No. 09/571,013, filed on May 15, 2000, now Pat. No. 6,811,773, which is a continuation of application No. 08/941,020, filed on Sep. 30, 1997, now abandoned, which is a continuation-in-part of application No. 08/722,723, filed on Sep. 30, 1996, now abandoned, which is a continuation-in-part of application No. 08/722,719, filed on Sep. 30, 1996, now Pat. No. 6,001,606, which is a continuation-in-part of application No. 08/468,775, filed on Jun. 6, 1995, now abandoned, and a continuation-in-part of application No. 08/465,682, filed on Jun. 6, 1995, now abandoned, and a continuation-in-part of application No. 08/446,881, filed on May 5, 1995, now abandoned, and a continuation-in-part of application No. 08/468,775, filed on Jun. 6, 1995, now abandoned, and a continuation-in-part of application No. 08/465,682, filed on Jun. 6, 1995, now abandoned, and a continuation-in-part of application No. 08/446,881, filed on May 5, 1995, now abandoned, and a continuation-in-part of application No. 08/173,209, filed on Dec. 22, 1993, now Pat. No. 5,556,767, and a continuation-in-part of application No. 08/208,339, filed on Mar. 8, 1994, now Pat. No. 5,504,003, and a continuation of application No. 08/446,881, filed on May 5, 1995, now abandoned, and a continuation-in-part of application No. 08/173,209, filed on Dec. 22, 1993, now Pat. No. 5,556,767, and a continuation-in-part of application No. 08/208,339, filed on Mar. 8, 1994, now Pat. No. 5,504,003, and a continuation of application No. 08/446,881, filed on May 5, 1995, now abandoned, and a continuation-in-part of application No. 08/173,209, filed on Dec. 22, 1993, now Pat. No. 5,556,767, and a continuation-in-part of application No. 08/208,339, filed on Mar. 8, 1994, now Pat. No. 5,504,003.

(60) Provisional application No. 60/027,300, filed on Sep. 30, 1996, provisional application No. 60/027,299, filed on Sep. 30, 1996.

(51) Int. Cl.
*C12N 5/10* (2006.01)
*C12N 5/12* (2006.01)
*G01N 33/53* (2006.01)
*C07K 16/24* (2006.01)

(52) U.S. Cl. .................. 435/7.1; 530/387.1; 530/387.3; 530/387.9; 530/388.23; 530/388.1; 435/325; 435/326

(58) Field of Classification Search ...................... None
See application file for complete search history.

(56) References Cited

U.S. PATENT DOCUMENTS 4,897,348 A 1/1990 Johnson et al.

(Continued)

FOREIGN PATENT DOCUMENTS

| DE | 4344397 A1 | 7/1995 |
|---|---|---|
| DE | 4427395 A1 | 2/1996 |
| DE | 19512463 A1 | 10/1996 |
| EP | 0 807 439 A2 | 11/1997 |

(Continued)

OTHER PUBLICATIONS

Bischoff, S. C., et al., "Monocyte Chemotactic Protein 1 Is a Potent Activator of Human Basophils," J. Exp. Med. 197:1271-1275 (1992).

(Continued)

*Primary Examiner*—Prema M Mertz
(74) *Attorney, Agent, or Firm*—Human Genome Sciences, Inc.

(57) ABSTRACT

There are disclosed therapeutic compositions and methods using isolated nucleic acid molecules encoding a human myeloid progenitor inhibitory factor-1 (MPIF-1) polypeptide (previously termed MIP-3 and chemokine β8 (CKβ8 or ckb-8)); a human monocyte-colony inhibitory factor (M-CIF) polypeptide (previously termed MIP1-γ and chemokine β1(CKβ1 or ckb-1)), and a macrophage inhibitory protein-4 (MIP-4), as well as MPIF-1, M-CIF and/or MIP-4 polypeptides themselves, as are vectors, host cells and recombinant methods for producing the same.

35 Claims, 69 Drawing Sheets

U.S. PATENT DOCUMENTS

| | | | |
|---|---|---|---|
| 5,268,463 | A | 12/1993 | Jefferson |
| 5,346,686 | A | 9/1994 | Lyle et al. |
| 5,504,003 | A | 4/1996 | Li et al. |
| 5,556,767 | A | 9/1996 | Rosen et al. |
| 5,874,211 | A | 2/1999 | Bandman et al. |
| 5,912,327 | A | 6/1999 | Li et al. |
| 6,001,606 | A | 12/1999 | Ruben et al. |
| 6,180,773 | B1 | 1/2001 | Forssmann et al. |
| 6,403,553 | B1 | 6/2002 | Opitz et al. |
| 6,451,562 | B1 | 9/2002 | Ruben et al. |
| 6,488,925 | B2 | 12/2002 | Ruben et al. |
| 6,495,129 | B1 | 12/2002 | Li et al. |
| 6,623,942 | B2 | 9/2003 | Ruben et al. |
| 6,811,773 | B1 | 11/2004 | Gentz et al. |
| 2003/0143191 | A1 | 7/2003 | Bell et al. |
| 2003/0147846 | A1 | 8/2003 | Ruben et al. |
| 2003/0158387 | A1 | 8/2003 | Forssmann et al. |

FOREIGN PATENT DOCUMENTS

| | | |
|---|---|---|
| WO | WO-90/02762 A1 | 3/1990 |
| WO | WO-91/04274 A1 | 4/1991 |
| WO | WO-92/00326 A1 | 1/1992 |
| WO | WO-92/00327 A1 | 1/1992 |
| WO | WO-92/05198 A1 | 4/1992 |
| WO | WO-92/13553 A2 | 8/1992 |
| WO | WO-92/20372 A1 | 11/1992 |
| WO | WO-93/09799 A1 | 5/1993 |
| WO | WO-95/17092 A1 | 6/1995 |
| WO | WO-95/18228 A1 | 7/1995 |
| WO | WO-96/16979 A1 | 6/1996 |
| WO | WO-96/22374 A1 | 7/1996 |
| WO | WO-96/32481 A1 | 10/1996 |
| WO | WO-96/34891 A1 | 11/1996 |
| WO | WO-97/12041 A1 | 4/1997 |
| WO | WO-97/15594 A1 | 5/1997 |
| WO | WO-97/41230 A2 | 11/1997 |
| WO | WO-98/14582 A1 | 4/1998 |
| WO | WO-98/25966 A1 | 6/1998 |
| WO | WO-01/31016 A2 | 5/2001 |
| WO | WO-02/97038 A1 | 12/2002 |

OTHER PUBLICATIONS

Blum, S., et al., "Three Human Homologues of a Murine Gene Encoding an Inhibitor of Stem Cell Proliferation," DNA and Cell Biology 9(8):589-602 (1990).

Chang, M., et al., "Cloning and Characterization of the Human Neutrophil-activating Peptide (ENA-78) Gene,"J. Biol. Chem. 269 (41):25277-25282 (1994).

Clements, J.M., et al., "Biological and Structural Properties of MIP-1.alpha. Expressed in Yeast," Cytokine 4:76-82 (Jan. 1992).

Derynck, R., et al., "Recombinant Expression, Biochemical Characterization, and Biological Activities of the Human MGSA/gro Protein," Biochem. 29:10225-10233 (Nov. 1990).

Glover, D.M., "The Principles of Cloning DNA,"in: Gene Cloning: The Mechanics of DNA Manipulation, Chapman and Hall, London, UK, pp. 1-20 (1984).

Graham, G. J. and Pragnell, I. B., "SCI/MIP-1.alpha.: A Potent Stem Cell Inhibitor with Potential Roles in Development," Developmental Biol. 151:377-381 (1992).

Harlow, E. and Lane, D., from "Antibodies. A Laboratory Manual,", Cold Spring Harbor Laboratory, Cold Spring Harbor, NY, p. 6 (1988).

Johnson, M. C., et al., "Cloning of Two Rabbit Gro Homologues and Their Expression in Alveolar Macrophage," Gene 151:337-338 (1994).

Jose, P.J., et al., "Eotaxin: A Potent Eosinophil Chemoattractant Cytokine Detected in a Guinea Pig Model of Allergic Airways Inflammation," J. Exp. Med. 179:881-887 (Mar. 1994).

Kuna, P. et al., "Monocyte Chemotactic and Activating Factor Is a Potent Histamine-releasing Factor for Human Basophils," J. Exp. Med. 175:489-493 (Feb. 1992).

Kwon, B.S., and Weissman, S.M., "cDNA Sequences of two Inducible T-cell Genes," Proc. Natl. Acad. Sci. USA 86:1963-1967 (Mar. 1989).

Lerner, R.A., "Tapping the Immunological Repertoire to Produce Antibodies of Predetermined Specificity," Nature 229:592-596 (Oct. 1982).

Lukacs, N. W., et al., "The Role of Macrophage Inflammatory Protein 1.alpha. in Schistosoma mansoni Egg-induced Granulomatous Inflammation," J. Exp. Med. 177:1551-1559 (1993).

Pardigol, A. et al., "HCC-2, a human chemokine: Gene structure, expression pattern, and biological activity," Proc. Nat. Acad. Sci. USA 95, 6308-6313 (May 1998).

Matsushima, K., et al., "Purification and Characterization of a Novel Monocyte Chemotactic and Activating Factor Produced by a Human Myelomonocytic Cell Line," J. Exp. Med. 169:1485-1490. (Apr. 1989).

Mikayama et al., "Molecular cloning and functional expression of a cDNA encoding glycosylation-inhibiting factor." Proc Natl Acad Sci U S A. 90(21):10056-60 (Nov. 1, 1993).

Nakao, M., et al., "Structures of Human Genes Coding for Cytokine LD78 and Their Expression," Molecular and Cellular Biology 10(10):3646-3658 (1990).

Obaru, K., et al., "A cDNA Clone Used to Study mRNA Inducible in Human Tonsillar Lymphocytes by a Tumor Promoter," J. Biochem. 99(3):885-894 (1986).

Pardigol, A. et al., "HCC-2, a human chemokine: Gene structure, expression pattern, and biological activity," Proc. Nat. Acad. Sci. USA 95, 6308-6313 (May 1998).

Poltorak, A., et al., "Molecular Cloning of MIP-1.gamma., A New Member of the Chemokine Family, through Diffrential Screening Based on Extinction of Macrophage Specific Genes," Clinical Research 42(2):306A XP000673113(Apr. 1994).

Poltorak, A. N., et al., "MIP-1.gamma.: Molecular Cloning, Expression, and Biological Activities of a novel CC Chemokine That Is Constitutively Secreted In Vivo," J. Inflam. 45:207-219 (1995).

Power, C.A., et al., "Cloning of a Full-Length Cdna Encoding the Neutrophil-activating Peptide Ena-78 from Human Platlets," Gene 151:333-334 (Jan. 1994).

Proost, P., et al., "Purification, Sequence Analysis, and Biological Characterization of a Second Bovine Monocyte Chemotactic Protein-1 (Bo MCP-1B)," Biochemistry33:13406-13412 (Nov. 1994).

Schall, T.J., "Biology of the RANTES/SIS Cytokine Family," Cytokine 3:165-183 (May 1991).

Schulz-Knappe, P. et al., "HCC-1, a novel chemokine from human plasma," J. Exp. Med. 183(1), 295-299 (1996).

Sudo, K., et al., "2058 Expressed Sequence Tags (ESTs) from a Human Fetal Lung cDNA Library," Genomics 24:276-279 (Nov. 1994).

Voet et al. Biochemistry. John Wiley & Sons, Inc., pp. 126-128 and 228-234, 1990.

Weber, M., et al., "Deletion of the NH.sub.2—Terminal Residue Converts Monocyte Chemotactic Protein 1 from an Activator of Basophil Mediator Release to an Eosinophil Chemoattractant," J. Exp. Med. 183:681-685 (Feb. 1996).

Wolpe, S.D., and Cerami, A., "Macrophage Inflammatory Proteins 1 and 2: Members of a Novel Superfamily of Cytokines," FASEB J. 3:2565-2573 (Dec. 1989).

Yoshida, T., et al., "Molecular Cloning of a Novel C or .gamma. Type Chemokine, SCM-1," FEBS Letters 360:155-159 (Feb. 1995).

Zipfel, P.F., et al., "Mitogenic Activation of Human T Cells Induces two Closely Related Genes Which Share Structural Similarities with a New Family of Secreted Factors," J. Immunol. 142:1582-1590 (Mar. 1989).

Search Report for EP 925671.3.

International Search Report for International Application No. PCT/US95/09058.

Derwent WPI, English language abstract for WO 95/18228.

```
ATGAAGGTCTCCGTGGCTGCCCTCTCCTGCCTCATGCTTGTTACTGCCCTTGGATCCCAG    60
 M  K  V  S  V  A  A  L  S  C  L  M  L  V  T  A  L  G  S  Q

GCCCGGGTCACAAAAGATGCAGAGACAGAGTTCATGATGTCAAAGCTTCCATTGGAAAAT   120
 A  R  V  T  K  D  A  E  T  E  F  M  M  S  K  L  P  L  E  N

CCAGTACTTCTGGACAGATTCCATGCTACTAGTGCTGACTGCTGCATCTCCTACACCCCA   180
 P  V  L  L  D  R  F  H  A  T  S  A  D  C  C  I  S  Y  T  P

CGAAGCATCCCGTGTTCACTCCTGGAGAGTTACTTTGAAACGAACAGCGAGTGCTCCAAG   240
 R  S  I  P  C  S  L  L  E  S  Y  F  E  T  N  S  E  C  S  K

CCGGGTGTCATCTTCCTCACCAAGAAGGGGCGACGTTTCTGTGCCAACCCCAGTGATAAG   300
 P  G  V  I  F  L  T  K  K  G  R  R  F  C  A  N  P  S  D  K

CAAGTTCAGGTTTGCATGAGAATGCTGAAGCTGGACACACGGATCAAGACCAGGAAGAAT   360
 Q  V  Q  V  C  M  R  M  L  K  L  D  T  R  I  K  T  R  K  N

TGA   363
 *
```

FIG. 1

ATGAAGATCTCCGTGGCTGCAATTCCCTTCTTCCTCCTCATCACCATCGCCCTAGGGACC
M  K  I  S  V  A  A  I  P  F  F  L  L  I  T  I  A  L  G  T

AAGACTGAATCCTCCTCACGGGGACCTTACCACCCCTCAGAGTGCTGCTTCACCTACACT
K  T  E  S  S  R  G  P  Y  H  P  S  E  C  C  F  T  Y  T

ACCTACAAGATCCCGCGTCAGCGGATTATGGATTACTATGAGACCAACAGCCAGTGCTCC
T  Y  K  I  P  R  Q  R  I  M  D  Y  Y  E  T  N  S  Q  C  S

AAGCCCGGAATTGTCTTCATCACCAAAAGGGGCCATTCCGTCTGTACCAACCCCAGTGAC
K  P  G  I  V  F  I  T  K  R  G  H  S  V  C  T  N  P  S  D

AAGTGGGTCCAGGACTATATCAAGGACATGAAGGAGAACTGA
K  W  V  Q  D  Y  I  K  D  M  K  E  N  *

FIG.2

```
1    ATGAAGGGCCTTGCAGCTGCCCTCCTTGTCCTCGTCTGCACCATGGCCCTCTGCTCCTGT    60
     M  K  G  L  A  A  A  L  L  V  L  V  C  T  M  A  L  C  S  C

61   GCACAAGTTGGTACCAACAAAGAGCTCTGCTGCCTCGTCTATACCTCCTGGCAGATTCCA   120
     A  Q  V  G  T  N  K  E  L  C  C  L  V  Y  T  S  W  Q  I  P

121  CAAAAGTTCATAGTTGACTATTCTGAAACCAGCCCCCAGTGCCCCAAGCCAGGTGTCATC   180
     Q  K  F  I  V  D  Y  S  E  T  S  P  Q  C  P  K  P  G  V  I

181  CTCCTAACCAAGAGAGGCCGGCAGATCTGTGCTGACCCCAATAAGAAGTGGGTCCAGAAA   240
     L  L  T  K  R  G  R  Q  I  C  A  D  P  N  K  K  W  V  Q  K

241  TACATCAGCGACCTGAAGCTGAATGCCTGA    270
     Y  I  S  D  L  K  L  N  A  *
```

FIG.3

```
CKβ-8    MKVSVAALSCLMLVTALGSQARVTKDAETEFMMSKLPLENPVLLDRFHAT    50
         |.||.|||..|: . ||..| ... .|:                       |
MIP-1α   MQVSTAALAVLLCTMALCNQFSASLAAD.....................T    29

CKβ-8    SADCCISYTPRSIPCSLLESYFETNSECSKPGVIFLTKKGRRFCANPSDK    100
         ...||:|||.| || .::..||||.|:||||||||||::|..||:||:.
MIP-1α   PTACCFSYTSRQIPQNFIADYFETSSQCSKPGVIFLTKRSRQVCADPSEE    79

CKβ-8    QVQVCMRMLKLDTRIKTRKN    120
         || ::. |.|..
MIP-1α   WVQKYVSDLELSA    92
```

FIG. 4

```
  1  MKGLAAALLVLVCTMALC....SCAQVGTNKELCCLVYTSWQIPQKFIVD  46
     |..·||| ||:||||||    |.: .:....||: |||:||||·||·|
  1  MQVSTAALAVLLCTMALCNQVLSAPLAADTPTACCFSYTSRQIPQNFIAD  50

47  YSETSPQCPKPGVILLTKRGRQICADPNKKWVQKYISDLKLNA  89
     | |||·||·||:||:|||||||:||||···|||||:|||·|:|
 51  YFETSSQCSKPSVIFLTKRGRQVCADPSEEWVQKYVSDLELSA  93
```

FIG.5

```
CKβ-1    MKISVAAIPFFLLITIALGTKTESSSRGPYHPSECCFTYTTYKIPRQRIM  50
         |.:|.||::  .||.|:||...  |.|  ::  |..|||.||. .||.. |
MIP-1α   MQVSTAALA.VLLCTMALCNQF.SASLAADTPTACCFSYTSRQIPQNFIA  48

CKβ-1    DYYETNSQCSKPGIVFITKRGHSVCTNPSDKWVQDYIKDMKEN  94
         ||:||.||||||||::|:|||::  ||..||.|||.|..|:.
MIP-1α   DYFETSSQCSKPGVIFLTKRSRQVCADPSEEWVQKYVSDLESA  93
```

FIG. 6

1 = mock, 2 and 3 = MIP1-γ-HA, 4 = IκB-HA
5 = mock, 6 = MIP1-γ-HA, 7 = IκB-HA

| TREATMENTS | NUMBERS OF CIRCULATING WBC PER MILLILITER OF BLOOD | | |
|---|---|---|---|
| | DAY 3 | DAY 6 | DAY 10 |
| Gr-1 (Saline) | $8.4 \times 10^6 \pm 3.0 \times 10^6$ | $10.2 \times 10^6 \pm 3.6 \times 10^6$ | $7.0 \times 10^6 \pm 9.9 \times 10^5$ |
| Gr-2, MPIF-1 ALONE | $7.8 \times 10^6 \pm 2.2 \times 10^6$ (100%) | $7.5 \times 10^6 \pm 6.5 \times 10^5$ (100%) | $10.6 \times 10^6$ (100%) |
| Gr-3, 5-Fu ALONE | $4.23 \times 10^6 \pm 2.8 \times 10^6$ (54) | $1.8 \times 10^6 \pm 1.4 \times 10^4$ (24) | $8.8 \times 10^6 \pm 4.9 \times 10^5$ (83) |
| Gr-4, MPIF-1 PLUS 5-Fu | $3.49 \times 10^6 \pm 6.5 \times 10^5$ (45) | $3.98 \times 10^6 \pm 4.3 \times 10^5$ (53) | $9.48 \times 10^6 \pm 9.4 \times 10^5$ (89) |

FIG.22

| GROUP | TREATMENTS | NUMBER OF COLONIES PER 2,000 CELLS | | | | | |
|---|---|---|---|---|---|---|---|
| | | DAY 6 | | | DAY 9 | | |
| | | HPP-CFC | LPP-CFC | | HPP-CFC | | LPP-CFC |
| 1 | SALINE | 10.5 ± 0.7 | 60 ± 9.8 | | 15 ± 2 | | 78 ± 3.5 |
| | SALINE | 12 ± 0.7 | 92 ± 11 | | 13 ± 1 | | 80 ± 14 |
| | SALINE | 14 ± 1.4 | 84 ± 1.4 | | 11 ± 2 | | 82 ± 0 |
| 2 | 5-Fu | 4.5 ± 3.5 | 3.5 ± 0.7 | | 7 ± 2 | | 5 ± 0 |
| | 5-Fu | 12 ± 2 | 37 ± 16 | | 6 ± 2 | | 2 ± 0 |
| | 5-Fu | 4 ± 2.8 | 6 ± 3 | | DEAD | | DEAD |
| 3 | 5-Fu PLUS MPIF-1 | 0 | 6.5 ± 3.5 | | 16 ± 1.4 | | 75 ± 1.4 |
| | " " " " | 0 | 105 ± 10 | | 12 ± 2.8 | | 46 ± 12 |
| | " " " " | 0 | 120 ± 1.4 | | 16 ± 0 | | 95 ± 2.8 |

FIG.24

```
         1          20         30         40         50         60         70         80
         MKVSVAALSC LMLVTALGSQ ARVTKDAETE FMMSKLPLEN PVLLDRFHAT SADCCISYTP RSIPCSLLES YFETNSECSK
1) Wild type:        RVTKDAE..
2) Mutant-1(+1):    MRVTKDAE..
3) Mutant-2(-δ 24):                                           RFHAT....
4) Mutant-3(-δ 23):                                          DRFHAT....
5) Mutant-4(-δ 26):                                     HAT SAD.....
6) Mutant-5(-δ 27):                                      AT SAD.....
7) Mutant-6(-δ 24):                                          MRFHAT....
8) Mutant-7(-δ 17):                                 EN PVLLD.....
9) Mutant-8(-δ 22):                                         LDRFHAT....
10)Mutant-9(-δ 25):                                         HAAGFHAT....
```

FIG. 25

```
gtcctcggccagccctgcctgcccaccaggaggatgaaggtctccgtggctgccctctcctgcctcatgctt
                              M K V S V A A L S C L M L gttactgcccttggatcccaggcccgggtcacaaaagatgcagagacagagttcatgatgtcaaagcttcca
V T A L G S Q A  R V T K D A E T E F M M S K L P ttggaaaatccagtacttctggacatgctctggaggagaaagattggtcctcagatgaccctttctcatgcc
L E N P V L L D M L W R R K I G P Q M T L S H A gcaggattccatgctactagtgctgactgctgcatctcctacaccccacgaagcatcccgtgttcactcctg
A G F H A T S A D C C I S Y T P R S I P C S L L gagagttactttgaaacgaacagcgagtgctccaagccgggtgtcatcttcctcaccaagaaggggcgacgt
E S Y F E T N S E C S K P G V I F L T K K G R R ttctgtgccaaccccagtgataagcaagttcaggtttgcatgagaatgctgaagctggacacacggatcaag
F C A N P S D K Q V Q V C M R M L K L D T R I K accaggaagaattgaacttgtcaaggtgaagggacacaagttgccagccaccaactttcttgcctcaactaa
T R K N *
cttcctgaattatttttttaagaagcatttattcttgtgttctggatttagagcaattcatcttttctcacc
tttaaaaaaaaaaaaaaaaaaa
```

FIG.26A

```
1   MKVSVAALSCLMLVTALGSQARVTKDAETEFMMSKLPLENPVLLDMLWRR    50    MPIF-1 variant
    ||||||||||||||||||||||||||||||||||||||||||||||
1   MKVSVAALSCLMLVTALGSQARVTKDAETEFMMSKLPLENPVLLDR....    46    MPIF-1

51  KIGPQMTLSHAAGFHATSADCCISYTPRSIPCSLLESYFETNSECSKPGV   100
                 ||||||||||||||||||||||||||||||||||||||
47  .............FHATSADCCISYTPRSIPCSLLESYFETNSECSKPGV    83

101 IFLTKKGRRFCANPSDKQVQVCMRMLKLDTRIKTRKN  137
    ||||||||||||||||||||||||||||||||||||
84  IFLTKKGRRFCANPSDKQVQVCMRMLKLDTRIKTRKN  120
```

FIG.26B

| MPIF-1 MUTANTS | CONCENTRATION (ng/ml) |
| --- | --- |
| WILD TYPE | 100 |
| PREPARATION K0871 | 10 |
| MUTANT-1 | 50 |
| MUTANT-6 | 100 |
| HG00300-B7 | 10 |
| MUTANT-9 | 10 |

FIG.27

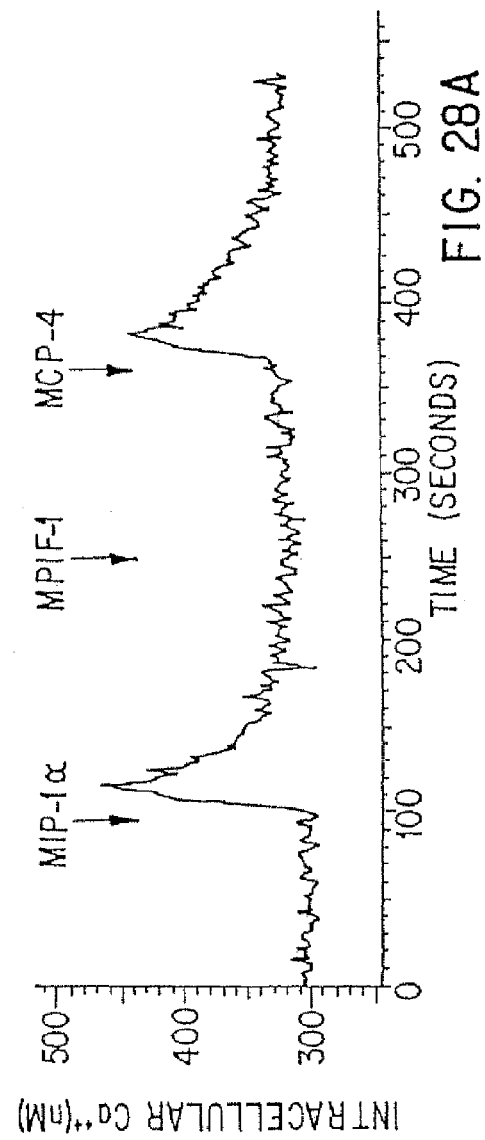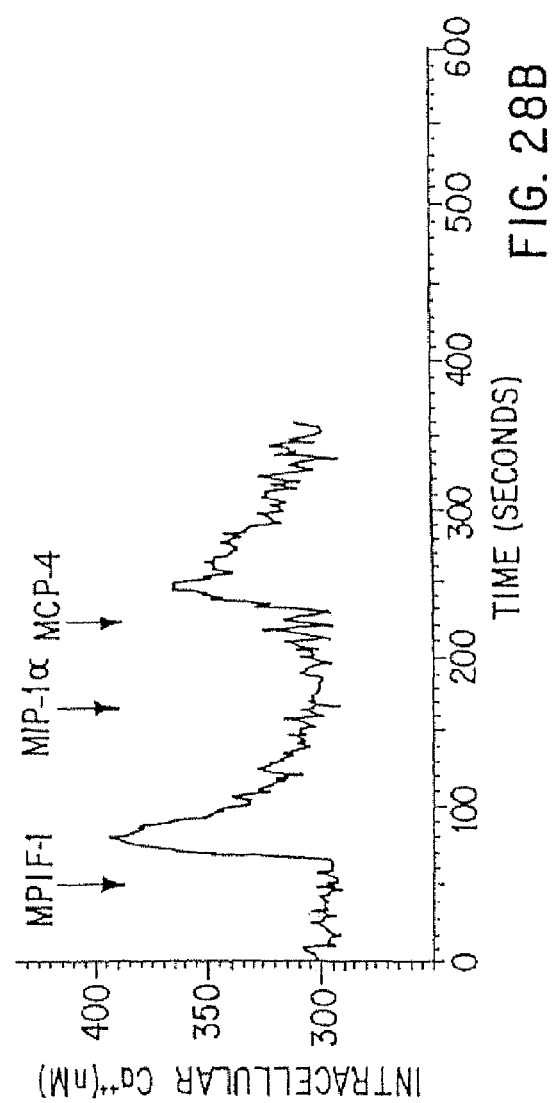

| ADDITIONS | CALCIUM MOBILIZATION RESPONSE |
|---|---|
| MIP-1α ALONE | + |
| MPIF-1 ALONE | + |
| MIP-1α FOLLOWED BY MPIF-1 | − |
| MPIF-1 FOLLOWED BY MIP-1α | − |
| | |
| MIP-1α FOLLOWED BY: | |
| PREPARATION K0871 | − |
| HG00300-B7 | − |
| MUTANT-6 | − |
| MUTANT-1 | − |
| MUTANT-9 | − |
| | |
| PREPARATION K0871 | + |
| K0871 FOLLOWED BY MIP-1α | − |
| HG00300-B7 | + |
| HG00300-B7 FOLLOWED BY MIP-1α | − |
| MUTANT-6 | + |
| MUTANT-6 FOLLOWED BY MIP-1α | − |
| MUTANT-1 | + |
| MUTANT-1 FOLLOWED BY MIP-1α | − |
| MUTANT-9 | + |
| MUTANT-9 FOLLOWED BY MIP-1α | − |

FIG.29

| PROTEINS | CHEMOTAXIS * |
|---|---|
| WILD TYPE | 50-100 ng/ml (3-4X) |
| PREPARATION K0871 | 10-30 ng/ml (6-7X) |
| MUTANT-1 | 50-100 ng/ml (3-4X) |
| MUTANT-6 | 50-100 ng/ml (5-7X) |
| HG00300-B7 | 10-30 ng/ml (4-5X) |

FIG.30

| ADDITIONS | CONCENTRATION REQUIRED FOR 50% OF MAXIMAL LPP-CFC INHIBITION (ng/ml) |
|---|---|
| MPIF-1, WILD TYPE | 10-20 |
| MUTANT-1 | 15-25 |
| MUTANT-6 | 1-10 |
| PREPARATION K0871 | 0.1-1.0 |
| HG00300-B7 | 0.1-1.0 |

FIG.31

STEM CELL MOBILIZATION IN RESPONSE TO ADMINISTERING MPIF-1 TO NORMAL MICE

| EXPERIMENT | TREATMENTS | WBC/ml BLOOD (x 10$^6$) | PHENOTYPE OF CELLS | |
|---|---|---|---|---|
| | | | Gr.1 | CD34$^+$Sca-1$^+$ |
| 1 | SALINE | 4.7 ± 0.36 | 10 | 0.20 |
| | MPIF-1 | 7.1 ± 0.63 | 39 | 8 |

FIG. 50

```
                                      -35          Operator 1
1   AAGCTT AAAAAACTGCAAAAAATAGT TTGACT TGTGAGCGGATAACAAT -10              Operator 2
50  TAAGAT GTACCCA ATTGTGAGCGGATAACAAT TTCACACATTAA

S/D
94  AGAGGAG AAATTA CATATG
```

ANTIBODIES TO MYELOID PROGENITOR INHIBITORY FACTOR-1 (MPIF-1)

CROSS REFERENCE TO RELATED APPLICATIONS

This application is a divisional of U.S. application Ser. No. 10/626,530, filed Jul. 25, 2003, now U.S. Pat. No. 7,041,460 which is a divisional U.S. application Ser. No. 09/571,013, filed May 15, 2000 (now U.S. Pat. No. 6,811,773, issued Nov. 2, 2004), which is a continuation of U.S. application Ser. No. 08/941,020, filed Sep. 30, 1997 (now abandoned), which claims benefit under 35 U.S.C. §119(e) of U.S. Provisional Application Nos. 60/027,299 and 60/027,300, both filed on Sep. 30, 1996; U.S. application Ser. No. 08/941,020 is also a continuation in part of U.S. application Ser. No. 08/722,723, filed Sep. 30, 1996 (now abandoned), and a continuation in part of U.S. application Ser. No. 08/722,719, filed Sep. 30, 1996 (now U.S. Pat. No. 6,001,606, issued Dec. 14, 1999); U.S. application Ser. No. 08/722,723 is a continuation in part of U.S. application Ser. No. 08/468,775, filed Jun. 6, 1995 (now abandoned), and a continuation in part of U.S. application Ser. No. 08/465,682, filed Jun. 6, 1995 (now abandoned), and a continuation in part of U.S. application Ser. No. 08/446,881 filed May 5, 1995 (now abandoned); U.S. application Ser. No. 08/722,719 is a continuation in part of U.S. application Ser. No. 08/468,775, filed Jun. 6, 1995 (now abandoned), and continuation in part of U.S. application Ser. No. 08/465,682, filed Jun. 6, 1995 (now abandoned), and a continuation in part of U.S. application Ser. No. 08/446,881, filed May 5, 1995 (now abandoned); U.S. application Ser. No. 08/468,775 is a continuation in part of U.S. application Ser. No. 08/173,209, filed Dec. 22, 1993 (now U.S. Pat. No. 5,556,767, issued Sep. 17, 1996), and a continuation in part of U.S. application Ser. No. 08/208,339, filed Mar. 8, 1994 (now U.S. Pat. No. 5,504,003, issued Apr. 2, 1996), and a continuation of U.S. application Ser. No. 08/446,881, filed May 5, 1995 (now abandoned); U.S. application Ser. No. 08/465,682 is a continuation in part of U.S. application Ser. No. 08/173,209, filed Dec. 22, 1993 (now 5,556,767, issued Sep. 17, 1996), and a continuation in part of U.S. application Ser. No. 08/208,339, filed Mar. 8, 1994 (now U.S. Pat. No. 5,504,003, issued Apr. 2, 1996), and a continuation of U.S. application Ser. No. 08/446,881, filed May 5, 1995 (now abandoned): U.S. application Ser. No. 08/446,881 is a continuation in part of U.S. application Ser. No. 08/173,209, filed Dec. 22, 1993 (now U.S. Pat. No. 5,556,767, issued Sep. 17, 1996), and a continuation in pan of U.S. application Ser. No. 08/208,339, filed Mar. 8, 1994 (now U.S. Pat. No. 5,504,003, issued Apr. 2, 1996).

U.S. Provisional Application Nos. 60/027,299 and 60/027,300 are herein incorporated by reference.

FIELD OF THE INVENTION

The present invention relates to novel chemokine polypeptides and encoding nucleic acids. More specifically, therapeutic compositions and methods are provided using isolated nucleic acid molecules encoding a human myeloid progenitor inhibitory factor-1 (MPIF-1) polypeptide (previously termed MIP-3 and chemokine , β8 (CKβ8 or ckb-8)), a human monocyte-colony inhibitory factor (M-CIF) polypeptide (previously termed MIP-1-γ and chemokine β1 (CKβ1 or ckb-1)), and a macrophage inhibitory protein-4 (MIP-4), as well as MPIF-1, M-CIF and/or MIP-4 polypeptides themselves, as are vectors, host cells and recombinant methods for producing the same.

BACKGROUND OF THE INVENTION

Chemokines, also referred to as intercrine cytokines, are a subfamily of structurally and functionally related cytokines. These molecules are 8-14 kd in size. In general chemokines exhibit 20% to 75% homology at the amino acid level and are characterized by four conserved cysteine residues that form two disulfide bonds. Based on the arrangement of the first two cysteine residues, chemokines have been classified into two subfamilies, alpha and beta. In the alpha subfamily, the first two cysteines are separated by one amino acid and hence are referred to as the "C—X—C" subfamily. In the beta subfamily, the two cysteines are in an adjacent position and are, therefore, referred to as the —C—C— subfamily. Thus far, at least eight different members of this family have been identified in humans.

The intercrine cytokines exhibit a wide variety of functions. A hallmark feature is their ability to elicit chemotactic migration of distinct cell types, including monocytes, neutrophils, T lymphocytes, basophils and fibroblasts. Many chemokines have proinflammatory activity and are involved in multiple steps during an inflammatory reaction. These activities include stimulation of histamine release, lysosomal enzyme and leukotriene release, increased adherence of target immune cells to endothelial cells, enhanced binding of complement proteins, induced expression of granulocyte adhesion molecules and complement receptors, and respiratory burst. In addition to their involvement in inflammation, certain chemokines have been shown to exhibit other activities. For example, macrophage inflammatory protein 1 (MIP-1 ) is able to suppress hematopoietic stem cell proliferation, platelet factor-4 (PF4) is a potent inhibitor of endothelial cell growth, Interleukin-8 (IL-8) promotes proliferation of keratinocytes, and GRO is an autocrine growth factor for melanoma cells.

In light of the diverse biological activities, it is not surprising that chemokines have been implicated in a number of physiological and disease conditions, including lymphocyte trafficking, wound healing, hematopoietic regulation and immunological disorders such as allergy, asthma and arthritis. An example of a hematopoietic lineage regulator is MIP-1, MIP-1 was originally identified as an endotoxin-induced proinflammatory cytokine produced from macrophages. Subsequent studies have shown that MIP-1 is composed of two different: but related, proteins MIP-1α and MIP-1β. Both MIP-1α and MIP-1β are chemo-attractants for macrophages, monocytes and T lymphocytes. Interestingly, biochemical purification and subsequent sequence analysis of a multipotent stem cell inhibitor (SCI) revealed that SCI is identical to MIP-1β. Furthermore, it has been shown that MIP-1β can counteract the ability of MIP-1α to suppress hematopoietic stein cell proliferation. This finding leads to the hypothesis that the primary physiological role of MIP-1 is to regulate hematopoiesis in hone marrow, and that the proposed inflammatory function is secondary. The mode of action of MIP-1α as a stem cell inhibitor relates to its ability to block the cell cycle at the $G_2S$ interphase. Furthermore, the inhibitory effect of MIP-1α seems to be restricted to immature progenitor cells and it is actually stimulatory to late progenitors in the presence of granulocyte macrophage-colony stimulating factor (GM-CSF).

Murine MIP-1 is a major secreted protein from lipopolysaccharide stimulated RAW 264.7, a murine macrophage tumor cell line. It has been purified and found to consist of two related proteins, MIP-1α and MIP-1β.

Several groups have cloned what are likely to be the human homologs of MIP-1α and MIP-1β. In all cases, cDNAs were isolated from libraries prepared against activated T-cell RNA.

MIP-1 proteins can be detected in early wound inflammation cells and have been shown to induce production of IL-1 and L6 from wound fibroblast cells. In addition, purified native MIP-1 (comprising MIP-1, MIP-1α and MIP-1β polypeptides) causes acute inflammation when injected either subcutaneously into the footpads of mice or intracisternally into the cerebrospinal fluid of rabbits (Wolpe and Cerami, *FASEB J.* 3:2565-73 (1989)). In addition to these proinflammatory properties of MIP-1, which can be direct or indirect, MIP-1 has been recovered during the early inflammatory phases of wound healing in an experimental mouse model employing sterile wound chambers (Fahey, et al. *Cytokine*, 2:92(1990)). For example, PCT application U.S. 92/05198 filed by Chiron Corporation, discloses a DNA molecule which is active as a template for producing mammalian macrophage inflammatory proteins (MIPs) in yeast.

The murine MIP-1α and MIP-1β are distinct but closely related cytokines. Partially purified mixtures of the two proteins affect neutrophil function and cause local inflammation and fever. MIP-1α has been expressed in yeast cells and purified to homogeneity. Structural analysis confirmed that MIP-la has a very similar secondary and tertiary structure to platelet factor 4 (PF4interleukin 8 (IL-8) with which it shares limited sequence homology. It has also been demonstrated that MIP-1α is active in vivo to protect mouse stem cells from subsequent in vitro killing by tritiated thymidine. MIP-1α was also shown to enhance the proliferation of more committed progenitor granulocyte macrophage colony-forming cells in response to granulocyte macrophage colony-stimulating factor. (Clemens, J. M. et al, *Cytokine* 4:76-82 (1992)).

The polypeptides of the present invention, M-CIF originally referred to as MIP-1γ and Ckβ-1 in the parent patent application, is a new member of the β chemokine family based on amino sequence homology. The MPIF-1 polypeptide, originally referred to as MIP-3 and Ckβ-8 in the parent application, is also a new member of the β chemokine family based on the amino acid sequence homology.

SUMMARY OF THE INVENTION

In accordance with one aspect of the present invention, there are provided novel full length or mature polypeptides which are MPIF-1, MIP-4 and/or M-CIF, as well as biologically active, diagnostically useful or therapeutically useful fragments, analogs and derivatives thereof The MPIF-1, MIP-4 and M-CIF of the present invention are preferably of animal origin, and more preferably of human origin.

In accordance with another aspect of the present invention, there are provided polynucleotides (DNA or RNA) which encode such polypeptides and isolated nucleic acid molecules encoding such polypeptides, including mRNAs, DNAs, cDNAs, genomic DNA as well as biologically active and diagnostically or therapeutically useful fragments, analogs and derivatives thereof MPIF-1 Polynucleotides. The present invention also provides isolated nucleic acid molecules comprising a polynucleotide encoding the MPIF-1 polypeptide having the amino acid sequence shown in FIG. 1 (SEQ ID NO:4) or the amino acid sequence encoded by the cDNA clone deposited as ATCC® Deposit Number 75676 on Feb. 9, 1994. The nucleotide sequence determined by sequencing the deposited MPIF-1 clone, which is shown in FIG. 1 (SEQ ID NO:3), contains an open reading frame encoding a polypeptide of 120 amino acid residues, with a leader sequence of about 21 amino acid residues, and a predicted molecula weight for the mature protein of about 11 kDa in non-glycosylated form, and about 11-14 kDa in glycosylated form, depending on the extent of glycoslyation. The amino acid sequence of the mature MPIF-1 protein is shown in FIG. 1 (SEQ ID NO:4).

Thus, one aspect of the invention provides an isolated nucleic acid molecule comprising a polynucleotide having a nucleotide sequence selected from the group consisting of: (1)(a) a nucleotide sequence encoding an MPIF-1 polypeptide having the complete amino acid sequence in FIG. 1 (SEQ ID NO:4); (1)(b) a nucleotide sequence encoding the MPIF-1 polypeptide having the complete amino acid sequence in FIG. 1 (SEQ ID NO:4) but minus the N-terminal methionine residue; (1)(c) a nucleotide sequence encoding the mature MPIF-1 polypeptide having the amino acid sequence at positions 22-120 in FIG. 1 (SEQ ID NO:4); (1)(d) a nucleotide sequence encoding the MPIF-1 polypeptide having the complete amino acid sequence encoded by the cDNA clone contained in ATCC® Deposit No. 75676, (1)(e) a nucleotide sequence encoding the mature MPIF-1 polypeptide having the amino acid sequence encoded by the cDNA clone contained in ATCC® Deposit No. 75676; and (1)(f) a nucleotide sequence complementary to any of the nucleotide sequences in (1)-(a), (b), (c), (d), or (e) above.

M-CIF Polynucleotides. In one aspect, the present invention provides isolated nucleic acid molecules comprising a polynucleotide encoding the M-CIF polypeptide having the amino acid sequence shown in FIG. 2 (SEQ ID NO:2) or the amino acid sequence encoded by the cDNA clone deposited as ATCC® Deposit Number 75572 on Oct. 13, 1993. The nucleotide sequence determined by sequencing the deposited M-CIF clone, which is shown in FIG. 2 (SEQ ID NO:1), contains an open reading frame encoding a polypeptide of 93 amino acid residues, with a leader sequence of about 19 amino acid residues, and a predicted molecular weight of about 9 kDa in non-glycosylated form, and about 9-14 kDa in glycosylated form, depending on the extent of glycoslyation. The amino acid sequence of the mature M-CIF protein is shown in FIG. 2 (SEQ ID NO:2).

Thus, one aspect of the invention provides an isolated nucleic acid molecule comprising a polynucleotide having a nucleotide sequence selected from the group consisting of: (2)(a) a nucleotide sequence encoding the M-CIF polypeptide having the complete amino acid sequence in FIG. 2 (SEQ ID NO:2); (2)(b) a nucleotide sequence encoding the M-CIF polypeptide having the complete amino acid sequence in FIG. 2 (SEQ ID NO:2) but minus the N-terminal methionine residue; (2)(c) a nucleotide sequence encoding the mature M-CIF polypeptide having the amino acid sequence at positions 20-93 in FIG. 2 (SEQ ID NO2); (2)(d) a nucleotide sequence encoding the M-CIF polypeptide having the complete amino acid sequence encoded by the cDNA clone contained in ATCC® Deposit No. 75572; (2)(e) a nucleotide sequence encoding the mature M-CIF polypeptide having the amino acid sequence encoded by the cDNA clone contained in ATCC® Deposit No. 75572; and (2)(t) a nucleotide sequence complementary to any of the nucleotide sequences in (2)-(a), (b), (c), (d), or (e) above.

MIP-4 Polynucleotides. The present invention further provides isolated nucleic acid molecules comprising a polynucleotide encoding the MIP-4 polypeptide having the amino acid sequence shown in FIG. 3 (SEQ ID NO:6) or the amino acid sequence encoded by the cDNA clone deposited as ATCC® Deposit Number 75675 on Feb. 9, 1994. The nucleotide sequence determined by sequencing the deposited MIP-4 clone, which is shown in FIG. 3 (SEQ ID NO:5), contains an open reading frame encoding a polypeptide of 89 amino acid residues, with a leader sequence of about 20 amino acid residues, and a predicted molecular weight of about 8 kDa in non-glycosylated form, and about 8-14 kDa in glycosylated form, depending on the extent of glycoslyation. The amino acid sequence of the mature MIP-4 protein is shown in FIG. 2 (SEQ ID NO:6).

Another aspect of the invention provides an isolated nucleic acid molecule comprising a polynucleotide having a nucleotide sequence selected from the group consisting of: (3)(a) a nucleotide sequence encoding the MIP-4 polypeptide having the complete amino acid sequence in FIG. 3 (SEQ ID NO:6); (3)(b) a nucleotide sequence encoding the MIP-4 polypeptide having the complete amino acid sequence in FIG. 3 (SEQ ID NO:6) but minus the N-terminal methionine residue; (3)(c) a nucleotide sequence encoding the mature MIP-4 polypeptide having the amino acid sequence at positions 21-89 in FIG. 3 (SEQ ID NO:6); (3)(d) a nucleotide sequence encoding the MIP-4 polypeptide having the complete amino acid sequence encoded by the cDNA clone contained in ATCC® Deposit No. 75675; (3)(e) a nucleotide sequence encoding the mature MIP-1 polypeptide having the amino acid sequence encoded by the cDNA clone contained in ATCC® Deposit No. 75675; and (3)(f) a nucleotide sequence complementary to any of the nucleotide sequences in (3)-(a), (b), (c), (d), or (e) above.

MPIF-1, M-CIF and MIP-4 Polynucleotide Variants. The present invention further relates to variants of the hereinabove described polynucleotides which encode for fragments, analogs and derivatives of the polypeptide having the deduced amino acid sequence of FIGS. 1, 2 and 3 (SEQ ID NOS:2, 4 and 6) or the polypeptides encoded by the cDNA of the deposited clone(s). The variants of the polynucleotides can be a naturally occurring allelic variant of the polynucleotides or a non-naturally occurring variant of the polynucleotides.

Homologous MPIF-1, M-CIF and MIP-4 Polynucleotides. Further embodiments of the invention include isolated nucleic acid molecules that comprise a polynucleotide having a nucleotide sequence at least 95%, 96%, 97%, 98% or 99% identical, to any of the nucleotide sequences in (1)-, (2)- or (3)-(a), (b), (c), (d), (e), or (f), above, or a polynucleotide which hybridized under stringent hybridization conditions to a polynucleotide in (1)-, (2)- or (3)-(a), (b), (c), (d), (e), or (f), above. These polynucleotides which hybridize do not hybridize under stringent hybridization conditions to a polynucleotide having a nucleotide sequence consisting of only A residues or of only T residues.

Nucleic Acid Probes. In accordance with yet another aspect of the present invention, there are also provided nucleic acid probes comprising nucleic acid molecules of sufficient length to specifically hybridize to the MPIF-1, M-CIF and/or MIP-4 nucleic acid sequences.

Recombinant Vectors, Host Cells and Expression. The present invention also relates to recombinant vectors, which include the isolated nucleic acid molecules of the present invention, and to host cells containing the recombinant vectors, as well as to methods of making such vectors and host cells and for using them for production of MPIF-1, M-CIF or MIP-4 polypeptides or peptides by recombinant techniques.

MPIF-1 Polypeptides. The invention further provides an isolated MPIF-1 polypeptide having an amino acid sequence selected from the group consisting of: (I)(a) the amino acid sequence of the MPIF-1 polypeptide having the complete 120 amino acid sequence, including the leader sequence shown in FIG. 1 (SEQ ID NO:4); (I)(b) the amino acid sequence of the MPIF-1 polypeptide having the complete 120 amino acid sequence, including the leader sequence shown in FIG. 1 (SEQ ID NO:4) but minus the N-terminal methionine residue; (I)(c) the amino acid sequence of the mature MPIF-1 polypeptide (without the leader) having the amino acid sequence at positions 22-120 in FIG. 1 (SEQ ID NO:4); (I)(d) the amino acid sequence of the MPIF-1 polypeptide having the complete amino acid sequence, including the leader, encoded by the cDNA clone contained in ATCC® Deposit No. 75676; and (I)(e) tie amino acid sequence of the mature MPIF-1 polypeptide having the amino acid sequence encoded by the cDNA clone contained in ATCC® Deposit No. 75676.

M-CIF Polypeptides. The invention further provides an isolated M-CIF polypeptide having an amino acid sequence selected from the group consisting of (II)(a) the amino acid sequence of the M-CIF polypeptide having the complete 93 amino acid sequence, including the leader sequence shown in FIG. 2 (SEQ ID NO:2); (I)(b) the amino acid sequence of the M-CIF polypeptide having the complete 93 amino acid sequence, including the leader sequence shown in FIG. 2 (SEQ ID NO:2) but minus the N-terminal methionine residue; (II)(c) the amino acid sequence of the mature M-CIF polypeptide (without the leader) having the amino acid sequence at positions 20-93 in FIG. 2 (SEQ ID NO:2); (II)(d) the amino acid sequence of the M-CIF polypeptide having the complete amino acid sequence, including the leader, encoded by the cDNA clone contained in ATCC® Deposit No. 75572; and (II)(e) the amino acid sequence of the mature M-CIF polypeptide having the amino acid sequence encoded by the cDNA clone contained in ATCC® Deposit No. 75572.

MIP-4 Polypeptides. The invention further provides an isolated MIP-4 polypeptide having an amino acid sequence selected from the group consisting of, (III)(a) the amino acid sequence of the MIP-4 polypeptide having the complete 89 amino acid sequence, including the leader sequence shown in FIG. 3 (SEQ ID NO:6); (III)(b) the amino acid sequence of the MIP-4 polypeptide having the complete 89 amino acid sequence, including the leader sequence shown in FIG. 3 (SEQ ID NO:6) but minus the N-terminal methionine residue; (III)(c) the amino acid sequence of the mature MIP-4 polypeptide (without the leader) having the amino acid sequence at positions 21-89 in FIG. 3 (SEQ ID NO:6); (III)(d) the amino acid sequence of the MIP-4 polypeptide having the complete amino acid sequence, including the leader, encoded by the cDNA clone contained in ATCC® Deposit No. 75675; and (III)(e) the amino acid sequence of the mature MIP-4 polypeptide having the amino acid sequence encoded by the cDNA clone contained in ATCC® Deposit No. 75675.

Homologous MPIF-1, M-CIF and MIP-4 Polypeptides. Polypeptides of the present invention also include homologous polypeptides having an amino acid sequence with at least 95% identity to those described in (I)-, (II)- and (III)(a), (b), (c), (d), or (e) above, as well as polypeptides having an amino acid sequence at least 95%, 96%, 97%, 98% or 99% identical to those above.

MPIF-1, M-CIF and MIP-4 Epitope Bearing Polypeptides and Encoding Polynucleotides. An additional embodiment of this aspect of the invention relates to a peptide or polypeptide which has the amino acid sequence of an epitope-bearing portion of an MPF-1, M-CIF or MIP-4 polypeptide having an amino acid sequence described in (I)-, (II)-, or (III)-(a), (b), (c), (d), or (e) above. Peptides or polypeptides having the amino acid sequence of an epitope-bearing portion of an MPIF-1, M-CIF or MIP-4 polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

An additional nucleic acid embodiment of the invention relates to an isolated nucleic acid molecule comprising a polynucleotide which encodes the amino acid sequence of an epitope-bearing portion of an MPIF-1, M-CIF or MIP-4 polypeptide having an amino acid sequence in (I)-, (II)- or (III)-(a), (b), (c), (d), or (e), above.

MPIF-1, M-CIF and MIP-4 Antibodies. In accordance with yet a further aspect of the present invention, there is provided an antibody against such polypeptides. In another embodiment, the invention provides an isolated antibody that binds specifically to an MPIF-1, M-CIF or MIP-4 polypeptide having an amino acid sequence described in (I)-, (II)-, and/or (III)-(a), (b), (c), (d), or (e), above.

The invention further provides methods for isolating antibodies that bind specifically to an MPIF-1, M-CIF or MIP-4 polypeptide having an amino acid sequence as described herein. Such antibodies are useful diagnostically or therapeutically as described below.

MPIF-1, M-CIF and MIP-4 Antagonists and Methods. In accordance with yet another aspect of the present invention, there are provided antagonists or inhibitors of such polypeptides, which can be used to inhibit the action of such polypeptides, for example, in the treatment of arteriosclerosis, autoimmune and chronic inflammatory and infective diseases, histamine-mediated allergic reactions, hyper-eosinophilic syndrome, silicosis, sarcoidosis, inflammatory diseases of the lung, inhibition of IL-1 and TNF, aplastic anaemia, and myelodysplastic syndrome. Alternatively, such polypeptides can be used to inhibit production of IL-1 and TNF-α, to treat aplastic anemia, myelodysplastic syndrome, asthma and arthritis.

Diagnostic Assays. In accordance with still another aspect of the present invention, there are provided diagnostic assays for detecting diseases related to the underexpression and overexpression of the polypeptides and for detecting mutations in the nucleic acid sequences encoding such polypeptides.

In accordance with yet another aspect of the present invention, there is provided a process for utilizing such polypeptides, or polynucleotides encoding such polypeptides, as research reagents for in vitro purposes related to scientific research, synthesis of DNA and manufacture of DNA vectors, for the purpose of developing therapeutics and diagnostics for the treatment of human disease.

The present invention also provides a screening method for identifying compounds capable of enhancing or inhibiting a cellular response induced by an MPIF-1, M-CIF or MIP-4 polypeptide, which involves contacting cells which express the MPIF-1, M-CIF or MIP-4 polypeptide with the candidate compound, assaying a cellular response, and comparing the cellular response to a standard cellular response, the standard being assayed when contact is made in absence of the candidate compound-, whereby, an increased cellular response over the standard indicates that the compound is an agonist and a decreased cellular response over the standard indicates that the compound is an antagonist.

For a number of disorders, it is believed that significantly higher or lower levels of MPIF-1, M-CIF or MIP-4 gene expression can be detected in certain tissues or bodily fluids (e.g., serum, plasma, urine, synovial fluid or spinal fluid) taken from an individual having such a disorder, relative to a "standard" MPIF-1, M-CIF or MIP-4 gene expression level, i.e., the MPIF-1, M-CIF or MIP-4 expression level in tissue or bodily fluids from an individual not having the disorder. Thus, the invention provides a diagnostic method useful during diagnosis of a disorder, which involves: (a) assaying MPIF-1, M-CIF or MIP-4 gene expression level in cells or body fluid of an individual; (b) comparing the MPIF-1, M-CIF or MIP-4 gene expression level with a standard MPIF-1, M-CIF or MIP-4 gene expression level, whereby an increase or decrease in the assayed MPIF-1, M-CIF or MIP-4 gene expression level compared to the standard expression level is indicative of a disorder. Such disorders include leukemia, chronic inflammation, autoimmune diseases, solid tumors.

Pharmaceutical Compositions. The present invention also provides, in another aspect pharmaceutical compositions comprising at least one of an MPIF-1, M-CIF or MIP-4: polynucleotide, probe, vector, host cell, polypeptide, fragment, variant, derivative, epitope bearing portion, antibody, antagonist, or agonist.

Therapeutic Methods. In accordance with yet a further aspect of the present invention, there is provided a process for utilizing such polypeptides, or polynucleotides encoding such polypeptides for therapeutic purposes, for example, to protect bone marrow stem cells from chemotherapeutic agents during chemotherapy, to remove leukemic cells, to stimulate an immune response, to regulate hematopoiesis and lymphocyte trafficking, treatment of psoriasis, solid tumors, to enhance host defenses against resistant and acute and chronic infection, and to stimulate wound healing.

An additional aspect of the invention is related to a method for treating an individual in need of an increased level of MPIF-1, M-CIF or MIP-4 activity in the body comprising administering to such an individual a composition comprising a therapeutically effective amount of an isolated MPIF-1, M-CIF or MIP-4 polypeptide of the invention or an agonist thereof, respectively.

A still further aspect of the invention is related to a method for treating an individual in need of a decreased level of MPIF-1, M-CIF or MIP-4 activity in the body comprising, administering to such an individual a composition comprising a therapeutically effective amount of an MPIF-1, M-CIF or MIP-4 antagonist. Preferred antagonists for use in the present invention are M-CIF-specific antibodies, respectively.

These and other aspects of the present invention should be apparent to those skilled in the art from the teachings herein.

BRIEF DESCRIPTION OF THE FIGURES

The following drawings are illustrative of embodiments of the invention and are not meant to limit the scope of the invention as encompassed by the claims.

FIG. 1 displays the EDNA sequence encoding MPIF-1 (SEQ ID NO:3) and the corresponding deduced amino acid sequence (SEQ ID NO:4). The initial 21 amino acids represents the putative leader sequence. All the signal sequences were as determined by N-terminal peptide sequencing of the baculovirus expressed protein.

FIG. 2 displays the cDNA sequence encoding M-CIF (SEQ ID NO: 1) and the corresponding deduced amino acid sequence (SEQ ID NO:2). The initial 19 amino acids represents a leader sequence.

FIG. 3 displays the cDNA sequence encoding MIP-4 (SEQ ID NO:5) and the corresponding deduced amino acid sequence (SEQ ID NO:6). The initial 20 amino acids represents a leader sequence.

FIG. 4 illustrates the amino acid homology between MPIF-1 (top) (SEQ ID NO:4) and human MIP-1α (bottom) (SEQ ID NO:55). The four cysteines characteristic of all chemokines are shown.

FIG. 5 displays two amino acid sequences wherein, the top sequence is the human MIP-4 amino acid sequence (SEQ ID NO:6) and the bottom sequence is human MIP-1α (Human Tonsillar lymphocyte LD78 Beta protein precursor) (SEQ ID NO:55).

FIG. 6 illustrates the amino acid sequence alignment between M-CIF (top) and human MIP-1α (bottom) (SEQ ID NO:55).

FIG. 9A depicts part of a three-step purification of MPIF-1 in a baculovirus expression system, while

FIGS. 16A-B show the effect of MPIF-1 and M-CIF on the generation of Gr.1 and Mac-1 (surface markers) positive population of cells from lineage depleted population of bone marrow cells, lin cells were incubated in growth medium supplemented with IL-3 (5 ng/ml) and SCF (100 ng/ml) alone (a) with MPIF-1 (50 ng/ml) (b) or M-CIF (50 ng/ml) (c). Cells were then stained with Monoclonal antibodies against myeloid differentiation Gr. 1, Mac-1, Sca-1, and CD45R surface antigens and analyzed by FACScan. Data is presented as percentage of positive cells in both large (FIG. 16A) and small (FIG. 16B) cell populations.

FIG. 20A shows an analysis of the MPIF-1 amino acid sequence (SEQ ID NO:4). Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues 21-30, 31-44, 49-55, 59-67, 72-83, 86-103 and 110-120 in FIG. 1 (SEQ ID NO:4), or any range or value therein, in FIG. 1 (SEQ ID NO:4) correspond to the shown highly antigenic regions of the MPIF-1 protein. FIG. 20B shows an analysis of the M-CIF amino acid sequence (SEQ ID NO:2). Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues 20-36, 42-52, 52-64, 67-75, 75-84 and/or 86-93 in FIG. 2 (SEQ ID NO:2), or any range or value therein, in FIG. 2 (SEQ ID NO:2) correspond to the shown highly antigenic regions of the M-CIF protein.

FIG. 21A shows the myeloprotective effect of MPIF-1 on the 5-Fu-induced killing of LPP-CFC cells. FIG. 21B shows the myeloprotective effect of MPIF-1 on the Ara-C induced killing of LPP-CFC cells.

FIG. 22 shows the effect of MPIF-1 pre-treatment of mice on the 5-Fu-induced reduction in the circulating WBC counts.

FIG. 24 shows the effect of administration of MPIF-1 prior to the second dose of 5-Fu on the HPP-CFC and LPP-CFC frequencies in the bone marrow.

FIG. 25 shows MPIF-1 variants. The first 80 out of 120 amino acids sequence of MPIF-1 (FIG. 1 (SEQ ID NO:4))

is shown using a single amino acid letter code of which the first 21 residues show characteristics of a signal sequence that is cleaved to give rise to a mature, wild type protein. Mutants-1 and -6 contain methionine as the N-terminal residue which is not present in the wild type. Also, the first four amino acids (HAAG) of Mutant-9 (residues 1 to 4 of SEQ ID NO:9) are not present in the wild type MPIF-1 protein. Mutants-1, -6 and, -9 correspond to SEQ ID NOS:7, 8 and 9, respectively. Mutant-2 corresponds to amino acid residues 46-120 in SEQ ID NO:4. Mutant-3 corresponds to amino acid residues 45-120 in SEQ ID NO:4). Mutants corresponds to amino acid residues 48-120 in SEQ ID NO:4. Mutant-5 corresponds to amino acid residues 49-120 in SEQ ID NO:4. Mutant-7 corresponds to amino acids residues 39-120 in SEQ ID NO:4. Mutant-8 corresponds to amino acid residues 44-120 in SEQ ID NO:4.

FIG. 26A-B. FIG. 26A shows the nucleotide sequence of a human MPIF-1 splice variant cDNA (SEQ ID NO:10), This cDNA sequence is shown along with the open reading frame encoding for a protein of 137 amino acids (SEQ ID NO:11) using a single letter amino acid code. The N-terminal 21 amino acids which are underlined represent the putative leader sequence. The insertion of 18 amino acids sequence not represented in the MPIF-1 sequence but unique to the splice variant are high-lighted in italics. FIG. shows the comparison of the amino acid sequence of the MPIF-1 variant (SEQ ID NO:11) with that of the wild type MPIF-1 molecule (SEQ ID NO:4).

FIG. 27 shows the concentrations of MPIF-1 mutant proteins required for 50% of maximal calcium mobilization response induced by MIP-1α in human monocytes.

FIG. 28 shows the changes in the intracellular free calcium concentration was measured in human monocytes in response to the indicated proteins at 100 ng/ml as described in the legend to FIG. 27.

FIG. 29 shows the ability of MPIF-1 mutants to desensitize MIP-1α stimulated calcium mobilization in human monocytes (summary).

FIG. 30 shows the chemotactic responses of human peripheral blood mononuclear cells (PBMC) to MPIF-1 mutants. Numbers within the parenthesis reflect fold stimulation of chemotaxis above background observed at the indicate concentration range.

FIG. 31 shows the effect of MPIF-1 variants on the growth and differentiation of Low Proliferative Potential Colony-forming Cells (LPP-CFC) in vitro.

Figure 32:
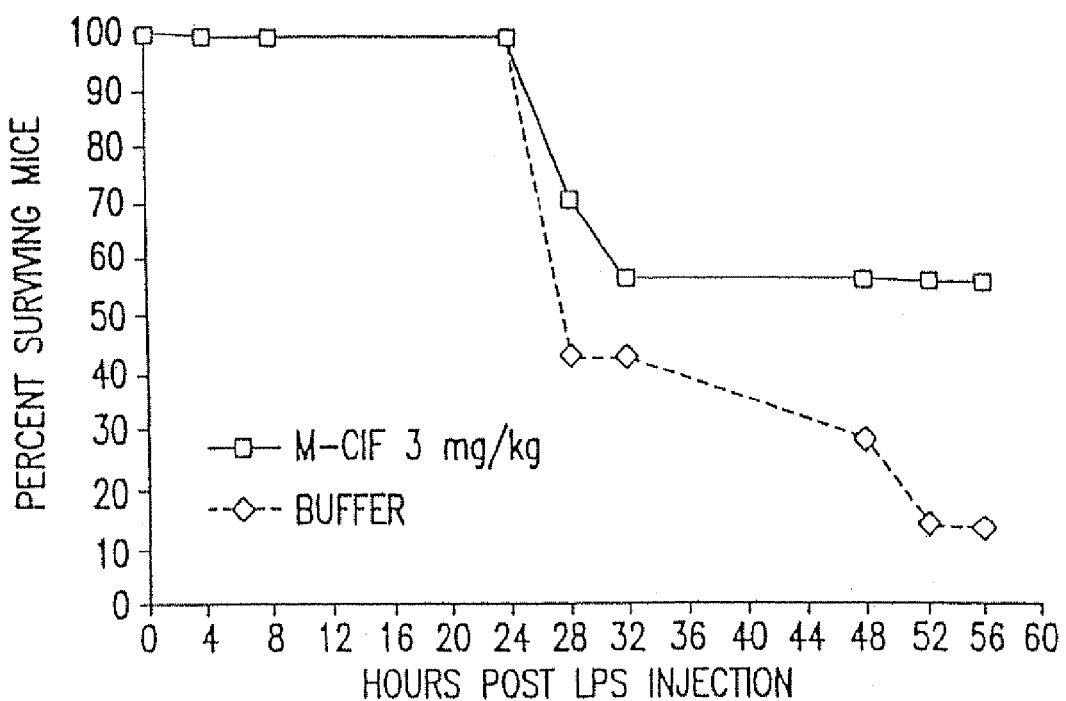

FIG. 32 shows protection against LPS-induced septic shock in mice by pretreatment with recombinant human M-CIF. Groups of Balb/c mice (n=7) were injected i.p. with 25 mg/kg of LPS on day 0. M-CIF was given i.p. daily at 3 mg/kg of body weight of for 3 consecutive days from one day before, on the same day, and one day after LPS challenge (−1, 0, +1). Mice receiving buffer only served as disease control. The kinetic of lethality was followed for 56 hours after LPS challenge.

Figure 33:
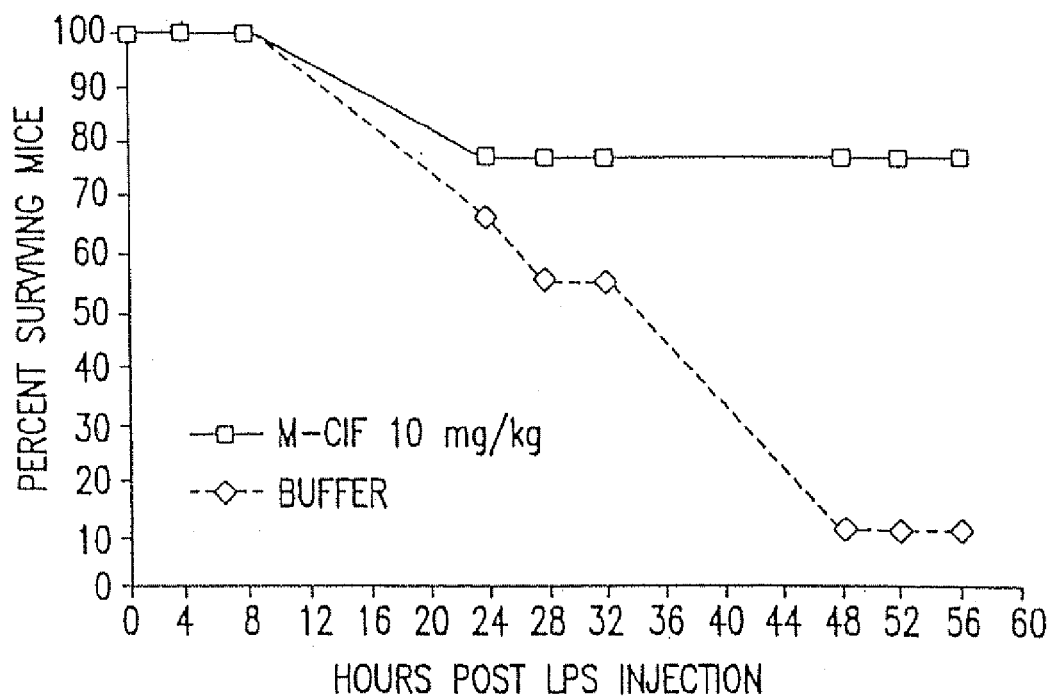

FIG. 33 shows the protective effect of M-CIF on lethal shock is dependent on LPS dose. Groups of Balb/c mice (n=9 ) were injected i.p. with 25 mg/kg of LPS on day 0 for different degrees of sepsis induction, 10 mg/kg of M-CIF was given i.p. daily for 3 consecutive day to each group of LPS-treated mice. The kinetic of lethality was followed for 56 hours after LPS challenge.

Figure 34:
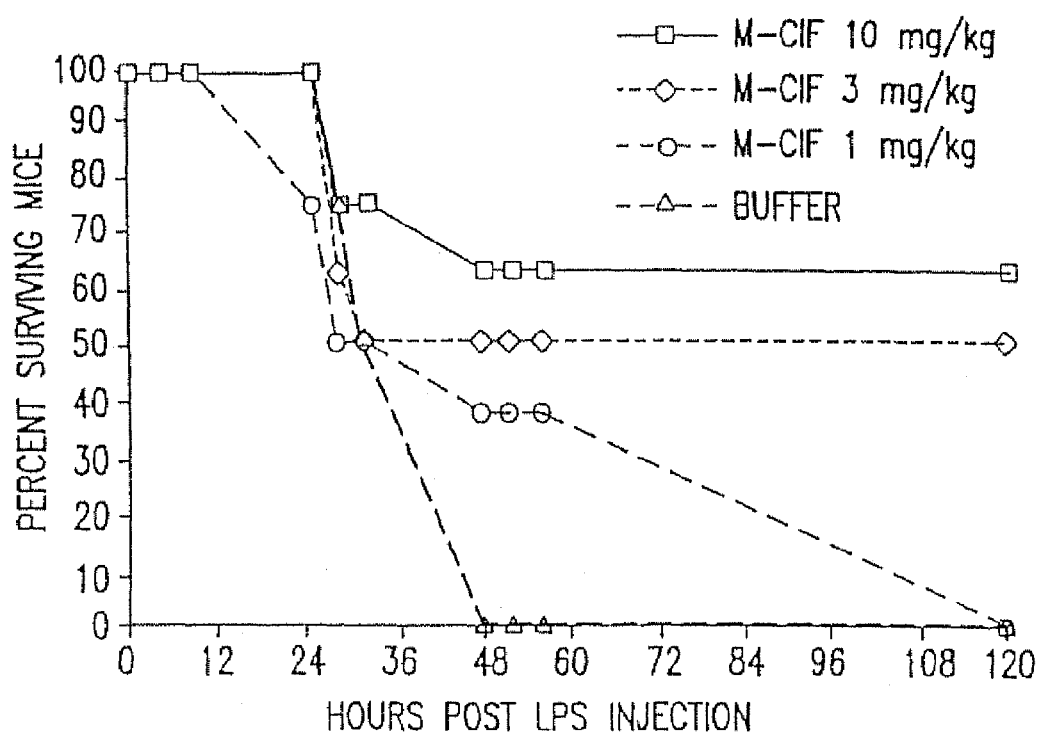

FIG. 34 shows protection against UPS-induced lethal shock in mice is dependent on M-CIF dose. Groups of Balb/c mice (n=8) were challenged i.p. with 25 mg/kg of LPS on day 0 and treated daily with different doses (1, 3 or 10 mg/kg) of M-CIF for 3 consecutive days (−1, 0, +1). Mice receiving buffer only served as a disease control. The kinetic of lethality was followed for 120 hours after LPS challenge.

Figure 35A:
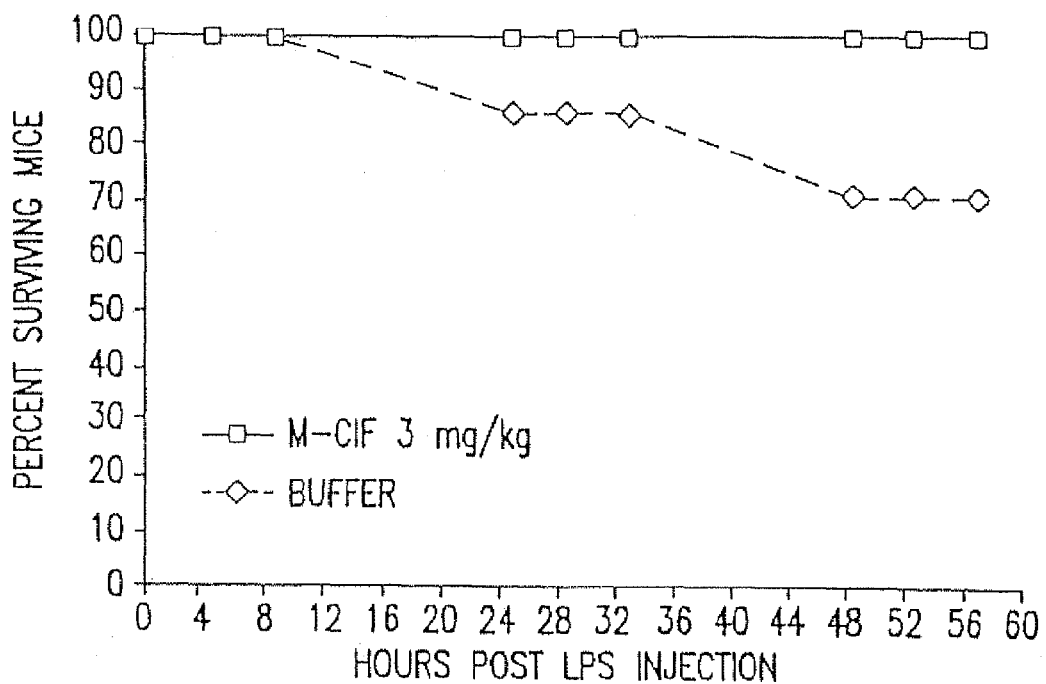
Figure 35B:
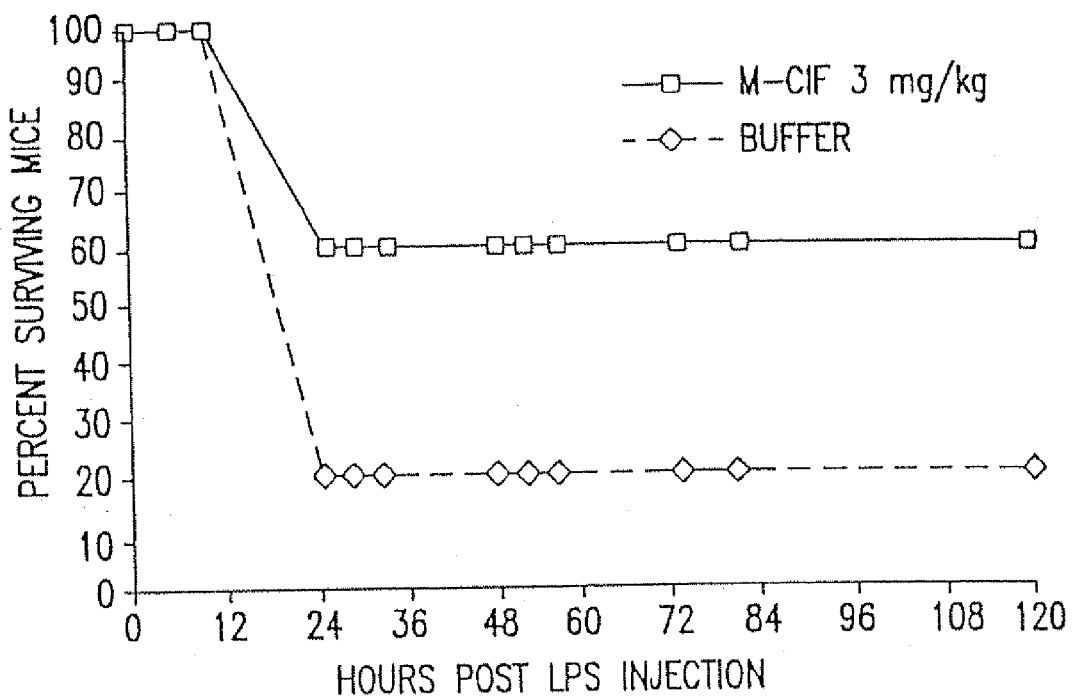

FIG. 35A-B shows the protective effect of M-CIF on LPS-induced shock in Balb/c SCID mice. Groups of Balb/c SCID mice (n=5-7) were challenged i.p. with 20, 30 or 40 mg/kg of LPS on day 0; and M-CIF treatment was given to each group of LPS-injected mice at 3 mg/kg daily dosing for 3 consecutive days (−1, 0, +1). The kinetic of lethality was followed for 120 hours after LPS challenge. The result of M-CIF pretreatment on 20 mg/kg of LPS-injected mice is the same as that of LPS-injection alone with no death occurring.

Figure 36:
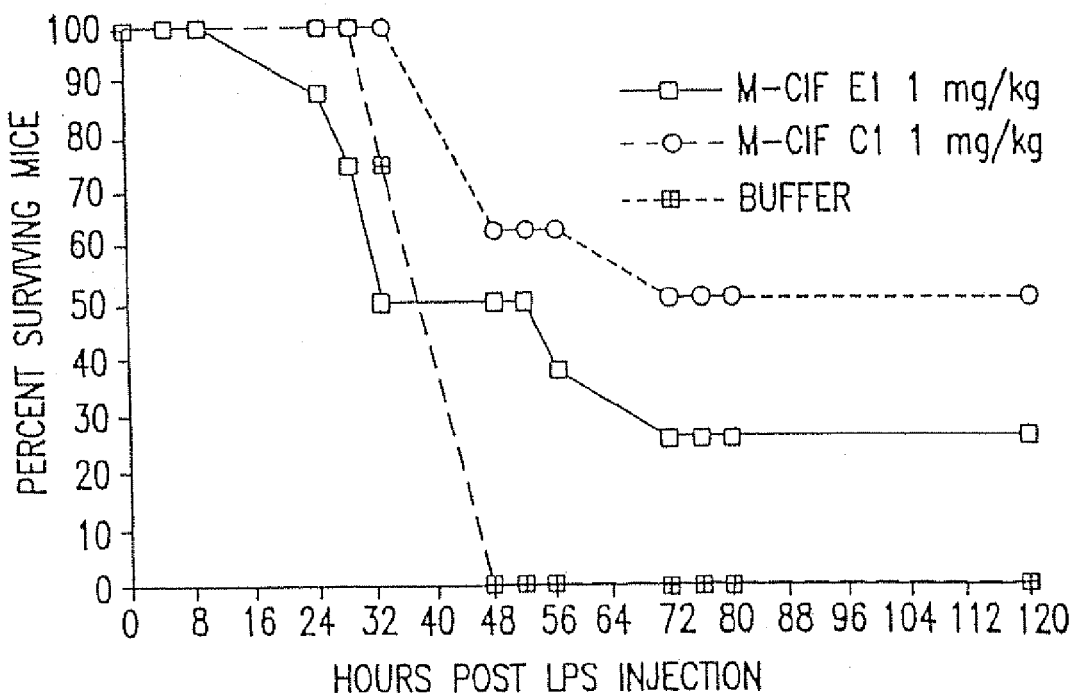

FIG. 36 shows the protective effect of M-CIF protein from E. coli and CHO expression vectors on sepsis. Groups of Balb/c mice (n=8) were injected with 25 mg/kg of LPS on day 0; and treated with two different batches (E1 and C1) of M-CIF at 1 mg/kg for 3 consecutive days (−1, 0, +1). Mice receiving buffer only served as a disease control. The kinetic of lethality was followed for 120 hours after LPS challenge.

Figure 37:
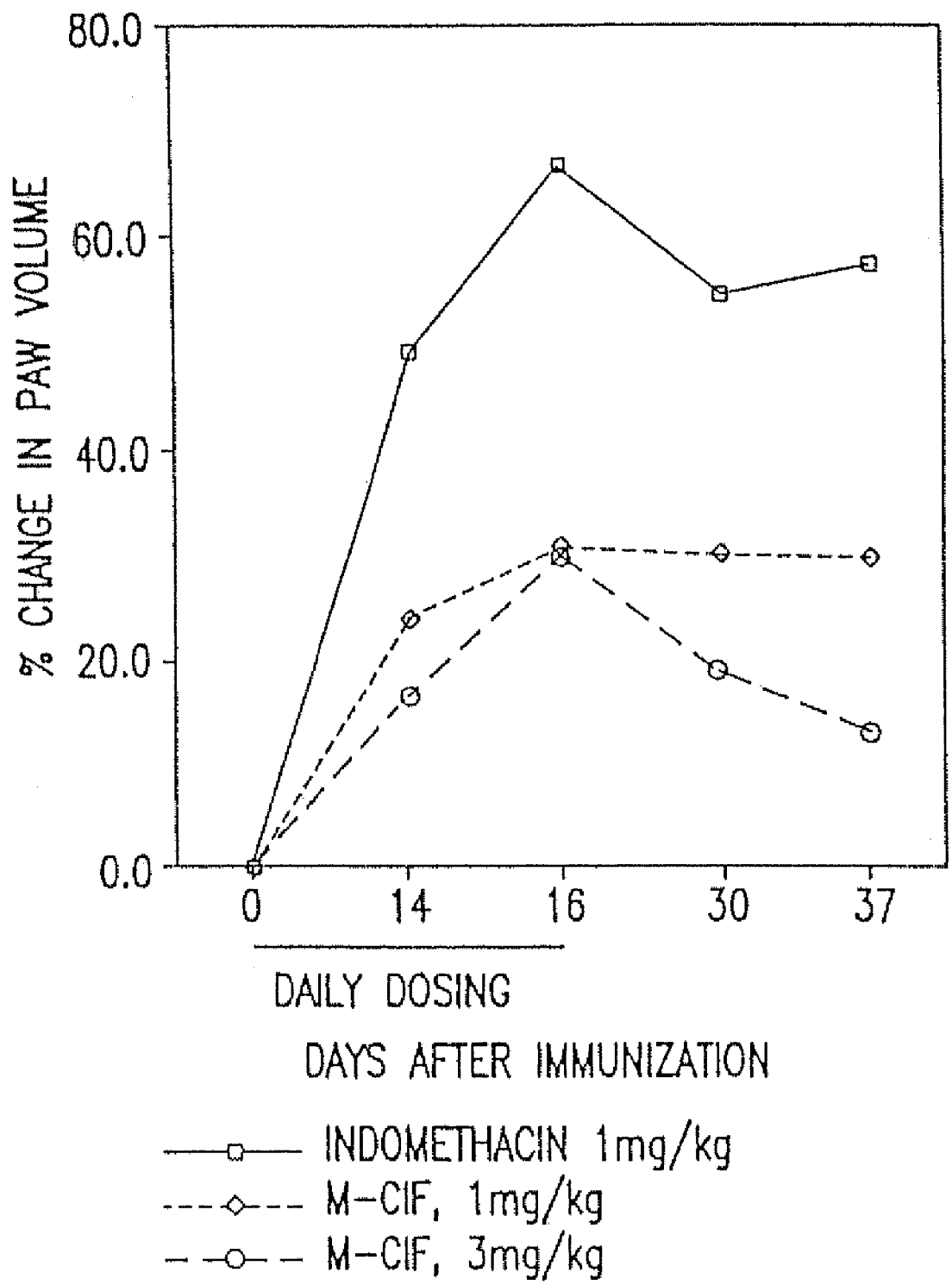

FIG. 37. Efficacy of M-CIF in reducing paw edema in adjuvant-induced arthritis model. Groups of Lewis rats (n=5) were injected intradermally at the base of the tail with 100 μl/rat of Freund's complete adjuvant containing 5 mg/ml Mycobacterium butyricum on day 0. Preventative treatment started on day 0 and continued daily (M-CIF, 5 times/week) for 16 days with i.p. M-CIF at 1 or 3 mg/kg in buffer (40 mM sodium acetate; 500 mM NaCl) or with p.o. indomethacin at 1 mg/kg in methyl cellulose, as drug control, daily dose (5 times/week) for 16 days. Rats receiving buffer or methyl cellulose only served as disease control. Swelling of both hind paws were monitored on the days as indicated using a plethysmometer chamber, and percentage of efficacy of testing drugs on paw volume were calculated.

Figure 38:
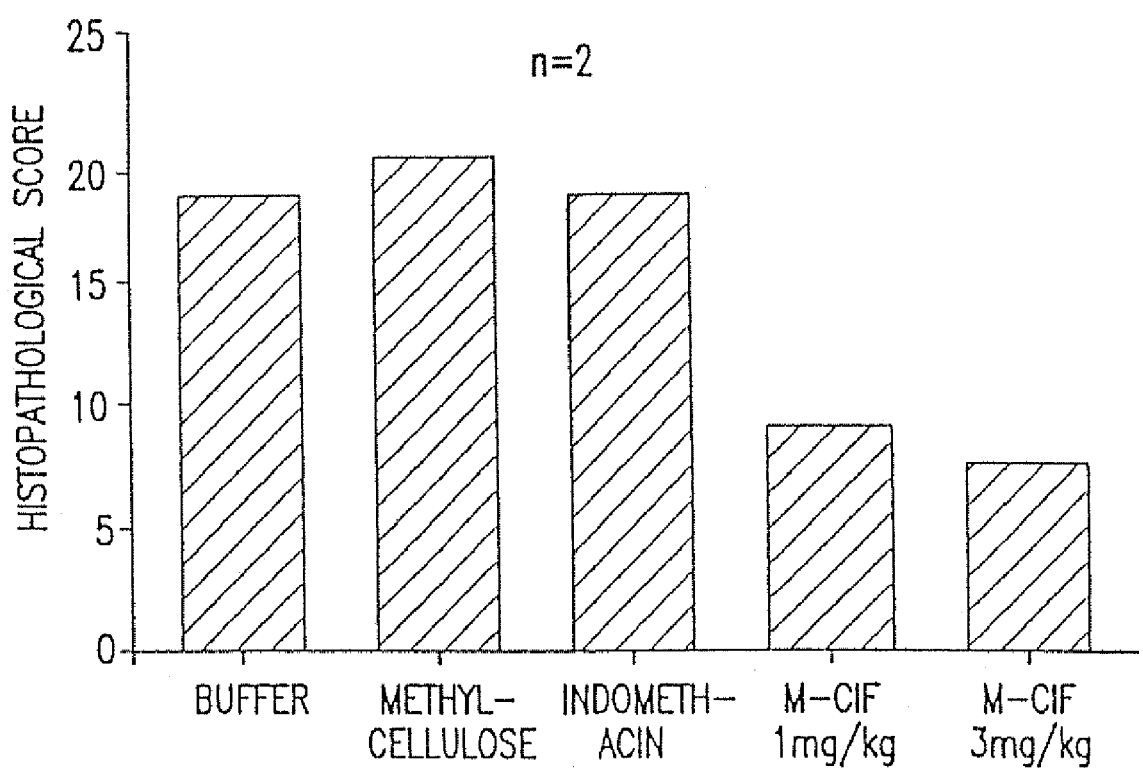

FIG. 38. Protective effect of M-CIF on total joint inflammation. At the end of the same experiment as FIG. 40, which was 40 days after adjuvant immunization, both hind limbs from two rats per group were collected for histopathological analysis. The results are expressed as mean of total histological score.

Figure 39:
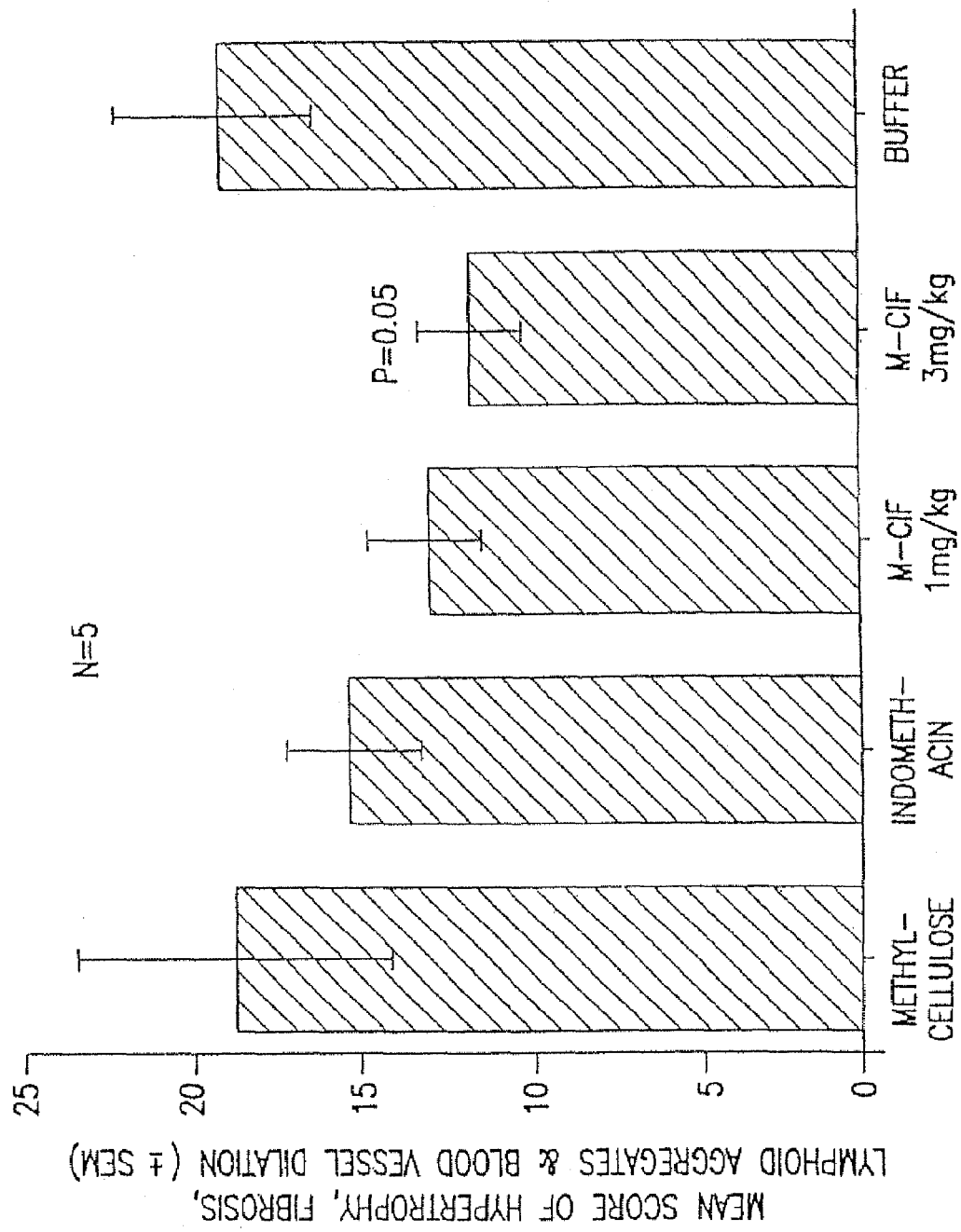

FIG. 39. Protective effect of M-CIF on chronic features of arthritis. A similar experiment as FIG. 40 with prolonged daily treatment of M-CIF or indomethacin to 40 days post adjuvant immunization, was conducted to further analyze chronic histopathological changes including hypertrophy, fibrosis, blood vessel dilation and lymphoid aggregates around blood vessels. The results were expressed as mean (n=5) of the total features mentioned above. An unpaired T test was employed for obtaining assessing statistical significance.

Figure 40:
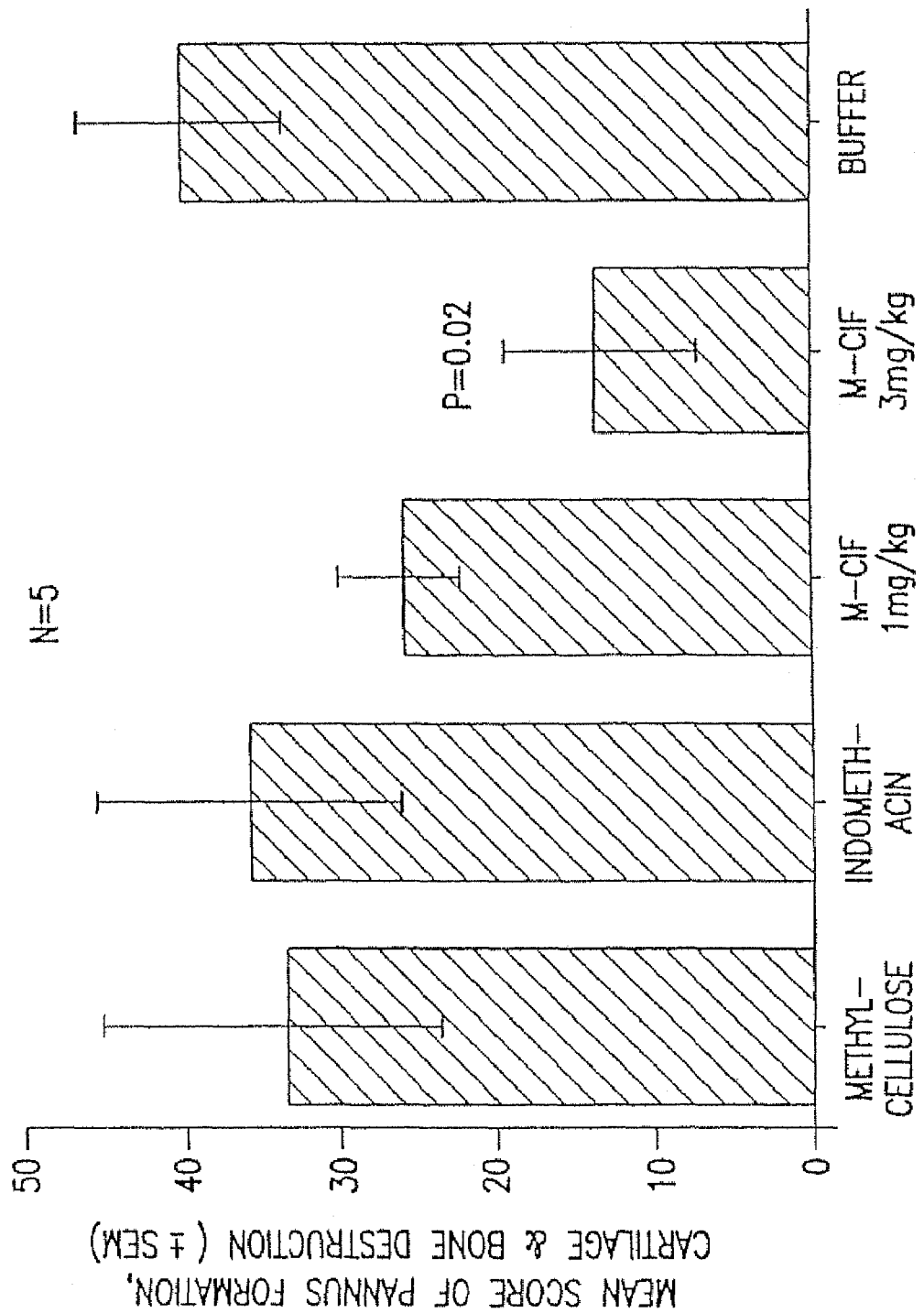

FIG. 40. Protective effect of M-CIF on bone and cartilage erosion. In the same experiment as FIG. 39, pannus formation, bone and cartilage destruction were evaluated. The results were expressed as mean (n=5) of the total features mentioned above. An unpaired T test was employed for assessing statistical significance.

Figure 41:
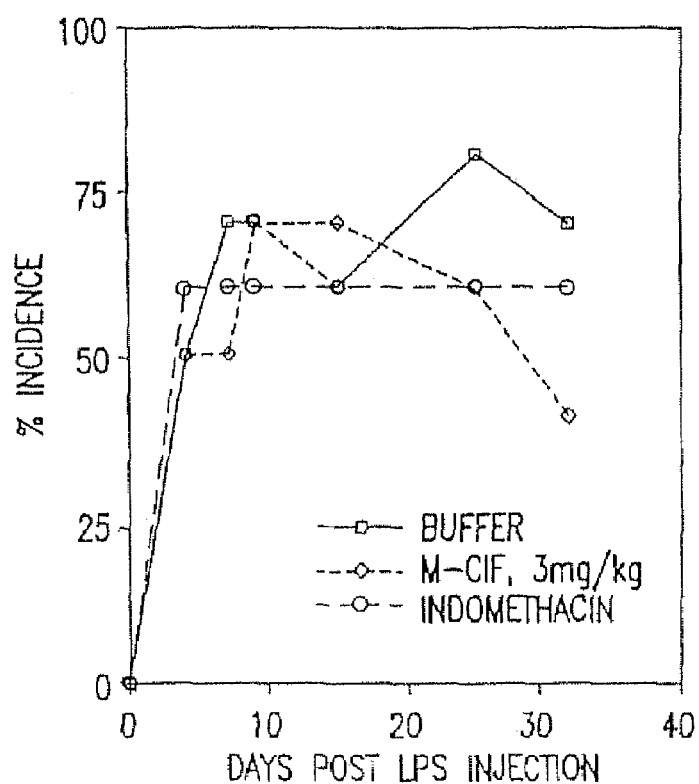

FIG. 41. M-CIF treatment prevents developing type 11 collagen-induced arthritis in DBA/I mice. Female DEA/ilacJ mice were immunized i.d. at the base of the tail with Bovine type 11 collagen emulsified in complete Freund's adjuvant. 20 days later, the mice were challenged with a s.c. injection of 60 mg/100 of LPS. Two days preceding LPS injection, 3 groups of animals (n=10 per 14 days. The animals were examined and their clinical presentation semiquantified. The % incidence is shown in this FIG.

Figure 42:
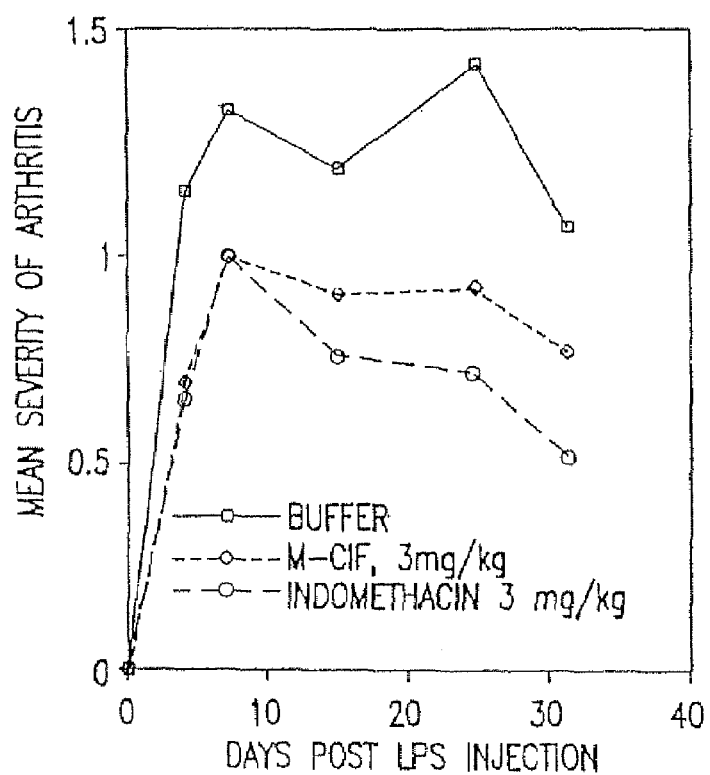
Figure 44:
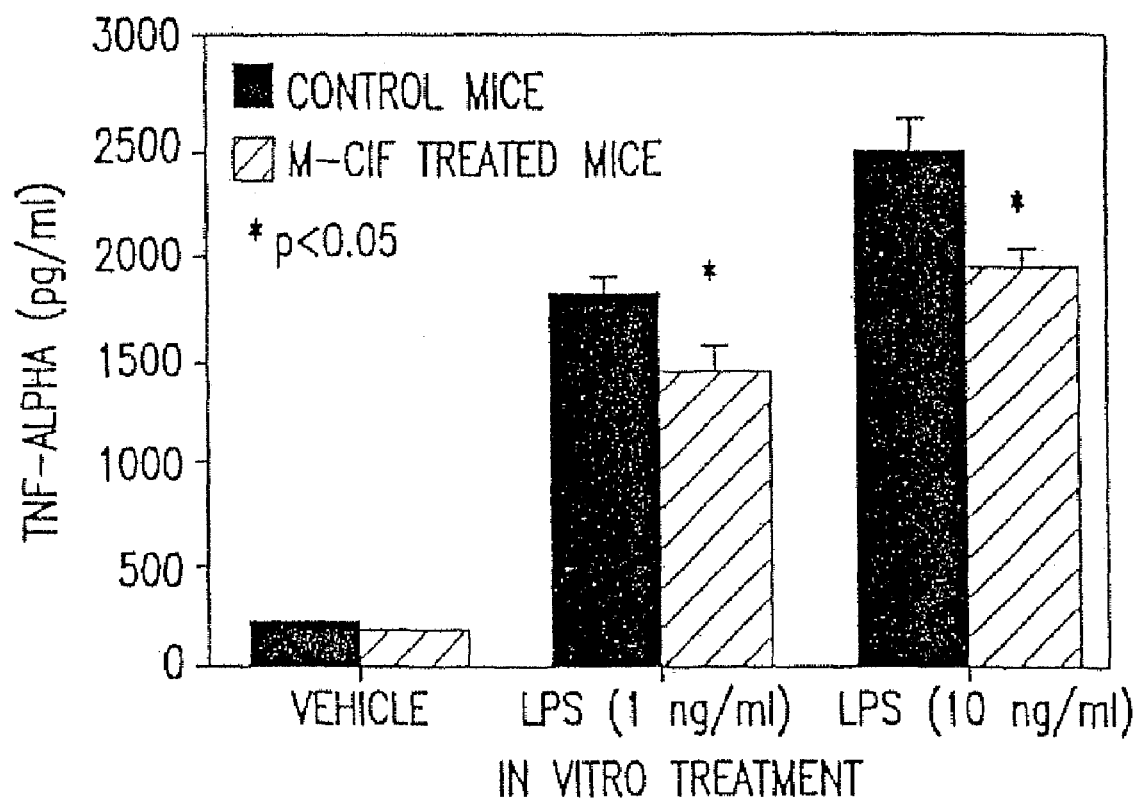

FIG. 42 Animals were immunized with bovine type II collagen as described in FIG. 44. The results are expressed as the mean severity.

Figure 43:
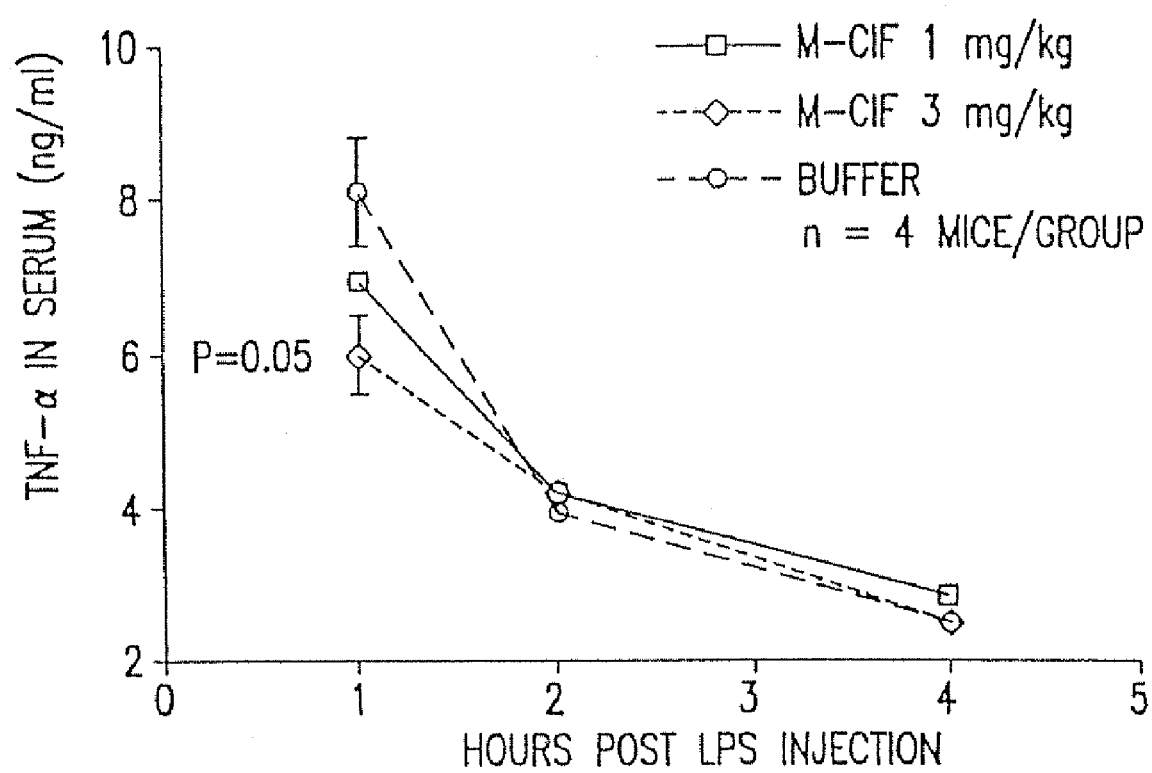

FIG. 43 shows the suppressive effect of M-CIF on systemic TNF-α production.

Groups of female Balb/c mice were challenged with 25 mg/kg of lipopolysaccharide (LPS) from *E. coli* serotype 0127:B8 (Sigma) in saline on Day 0. M-CIF or buffer was administered one day before and the same day (1 hour before) of LPS injection. Serum was collected at various time points after LPS administration and the TNF-α level determined. The results were analyzed with an unpaired T test and the data expressed as the mean±SEM.

FIG. 44 shows the decrease in TNF-(α) production from peritoneal cells isolated from M-CIF treated mice. Mice were treated with M-CIF at 3 mg/kg for two days. One hour after the second M-CIF injection, the peritoneal cells were harvested and put into culture to assay for cytokine production in the presence or absence of LPS. TNF-α levels were measured by ELISA.

Figure 45:
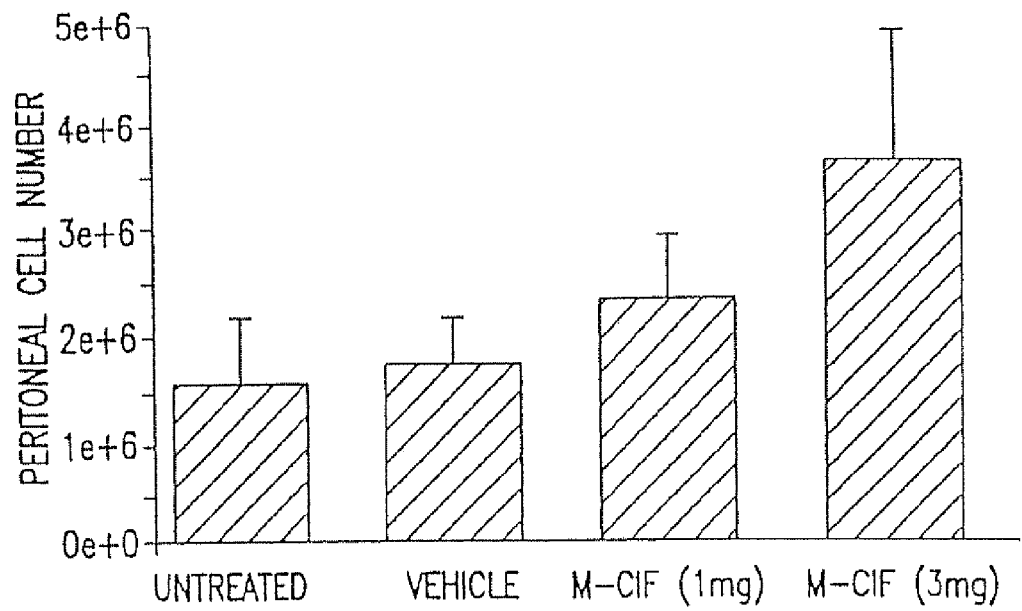

FIG. 45 shows the increased total cell number in the peritoneal cavity of M-CIF treated mice. Mice were untreated, treated with vehicle control or treated with M-CIF at 1 mg/kg and 3 mg/kg daily for six consecutive days. On the seventh day, mice were sacrificed and the peritoneal cells harvested and quantitated.

Figure 46:
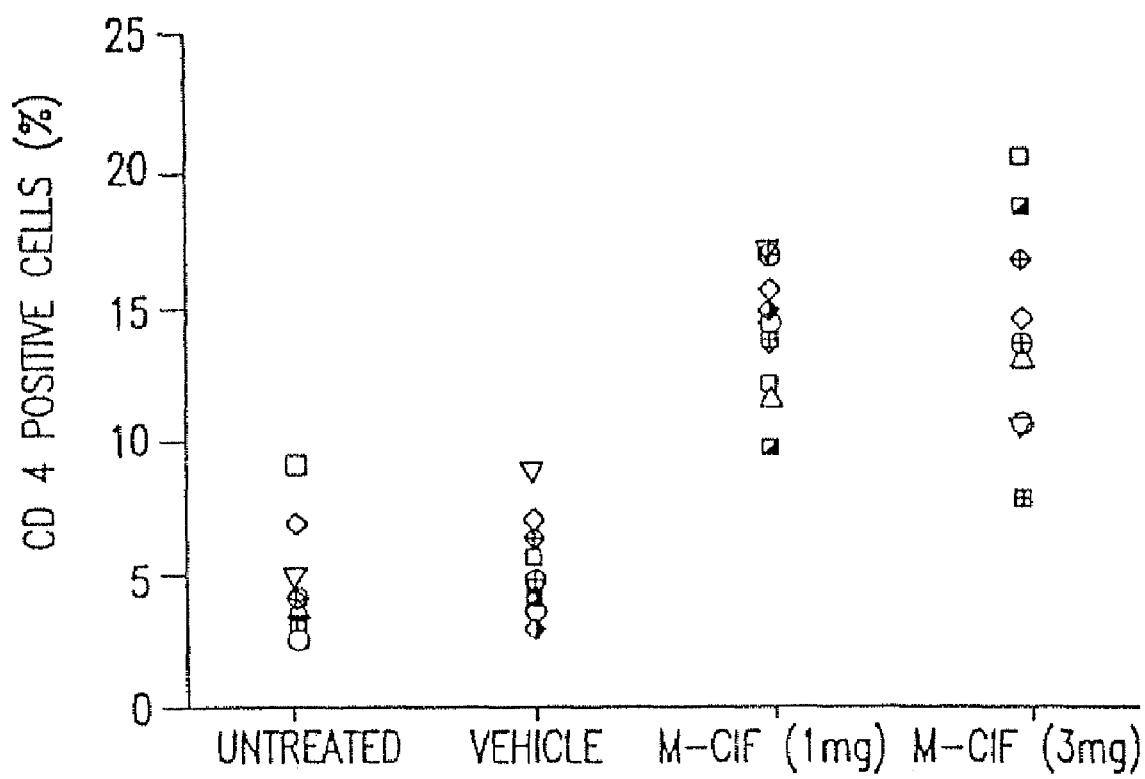

FIG. 46 shows the specific increase in CD4 positive T-lymphocytes in the peritoneal cavity of M-CIF treated mice. Mice were treated as described in FIG. 48. Each animal is represented by a different symbol from the untreated, vehicle treated, 1 mg/kg M-CIF, and 3 mg/kg M-CIF groups. Each group contained 10 animals each, with the cells from each animal analyzed by cell surface staining using antibodies directed at CD4, CD5, CD8, Mac1, MHC class II, B220, IgM, Gr 1 and CD 14.

Figure 47:
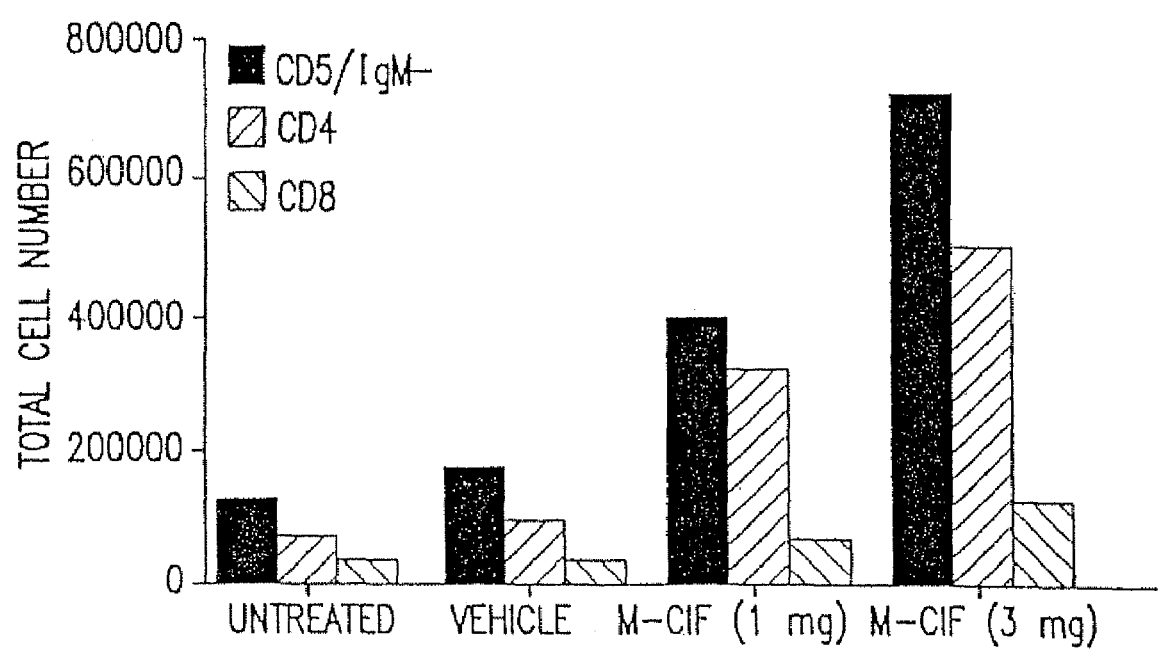

FIG. 47 shows an increase in total T-lymphocyte cell numbers (CD5/IgM-, CD4, and CD8) in the peritoneal cavity M-CIF treated mice.

Figure 48A:
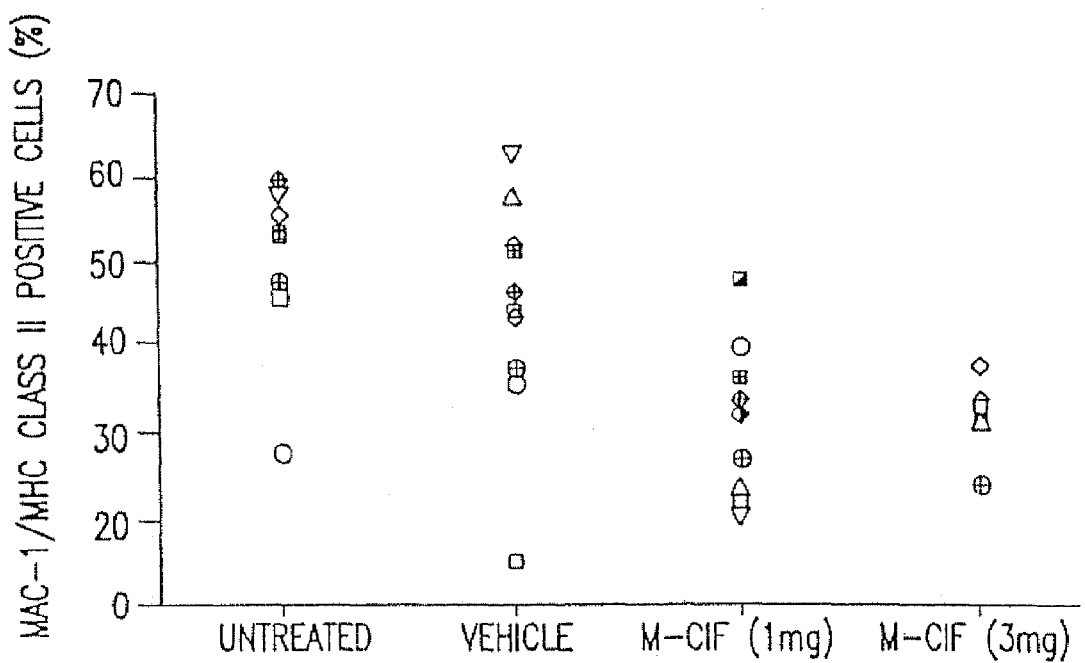
Figure 48B:
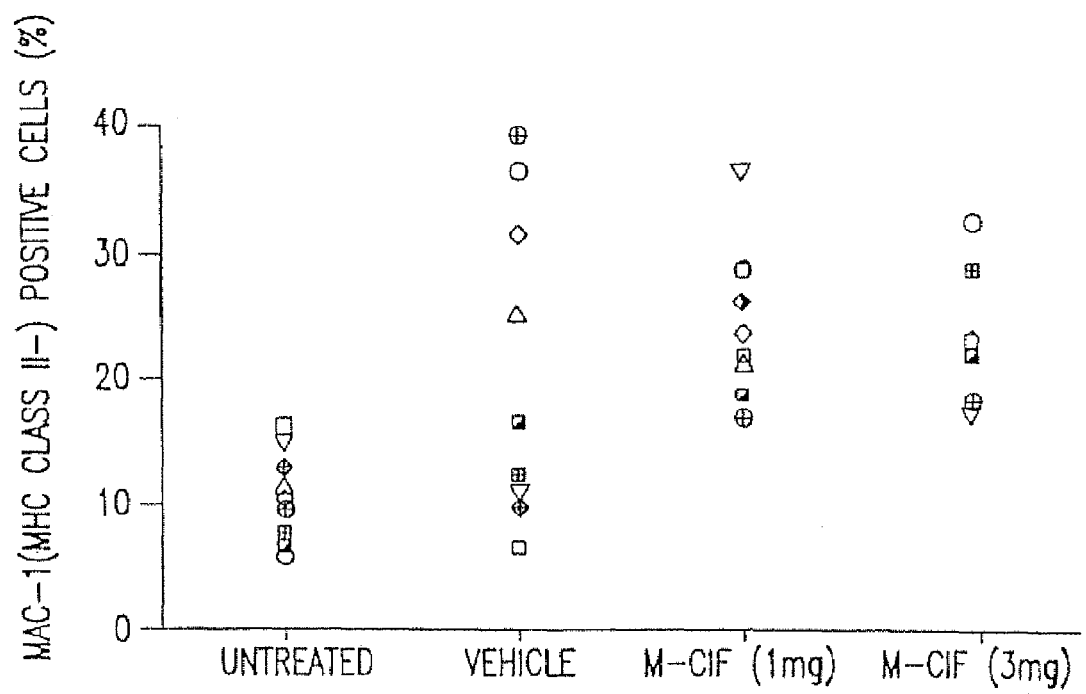

FIG. 48 shows a decrease in the percentage of Mac1+/MHC class II+ cells in the peritoneal cavity of M-CIF treated mice with a corresponding increase in the percentage of Mac1+/MHC class II cells.

Figure 49:
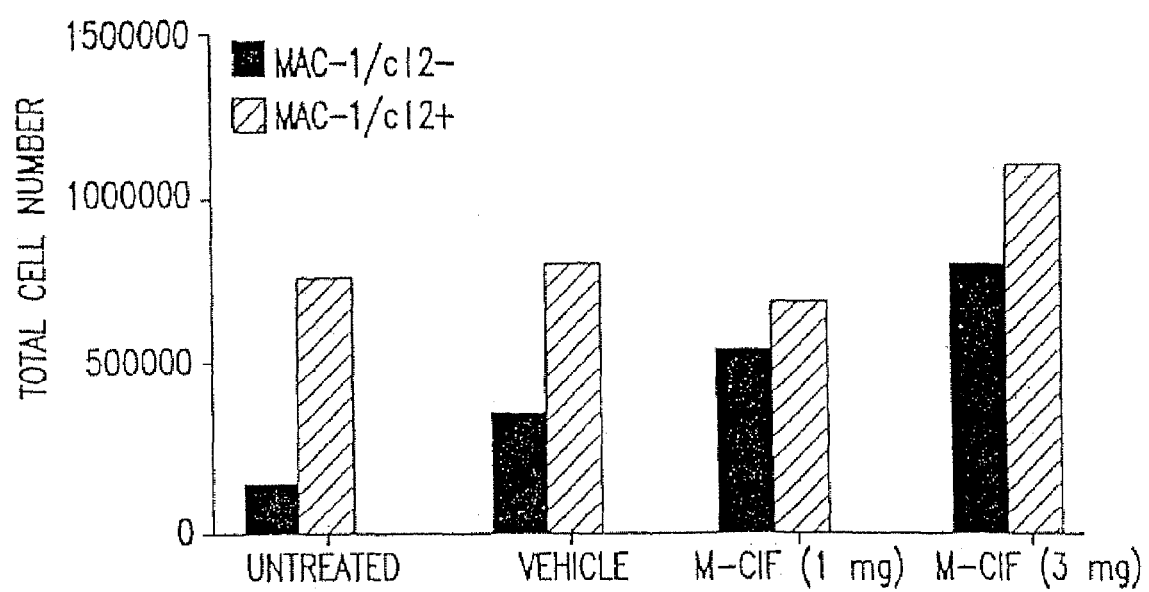

FIG. 49 shows an increase in the total number of Mac1+/MHC class II-cells in the peritoneal cavity of M-CIF treated mice.

FIG. 50 shows the stem cell mobilization in normal mice in response to the administration of MPIF-1.

Figure 51:
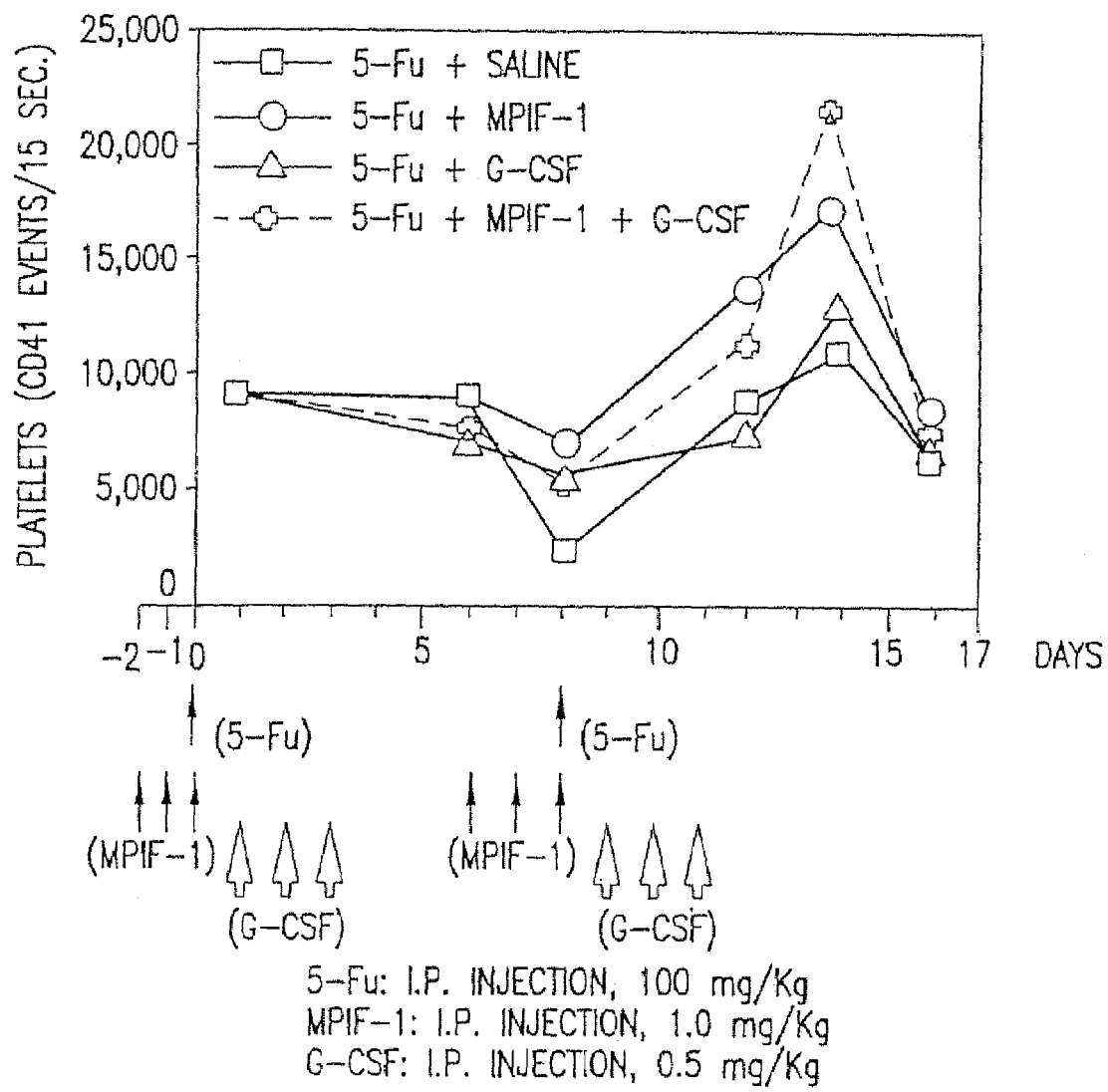

FIG. 51 shows a comparison of the effect of MPIF-1 with G-CSF on the recovery of platelets following two cycles of 5-Fu treatment as determined by FACS Vantage method.

Figure 52:
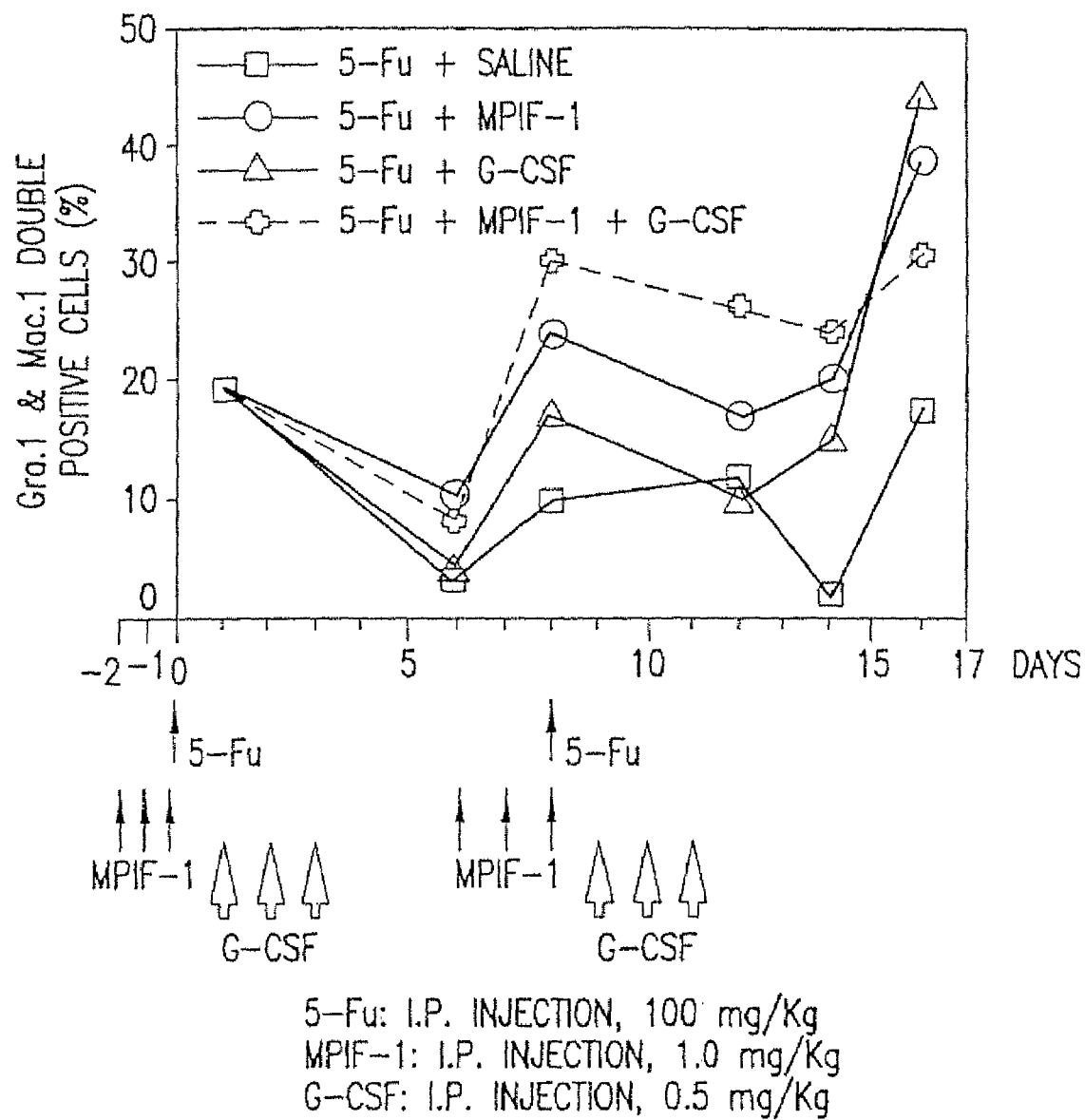

FIG. 52 shows a comparison of the effect of MPIF-1 with G-CSF on the recovery of Gra. 1 and Mac. 1 double positive cells in the blood following two cycles of 5-Fu treatment.

Figure 53:
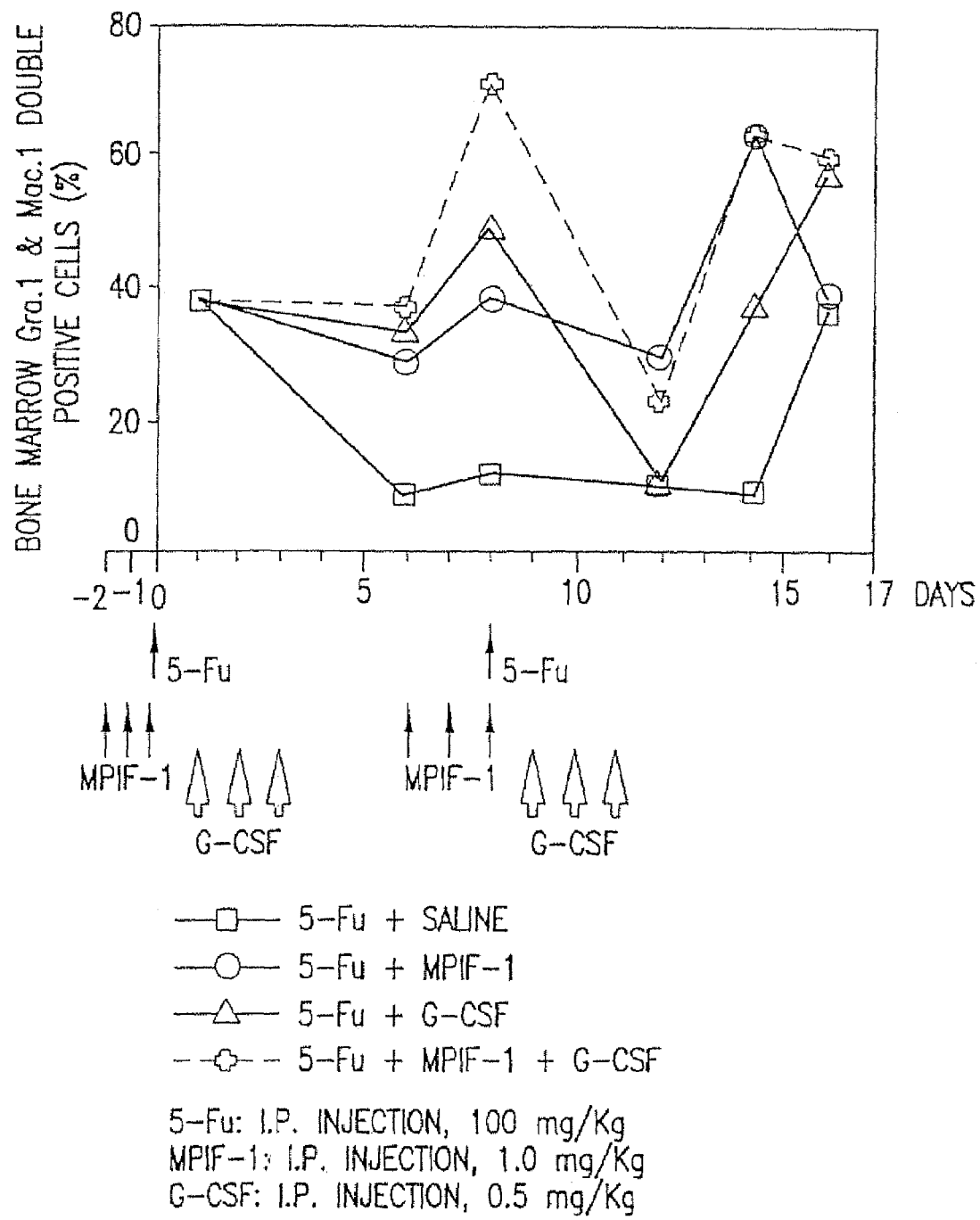

FIG. 53 shows a comparison of the effect of MPIF-1 with G-CSF on the recovery of Gra. 1 and Mac. 1 double positive cells in the bone marrow following two cycles of 5-Fu treatment as determined by FACS Vantage method.

Figure 54:
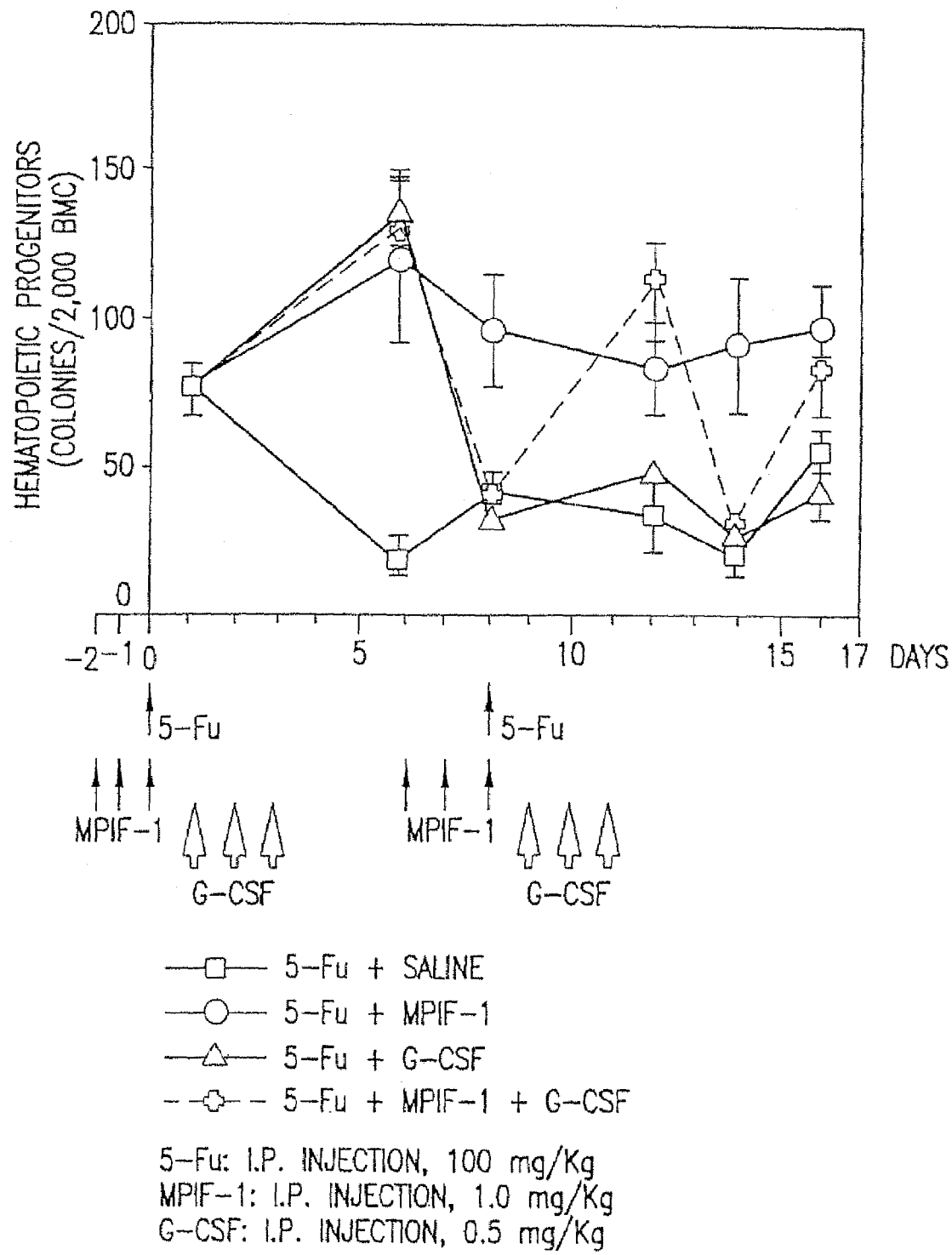

FIG. 54 shows a comparison of the effect of MPIF-1 with G-CSF on the recovery of hematopoietic progenitors in the bone marrow during following two cycles of 5-Fu treatment.

Figure 55:
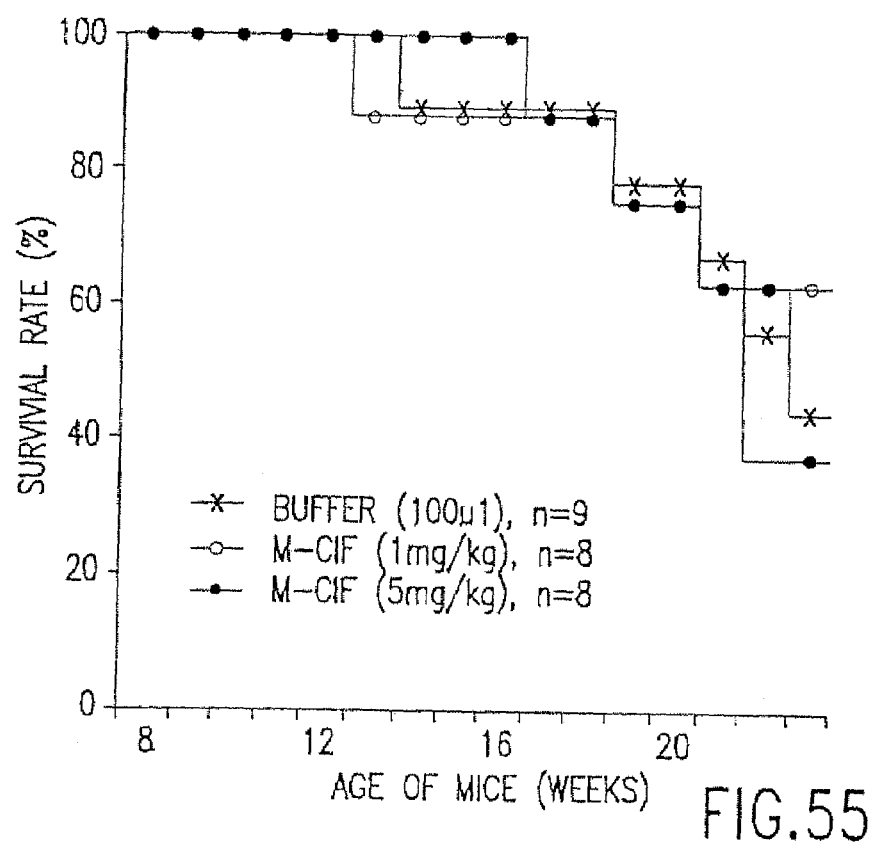

FIG. 55. Time course of survival rates of MRL lpr mice (8 weeks old) in 3 different groups treated i.p. daily (5 days/week) with 1 or 5 mg/kg of M-CIF (n=8) or buffer (n=9) for 14 weeks.

Figure 56:
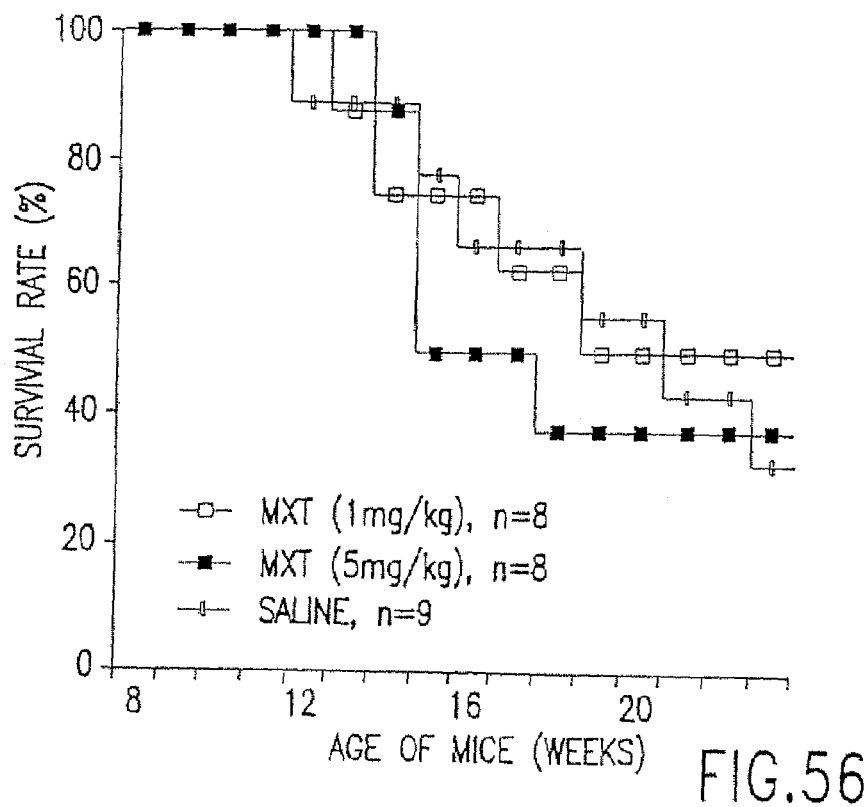

FIG. 56. Time course of survival rates of MRL lpr mice (8 weeks old) in 3 different groups treated i.p. once per day, 3 days/week with 1 or 5 mg/kg of M-CIF (n=8) or buffer (n=9) for 14 weeks.

Figure 57:
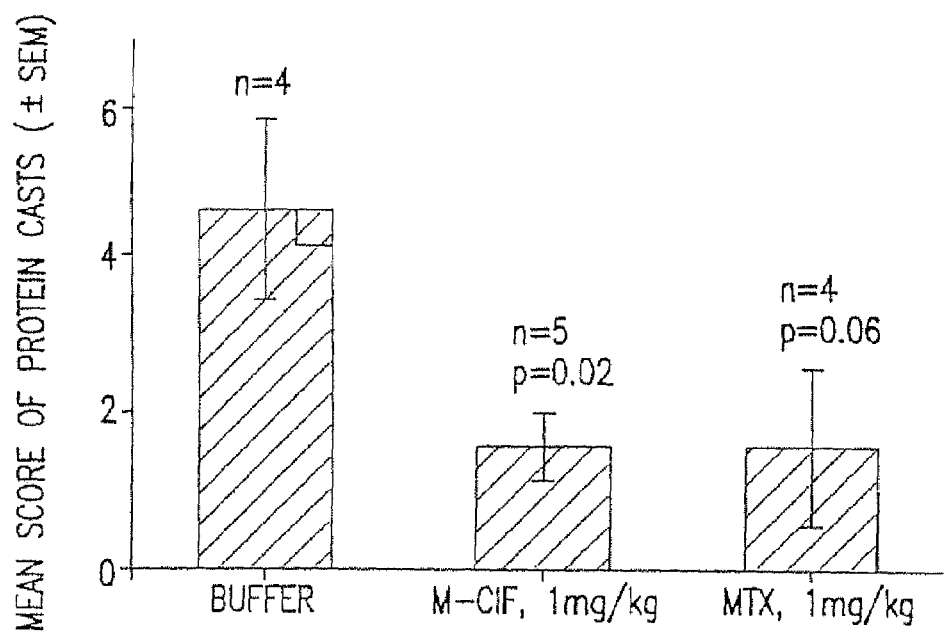

FIG. 57. Changes in the protein cast formation by multi-blinded histological evaluation of both kidneys of 23 week-old MRL lpr/lpr mice treated with buffer control, rhM-CIF or methotrexate (MTX) at 1 mg/kg, daily (5 days each week) for 14 weeks since mice were 8 weeks old. Values are the mean of 4-5 mice per group±SEM.

Figure 58:
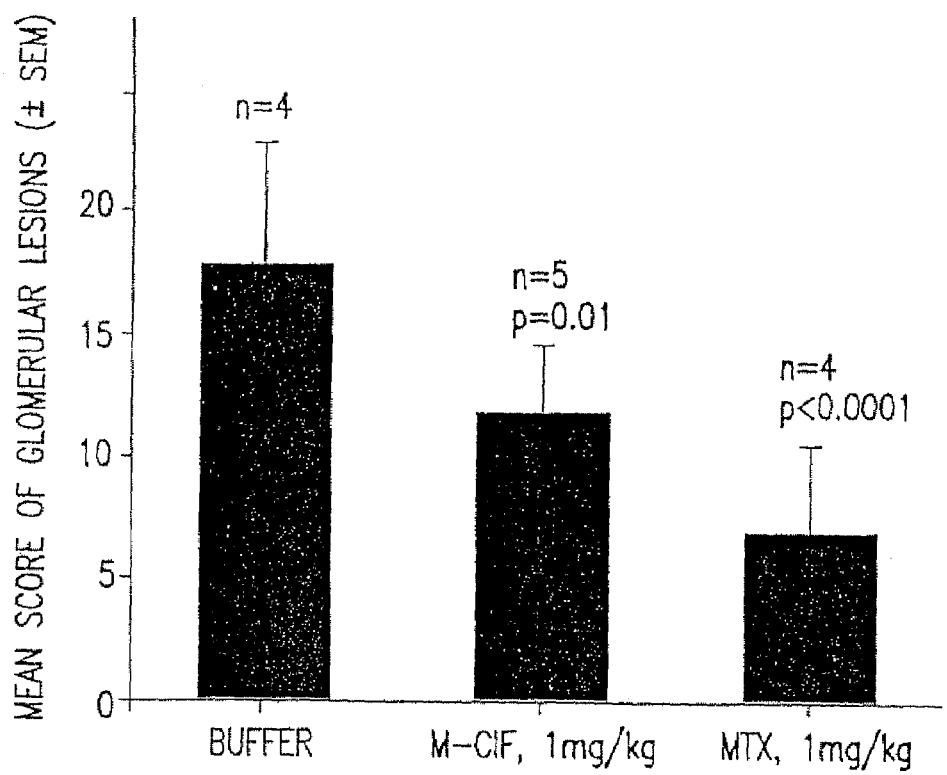

FIG. 58. Changes in the glomerular lesions by multi-blinded histological evaluation of both kidneys of 23 week-old MRL lpr/lpr mice treated with buffer control, rhM-CIF or methotrexate (MTX) at 1 mg/kg, daily (5 days each week) for 14 weeks since mice were 8 weeks old. Glomerular lesions assessed by multi-blinded histological evaluation represent the sum of basement membrane thickening, crescent formation and scarring, hypercellularity, fibrosis and karyorrhexis. Values are the mean of 4-5 mice per group±SEM.

Figure 59:
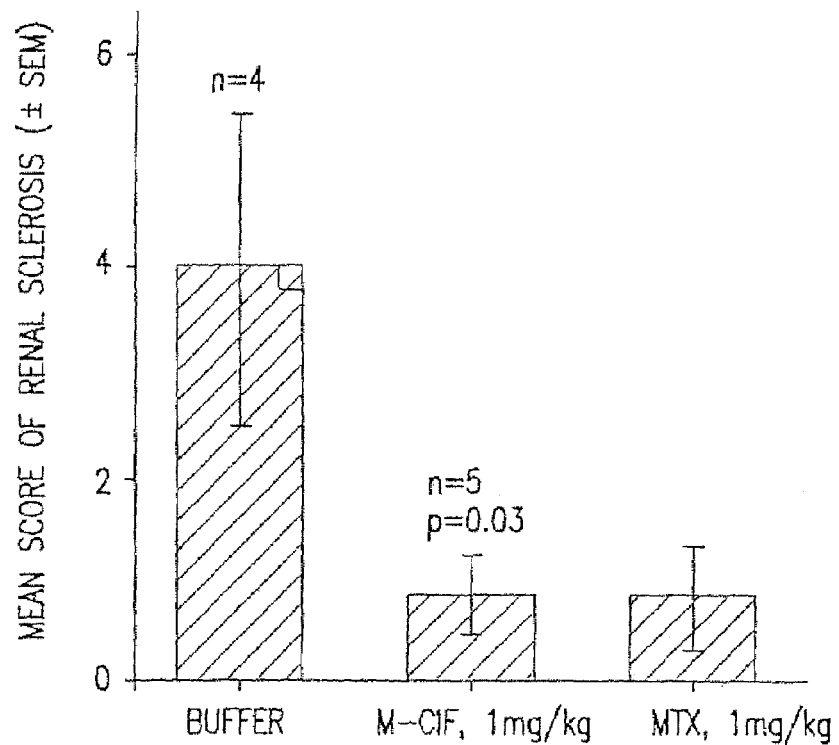

FIG. 59. Changes of renal sclerosis by multi-blinded histological evaluation of both kidneys of 23 week-old MRL lpr/lpr mice treated with buffer control, rhM-CIF or methotrexate (MTX) at 1 ng/kg, daily (5 days each week) for 14 weeks since mice were 8 weeks old. Values are the mean of 4-5 mice per group +SEM.

Figure 60:
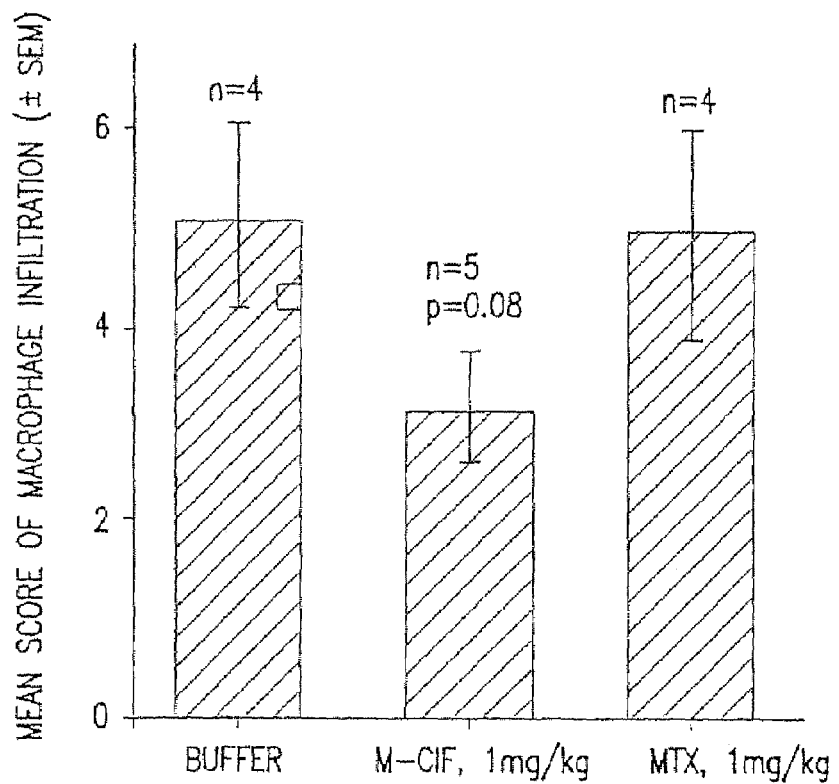

FIG. 60. Changes of macrophage infiltration by immunohistological evaluation of both kidneys of 23 week-old MRL lpr/lpr mice treated with buffer control, rhM-CIF or methotrexate (MTX) at 1 mg/kg, daily (5 days each week) for 14 weeks since mice were 8 weeks old. Values are the mean of 4-5 mice per group±SEM.

Figure 61:
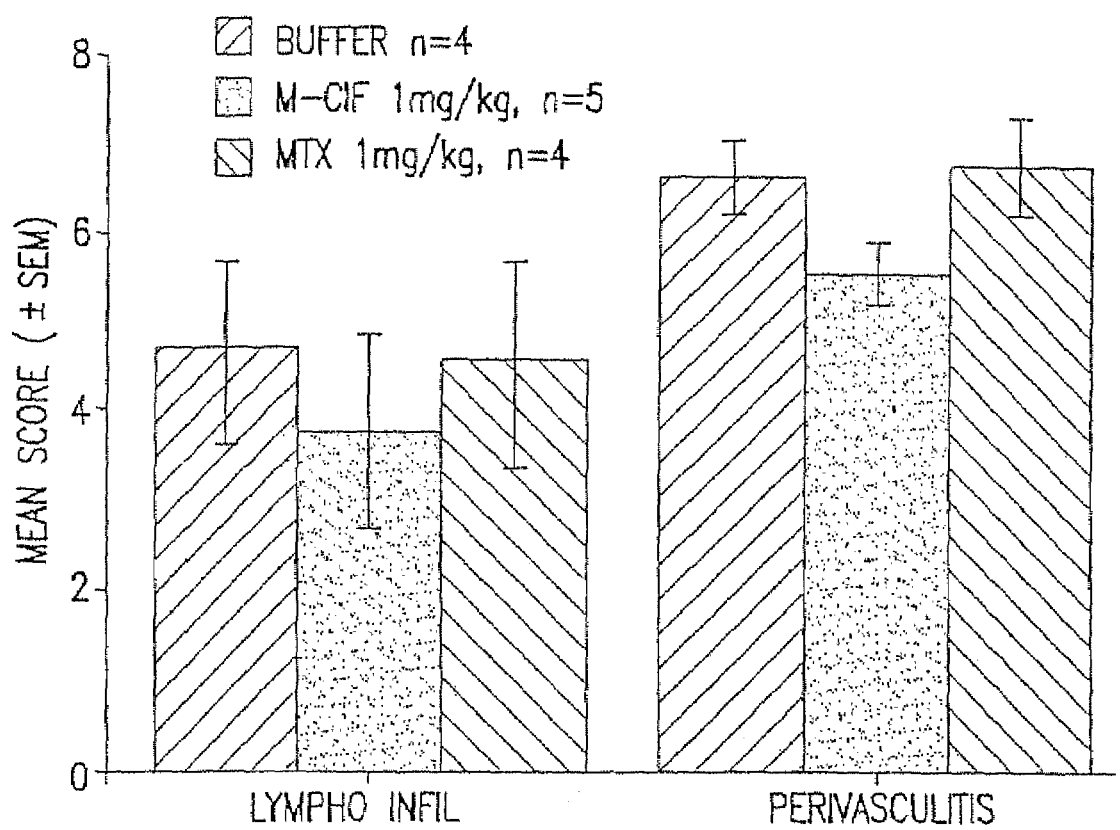

FIG. 61. Changes of lymphocyte infiltration and perivasculitis by multi-blinded histological evaluation of both kidneys of 23 week-old MRL lpr/lpr mice treated with buffer control, rhM-CIF or methotrexate (MTX) at 1 mg/kg, daily (5 days each week) for 14 weeks since mice were 8 weeks old. Values are the mean of 4-5 mice per group±SEM.

Figure 62:
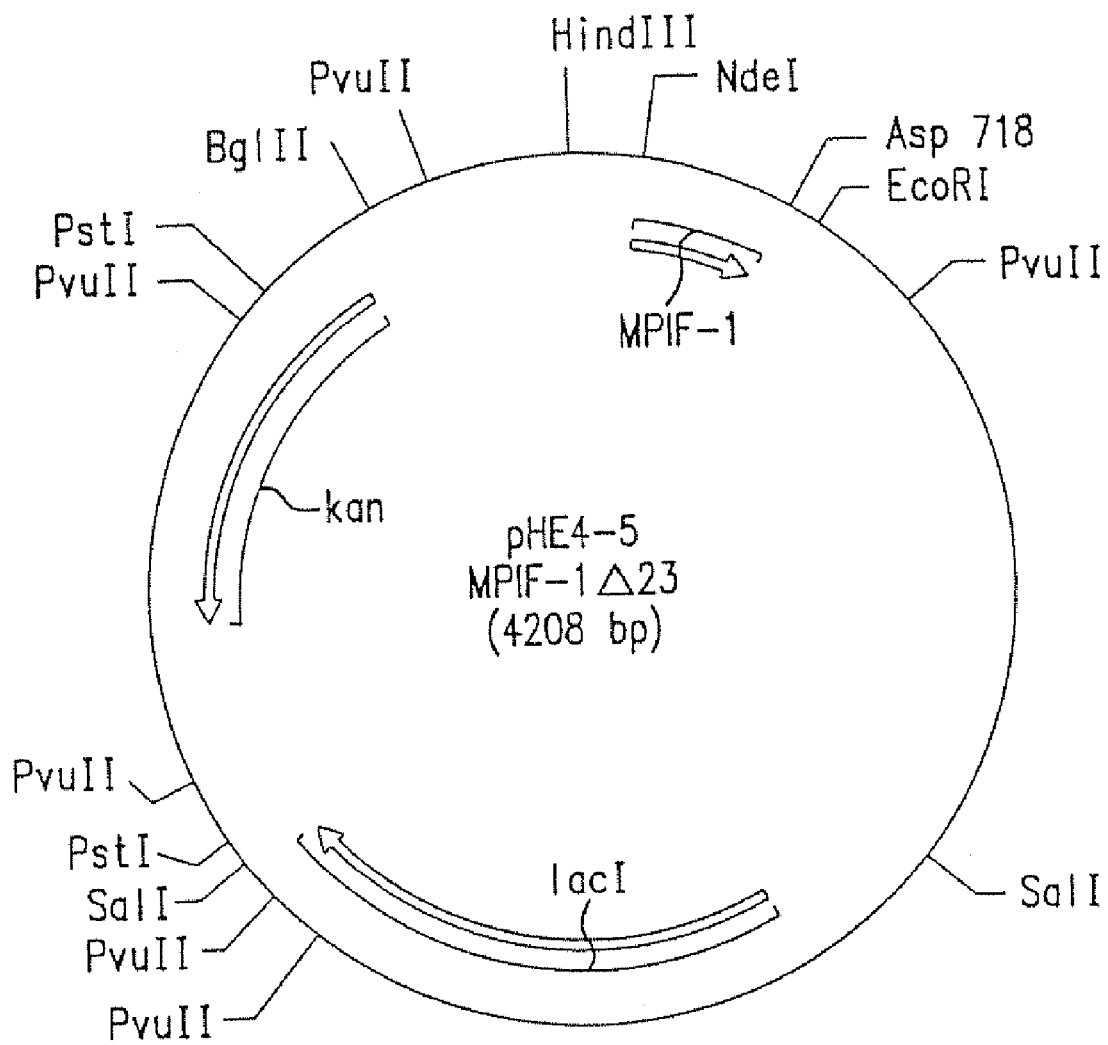

FIG. 62 shows a schematic representation of the pHE4-5 expression vector (SEQ ID NO:56) and the subcloned MPIF-1Δ23 cDNA coding sequence. The locations of the kanamycin resistance marker gene, the MPIF-1Δ23 coding sequence, the oriC sequence, and the lacIq coding sequence are indicated.

Figure 63:
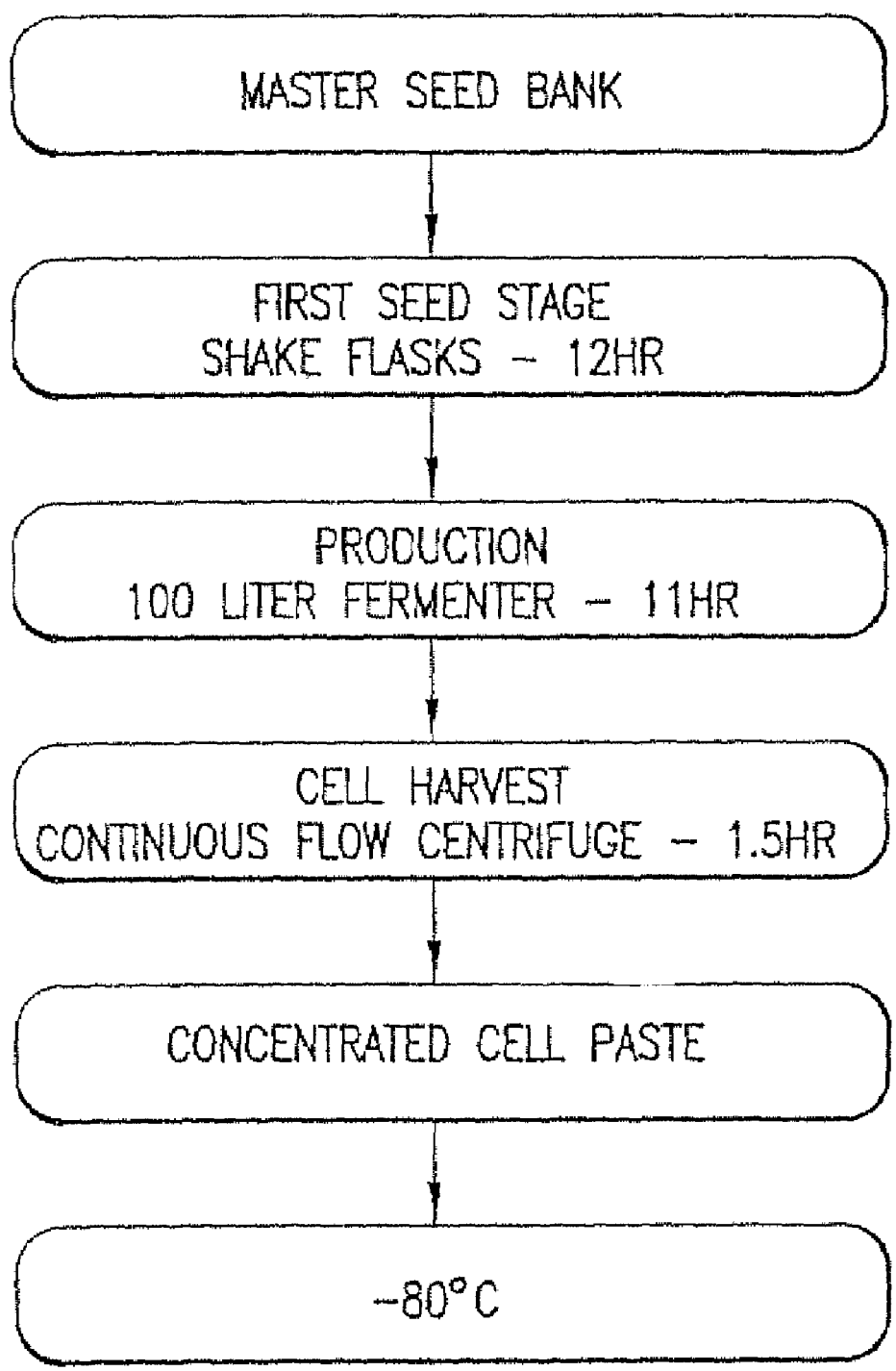

FIG. 63 shows an overview of the fermentation process for the production of MPIF-1Δ23.

Figure 64:
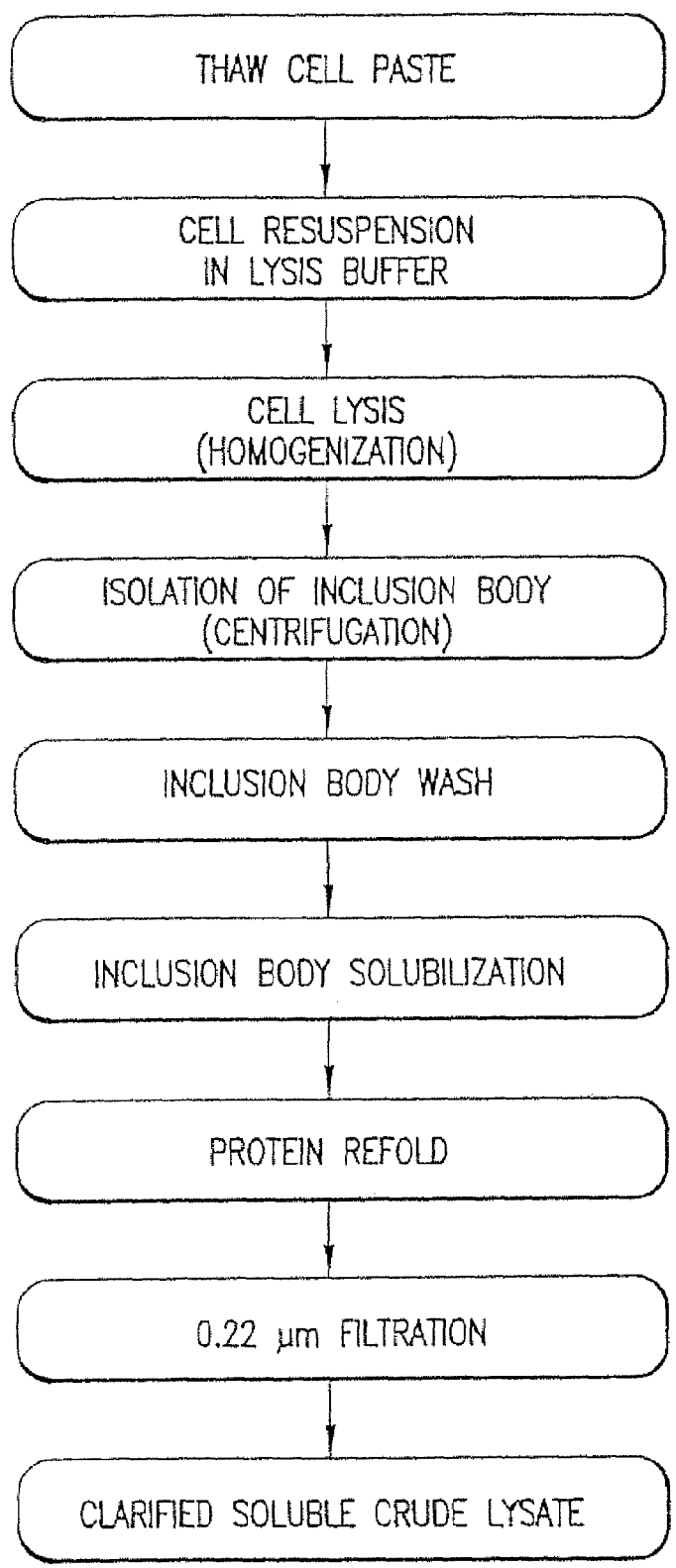

FIG. 64 shows a flow diagram of the methods used to recover MPIF-1Δ3 produced by the process shown in FIG. 63.

Figure 65:
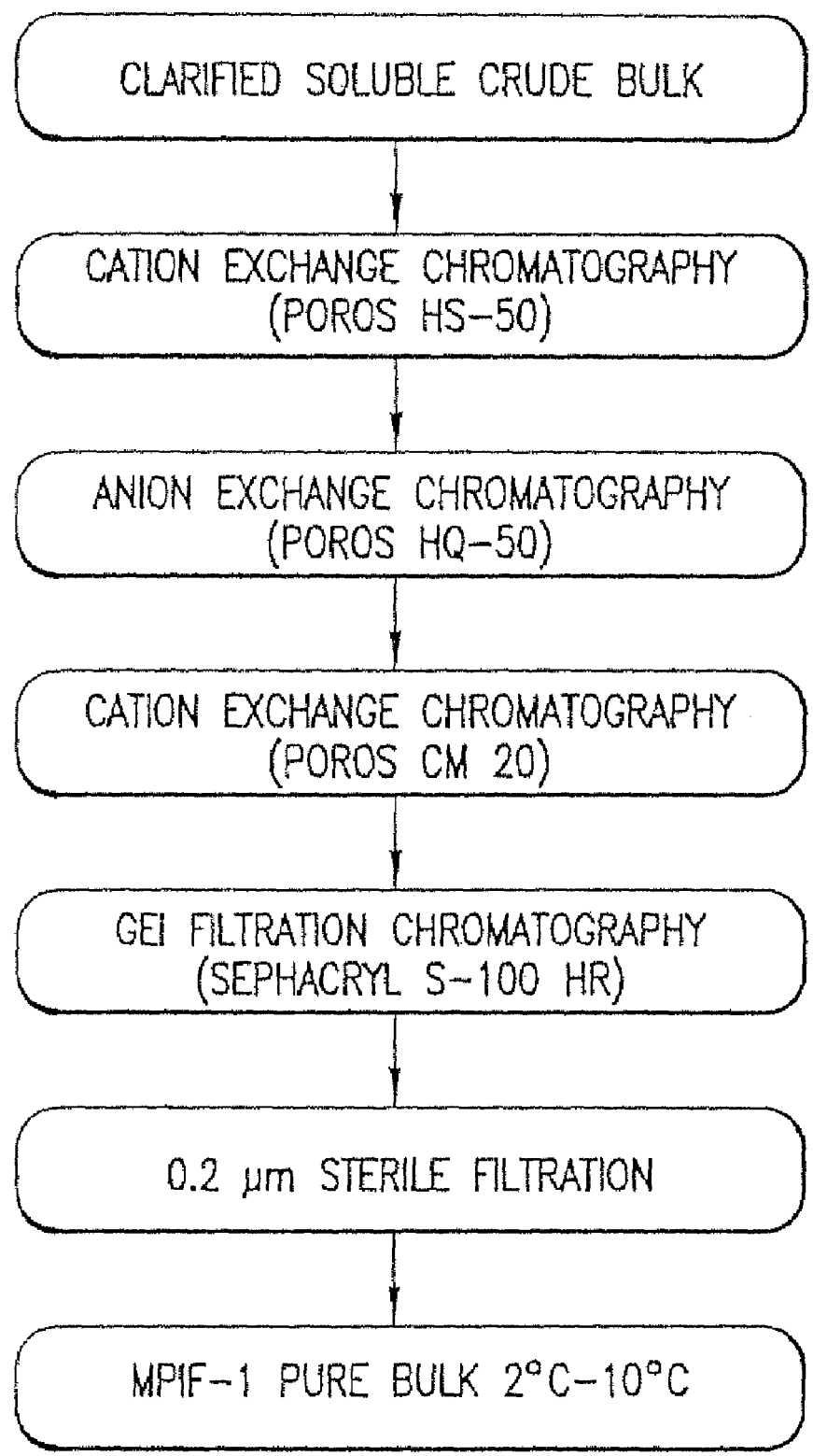

FIG. 65 shows the process for the purification of MPIF-1Δ23 produced and recovered by the processes shown in FIGS. 63 and 64.

FIG. 66 shows the nucleotide sequence of the regulatory elements of the pHE promoter (SEQ ID NO:57). The two lac operator sequences, the Shine-Delgarno sequence (S/D), and the terminal HindIII and NdeI restriction sites (italicized) are indicated.

Figure 67A:
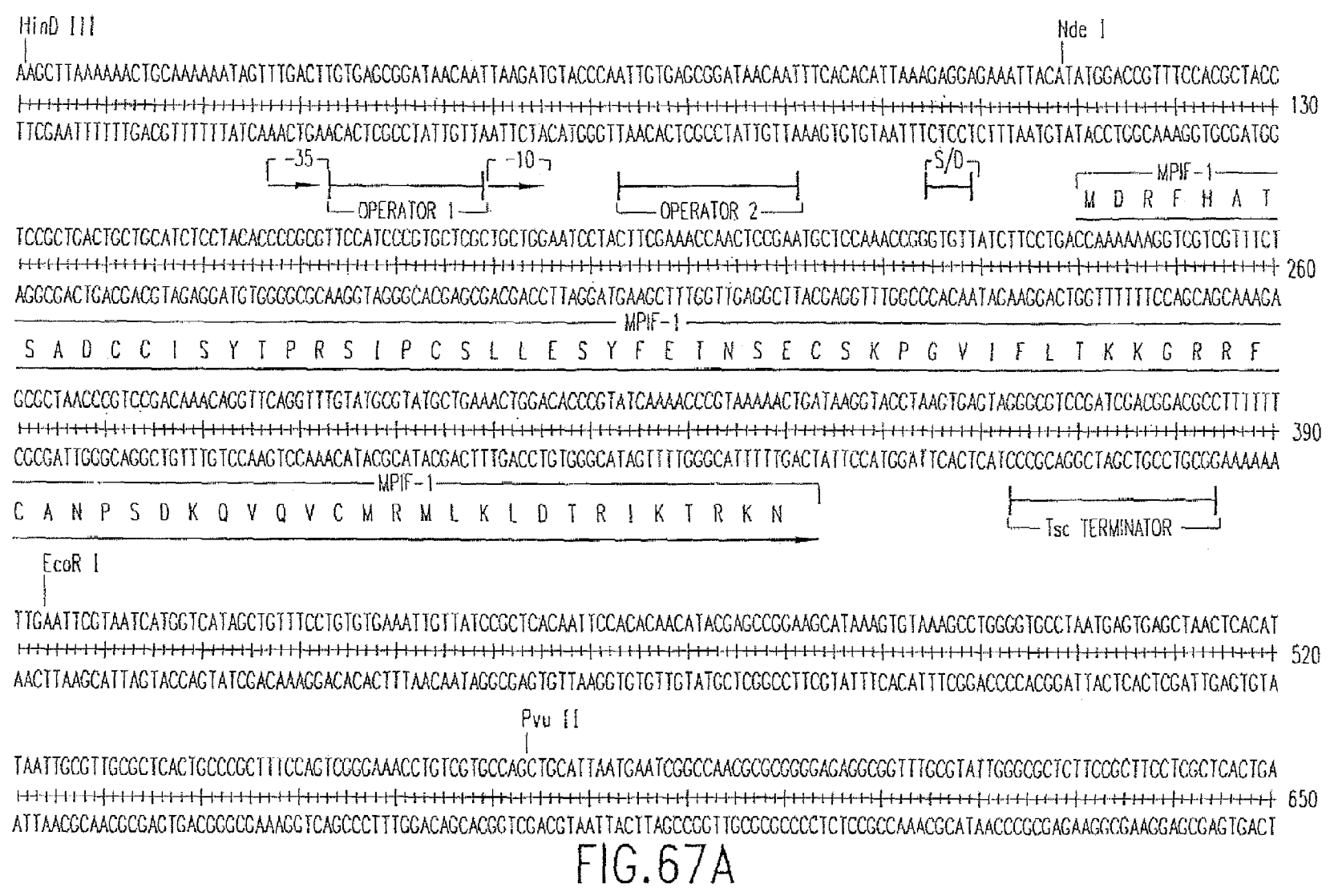
Figure 67B:
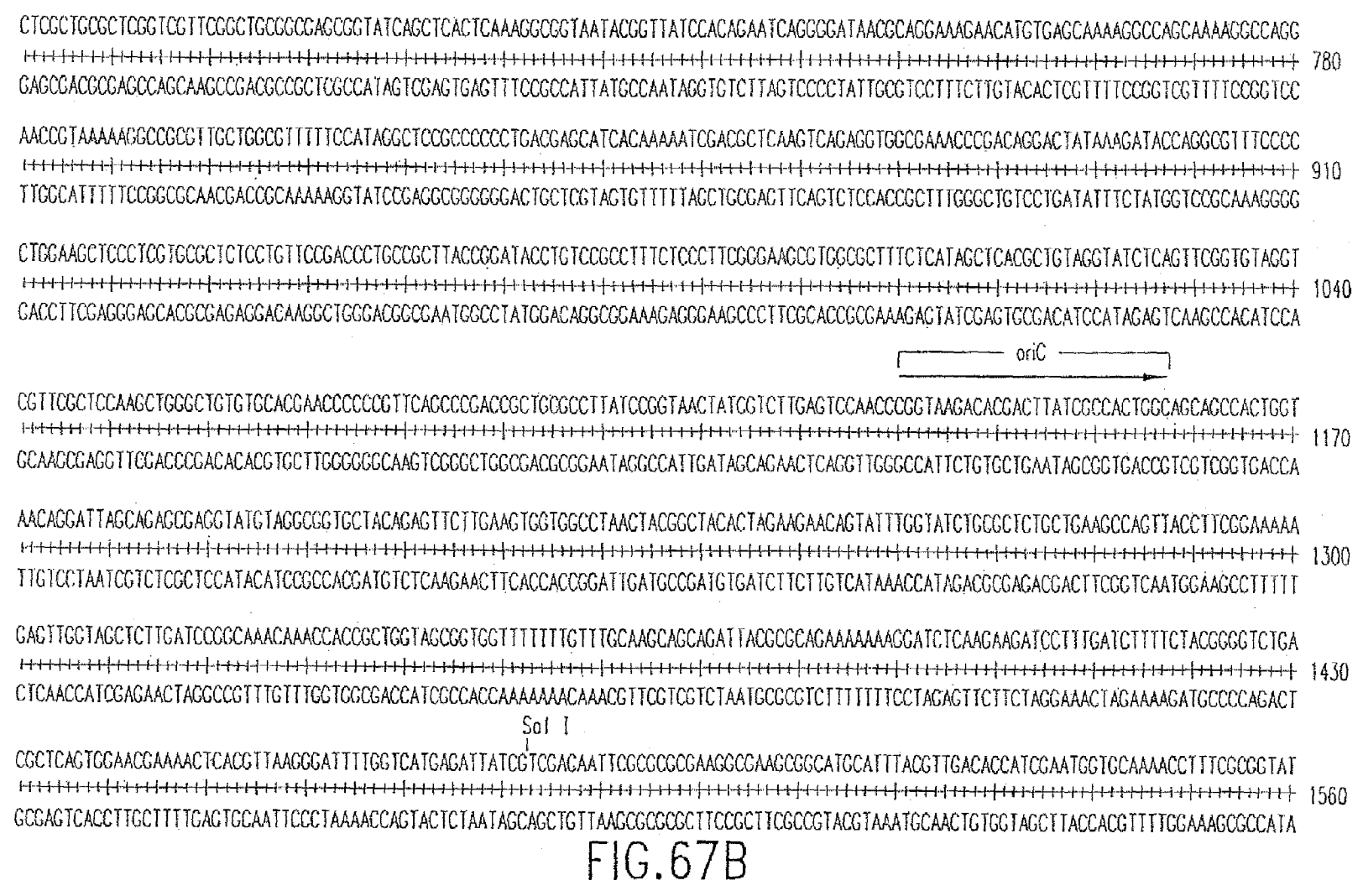
Figure 67F:
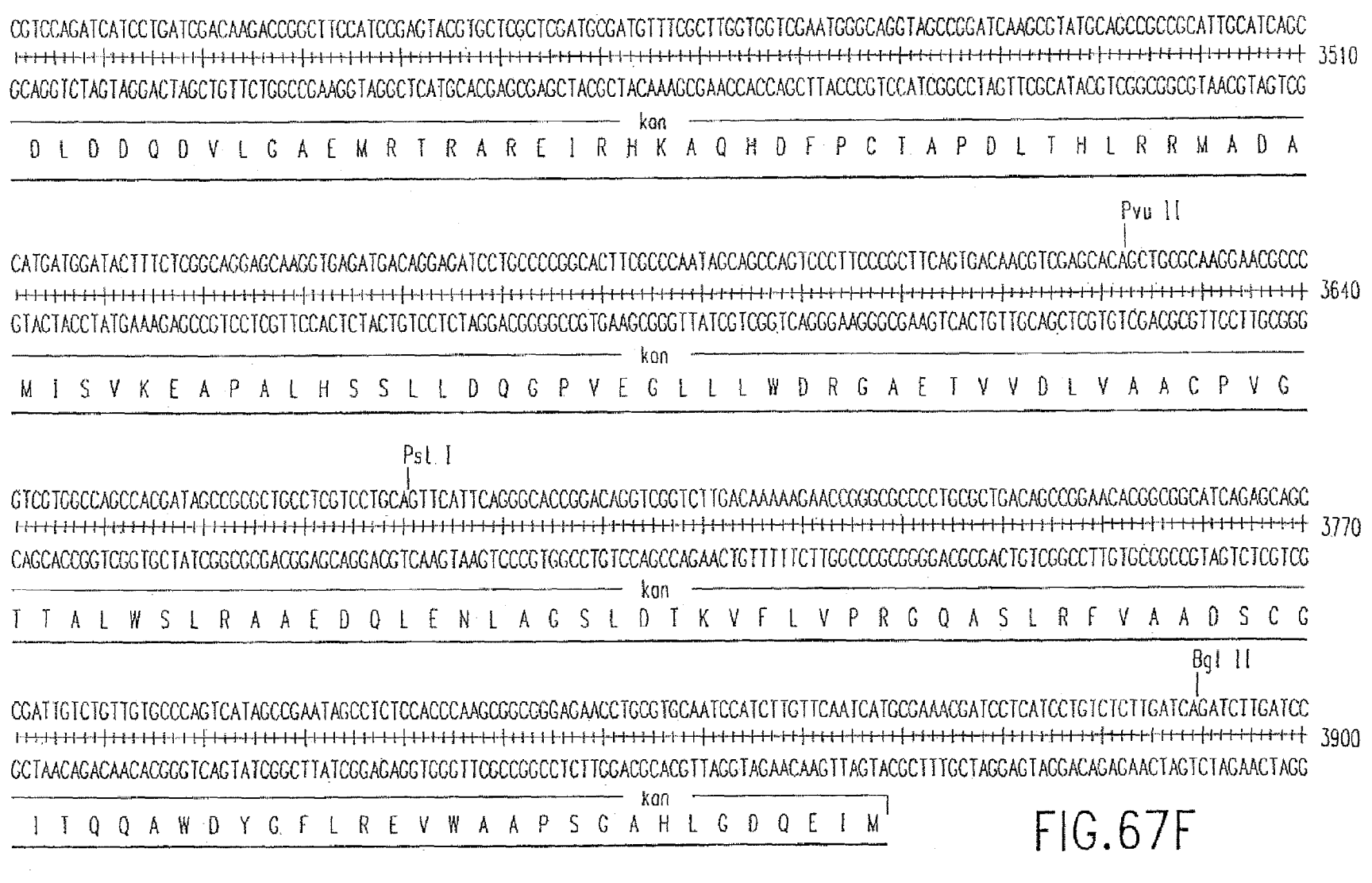
Figure 67G:
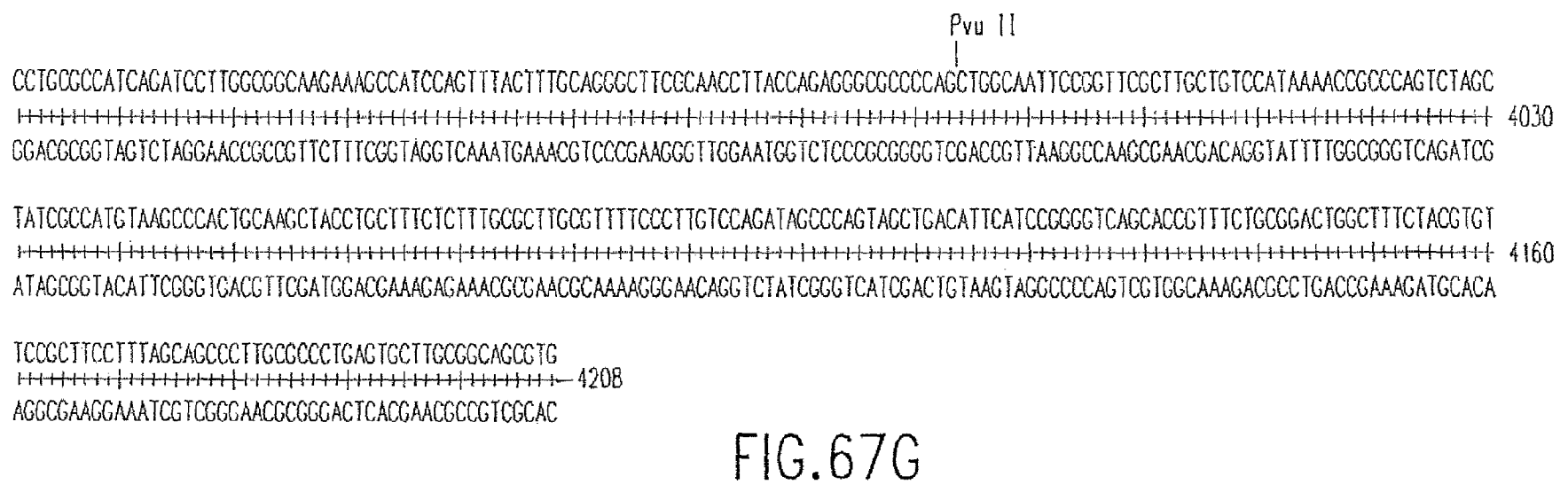

FIG. 67A-G show the complete nucleotide sequence of the pHE4-5 vector (SEQ ID NO:56).

DETAILED DESCRIPTION

The present invention provides diagnostic or therapeutic compositions and methods that utilize isolated polynucleotide molecules encoding polypeptides, or the polypeptides themselves, as: (i) a human monocyte-colony inhibitory factor (M-CIF) polypeptides (previously termed MIP1-γ and chemokine β1(CKβ1 or ckb-1)); (ii) human myeloid progenitor inhibitory factor-1 (MPIF-1) polypeptides (previously termed MIP-3 and chemokine β8(CKβ8 or ckb-8)); and/or (iii) macrophage inhibitory protein-4 (MIP-4), as are vectors, host cells and recombinant or synthetic methods for producing the same.

MPIF-1, M-CIF and MIP-4 Polynucleotides

In accordance with an aspect of the present invention, there are provided isolated nucleic acids (polynucleotides) which encode for the full-length or mature MPIF-1, M-CIF or MIP-4 polypeptide having the deduced amino acid sequence of, respectively, FIG. 1, 2 or 3 (SEQ ID NOS:4, 2, and 6) and for the mature MPIF-1 polypeptide encoded by the cDNA of the clone(s) deposited as ATCC® Deposit No. 75676 on Feb. 9, 1994, and for the mature MIP-4 polypeptide encoded by the cDNA of the clone deposited as ATCC® Deposit No. 75675 on Feb. 9, 1994 and for the mature M-CIF polypeptide encoded by the cDNA of the clone deposited as ATCC® No. 75572, deposited on Oct. 13, 1993. The present address of the American Type Culture Collection (ATCC®) is 10801 University Boulevard, Manassas, Va. 20110-2209, USA. The deposited clones are contained in the pBluescript SK(−) plasmid (Stratagene, LaJolla, Calif.).

The deposit(s) referred to herein will be maintained under the terms of the Budapest Treaty on the International Recognition of the Deposit of Micro-Organisms for Purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with description of sequences herein. A license can be required to make, use or sell the deposited materials, and no such license is hereby granted.

Polynucleotides encoding polypeptides of the present invention are structurally related to the pro-inflammatory supergene "intercrine" which is in the cytokine or chemokine family. Both MPIF-1 and MIP-4 are M-CIF homologues and are more homologous to MIP-1α than to MIP-1β. The polynucleotide encoding for MPIF-1 was derived from an aortic endothelium cDNA library and contains an open reading frame encoding a polypeptide of 120 amino acid residues, which exhibits significant homology to a number of chemokines. The top match is to the human macrophage inflammatory protein I alpha, showing 36% identity and 66% similarity (FIG. 4).

The polynucleotide encoding MIP-4 (SEQ ID NO:5) was derived from a human adult lung cDNA library and contains an open reading frame encoding a polypeptide of 89 amino acid residues (SEQ ED NO:6), which exhibits significant homology to a number of chemokines. The top match is to the human tonsillar lymphocyte LD78 beta protein (SEQ ID NO:55), showing 60% identi and 89% similarity (FIG. 5). Furthermore, the four cysteine residues occurring in all chemokines in a characteristic motif are conserved in both clone(s). The fact that the first two cysteine residues in the genes are in adjacent positions classifies them as "C—C" or β subfamily of chemokines. In the other subfamily, the "CXC" or α subfamily, the first two cysteine residues are separated by one amino acid.

The polynucleotide encoding from M-CIF (SEQ ID NO:1) contains and open reading frame encoding a polypeptide of 93 amino acids (SEQ ID NO:2), of which the first about 19 are a leader sequence such that the mature peptide contains about 74 amino acid residues. M-CIF exhibits significant homology to human macrophage inhibitory protein-α, with 48% identity and 72% similarit over a stretch of 80 amino acids. Further, the four cysteine residues comprising a characteristic motif are conserved.

The polynucleotides of the present invention can be in the form of RNA or in the form of DNA, which DNA includes cDNA, genomic DNA, and synthetic DNA. The DNA can be double-stranded or single-stranded, and if single stranded can be the coding strand or noncoding (anti-sense) strand. The coding sequence which encodes the mature polypeptides can be identical to the coding sequence shown in FIGS. 1, 2 and 3 (SEQ ID NOS:3, 1, and 5, respectively) or that of the deposited clone(s) or can be a different coding sequence which coding sequence, as a result of the redundancy or degeneracy of the genetic code, encodes the same, mature polypeptides as the DNA of FIGS. 1, 2 and 3 (SEQ ID NOS:3, 1 and 5) or the deposited cDNAs.

The polynucleotides which encode for the mature polypeptides of FIGS. 1, 2 and 3 (SEQ ID NOS:4, 2, and 6the mature polypeptides encoded by the deposited cDNA can include: only the coding sequence for the mature polypeptide; the coding sequence for the mature polypeptides and additional coding sequence such as a leader or secretory sequence or a proprotein sequence; the coding sequence for the mature polypeptides (and optionally additional coding sequence) and non-coding sequence, such as introns or non-coding sequence 5' and/or 3' of the coding sequence for the mature polypeptides.

Thus, the term "polynucleotide encoding a polypeptide" encompasses a polynucleotide which includes only coding sequence for the polypeptide as well as a polynucleotide which includes additional coding and/or non-coding sequence.

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO:1, 3 or 5, as set forth using deoxyribonucleotide abbreviations, is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U.

Using the information provided herein, such as the nucleotide sequence in FIG. 1, 2, or 3, a nucleic acid mole the present invention encoding an MPIF-1, M-CIF or MIP-4 (respectively) polypeptide may be obtained using standard cloning and screening procedures, such as those for cloning cDNAs using mRNA as starting material.

The present invention further relates to variants of the hereinabove described polynucleotides which encode for fragments, analogs and derivatives of the polypeptide having the deduced amino acid sequence of FIGS. 1, 2 and 3 (SEQ D NOS:4, 2 and 6) or the polypeptides encoded by the cDNA of the deposited clone(s). The variants of the polynucleotides can be a naturally occurring allelic variant of the polynucleotides or a non-naturally occurring variant of the polynucleotides.

The present invention also includes polynucleotides encoding the same mature polypeptides as shown in FIGS. 1, 2 and 3 (SEQ ID NOS:4, 2 and 6) or the same mature polypeptides encoded by the cDNA of the deposited clone(s) as well as variants of such polynucleotides which variants encode for a fragment, derivative or analog of the polypeptides of FIGS. 1, 2 and 3 (SEQ ID NOS:4, 2 and 6) or the polypeptides encoded by the cDNA of the deposited clone(s). Such nucleotide variants include deletion variants, substitution variants and addition or insertion variants.

As hereinabove indicated, the polynucleotide can have a coding sequence which is a naturally occurring allelic variant of the coding sequence shown in FIGS. 1, 2 and 3 (SEQ ID NOS:4, 2 and 6) or of the coding sequence of the deposited clone(s). As known in the art, an allelic variant is an alternate form of a polynucleotide sequence which can have a substitution, deletion or addition of one or more nucleotides, which does not substantially alter the function of the encoded polypeptide.

The present invention also includes polynucleotides, wherein the coding sequence for the mature polypeptides can be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotides of the present invention can encode for a mature protein, or for a protein having a prosequence or for a protein having both a prosequence and a presequence (leader sequence).

The polynucleotides of the present invention can also have the coding sequence fused in frame to a marker sequence which allows for purification of the polypeptides of the present invention. The marker sequence can be a hexa-histidine tag supplied by a pQE-9 vector to provide for purification of the mature polypeptides fused to the marker in the case of a bacterial host, or, for example, the marker sequence can be a hemagglutinin (HA) tag when a mammalian host, e.g. COS-7 cells, is used. The HA tag corresponds to an epitope derived from the influenza hemagglutinin protein (Wilson, I, et al, *Cell*, 37:767 (1984)).

The term "gene" means the segment of DNA involved in producing a polypeptide chain; it includes regions preceding and following the coding region (leader and trailer) as well as intervening sequences (introns) between individual coding segments (exons).

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

The term "isolated" means that the material is removed from its original environment (e.g., the natural environment if it is naturally occurring). For example, a naturally-occurring polynucleotide or polypeptide present in a living animal is not isolated, but the same polynucleotides or DNA or polypeptides, separated from some or all of the coexisting materials in the natural system, is isolated. Such polynucleotides could be part of a vector and/or such polynucleotides or polypeptides could be part of a composition, and still be isolated in that such vector or composition is not part of its natural environment. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) for a MPIF-1, M-CIF or MIP-4 cDNA; DNA molecules comprising the coding sequence for a mature M-CIF, MPIF-1 or MIP-4 protein, and DNA molecules which comprise a sequence substantially different from those described above but which, due to the degeneracy of the genetic code, still encode an MPIF-1, M-CIF or MIP-4 polypeptide. Of course, the genetic code is well known in the art. Thus, it would be routine for one skilled in the art to generate the degenerate variants described above.

The present invention further relates to polynucleotides which hybridize to the hereinabove-described sequences if there is at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNAs of FIGS. 1, 2 and 3 (SEQ ID NO:3, 1, and 5) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, 3 and 5, for example, for recovery of the polynucleotide or as a diagnostic probe or as a PCR primer.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC® Deposit 75572 (M-CIF); ATCC® Deposit 75676 (MPIF-1); or ATCC® Deposit 75675 (MIP-4). By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 g/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. These are useful as diagnostic probes and primers as discussed above and in more detail below.

Of course, polynucleotides hybridizing to a larger portion of the reference polynucleotide (e.g. the deposited cDNA clone), for instance, a portion 50-750 nt in length, or even to the entire length of the reference polynucleotide, are also useful as probes according to the present invention, as are polynucleotides corresponding to most, if not all, of the nucleotide sequence of the deposited cDNA or the nucleotide sequence as shown in SEQ ID NO:1 (M-CIF); SEQ ID NO:3 (MPIF-1); or SEQ ID NO:5 (MIP-4). By a portion of a polynucleotide of "at least 20 nt in length," for example, is intended 20 or more contiguous nucleotides from the nucleotide sequence of the reference polynucleotide. As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual*, 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference.

Since a MPIF-1, M-CIF and MIP-4 cDNA clones have been deposited and its determined nucleotide sequence provided, generating polynucleotides which hybridize to a portion of the MPIF-1, M-CIF or MIP-4 cDNA molecules would be routine to the skilled artisan. For example, restriction endonuclease cleavage or shearing by sonication of a MPIF-1, M-CIF or MIP-4 cDNA clone could easily be used to generate DNA portions of various sizes which are polynucleotides that hybridize, respectively, to a portion of the MPIF-1, M-CIF or MIP-4 cDNA molecules.

Alternatively, the hybridizing polynucleotides of the present invention could be generated synthetically according to known techniques. Of course, a polynucleotide which hybridizes only to a poly A sequence (such as the 3' terminal poly(A) tract of a cDNA, or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g. practically any double-stranded cDNA clone).

As indicated, nucleic acid molecules of the present invention which encode an MPIF-1, M-CIF or MIP-4 polypeptide may include, but are not limited to those encoding the amino acid sequence of the mature polypeptide, by itself; the coding sequence for the mature polypeptide and additional sequences, such as those encoding the leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821-824 (1989), for instance, hexa-histidine provides for convenient purification of the fusion protein. The "HA" tag peptide useful for purification which corresponds to an epitope derived from the influenza hemagglutinin protein, which has been described by Wilson et al., *Cell* 37: 767 (1984). As discussed below, other such fusion proteins include at least one of an MPIF-1, M-CIF or MIP-4 polypeptide or fragment fused to Fc at the N- or C-terminus.

The present invention further relates to variants of the nucleic acid molecules of the present invention, which encode portions, analogs or derivatives of an MPIF-1, M-CIF or MIP-4 polypeptide. Variants may occur naturally, such as a natural allelic variant By an "allelic variant" is intended one of several alternate forms of a gene occupying a given locus on a chromosome of an organism. *Genes V.* Lewin, B., ed., Oxford University Press, New York (1994). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of an MPIF-1, M-CIF or MIP-4 polypeptide or portions thereof. Also especially preferred in this regard are conservative substitutions. Most highly preferred are nucleic acid molecules encoding the mature protein or the mature amino acid sequence encoded by the deposited cDNA clone, as described herein.

MPIF-1, M-CIF and MIP-4 Homolog Polynucleotides. The present invention is further directed to polynucleotides having at least 95% identity to a polynucleotide which encodes the polypeptide of SEQ ID NO:2, 4 and 6 as well as fragments thereof, which fragments have at least 30 bases and preferably at least 50 bases and to polypeptides encoded by such polynucleotides.

Further embodiments of the invention include isolated nucleic acid molecules comprising a polynucleotide having a nucleotide sequence at least 95%/, 96%, 97%, 98% or 99% identical to (a) a nucleotide sequence encoding an MPIF-1. M-CIF or MIP-4 polypeptide or fragment, having an amino acid sequence of SEQ ID NO:4, SEQ ID NO:2, or SEQ ID NO:6, respectively, including the predicted leader sequence; (b) a nucleotide sequence encoding an MPIF-1, M-CIF or MIP-4 polypeptide or fragment, having an amino acid sequence of SEQ ID NO;4, SEQ ID NO:2, or SEQ ID NO:6, respectively, including the predicted leader sequence, but minus the N-terminal methionine residue; (c) a nucleotide sequence encoding the mature MPIF-1, M-CIF or MIP-4 polypeptide (full-length polypeptide with the leader removed), (d) a nucleotide sequence encoding the full-length polypeptide having the complete amino acid sequence including the leader encoded by the deposited cDNA clone; (e) a nucleotide sequence encoding the mature polypeptide having the amino acid sequence encoded by the deposited cDNA clone; or (f) a nucleotide sequence complementary to any of the nucleotide sequences in (a), (b), (c), (d), or (e).

By a polynucleotide having a nucleotide sequence at least, for example, 95% "identical" to a reference nucleotide sequence encoding an MPIF-1, M-CIF or MIP-4 polypeptide is intended that the nucleotide sequence of the polynucleotide is identical to the reference sequence except that the polynucleotide sequence may include up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in FIG. 1, 3 or 5, or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482-489 (198 1), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

As one of ordinary skill would appreciate, due to the possibilities of sequencing errors discussed above, as well as the variability of cleavage sites for leaders in different known proteins, the mature M-CIF polypeptide encoded by the deposited cDNA comprises about 74 amino acids, but may be anywhere in the range of 69-93 amino acids; and the actual leader sequence of this protein is about 19 amino acids, but may be anywhere in the range of about 15 to about 24 amino acids.

As one of ordinary skill would appreciate, due to the possibilities of sequencing errors discussed above, as well as the variability of cleavage sites for leaders in different known proteins, the mature MPIF-1 polypeptide encoded by the deposited cDNA comprises about 99 amino acids, but may be anywhere in the range of 75-120 amino acids; and the actual leader sequence of this protein is about 21 amino acids, but may be anywhere in the range of about 15 to about 35 amino acids.

As one of ordinary skill would appreciate, due to the possibilities of sequencing errors discussed above, as well as the variability of cleavage sites for leaders in different known proteins, the mature MIP-1 polypeptide encoded by the deposited cDNA comprises about 69 amino acids, but may be anywhere in tie range of 60-89 amino acids; and the actual leader sequence of this protein about 20 amino acids, but may be anywhere in the range of about 15 to about 30 amino acids.

Nucleic Acid Probes. Such isolated molecules, particularly DNA molecules, are useful as probes for gene mapping, by in situ hybridization with chromosomes, and for detecting expression of a MPIF-1, M-CIF and/or MIP-4 gene in human tissue, for instance, by Northern blot analysis. The present invention is further directed to fragments of the isolated nucleic acid molecules described herein. By a fragment of an isolated nucleic acid molecule having the nucleotide sequence of the deposited MPIF-1, M-CIF or MIP-4 cDNAs, or a nucleotide sequence shown in any or all of FIGS. 1, 2 and 3 (SEQ ID NOS:3, 1 and 5), respectively, is intented fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50-500 nt in length are also useful according to the present invention as are fragments corresponding to most, if not all, of a nucleotide sequence of the deposited MPIF-1, M-CIF or MIP-4 cDNAs, or as shown in FIGS. 1, 2 aid 3 (SEQ ID NOS:3, 1 and 5). By a fragment at least 20 nt in length, for example, is intended fragments which include 20 or more contiguous bases from the nucleotide sequence of the deposited cDNA or the nucleotide sequence as shown in FIGS. 1, 2 and 3 (SEQ ID NOS:3, 1 and 5). Since the gene has been deposited and the nucleotide sequences shown in FIGS. 1, 2 and 3 (SEQ ID NOS:3, 1 and 5) are provided, generating such DNA fragments would be routine to the skilled artisan. For example, restriction endonuclease cleavage or shearing by sonication could easily be used to generate fragments of various sizes. Alternatively, such fragments could be generated synthetically.

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

Vectors, Host Cells, and Protein Expression. The present invention also relates to vectors containing the isolated nucleic acid molecules of the present invention, genetically engineered host cells containing the recombinant vectors, and the production of MPIF-1, M-CIF or MIP-4 polypeptides or fragments thereof by recombinant techniques. The present invention further relates to novel expression vectors useful for the production of proteins in bacterial systems. These novel vectors are exemplified by the pHE4 series of vectors and, in particular, the pHE4-5 vector (FIGS. 62 and 67A-G).

The polynucleotides encoding the proteins of the present invention may be joined to a vector containing a selectable marker for propagation in a host. As discussed in detail below, generally, a plasmid vector is introduced into a host cell in a precipitate, such as a calcium phosphate precipitate, or in a complex with a charged lipid. If the vector is a virus, it may be packaged in vitro using an appropriate packaging cell line and then transduced into host cells.

Preferred for use in the practice of the present invention are vectors comprising cis-acting control regions operatively linked to the polynucleotide of interest. Cis-acting control regions include operator and enhancer sequences. As used herein, the term "operator" refers to a nucleotide sequence, usually composed of DNA, which controls the transcription of an adjacent nucleotide sequence. Operator sequences are generally derived from bacterial chromosomes.

Transcription of the nucleotide sequences encoding the polypeptides of the present invention by higher eukaryotes may be increased by inserting an enhancer sequence into the vector. Enhancers are cis-acting elements usually about from 10 to 300 bp that act to increase transcriptional activity of a promoter in a given host cell-type. Examples of enhancers include the SV40 enhancer, which located on the late side of the replication origin at bp 100 to 270, the cytomegalovirus early promoter enhancer, the polyoma enhancer on the late side of the replication origin, and adenovirus enhancers.

Appropriate trans-acting factors may be supplied by the host, supplied by a complementing vector, or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives. Also preferred for the expression of MPIF-1 is the pHE4-5 vector described in Example 30.

Additional expression vectors useful in the present invention include chromosomal-, episomal- and virus-derived vectors, e.g., vectors derived from bacterial plasmids, bacteriophage, yeast episomes, yeast chromosomal elements, viruses such as baculovirus, papova viruses, vaccinia viruses, adenoviruses, fowl pox viruses, pseudorabies viruses and retroviruses, and vectors derived from combinations thereof, such as cosmids and phagemids.

The appropriate nucleic acid sequence can be inserted into the vector by a variety of procedures. In general, the nucleic acid sequence is inserted into an appropriate restriction endonuclease site(s) by procedures known in the art. Such procedures and others are deemed to be within the scope of those skilled in the art.

The nucleic acid insert should be operatively linked to an appropriate promoter, such as the phage lambda PL promoter, the *E. coli* lac, trp and tac promoters, the SV40 early and late promoters and promoters of retroviral LTRs, and other promoters known to control expression of genes in prokaryotic or eukaryotic cells or their viruses. Other suitable promoters will be known to the skilled artisan. As used herein, the term "promoter" refers to a nucleotide sequence or group of nucleotide sequences which, at a minimum, provides a binding site or initiation site for RNA polymerase action. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated. The vector can also include appropriate sequences for amplifying expression.

As used herein, the phrase "operatively linked" refers to a linkage in which a nucleotide sequence is connected to another nucleotide sequence (or sequences) in such a way as to be capable of altering the functioning of the sequence (or sequences). For example, a protein coding sequence which is operatively linked to a promoter/operator places expression of the protein coding sequence under the influence or control of these sequences. Two nucleotide sequences (such as a protein encoding sequence and a promoter region sequence linked to the 5' end of the encoding sequence) are said to be operatively linked if induction of promoter function results in the transcription of the protein encoding sequence mRNA and if the nature of the linkage between the two nucleotide sequences does not (1) result in the introduction of a frame-shift mutation nor (2) prevent the expression regulatory sequences to direct the expression of the mRNA or protein. Thus, a promoter region would be operatively linked to a nucleotide sequence if the promoter were capable of effecting transcription of that nucleotide sequence.

As used herein, the phrase "cloning vector" refers to a plasmid or phage nucleic acid or other nucleic acid sequence which is able to replicate autonomously in a host cell, and which is characterized by one or a small number of endonuclease recognition sites at which such nucleic acid sequences may be cut in a determinable fashion without loss of an essential biological function of the vector, and into which nucleic acid may be spliced in order to bring about its replication and cloning. The cloning vector may further contain a marker suitable for use in the identification of cells transformed with the cloning vector. Markers, for example, are erythromycin and kanamycin resistance. The term "vehicle" is sometimes used for "vector."

As used herein, the phrase "expression vector" refers to a vector similar to a cloning vector which is capable of expressing a structural gene cloned into the expression vector, after transformation of the expression vector into a host. In an expression vector, the cloned structural gene (any coding sequence of interest) is placed under the control of (i.e., operatively linked to) certain sequences which allow such gene to be expressed in a specific host. In the pHE4-5 vector, for example, the structural gene is operatively linked to a T5 phage promoter sequence and two lac operator sequences. Expression control sequences will vary, and may additionally contain transcriptional elements such as termination sequences and/or translational elements such as initiation and termination sites.

As indicated above, the expression vectors will preferably include at least one selectable marker. Such markers include dihydrofolate reductase or neomycin resistance for eukaryotic cell culture and tetracycline, kanamycin, or ampicillin resistance genes for culturing in *E. coli* and other bacteria. Representative examples of appropriate hosts include, but are not limited to, bacterial cells, such as *E. coli*, *Streptomyces* and *Salmonella typhimurium* cells; fungal cells, such as yeast cells, insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

In addition to the use of expression vectors in the practice of the present invention, the present invention further includes novel expression vectors comprising operator and promoter elements operatively linked to nucleotide sequences encoding a protein of interest One example of such a vector is pHE4-5 (SEQ ID NO:56) which is described in detail both below and in Example 30. The pHE4-5 vector was deposited on Sep. 30, 1997 at the American Type Culture Collection (ATCC®), 10801 University Boulevard, Manassas, Va. 20110-2209, USA (present address), and given ATCC® accession number 20931.

As summarized in FIGS. 62 and 67, components of the pHE4-5 vector (SEQ D NO:56) include: 1). a neomycin-phosphotransferase gene as a selection marker, 2). an *E. coli* origin of replication, 3). a T5 phage promoter sequence, 4). two lac operator sequences, 5). a nucleotide sequence encoding MPIF-1Δ23 (SEQ ID NO:27), 6). a Shine-Delgarno sequence, 7). the lactose operon repressor gene (lacIq). The origin of replication (oriC) is derived from pUC19 (LTI, Gaithersburg, Md.). The promoter sequence was and operator sequences were made synthetically. Synthetic production of nucleic acid sequences is well known in the art. CLONTECH 95196 Catalog, pages 215-216, CLONTECH, 1020 East Meadow Circle, Palo Alto, Calif. 94303.

As noted above, the pHE4-5 vector contains a lacIq gene. LacIq is an allele of the lacd gene which confers tight regulation of the lac operator, Amann, E. et al., *Gene* 69:301-315 (1988); Stark, M., *Gene* 51255-267 (1987).The lacIq gene encodes a repressor protein which binds to lac operator sequences and blocks transcription of down-stream (i e., 3') sequences. However, the lacIq gene product dissociates from the lac operator in the presence of either lactose or certain lactose analogs, e.g., isopropyl B-D-thiogalacto-pyranoside (IPTG). MPIF-1Δ23 thus is not produced in appreciable quantities in uninduced host cells containing the pHE4vector. Induction of these host cells by the addition of an agent such as IPTG, however, results in the expression of the MPIF-1Δ23 coding sequence.

The promoter/operator sequences of the pHE4-5 vector (SEQ ID NO:57) comprise a T5 phage promoter and two operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located downstream from the lac operators may be induced by the addition of a lac operon inducer, such as IPTG. Binding of a lac inducer to the facIq proteins results in their release from the lac operator sequences and the initiation of transcription of operatively linked sequences, Lac operon regulation of gene expression is reviewed in Devlin, T., TEXTBOOK OF BIOCHEMISTRY WITH CLINICAL CORRELATIONS, 4the Edition (1997), pages 802-807.

The pHE4 series of vectors contain all of the components of the pHE4-5 vector except for the MPIF-1Δ23 coding sequence. Features of the pHE4 vectors include optimized synthetic T5 phage promoter, lac operator, and Shine-Delgarno sequences. Further, these sequences are also optimally spaced so that expression of an inserted gene may be tightly regulated and high level of expression occurs upon induction.

Among known bacterial promoters suitable for use in the production of proteins of the present invention include the *E. coli* lacI and lacZ promoters, the T3 and T7 promoters, the trp promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4-5 vector also contains a Shine-Delgarno sequence 5' to the AUG initiation codon. Shine-Delgarno sequence are short sequences generally located about 10 nucleotides up-stream (i.e., 5') from the AUG initiation codon. These sequences essentially direct prokaryotic ribosomes to the AUG initiation codon.

Thus, the present invention is also directed to expression vector useful for the production of the proteins of the present invention. This aspect of the invention is exemplified by the pHE4-5 vector (SEQ ID NO;56).

Additional vectors preferred for use in the expression of the proteins of the present invention in bacteria include pQE70, pQE60 and pQE-9, (Qiagen); pBS vectors, pD10, Phagescript vectors, pBluescript vectors, pNH8A, pNH16a, pNH18A, pNH46A, available from Stratagene; and ptrc99a, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVM available from Pharmacia.

Other suitable vectors will be readily apparent to the skilled artisan and include pBR322 (ATCC® 37017), pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed. Following transformation of a suitable host strain and growth of the host strain to an appropriate cell density, the selected promoter is induced by appropriate means (e.g. temperature shift or chemical induction) and cells are cultured for an additional period.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., BASIC METHODS IN MOLECULAR BIOLOOY (1986).

Recombinant constructs may be introduced into host cells using well known techniques such infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

Host cells are genetically engineered (transduced or transformed or transfected) with the vectors of this invention which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants or amplifying the MPIF-1, MIP-4 and M-CIF genes. The culture conditions, such as temperature, pH and the like, are those previously used with the host cell selected for expression, and will be apparent to the ordinarily skilled artisan.

The polynucleotides of the present invention can be employed for producing polypeptides by recombinant techniques. Thus, for example, the polynucleotide sequence can be included in any one of a variety of expression vehicles, in particular vectors or plasmids for expressing a polypeptide. Such vectors include chromosomal, nonchromosomal and synthetic nucleic acid sequences, e.g., derivatives of SV4O0 bacterial plasmids; phage nucleic acid; yeast plasmids; vectors derived from combinations of plasmids and phage nucleic acid, viral nucleic acid such as vaccinia, adenovirus, fowl pox virus, alphaviruses and pseudorabies. However, any other plasmid or vector can be used as long as they are replicable and viable in the host.

As noted above, the vector containing the appropriate nucleic acid sequence as hereinabove described, as well as an appropriate promoter or control sequence, can be employed to transform an appropriate host to permit the host to express the protein.

As representative examples of appropriate hosts, there can be mentioned: bacterial cells, such as *E. coli, Streptomyces, Salmonella typhimurium*; fungal cells, such as yeast; insect cells such as Drosophila and Sf9; animal cells such as CHO, COS or Bowes melanoma; plant cells, etc. The selection of an appropriate host is deemed to be within the scope of those skilled in the an from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operatively linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pBluescript SK, pbsks, pNH8A, pNH16a, pNH18A, pNH46A (Stratagene); ptrc99a, pKK223-3, pKK233-3, pDR540, pRITS (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector can be used as long as they are replicable and viable in the host The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the nucleic acid constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural nucleic acid sequence encoding desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus sublriis, Salmonella typhimurium* and various species within the genera *Pseudomonas, Streptomyces*, and *Staphylococcus*, although others can also be employed as a matter of choice.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3t3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. Nucleic acid sequences derived from the SV4O splice, and polyadenylation sites can be used to provide the required nontranscribed genetic elements.

Polypeptides and Polypeptide Fragments. The invention further provides an isolated MPIF-1, M-CIF, or MIP-4 polypeptide having the amino acid sequence encoded by the deposited cDNA, or the amino acid sequence in FIG. 1, 2 or 3 (SEQ ID NOS:4, 2 or 6, respectively), or a peptide or polypeptide comprising a portion of the above polypeptides. The terms "peptide" and "oligopeptide" are considered synonymous (as is commonly recognized) and each term can be used interchangeably as the context requires to indicate a chain) of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

Figure 11:
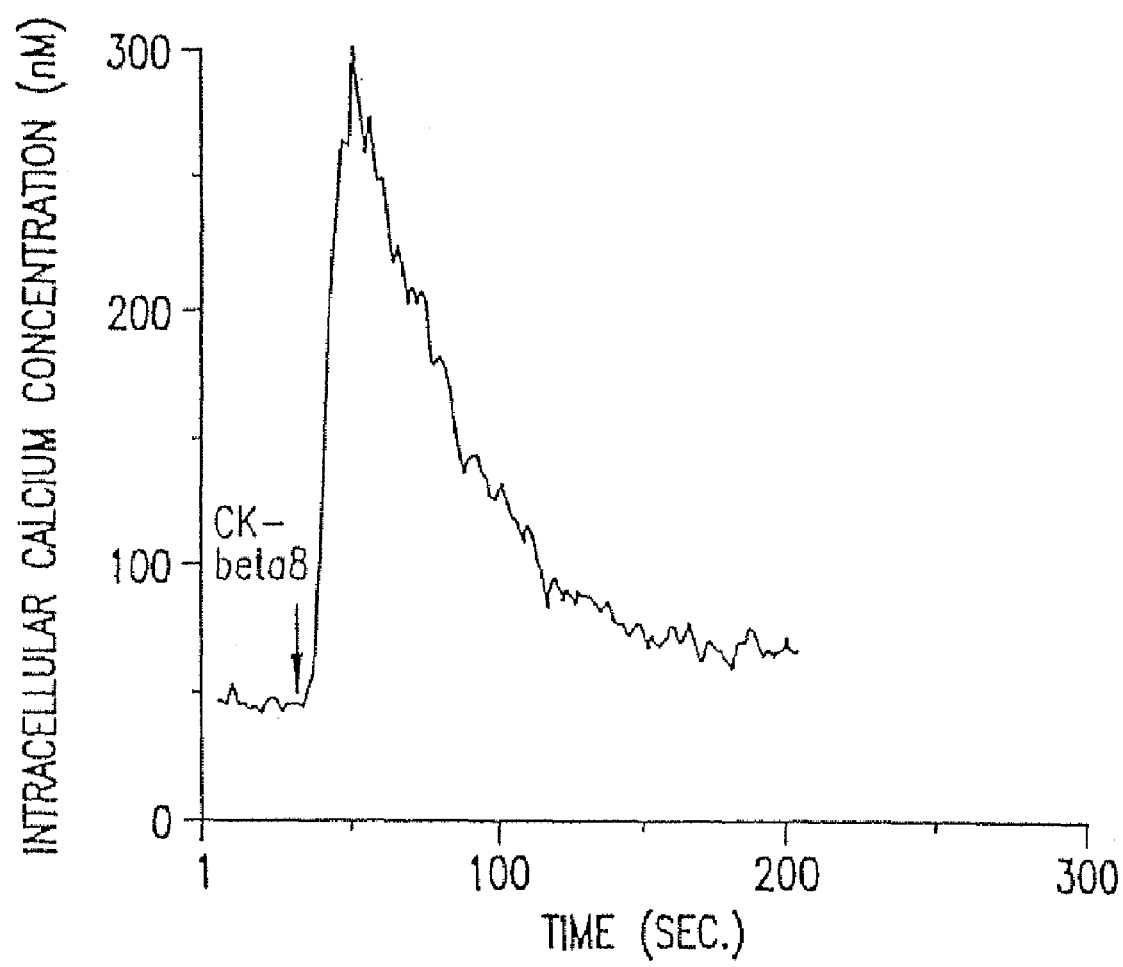
FIG. 11. Change in intracellular calcium concentration in response to MPIF-1 was determined using a Hitachi F-2000 fluorescence spectrophotometer. Bacterial expressed MPIF-1 was added to Indo-1 loaded THP-1 cells to a final concentration of 50 nM and the intracellular level of calcium concentration was monitored.

By "a polypeptide having MPIF-1 activity" is intended polypeptides exhibiting activity similar, but not necessarily identical, to an activity of the MPIF-1 protein of the invention (either the full-length protein or, preferably, the mature protein), as measured in a particular biological assay. MPIF-1 protein activity can be measured by the assays set forth in Examples 15, 16, as well as FIG. 11. For example, MPIF-1 protein activity measured using the in vitro myeloprotection assay disclosed in Example 15, infra.

Briefly, lineage-depleted populations of cells (Lin cells) are isolated from mouse bone marrow and incubated in the presence of multiple cytokines with or without MPIF-1. After 48 hours, one set of each culture receives 5-Fu and the incubation is then continued for additional 24 hours, at which point the numbers of surviving low proliferative potential colony-forming cells (LPP-CFC) are determined by any suitable clonogenic assay known to those of skill in the art. A large percentage (e.g., ≧30-50%, such as ≧40%) of LPP-CFC are protected from the 5-Fu-induced cytotoxicity in the presence of MPIF-1, whereas little protection (<5%) of LPP-CFC will be observed in the absence of MPIF-1 or in the presence of an unrelated protein. In such an assay, high proliferative potential colony-forming cells (HPP-CFC) can additionally be protected from the 5-Fu-induced cytotoxicity in the presence, of MPIF-1, but in some cases are not. HPP-CFC are generally not protected when LPP-CFC are not protected.

Thus, "a polypeptide having MPIF-1 protein activity" includes polypeptides that exhibit MPIF-1 activity, in the above-described assay. Although the degree of activity need not be identical to that of the MPIF-1 protein, preferably, "a polypeptide having MPIF-1 protein activity" will exhibit substantially similar activity as compared to the MPIF-1 protein (i.e., the candidate polypeptide will exhibit greater activity or not more than about twenty-fold less and, preferably, not more than about ten-fold less activity relative to the reference MPIF-1 protein).

By "a polypeptide having M-CIF activity" is intended polypeptides exhibiting activity similar, but not necessarily identical, to an activity of the M-CIF protein of the invention (either the lull-length protein or, preferably, the mature protein), as measured in a particular biological assay. For example, M-CIF protein activity can be measured using the in vitro inhibition of M-CSF-induced colony formation by animal cells, such as bone marrow cells, in an assay as described in Example 25, infra.

Thus, "a polypeptide having M-CIF protein activity" includes polypeptides that exhibit M-CIF activity, in the above-described assay. Although the degree of activity need not be identical to that of the M-CIF protein, preferably, "a polypeptide having M-CIF protein activity" will exhibit substantially similar activity as compared to the M-CIF protein (i.e., the candidate polypeptide will exhibit greater activity or not more than about twenty-fold less and, preferably, not more than about ten-fold less activity relative to the reference M-CIF protein).

The present invention further relates to MPIF-1, M-CIF and MIP-4 polypeptides which have the deduced amino acid sequence of FIGS. 1, 2 and 3 (SEQ ID NOS:4, 2 and 6) or which have the amino acid sequence encoded by the deposited cDNA, as well as fragments, analogs and derivatives of such polypeptide.

The terms "fragment," "derivative" and "analog" when referring to the polypeptides of FIGS. 1, 2 and 3 (SEQ ID NOS:4, 2 and 6) or that encoded by the deposited cDNA, means a polypeptide which retains essentially the same biological function or activity as such polypeptide. Thus, an analog includes a proprotein which can he activated by cleavage of the proprotein portion to produce art active mature polypeptide.

The polypeptides of the present invention can be a recombinant polypeptide, a natural polypeptide or a synthetic polypeptide, preferably a recombinant polypeptide.

The fragment, derivative or analog of the polypeptides of FIGS. 1, 2 and 3 (SEQ ID NOS:4, 2 and 6) by the deposited EDNA can be (i) one in which one or more of the amino acid residues are substituted with a conserved or non-conserved amino acid residue (preferably a conserved amino acid residue) and such substituted amino acid residues is or is not be one encoded by the genetic code, or (ii) one in which one or more of the amino acid residues includes a substituent group, or (iii) one in which the mature polypeptides are fused with another compound, such as a compound to increase the half-life of the polypeptide (for example, polyethylene glycol), or (iv) one in which the additional amino acids are fused to the mature polypeptides, such as a leader or secretory sequence or a sequence which is employed for purification of the mature polypeptides or a proprotein sequence. Such fragments, derivatives and analogs are deemed to be within the scope of those skilled in the art from the teachings herein.

The polypeptides of the present invention are preferably provided in an isolated form, and preferably are purified to homogeneity.

The polypeptides of the present invention include the polypeptide of SEQ ID NOS:2, 4 and 6 (in particular the mature polypeptide) as well as polypeptides which have at least 95% similarity (still more preferably at least 95% identity) to the polypeptide of SEQ ID NOS:2, 4 and 6 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Of course, due to the degeneracy of the genetic code, one of ordinary skill in the art will immediately recognize that a large number of the nucleic acid molecules having a sequence at least 95%, 96%, 97%, 98, or 99% identical to the nucleic acid sequence of the deposited cDNA (ATCC® 75676) or the nucleic acid sequence shown in FIG. 1 (SEQ ID NO:3) will encode a polypeptide "having MPIF-1 protein activity." One of ordinary skill in the art will also immediately recognize that a large number of the nucleic acid molecules having a sequence at least 95%, 96%, 97%, 98%, or 99% identical to the nucleic acid sequence of the deposited cDNA (ATCC® 75572) or the nucleic acid sequence shown in FIG. 2 (SEQ ID NO: 1) will encode a polypeptide "having M-CIF protein activity." Additionally, one of ordinary skill in the art will immediately recognize that a large number of the nucleic acid molecules having a sequence at least 95%, 96%, 97%, 98%, or 99% identical to the nucleic acid sequence of the deposited cDNA (ATTC® 75675) or the nucleic acid sequence shown in FIG. 3 (SEQ ID NO:5) will encode a polypeptide "having MIP-4 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having MPIF-1, M-CIF or MIP-4 protein activity. This is because the skilled artisan is fully aware of amino acid substitutions that are either less likely or not likely to significantly effect protein function (e.g. replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306-1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fe part after the fusion protein has been expressed, detected and purified in the advantageous manner described. This is the case when Fe portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL5. See, D. Bennett et al., *Journal of Molecular Recognition*, Vol. 8: 52-58 (1995) and K. Johanson et al., *The Journal of Biological Chemistry*. Vol. 270, No. 16:9459-9471 (1995).

The MPIF-1, M-CIF or MIP-4 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

MPIF-1, M-CIF and MIP-4 Polypeptide Variants. It wilt be recognized in the art that some amino acid sequences of the MPIF-1, M-CIF or MIP-4 polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of an MPIF-1, M-CIF or MIP-4 polypeptide which show, respectively, substantial MPIF-1, M-CIF or MIP-4 polypeptide activity or which include regions, respectively, of an MPIF-1, M-CIF or MIP-4 protein such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Tht, exchange of the acidic residues Asp and Glu, substitution between the amide residues Asn and Gln, exchange of the basic residues Lys and Arg and replacements among the aromatic residues Phe, Tyr.

Of additional special interest are also substitutions of charged amino acids with another charged amino acid or with neutral amino acids. This may result in proteins with improved characteristics such as less aggregation. Prevention of aggregation is highly desirable. Aggregation of proteins cannot only result in a reduced activity but be problematic when preparing pharmaceutical formulations because they can be immunogenic (Pinckard et al., Clin. Exp. Immunol. 2:331-340 (1967), Robbins et al., Diabetes 36:838-845 (1987), Cleland et al., Crit. Rev. Therapeutic Drug Carrier Systems 10:307-377 (1993).

The replacement of amino acids can also change the selectivity of the binding to cell surface receptors. Ostade et al., Nature 361: 266-268 (1993), described certain TNF alpha mutations resulting in selective binding of TNF alpha to only one of known TNF receptors.

As indicated in detail above, further guidance concerning which amino acid changes are likely to be phenotypically silent (i.e., are not likely to have a significant deleterious effect on a function) can be found in Bowie, J. U., et al., "Deciphering the in Protein Sequences: Tolerance to Amino Acid Substitutions," *Science* 247:1306-1310 (1990) (see Table 1).

As indicated, changes are preferably of a minor nature, such as conservative amino acid substitutions that do not significantly affect the folding or activity of the protein (see Table 1).

TABLE 1

| Conservative Amino Acid Substitutions. | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above and below. Generally speaking, the number of substitutions for any given MPIF-1 or M-CIF polypeptide or mutant thereof will not be more than 50,40, 30, 20, 10, 5, or 3, depending on the objective. Specific MPIF-1 and M-CIF amino acid substitutions are described below.

MPIF-1 Variants. In addition, variants of MPIF-1 have been identified and characterized. Several of these analogs comprise amino terminal truncations. In addition, an, MPIF-1 analog apparently resulting from an alternative splice site has also been identified and characterized (FIG. 26 (SEQ ID NO:11)). Example 17 discloses the biological activities of these MPIF-1 analogs. The sequences of these analogs are shown in FIG. 25 (SEQ ID NOS:7, 8, and 9, as well amino acid residues 46-120, 45-120, 48-120, 49-120, 39-120, and 44-120 in SEQ ID NO:4).

In order to improve or alter the characteristics of the MPIF-1 polypeptide(s), protein engineering may be employed. Recombinant DNA technology known to those skilled in the art can be used to create novel proteins. Muteins and deletions or fusion proteins can show, e.g., enhanced activity or increased stability. In addition, they could be purified in higher yields and show better solubility at least under certain purification and storage conditions. Set below are additional examples of mutations that can be constructed.

MPIF-1 Aminoterminal and carboxyterminal deletions: Interferon gamma shows up to ten times higher activities by deleting 8-10 amino acid residues from the carboxy terminus of the protein (Döbeli et al., *J. of Biotechnology* 7:199-216 (1988). Ron et al., *J. Biol. Chem.,* 268(4):2984-2988 (1993) reported modified KGF proteins that had heparin binding activity even if 3, 8, or 27 amino terminal amino acid residues were missing. Many other examples are known to anyone skilled in the art.

Particularly preferred MPIF-1 polypeptides of the amino acid sequence shown in FIG. 1 (SEQ ID NO:4) are shown below:

| | |
|---|---|
| Val (23) - Asn (120) | Val (23) - Lys (119) |
| Thr (24) - Asn (120) | Thr (24) - Arg (118) |
| Lys (25) - Asn (120) | Lys (25) - Thr (117) |
| Asp (26) - Asn (120) | Asp (26) - Lys (116) |
| Ala (27) - Asn (120) | Ala (27) - Ile (115) |
| Glu (28) - Asn (120) | Glu (28) - Arg (114) |
| Thr (29) - Asn (120) | Thr (29) - Thr (113) |
| Glu (30) - Asn (120) | Thr (29) - Asp (112) |
| Phe (31) - Asn (120) | Thr (29) - Leu (111) |
| Met (32) - Asn (120) | Thr (29) - Lys (110) |
| Met (33) - Asn (120) | Met (33) - Leu (109) |
| Ser (34) - Asn (120) | Ser (34) - Met (108) |
| Lys (35) - Asn (120) | Ser (34) - Arg (107) |
| Leu (36) - Asn (120) | Ser (34) - Met (106) |
| Pro (37) - Asn (120) | Ser (34) - Cys (105) |
| Leu (38) - Asn (120) | Ser (34) - Val (104) |
| Glu (39) - Asn (120) | Ser (34) - Gln (103) |
| Asn (40) - Asn (120) | Ser (34) - Val (102) |
| Pro (41) - Asn (120) | Ser (34) - Gln (101) |
| Val (42) - Asn (120) | Ser (34) - Lys (100) |
| Leu (43) - Asn (120) | Ser (34) - Asp (99) |
| Leu (44) - Asn (120) | Ser (34) - Ser (98) |
| Asp (45) - Asn (120) | Ser (34) - Pro (97) |
| Arg (46) - Asn (120) | Ser (34) - Asn (96) |
| Phe (47) - Asn (120) | Ser (34) - Ala (95) |
| His (48) - Asn (120) | Ser (34) - Cys (94) |
| Ala (49) - Asn (120) | Ser (34) - Phe (93) |
| Thr (50) - Asn (120) | Ser (34) - Arg (92) |
| Ser (51) - Asn (120) | Ser (34) - Arg (91) |
| Ala (52) - Asn (120) | Ser (34) - Gly (90) |
| Asp (53) - Asn (120) | Ser (34) - Lys (89) |
| | Ser (34) - Ile (84) |
| | Ser (34) - Ser (79) |
| | Ser (34) - Asn (75) |
| | Ser (34) - Phe (72) |
| | Ser (34) - Leu (68) |

Thus, in one aspect, MPIF-1 N-terminal deletion mutants are provided by the present invention. Such mutants include those comprising an amino acid sequence shown in FIG. 1 (SEQ ID NO:4) having a deletion of at least the first 22 N-terminal amino acid residues (i.e., a deletion of at least Met (1)—Arg (22)) but not more than the first 60 N-terminal amino acid residue (SEQ ID NO:4). Alternatively, the deletion will include at least the first 22 N-terminal amino acid residues but not more than die first 53 N-terminal amino acid residues of FIG. 1 (SEQ ID NO:4). Alternatively, the deletion will include at least the first 33 N-terminal amino acid residues but not more than the first 53 N-terminal amino acid residues of FIG. 1 (SEQ ID NO:4). Alternatively, the deletion will include at least tie first 37 N-terminal amino acid residues (i.e., a deletion of at least Met (1)—Pro (37)) but not more the first 53 N-terminal amino acid residues of FIG. 1 (SEQ ID NO:4). Alternatively, the deletion will include at least the first 48 N-terminal amino acid residues but not more than the first 53 N-terminal amino acid residues of FIG. 1 (SEQ ID NO:4).

In addition to the ranges of MPIF-1 N-terminal deletion mutants described above, the present invention is also directed to all combinations of the above described ranges, e.g., deletions of at least the first 22 N-terminal amino acid residues but not more than the first 48 N-terminal amino acid residues of FIG. 1 (SEQ ID NO:4); deletions of at least the first 37 N-terminal amino acid residues but not more than the first 48 N-terminal amino acid residues of FIG. 1 (SEQ ID NO:4); deletions of at least the first 22 N-terminal amino acid residues but not more than the first 37 N-terminal amino acid residues of FIG. 1 (SEQ ID NO:4); deletions of at least the first 22 N-terminal amino acid residues but not more than the first 33 N-terminal amino acid residues of FIG. 1 (SEQ ID NO:4); deletions of at least the first 33 N-terminal amino acid residues but not more than the first 37 N-terminal amino acid residues of FIG. 1 (SEQ ID NO:4); and deletions of at least the first 33 N-terminal amino acid residues but not more than the first 48 N-terminal amino acid residues of FIG. 1 (SEQ 1) NO:4)

In another aspect, MPIF-1 C-terminal deletion mutants are provided by the present invention. Preferably, the N-terminal amino acid residue of said MPIF-1 C-terminal deletion mutants is amino acid residue 1 (Met) or 22 (Arg) of FIG. 1 (SEQ ID NO:4). Such mutants include those comprising an amino acid sequence shown in FIG. 1 (SEQ ID NO:4) having a deletion of at least the last C-terminal amino acid residue (Asn (120)) but not more than the last 52 C-terminal amino acid residues (e.g., a deletion of amino acid residues Glu (69) Asn (120) of FIG. 1 (SEQ ID NO:4)). Alternatively, the deletion will include at least the last 10 or 15 C-terminal amino acid residues but not more than the last 52 C-terminal amino acid residues of FIG. 1 (SEQ ID NO:4). Alternatively, the deletion will include at least the last 20 C-terminal amino acid residues but not more than the last 52 C-terminal amino acid residues of FIG. 1 (SEQ ID NO:4). Alternatively, the deletion will include at least the last 30 C-terminal amino acid residues but not more than the last 52 C-terminal amino acid residues of FIG. 1 (SEQ ID NO:4). Alternatively, the deletion will include at least the last 36 C-terminal amino acid residues but not more than the last 52 C-terminal amino acid residues of FIG. 1 (SEQ ID NO:4). Alternatively, the deletion will include at least the last 41 C-terminal amino acid residues but not more than the last 52 C-terminal amino acid residues of FIG. 1 (SEQ ID NO:4). Alternatively, the deletion will include at least the last 45 C-terminal amino acid residues but not more than the last 52 C-terminal amino acid residues of FIG. 1 (SEQ ID NO:4). Alternatively, the deletion will include at least the last 48 C-terminal amino acid residues but not more than the last 52 C-terminal amino acid residues of FIG. 1 (SEQ ID NO:4).

In addition to the ranges of C-terminal deletion mutants described above, the present invention is also directed to all combinations of the above described ranges, e.g., deletions of at least the last C-terminal amino acid residue but not more than the last 48 C-terminal amino acid residues of FIG. 1 (SEQ ID NO:4); deletions of at least the last C-terminal amino acid residue but not more than the last 45 C-terminal amino acid residues of FIG. 1 (SEQ ID NO:4), deletions of at least the last C-terminal amino acid residue but not more than the last 41 C-terminal amino acid residues of FIG. 1 (SEQ ID NO:4); deletions of at least the last C-terminal amino acid residue but not more than the last 36 C-terminal amino acid residues of FIG. 1 (SEQ ID NO:4); deletions of at least the last C-terminal amino acid residue but not more than the last 10 C-terminal amino acid residues of FIG. 1 (SEQ ID NO:4); deletions of at least the last 10 C-terminal amino acid residues but not more than the last 20 C-terminal amino acid residues of FIG. 1 (SEQ ID NO:4); deletions of at least the last 10 C-terminal amino acid residues but not more than the last 30 C-terminal amino acid residues of FIG. 1 (SEQ ID NO:4); deletions of at least the last 10 C-terminal amino acid residues but not more than the last 36 C-terminal amino acid residues of FIG. 1 (SEQ ID NO:4); deletions of at least the last 20 C-terminal amino acid residues but not more than the last 30 C-terminal amino acid residues of FIG. 1 (SEQ ID NO:4); etc. etc. etc. . . . .

In yet another aspect, also included by the present invention are MPIF-1 deletion mutants having amino acids deleted from both the N-terminal and C-terminal residues. Such mutants include all combinations of the N-terminal deletion mutants and C-terminal deletion mutants described above. Such mutants include those comprising an amino acid sequence shown in FIG. 1 (SEQ ID NO:4) having a deletion of at least the first 22 N-terminal amino acid residues but not more than the first 52 N-terminal amino acid residues of FIG. 1 (SEQ ID NO:4) and a deletion of at least the last C-terminal amino acid residue but not more than the last 52 C-terminal amino acid residues of FIG. 1 (SEQ ID NO:4). Alternatively, a deletion can include at least the first 33, 37, or 48 N-terminal amino acids but not more than the first 52 N-terminal amino acid residues of FIG. 1 (SEQ ID) NO:4) and a deletion of at least the last 10, 20, 30, 36, 41, 45, or 48 C-terminal amino acid residues but not more than the last 52 C-terminal amino acid residues of FIG. 1 (SEQ ID NO:4). Further included are all combinations of the above described ranges.

Substitution of amino acids: A further aspect of the present invention also includes the substitution of amino acids. Of special interest are conservative amino acid substitutions that do not significantly affect the folding of the protein. Examples of conservative amino acid substitutions known to those skilled in the art are set forth Table 1, above.

Of additional special interest are also substitutions of charged amino acids with another charged amino acid or with neutral amino acids. This may result in proteins with improved characteristics such as less aggregation. Prevention of aggregation is highly desirable. Aggregation of proteins cannot only result in a reduced activity but be problematic when preparing pharmaceutical formulations because they can be immunogenic (Pinckard et al., *Clin. Exp. Immunol.* 2:331-340 (1967), Robbins et al., *Diabetes* 36:83 8-845 (1987), Cleland et al, *Crit. Rev, Therapeutic Drug Carrier Systems* 10:307-377 (1993).

The MPIF-1 protein may contain one or several amino acid substitutions, deletions or additions, either from natural mutation or human manipulation. Examples of some preferred mutations of the amino acid sequence shown in FIG. 1 (SEQ ID NO:4) are provided below. (By the designation, for example, Ala (21) Met is intended that the Ala at position 21 of FIG. 1 (SEQ ID NO:4) is replaced by Met.)

Ala (21) Met
Thr (24) Ala
Lys (25) Asn
Asp (26) Ala
Asp (45) Ala
Asp (45) Gly
Asp (45) Ser
Asp (45) Thr
Asp (45) Met
Asp (53) Ala
Asp (53) Gly
Asp (53) Ser
Asp (53) Thr
Asp (53) Met
Ser (51) Gly
Ser (34) Gly
Glu (30) Gin
Slu (28) Gln
Pro (60) Thr
Ser (70) Ala

Aminoterminal Deletions of the MPIF-1 137 Amino Acid Splice Variant:

As indicated above, the present invention further provides a human MPIF-1 splice variant. The cDNA sequence and the 137 amino acid sequence are shown in FIG. 26A (SEQ ID NOs:10 and 11, respectively). Using eukaryotic expression systems, the present inventors have discovered three N-terminal deletion mutants of this MPIF-1 splice variant. These include His (60)—Asn (137); Met (46)—Asn (137); and Pro (54)—Asn (137). Thus, in a further aspect, MPIF-1 splice variant N-terminal deletion mutants are provided by the present invention. Such mutants include those comprising an amino acid sequence shown in FIG. 26A (SEQ ID NO:11) having a deletion of at least the first 45 N-terminal amino acid residues but not more than the first 59 N-terminal amino acid residues of FIG. 26A (SEQ ID NO:11). Alternatively, the deletion will include at least the first 53 N-terminal amino acid residues but not more than the first 59 N-terminal amino acid residues of FIG. 26A (SEQ ID NO:11). Alternatively, the deletion will include at least the first 45 N-terminal amino acid residues but not more than the first 53 N-terminal amino acid residues of FIG. 26A (SEQ ID NO:11).

M-CIF Variants. In order to improve or alter the characteristics of the M-CIF polypeptide(s), protein engineering may be employed. Recombinant DNA technology known to those skilled in the art can be used to create novel proteins. Muteins and deletions or fusion proteins can show, e g., enhanced activity or increased stability. In addition, they could be purified in higher yields and show better solubility at least under certain purification and storage conditions. Set below are examples of mutations that can be constructed.

M-CIF Amino terminal and carboxyterminal deletions: Interferon gamma shows up to ten times higher activities by deleting 8-10 amino acid residues from the carboxy terminus of the protein (Döbeli et al., J. of Biotechnology 7:199-216 (1988) Ron et al., J. Biol. Chem., 268(4):2984-2988 (1993) reported modified KGF proteins that had heparin binding activity even if 3, 8, or 27 amino terminal amino acid residues were missing. Many other examples are known to anyone skilled in the art.

Particularly preferred variants of M-CIF polypeptides of some preferred mutations of the amino acid sequence shown in FIG. 2 (SEQ ID NO:2) are:

```
        Gly (19) --- Asn (93)

Gly (19) --- Glu (92)

Thr (20) --- Asn (93)

Thr (20) --- Glu (92)

Lys (21) --- Asn (93)

Thr (20) --- Lys (91)

Thr (22) --- Asn (93)

Thr (20) --- Lys (81)

Glu (23) --- Asn (93)

Thr (20) --- Cys (75)

Ser (24) --- Asn (93)

Lys (21) --- Glu (92)

Ser (25) --- Asn (93)
```

-continued

```
        Thr (22) --- Lys (91)

Ser (26) --- Asn (93)

Glu (23) --- Lys (91)

Arg (27) --- Asn (93)

Ser (24) --- Lys (91)

Gly (28) --- Asn (93)

Ser (25) --- Glu (92)

Pro (29) --- Asn (93)

Ser (25) --- Lys (91)

Tyr (30) --- Asn (93)

Ser (25) --- Met (90)

His (31) --- Asn (93)

Ser (25) --- Lys (88)

Pro (32) --- Asn (93)

Ser (25) --- Lys (81)

Ser (33) --- Asn (93)

Ser (25) --- Cys (75)

Glu (34) --- Asn (93)

Ser (26) --- Cys (75)
```

Thus, in one aspect, M-CIF N-terminal deletion mutants are provided by the present invention. Such mutants include those comprising an amino acid sequence shown in FIG. 2 (SEQ ID NO:2) having a deletion of at least the first 20 N-terminal amino acid residues (i.e., a deletion of at least Met (1)—Thr (20)) but not more than the first 40 N-terminal amino acid residues of FIG. 2 (SEQ ID NO:2). Alternatively, the deletion will include at least the first 20 N-terminal amino acid residues but not more than the first 33 N-terminal amino acid residues of FIG. 2 (SEQ ED NO:2). Alternatively, the deletion will include at least the first 23 N-terminal amino acid residues but not more than the first 33 N-terminal amino acid residues of FIG. 2 (SEQ ID NO;2). Alternatively, the deletion will include at least the first 28 N-terminal amino acid residues but not more than the first 3 3 N-terminal amino acid residues of FIG. 2 (SEQ ID NO:2).

In addition to the ranges of M-CIF N-terminal deletion mutants described above, the present invention is also directed to all combinations of the above described ranges, e.g., deletions of at least the first 20 N-terminal amino acid residues but not more than the first 28 N-terminal amino acid residues of FIG. 2 (SEQ ID NO:2); deletions of at least the first 20 N-terminal amino acid residues but not more than the first 23 N-terminal amino acid residues of FIG. 2 (SEQ ID NO:2); and deletions of at least the first 28 N-terminal amino acid residues but not more than the first 33 N-terminal amino acid residues of FIG. 2 (SEQ ID NO:2).

In another aspect, M-CIF C-terminal deletion mutants are provided by the present invention. Preferably, the N-terminal amino acid residue of said M-CIF C-terminal deletion mutants is amino acid residue 1 (Met) or 20 (Thr) of FIG. 2 (SEQ ID NO:2). Such mutants include those comprising an amino acid sequence shown in FIG. 2 (SEQ ID NO:2) except for a deletion of at least the last C-terminal amino acid residue (Asn (93)) but not more than the last 25 C-terminal amino acid residues (e.g., a deletion of amino acid residues Lys (69)—Mn (93)) of FIG. 2 (SEQ ID NO:2). Alternatively, the deletion will include at least the last C-terminal amino acid residue but not more than the last 18 C-terminal amino acid residues of FIG. 2 (SEQ ID NO:2). Alternatively, the deletion will include at least the last 3 C-terminal amino acid residues but not more than the last 18 C-terminal amino acid residues of FIG. 2 (SEQ ID NO:2). Alternatively, the deletion will include at least the last 5 C-terminal amino acid residues but not more than the last 18 C-terminal amino acid residues of FIG. 2 (SEQ ID NO 2). Alternatively, the deletion will include at least the last 12 C-terminal amino acid residues but not more than the last 18 C-terminal amino acid residues of FIG. 2 (SEQ ID NO:2). Alternatively, the deletion will include at least the last 5 C-terminal amino acid residues but not more than the last 12 C-terminal amino acid residues of FIG. 2 (SEQ ID NO:2).

In yet another aspect, also included by the present invention are M-CIF deletion mutants having amino acids deleted from both the N-terminal and C-terminal residues. Such mutants include all combinations of the N-terminal deletion mutants and C-terminal deletion mutants described above. Such mutants include those comprising an amino acid sequence shown in FIG. 2 (SEQ ID NO:2) having a deletion of at least the first 20 N-terminal amino acid residues but not more than the first 33 N-terminal amino acid residues of FIG. 2 (SEQ ID NO:2) and a deletion of at least the last C-terminal amino acid residue but not more than the last 18 C-terminal amino acid residues of FIG. 2 (SEQ ID NO:2) Alternatively, a deletion can include at least the first 23 or 28 N-terminal amino acids but not more than the first 33 N-terminal amino acid residues of FIG. 2 (SEQ ID NO:2) and a deletion of at least the last 3, 5, or 12 C-terminal amino acid residues but not more than the last 18 C-terminal amino acid residues of FIG. 2 (SEQ ID NO:2). Further included are all combinations of the above described ranges.

An M-CIF polypeptide can contain one or several amino acid substitutions, deletions or additions, either from natural mutation or human manipulation. Examples of some preferred mutations of the amino acid sequence shown in FIG. 2 (SEQ ID NO:2) are:

Gly (19) Met
Thr (20) Ala
Lys (21) Asn
Glu (23) Gln
Ser (24) Ala
Ser (24) Met
Ser (25) Ala
Ser (25) Gly
Glu (34) Gln
Lys (43) Ala
Asp (51) Ala
Asp (51) Gly
Asp (51) Ser
Asp (51) Thr
Asp (51) Met
Lys (81) Asn
Lys (81) Ala
Lys (88) Asn
Lys (88) Ala
Lys (91) Ala
Pro (32) Glu
Set (33) Leu
Glu (34) Arg

The polypeptides of the present invention are preferably provided in an isolated form, and preferably are substantially purified. A recombinantly produced version of the MPIF-1, M-CIF or MIP-4 polypeptide can be substantially purified by the one-step method described in Smith and Johnson, *Gene* 67:31-40 (1988).

The polypeptides of the present invention include the polypeptide encoded by the deposited cDNA including the leader, the mature polypeptide encoded by the deposited the cDNA minus the leader (Le., the mature protein), the polypeptide of FIG. 1 (SEQ ID NO:4), FIG. 2 (SEQ ID NO:2) or FIG. 3 (SEQ ID NO:6) including the leader, the polypeptide of FIG. 1 (SEQ ID NO:4), FIG. 2 (SEQ ID NO:2) or FIG. 3 (SEQ ID NO:6) including the leader but minus the N-terminal methionine residue, the polypeptide of FIG. 1 (SEQ ID NO:4), FIG. 2 (SEQ ID NO:2) or FIG. 3 (SEQ ID NO:6) minus the leader, as well as polypeptides which have at least 95% similarity, and still more preferably at least 96%, 97%, 98% or 99% similarity to those described above. Further polypeptides of the present invention include polypeptides at least 95% identical, still more preferably at least 96%, 97%, 98% or 99% indentical to the polypeptide encoded by the deposited cDNA, to the polypeptide of FIG. 1 (SEQ ID NO:4), FIG. 2 (SEQ ID NO:2) or FIG. 3 (SEQ ID NO:6) and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (*Advances in Applied Mathematics* 2:482-489, 1981) to find the best segment of similarity between two sequences.

By a polypeptide having an amino acid sequence at least, for example, 95% "identical" to a reference amino acid sequence of an MPIF-1, M-CIF or MIP-4 polypeptide is intended that the amino acid sequence of the polypeptide is identical to the reference sequence except that the polypeptide sequence may include up to five amino acid alterations per each 100 amino acids of the reference amino acid of the MPIF-1, M-CIF or MIP-4 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% indentical to, for instance, the amino acid sequence shown in FIG. 1 (SEQ ID NO:4), FIG. 2 (SEQ ID NO:2) or FIG. 3 (SEQ ID NO:6) or to the amino acid sequence encoded by deposited cDNA clones can be determined conventionally using known computer programs such the Besrfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set of course, such, that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polygonal and monoclonal antibodies, which are useful in assays for detecting MPIF-1, M-CIF or MIP-4 protein expression as described below or as agonists and antagonists capable of enhancing or inhibiting MPIF-1, M-CIF or MIP-4 protein function. Further, such polypeptides can be used in the yeast two-hybrid system to "capture" MPIF-1, M-CIF or MIP-4 protein binding proteins which are also candidate agonist and antagonist according to the present invention. The yeast two hybrid system is described in Fields and Song, *Nature* 340:245-246 (1989).

MPIF-1, M-CIF and MIP-4 Epitope-Bearing Polypeptides. In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998-4002 (1983).

As to the selection of peptides or polypeptides bearing an antigenic epitope (i e., that contain a region of a protein molecule to which an antibody can bind), it is well known in that art that relatively short synthetic peptides that mimic part of a protein sequence are routinely capable of eliciting an antiserum that reacts with the partially mimicked protein. See, e.g., Sutcliffe, J. G., Shinnick, T. M., Green, N. and Learner, R. A., *Science* 219:660-666 (1983).

Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to he mimicked protein, longer, peptides, especially those containing proline residues, usually are effective, Sutcliffe et al., supra, at 661. For instance, 18 of 20 peptides designed according to these guidelines, containing 8-39 residues covering 75% of the sequence of the influenza virus hemagglutinin HA1 polypeptide chain, induced antibodies that reacted with the HA1 protein or intact virus; and 12/12 peptides from MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g. about 9 amino acids) can bind and displace the larger peptides in immunoprecipitation assays. See, for instance, Wilson et at., *Cell* 37:767-778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred Non-limiting examples of antigenic polypeptides or peptides that can be used to generate MPIF-1-specific antibodies include: a polypeptide comprising amino acid residues from about 21 to about 30 in SEQ ID NO:4; a polypeptide comprising amino acid residues from about 31 to about 44 in SEQ ID NO:4; a polypeptide comprising amino acid residues from about 49 to about 55 in SEQ ID NO:4; a polypeptide comprising amino acid residues from about 59 to about 67 in SEQ ID NO:4; a polypeptide comprising amino acid residues from about 72 to about 83 in SEQ ID NO:4; a polypeptide comprising amino acid residues from about 86 to about 103 in SEQ ID NO:4; a polypeptide comprising amino acid residues from about 110 to about 120 in SEQ ID NO:4. As indicated above, the inventors have determined that the above polypeptide fragments are antigenic regions of the MPIF-1 protein.

Non-limiting examples of antigenic polypeptides or peptides that can be used to generate M-CIF-specific antibodies include: a polypeptide comprising amino acid residues from about 20 to about 36 in SEQ ID NO:2; a polypeptide comprising amino acid residues from about 42 to about 52 in SEQ ID NO:2; a polypeptide comprising amino acid residues from about 52 to about 64 in SEQ ID NO:2; a polypeptide comprising amino acid residues from about 67 to about 75 in SEQ ID NO:2; a polypeptide comprising amino acid residues from about 75 to about 84 in SEQ ID NO:2; and a polypeptide comprising amino acid residues from about 86 to about 93 in SEQ ID NO:2. As indicated above, the inventors have determined that the above polypeptide fragments are antigenic regions of the M-CIF protein.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10-20 mg of 248 different 13 residue peptides representing single amino acid variants of a segment of the HA1 polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131-5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500-1000 or more syntheses to be conducted simultaneously. Houghten et al., supra, at 5134.

Preferred nucleic acid fragments of the present invention include nucleic acid molecules encoding epitope-bearing portions of the MPIF-1, M-CIF or MIP-4 protein. In particular, such nucleic acid fragments of the MPIF-1 of the present invention include nucleic acid molecules encoding: a polypeptide comprising amino acid residues from about 21 to about 30 in SEQ ID NO:4; a polypeptide comprising amino acid residues from about 31 to about 44 in SEQ ID NO:4; a polypeptide comprising amino acid residues from about 49 to about 55 in SEQ ID NO:4; a polypeptide comprising amino acid residues from about 59 to about 67 in SEQ ID NO:4; a polypeptide comprising amino acid residues from about 72 to about 83 in SEQ ID NO:4; a polypeptide comprising amino acid residues from about 86 to about 103 in SEQ ID NO:4; a polypeptide comprising amino acid residues from about 110 to about 120 in SEQ ID NO:4, or any range or value therein.

In particular, such nucleic acid fragments of the M-CIF of the present invention include nucleic acid molecules encoding: a polypeptide comprising amino acid residues from about 20 to about 36 in SEQ ID NO:2; a polypeptide comprising amino acid residues from about 42 to about 52 in SEQ ID NO:2; a polypeptide comprising amino acid residues from about 52 to about 64 in SEQ ID NO:2; a polypeptide comprising amino acid residues from about 67 to about 75 in SEQ ID NO:2; a polypeptide comprising amino acid residues from about 75 to about 84 in SEQ ID NO:2; and a polypeptide comprising amino acid residues from about 86 to about 93 in SEQ ID NO:2, or any range or value therein.

The inventors have determined that the above polypeptide fragments are antigenic regions of the MPIF-1 and M-CIF proteins. Methods for determining other such epitope-bearing portions of the MPIF-1, M-CIF or MIP-4 protein are described in detail below.

Epitope-bearing peptides and polypeptides of the invention are used to induce antibodies according to methods well known in the art, See, for instance, Sutcliffe et al., supra; Wilson et al., supra; Chow, M. et al., *Proc. Natl. Acad Sci.* *USA* 82:910-914; and Bittle, F. J. et al, *J. Gen. Virol* 66:2347-2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 g peptide or carrier protein and Freund's adjuvant. Several booster injections may be needed, for instance, at intervals of about two weeks, to provide a useful titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$-$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The entire disclosure of each document cited in this section on "Polypeptides and Peptides" is hereby incorporated herein by reference.

As one of skill in the art will appreciate, MPIF-1, M-CIF or MIP-4 polypeptides of the present invention and the epitope-bearing, fragments thereof described above can be combined with parts of the constant domain of immunoglobulins (IgG), resulting in chimeric polypeptides. These fusion proteins facilitate purification and show an increased half-life in vivo. This has been shown, e.g. for chimeric proteins consisting of the first two domains of the human CD4-polypeptide and various domains of the constant regions of the heavy or light chains of mammalian immunoglobulins (EPA 394,827; Traunecker et al., Nature 331: 84-86 (1988)). Fusion proteins that have a disulfide-linked dimeric structure due to the IgG part can also be more efficient in binding and neutralizing other molecules than the monomeric MPIF-1, M-CIF or MIP-4 protein or protein fragment alone (Fountoulakis et al., J Biochem 270:3958-3964 (1995)).

Polypeptide Purification and Isolation. MPIF-1, MIP-4 and M-CIF are recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention can be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention can be glycosylated with mammalian or other eukaryotic carbohydrates or can be non-glycosylated. Polypeptides of the invention can also include an initial methionine amino acid residue.

Antibodies. MPIF-1, M-CIF or MIP-4-protein specific antibodies for use in the present invention can be raised against the intact MPIF-1, M-CIF or MIP-4 protein or an antigenic polypeptide fragment thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')$_2$ fragments) which are capable of specifically binding to MPIF-1, M-CIF or MIP-4 protein. Fab and F(ab')$_2$ fragments lack the Fc fragment of intact antibody, clear more rapidly from the circulation, and may have less non-specific tissue binding of an intact antibody (Wahl et al., J. Nucl. Med. 24:316-325 (1983)). Thus, these fragments are preferred.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain and humanized antibodies, as well as Fab fragments, or the product of an Fab expression library. Various procedures known in the art can be used for the production of such antibodies and fragments.

Antibodies generated against the polypeptides corresponding to a sequence of the present invention or its in vivo receptor can be obtained by direct injection of the polypeptides into an animal or by administering the polypeptides to an animal, preferably a nonhuman. The antibody so obtained will then bind the polypeptides itself, In this manner, even a sequence encoding only a fragment of the polypeptides can be used to generate antibodies binding the whole native polypeptides. Such antibodies can then be used to isolate the polypeptides from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495-497), the trioma technique, the human B-cell hybridoma technique (Kozbor et al., 1983, Immunology Today 4;72), and the EBV-hybridoma technique to produce human monoclonal antibodies (Cole, et al., 1985, in Monocolonal Antibodies and Cancer Therapy, Alan R. Liss, Inc. pp. 77-96).

Techniques described for the production of single chain antibodies (U.S. Pat. 4,946,778) can be adapted to produce single chain antibodies to immunogenic polypeptides products of this invention.

The antibodies of the present invention may be prepared by any of a variety of methods. For example, cells expressing the MPIF-1, M-CIF or MIP-4 protein or an antigenic fragment thereof can be administered to an animal in order to induce the production of sera containing polyclonal antibodies. In a preferred method, a preparation of MPIF-1, M-CIF or MIP-4 protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or MPIF-1, M-CIF or MIP-4 protein binding fragments thereof). Such monoclonal antibodies can be prepared using hybridoma technology (Kohler et al., Nature 256:495 (1975); Kohler et al., Eur. J. Immunol. 6:511 (1976); Kohler et al., Eur. J. Immunol. 6:292 (1976); Hammerling et al., In: Monoclonal Antibodies and T-Cell Hybridomas, Elsevier, N.Y., (1981) pp. 563-681). In general, such procedures involve immunizing an animal (preferably a mouse) with an MPIF-1, M-CIF or MIP-4 protein antigen or, more preferably, with an MPIF-1, M-CIF or MIP-4 protein-expressing cell. Suitable cells can be recognized by their capacity to bind anti-MPIF-1, M-CIF or MIP-4 protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 g/ml of streptomycin. The splenocytes of such mice are extracted and fused with a suitable myeloma cell line. Any suitable myeloma cell line may be employed in accordance with the present invention; however, it is preferable to employ the parent myeloma cell line (SP2O), available from the American Type Culture Collection, 10801 University Boulevard, Manassas, Va. 20110-2209, USA (present address). After fusion, the resulting hybridoma cells are selectively maintained in HAT medium, and then cloned by limiting dilution as described by Wands et al. (Gastroenterology 80:225-232 (1981)), The hybridoma cells obtained through such a selection are then assayed to identify clones which secrete antibodies capable of binding the MPIF-1, M-CIF or MIP-4 protein antigen.

Alternatively, additional antibodies capable of binding to the MPIF-1, M-CIF or MIP-4 protein antigen may be produced in a two-step procedure through the use of anti-idiotypic antibodies. Such a method makes use of the fact that antibodies are themselves antigens, and that, therefore, it is possible to obtain an antibody which binds to a second antibody, In accordance with this method, MPIF-1, M-CIF or MIP-4-protein specific antibodies are used to immunize an animal, preferably a mouse. The splenocytes of such an animal are then used to produce hybridoma cells, and the hybridoma cells are screened to identify clones which produce an antibody whose ability to bind to the MPIF-1, M-CIF or MIP-4 protein-specific antibody can be blocked by the MPIF-1, M-CIF or MIP-4 protein antigen. Such antibodies comprise anti-idiotypic antibodies to the MPIF-1, M-CIF, or MIP-4 protein-specific antibody and can be used to immunize an animal to induce formation of further MPIF-1, M-CIF or MIP-4 protein-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, MPIF-1, M-CIF or MIP-4 protein-binding fragments can be produced through the application of recombinant DNA technology or through synthetic chemistry.

It may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *Bio-Techniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984), Neuberger et al., *Nature* 314:268 (1985).

Further suitable labels for the MPIF-1, M-CIF or MIP-4 protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging (Perkins el al., *Eur. J. Nucl. Med.* 10:296-301 (1985); Carasquillo et al., *J. Nucl. Med.* 28:281-287 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldelhyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al., *Clin. Chim. Acta* 70:1-31 (1976), and Schurs et al., *Clin. Chim. Acta* 81:140 (1977). Coupling techniques mentioned in the latter are the glutaraldehyde method, the periodate method, the dimaleimide method, the m-maleimidobenzyl-N-hydroxy-succinimide ester method, all of which methods are incorporated by reference herein.

Chromosome Assays. The nucleic acid molecules of the present invention are also valuable for chromosome identification. The sequence is specifically targeted to and can hybridize with a particular location on an individual human chromosome, Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of an MPIF-1, M-CIF or MIP-4 protein gene. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error may be necessary to identify a genomic probe that gives a good in situ hybridization signal.

Briefly, sequences can be mapped to chromosomes by preparing PCR primers (preferably 15-25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of portions from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Venna et al., *Human Chromosomes: A Manual Of Basic Techniques*, Pergamon Press, New York (1998).

Once a sequence has been mapped to a precise chromosomal location, the physical position of the sequence on the chromosome can he correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. This assumes 1 megabase mapping resolution and one gene per 20 kb.

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The present invention is further directed to inhibiting MPIF-1, MIP-4 and M-CIF in vivo by the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of MPIF-1, MIP-4 and M-CIF. The antisense RNA oligonucleotide hybridizes to the mRNA in vivo and blocks translation of the mRNA molecule into the MPIF-1, MIP-4 and M-CIF (antisense—Okano, J. Neurochem., 56:560 (1991); Oligodeoxynucleotides as Antisense Inhibitors of Gene Expression, CRC Press, Boca Raton, Fla. (1988)).

Alternatively, the oligonucleotides described above can be delivered to cells by procedures in the art such that the antisense RNA or DNA can be expressed in vivo to inhibit production of MPIF-1, MIP-4 and M-CIF in the manner described above.

Accordingly, antisense constructs to the MPIF-1, MIP-4 and M-CIF can be used to treat disorders which are either MPIF-1-, MIP-4- and/or M-CIF-induced or enhanced, for example, atherosclerosis, auto-immune, e.g. multiple sclerosis and insulin-dependent diabetes, and chronic inflammatory and infective diseases, histamine-mediated allergic reactions, rheumatoid arthritis, silicosis, sarcoidosis, idiopathic pulmonary fibrosis and other chronic inflammatory diseases of the lung, idiopathic hyper-eosinophilic syndrome, endotoxic shock, histamine-mediated allergic reactions, prostaglandin-independent fever, and a plastic anemia and other cases of bone marrow failure.

Antagonists, Agonists and Methods. This invention further provides methods for screening compounds to identify agonists and antagonists to the chemokine polypeptides of the present invention. An agonist is a compound which has similar biological functions, or enhances the functions, of the polypeptides, while antagonists block such functions. Chemotaxis may be assayed by placing cells, which are chemoattracted by either of the polypeptides of the present invention, on top of a filter with pores of sufficient diameter to admit the cells (about 5 µm). Solutions of potential agonists are place in the bottom of the chamber with an appropriate control medium in the upper compartment, and thus a concentration gradient of the agonist is measured by counting cells that migrate into or through the porous membrane over time.

When assaying for antagonists, the chemokine polypeptides of the present invention are placed in the bottom chamber and the potential antagonist is added to determine if chemotaxis of the cells is prevented.

Alternatively, a mammalian cell or membrane preparation expressing the receptors of the polypeptides would be incubated with a labeled chemokine polypeptide, e.g. radioactivity, in the presence of the compound. The ability of the compound to block this interaction could then be measured. When assaying for agonists in this fashion, the chemokines would be absent and the ability of the agonist itself to interact with the receptor could be measured.

Examples of potential MPIF-1, MIP-4 and M-CIF antagonists include antibodies, or in some cases, oligonucleotides, which bind to the polypeptides. Another example of a potential antagonist is a negative dominant mutant of the polypeptides. Negative dominant mutants are polypeptides which bind to the receptor of the wild-type polypeptide, but fail to retain biological activity.

Antisense constructs prepared using antisense technology are also potential antagonists. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple-helix, see Lee et al., *Nucl. Acids Res.* 6:3073 (1979); Cooney et al, *Science* 241:456 (1988); and Dervan et al., *Science* 251: 1360 (1991)), thereby preventing transcription and the production of the chemokine polypeptides. The antisense RNA oligonucleotide hybridizes to the mRNA in vivo and blocks translation of the mRNA molecule into the polypeptides (antisense—Okano, *J. eurochem*. 56:560 (1991); oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the chemokine polypeptides.

Another potential chemokine antagonist is a peptide derivative of the polypeptides which are naturally or synthetically modified analogs of the polypeptides that have lost biological function yet still recognize and bind to the receptors of the polypeptides to thereby effectively block the receptors. Examples of peptide derivatives include, but are not limited to, small peptides or peptide-like molecules.

The antagonists may be employed to treat disorders which are either MPIF-1-, MIP-4- and M-CIF-induced or enhanced, for example, auto-immune and chronic inflammatory and infective diseases. Examples of auto-immune diseases include multiple sclerosis, and insulin-dependent diabetes.

The antagonists may also be employed to treat infectious diseases including silicosis, sarcoidosis, idiopathic pulmonary fibrosis by preventing the recruitment and activation of mononuclear phagocytes. They may also be employed to treat idiopathic hyper-eosinophilic syndrome by preventing eosinophil production and migration. Endotoxic shock may also be treated by the antagonists by preventing the migration of macrophages and their production of the chemokine polypeptides of the present invention.

The antagonists may also be employed for treating atherosclerosis, by preventing monocyte infiltration in the artery wall.

The antagonists may also be employed to treat histamine mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated.

The antagonists may also be employed to treat chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung.

Antagonists may also be employed to treat rheumatoid arthritis by preventing the attraction of monocytes into synovial fluid in the joints of patients. Monocyte influx and activation plays a significant role in the pathogenesis of both degenerative and inflammatory anthropathies.

The antagonists may be employed to interfere with the deleterious cascades attributed primarily to IL-1 and TNF, which prevents the biosynthesis of other inflammatory cytokines. In this way, the antagonists may be employed to prevent inflammation. The antagonists may also be employed to inhibit prostaglandin-independent fever induced by chemokines.

The antagonists may also be employed to treat cases of bone marrow failure, for example, aplastic anemia and myelodysplastic syndrome.

The antagonists may also be employed to treat asthma and allergy by preventing eosinophil accumulation in the lung. The antagonists may also be employed to treat subepitlelial basement membrane fibrosis which is a prominent feature of the asthmatic lung.

Agonists. M-CIF, MPIF-1 and/or MIP-4 agonists include any small molecule that has an activity similar to any one or more of these polypeptides, as described herein. For example, MPIF-1 agonists can be used to enhance MPIF-1 activity. For example, to enhance MPIF-1 induced myeloprotection in patients undergoing chemotherapy or bone marrow transplantation. As another example, M-CIF agonists can provide one or more of antiinflammatory activity, anti-TNFα activity, and the like, as described herein for various functional activities of M-CIF.

Disease Diagnosis and Prognosis. Certain diseases or disorders, as discussed below, may be associated with enhanced levels of the MPIF-1, M-CIF or MIP-4 protein and mRNA encoding the MPIF-1, M-CIF or MIP-4 protein when compared to a corresponding "standard" mammal, i.e., a mammal of the same species not having the disease or disorder. Further, it is believed that enhanced levels of the MPIF-1, M-CIF or MIP-4 protein can be detected in certain body fluids (e.g. sera, plasma, urine, and spinal fluid) from mammals with a disease or disorder when compared to sera from mammals of the same species not having the disease or disorder, Thus, the invention provides a diagnostic method, which involves assaying the expression level of the gene encoding the MPIF-1, M-CIF or MIP-4 protein in mammalian cells or body fluid and comparing the gene expression level with a standard MPIF-1, M-CIF or MIP-4 gene expression level, whereby an increase in the gene expression level over the standard is indicative of certain diseases or disorders.

Where a disease or disorder diagnosis has already been made according to conventional methods, the present invention is useful as a prognostic indicator, whereby patients exhibiting enhanced MPIF-1, M-CIF or MIP-4 gene expression will experience a worse clinical outcome relative to patients expressing the gene at a lower level.

By "assaying the expression level of the gene encoding the MPIF-1, M-CIF or MIP-4 protein" is intended qualitatively or quantitatively measuring or estimating the level of the MPIF-1, M-CIF or MIP-4 protein or the level of the mRNA encoding the MPIF-1, M-CIF or MIP-4 protein in a first biological sample either directly (e.g. by determining or estimating absolute protein level or mRNA level) or relatively (e.g. by comparing to the MPIF-1, M-CIF or MIP-4 protein level or mRNA level in a second biological sample).

Preferably, the MPIF-1, M-CIF or MIP-4 protein level or mRNA level in the first biological sample is measured or estimated and compared to a standard MPIF-1, M-CIF or MIP-4 protein level or mRNA level, the standard being taken from a second biological sample obtained from an individual not having the disease or disorder. As will be appreciated in the art, once a standard MPIF-1, M-CIF or MIP-4 protein level or mRNA level is known, it can be used repeatedly as a standard for comparison.

By "biological sample" is intended any biological sample obtained from an individual, cell line, tissue culture, or other source which contains MPIF-1, M-CIF or MIP-4 protein or mRNA. Biological samples include mammalian body fluids (such as sera, plasma, urine, synovial fluid and spinal fluid) which contain secreted mature MPIF-1, M-CIF or MIP-4 protein, and ovarian, prostate, heart, placenta, pancreas, ascites, muscle, skin, glandular, kidney, liver, spleen, lung, bone, bone marrow, ocular, peripheral nervous, central nervous, breast and umbilical tissue. Methods for obtaining tissue biopsies and body fluids from mammals are well known in the art. Where the biological sample is to include mRNA, a tissue biopsy is the preferred source.

The present invention is useful for detecting disease in mammals. In particular the invention is useful during useful for diagnosis or treatment of various immune system-related disorders in mammals, preferably humans. Such disorders include tumors, cancers, and any disregulation of immune cell function including, but not limited to, autoimmunity, arthritis, leukemias, lymphomas, immunosuppression, sepsis, wound healing, acute and chronic infection, cell mediated immunity, humoral immunity, inflammatory bowel disease, myclosuppression, and the like. Preferred mammals include monkeys, apes, cats, dogs, cows, pigs, horses, rabbits and humans. Particularly preferred are humans.

Total cellular RNA can be isolated from a biological sample using any suitable technique such as the single-step guanidinium-thiocyanate-phenol-chloroform method described in Chomczynski and Sacchi, *Anal Biochem*. 162: 156-159 (1987). Levels of mRNA encoding the MPIF-1, M-CIF or MIP-4 protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., *Cell* 63:303-312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. MPIF-1, M-CIF or MIP-4 protein cDNA labeled according to any appropriate method (such as the $^{32}$P-multiprimed DNA labeling system (Amersham)) is used as probe. After hybridization overnight the filter is washed and exposed to x-ray film. cDNA for use as probe according to the present invention is described in the sections above and will preferably at least 15 bp in length.

S1 mapping can be performed as described in Fujita et al., *Cell* 49:357-367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the MPIF-1, M-CIF or MIP-4 protein). Northern blot analysis can be performed as described above.

Preferably, levels of mRNA encoding the MPIF-1, M-CIF or MIP-4 protein are assayed using the RT-PCR method described in Makino et al, *Technique* 2:295-301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers, Alternatively, rather than labeling the primers, a labeled dNTP can be included in the PCR reaction mixture. PCR amplification can be performed ill a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the MPIF-1, M-CIF or MIP-4 protein)) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying MPIF-1, M-CIF or MIP-4 protein levels in a biological sample can occur using any art known method. Preferred for assaying MPIF-1, M-CIF or MIP-4 protein levels in a biological sample are antibody-based techniques. For example, MPIF-1, M-CIF or MIP-4 protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g. with urea and neutral detergent, for the liberation of MPIF-1, M-CIF or MIP-4 protein for Western-blot or dot/slot assay (Jalkanen, M., et al., *J. Cell. Biol.* 101:976-985 (1985), Jalkanen, M., et al. *J. Cell. Biol.* 105:3087-3096 (1987)). In this technique, which is based on the use of cationic solid phases quantitation of MPIF-1, M-CIF or MIP-4 protein can be accomplished using isolated MPIF-1, M-CIF or MIP-4 protein as a standard. This technique can also be applied to body fluids. With these samples, a molar concentration of MPIF-1, M-CIF or MIP-4 protein will aid to set standard values of MPIF-1, M-CIF or MIP-4 protein content for different body fluids, like serum, plasma, urine, spinal fluid, etc. The normal appearance of MPIF-1, M-CIF or MIP-4 protein amounts can then be set using values from healthy individuals, which can be compared to those obtained from a test subject.

Other antibody-based methods useful for detecting MPIF-1, M-CIF or MIP-4 protein gene expression include immunoassays, such as the enzyme linked immunosorbent assay (ELISA) and the radioimmunoassay (RIA). For example, an MPIF-1, M-CIF or MIP-4 protein-specific monoclonal antibodies can be used both as an immunoabsorbent and as an enzyme-labeled probe to detect and quantify the MPIF-1, M-CIF or MIP-4 protein. The amount of MPIF-1, M-CIF or MIP-4 protein present in the sample can be calculated by reference to the amount present in a standard preparation using a linear regression computer algorithm. In another ELISA assay, two distinct specific monoclonal antibodies can be used to detect MPIF-1, M-CIF or MIP-4 protein in a body fluid. In this assay, one of the antibodies is used as the immunoabsorbent and the other as the enzyme-labeled probe.

The above techniques may be conducted essentially as a "one-step" or "two-step" assay. The "one-step" assay involves contacting MPIF-1, M-CIF or MIP-4 protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

The polypeptides of the present invention, and polynucleotides encoding such polypeptides, may be employed as research reagents for in vitro purposes related to scientific research, synthesis of DNA and manufacture of DNA vectors, and for the purpose of developing therapeutics and diagnostics for the treatment of human disease. For example, M-CIF and MPIF-1 may be employed for the expansion of immature hematopoietic progenitor cells, for example, granulocytes, macrophages or monocytes, by temporarily preventing their differentiation. These bone marrow cells may be cultured in vitro.

Fragments of the full length MPIF-1, MIP-4 or M-CIF genes may be used as a hybridization probe for a cDNA library to isolate the full length gene and to isolate other genes which have a high sequence similarity to the gene or similar biological activity. Preferably, however, the probes have at least 30 bases and may contain, for example, 50 or more bases. The probe may also be used to identify a cDNA clone corresponding to a full length transcript and a genomic clone or clones that contain the complete genes including regulatory and promoter regions, exons, and introns. An example of a screen comprises isolating the coding region of the genes by using the known DNA sequence to synthesize an oligonucleotide probe. Labeled oligonucleotides having a sequence complementary to that of the genes of the present invention are used to screen a library of human cDNA, genomic DNA or mRNA to determine which members of the library the probe hybridizes to.

This invention is also related to the use of the MPIF-1, MIP-4 and M-CIF gene as part of a diagnostic assay for detecting diseases or susceptibility to diseases related to the presence of mutations in the nucleic acid sequences. Such diseases are related to under-expression of the chemokine polypeptides.

Individuals carrying mutations in the MPIF-1, MIP-4 and M-CIF may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature 324:163-166 (1986)) prior to analysis. RNA or cDNA may also be used for the same purpose. As an example, PCR primers complementary to the nucleic acid encoding MPIF-1, MIP-4 and M-CIF can be used to identity and analyze MPIF-1, MIP-4 and M-CIF mutations. For example, deletions and insertions can be detected by a change in size of the amplified product in comparison to the normal genotype. Point mutations can be identified by hybridizing amplified DNA to radiolabeled MPIF-1, MIP-4 and M-CIF RNA or alternatively, radiolabeled MPIF-1, MIP-4 and M-CIF antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g. Myers et al., *Science* 230:1242 (1985)).

Sequence changes at specific locations may also be revealed by nuclease protection assays, such as RNase and S1 protection or the chemical cleavage method (e.g. Cotton et al., *PNAS, USA* 85:4397-4401 (1985)).

Thus, the detection of a specific DNA sequence may be achieved by methods such as hybridization, RNase protection, chemical cleavage, direct DNA sequencing or the use of restriction enzymes, (e.g. Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of MPIF-1, MIP-4 and M-CIF protein in various tissues since an over-expression of the proteins compared to normal control tissue samples may detect the presence of a disease or susceptibility to a disease, for example, a tumor, Assays used to detect levels of MPIF-1, MIP-4 and M-CIF protein in a sample derived from a host are well-known to those of skill in the art and include radioimmunoassays, competitive-binding assays, Western Blot analysis, ELISA assays and "sandwich" assay. An ELISA assay (Coligan, et al., *Current Protocols in Immunology* 1(2), Chapter 6, (1991)) initially comprises preparing an antibody specific to the MPIF-1 MIP-4 and M-CIF antigens, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g, a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any MPIF-1, MIP-4 and M-CIF proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to MPIF-1, MIP-4 and M-CIF. Unattached reporter antibody is then washed out. Peroxidase substrates are then added to the dish and the amount of color developed in a given time period is a measurement of the amount of MPIF-1, MIP-4 and M-CIF protein present in a given volume of patient sample when compared against a standard curve.

A competition assay may be employed wherein antibodies specific to MPIF-1, MIP-4 and M-CIF are attached to a solid support and labeled MPIF-1, MIP-4 and M-CIF and a sample derived from the host are passed over the solid support and the amount of label detected, for example by liquid scintillation chromatography, can be correlated to a quantity of protein in the sample.

A "sandwich" assay is similar to an ELISA assay. In a "sandwich" assay MPIF-1, MIP-4 and M-CIF is passed over a solid support and binds to antibody attached to a solid support. A second antibody is then bound to the MPIF-1, MIP-4 and M-CIF. A third antibody which is labeled and specific to the second antibody is then passed over the solid support and binds to the second antibody and an amount can then be quantified.

This invention provides a method for identification of the receptors for the chemokitte polypeptides. The gene encoding the receptor can be identified by numerous methods known to those of skill in the art, for example, ligand panning and FACS sorting (Coligan, et al., *Current Protocols in Immun*. 1(2), Chapter 5, (1991)). Preferably, expression cloning is employed wherein polyadenylated RNA is prepared from a cell responsive to the polypeptides, and a cDNA library created from this RNA is divided into pools and used to transfect COS cells or other cells that are not responsive to the polypeptides. Transfected cells which are grown on glasss slides are exposed to the labeled polypeptides. The polypeptides can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Therapeutics. Polypeptides of the present invention can be used in a variety of immunoregulatory and inflammatory functions and also in a number of disease conditions. MPIF-1, MIP-4 and M-CIF are in the chemokine family and therefore they are a chemo-attractant for leukocytes (such as monocytes, neutrophils: T lymphocytes, eosinophils, basophils, etc.).

Northern Blot analyses show that MPIF-1, MIP-4 and M-CIF are expressed predominantly is tissues of hemopoietic origin.

Figure 19:
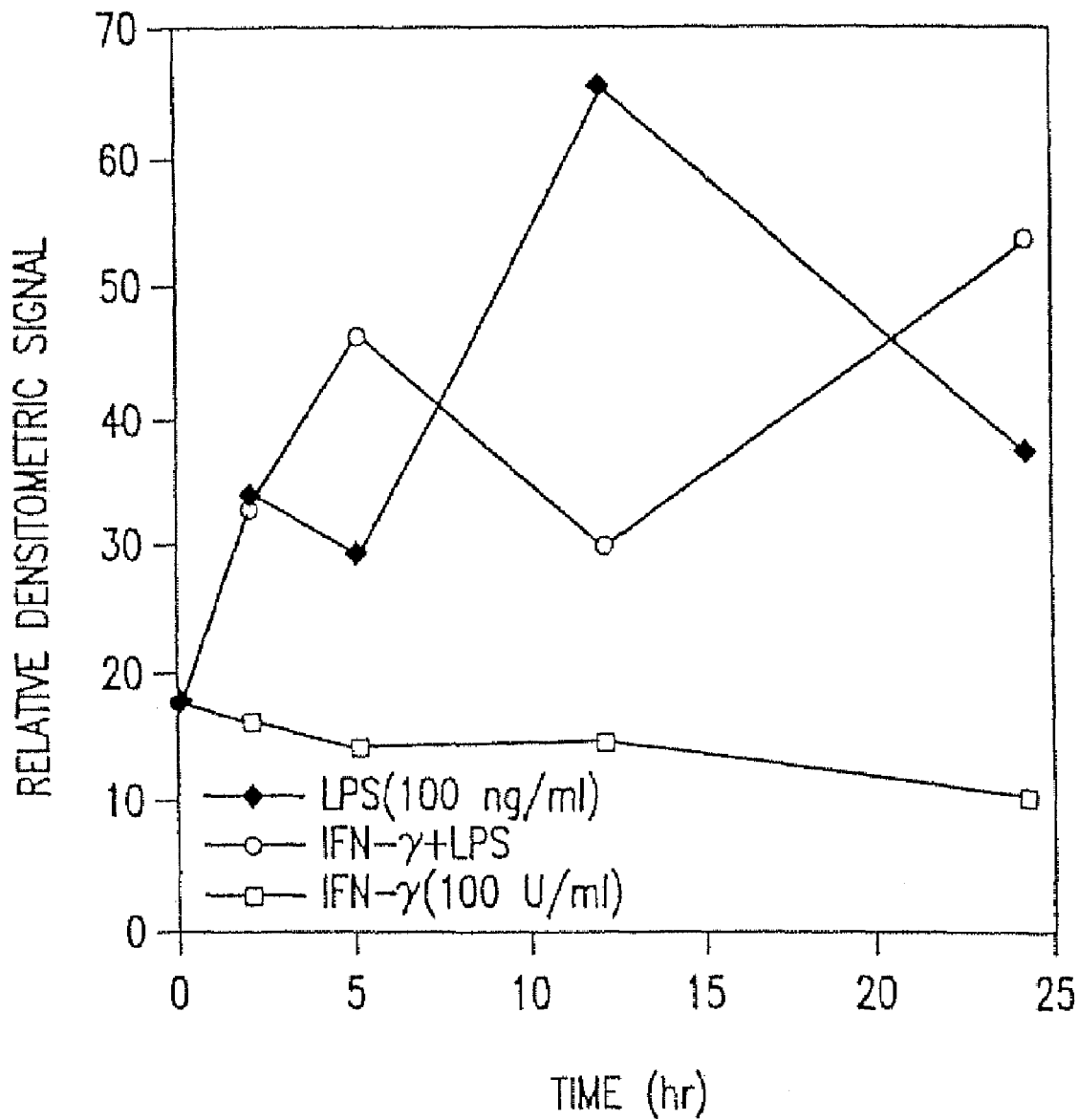
FIG. 19. Expression of RNA encoding MPIF-1 in human monocytes. Total RNA from fresh elutriated monocytes was isolated and treated with 100 U/ml hu rIFN-g, 100 ng/ml LPS, or both. RNA (8 μg) from each treatment was separated electrophoretically on a 1.2% agarose gel and transferred to a nylon membrane. MPIF-1 inRNA was quantified by probing with $^{32}$P-labeled cDNA and the bands on the resulting autoradiograph were quantified densitometrically.
Figure 20A:
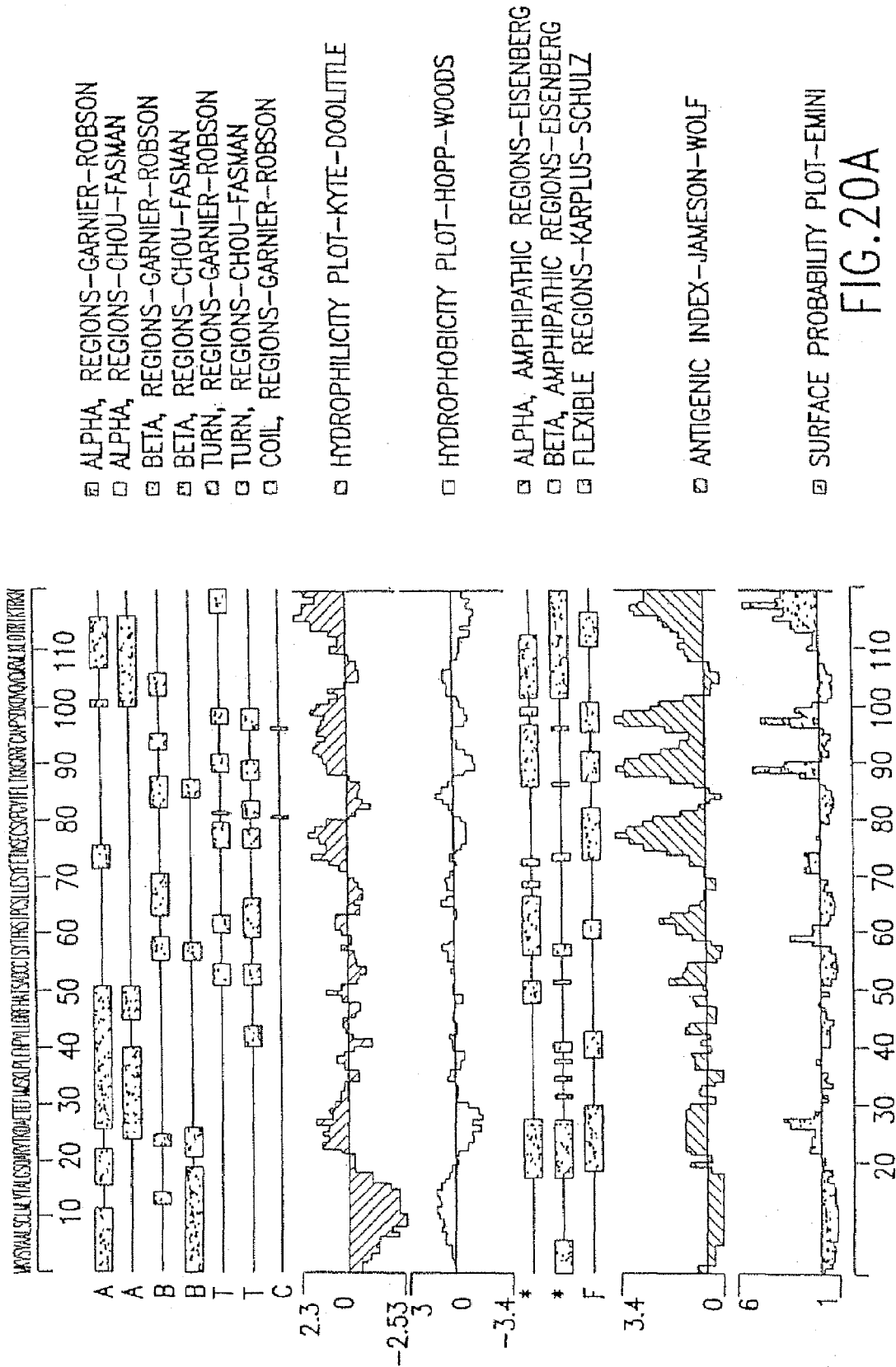
FIG. 20A-B.
Figure 20B:
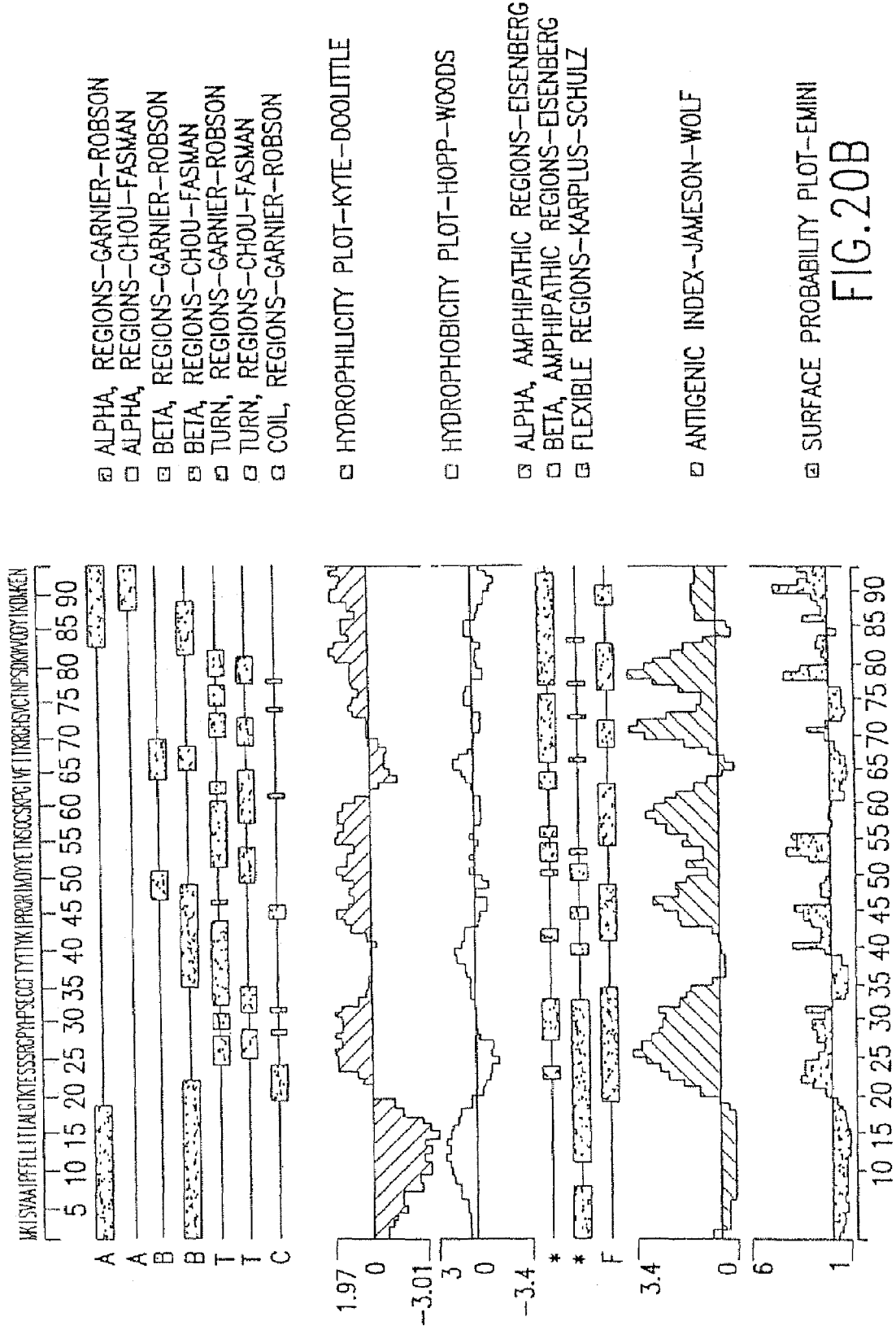

MPIF-1 Therapeutic/Diagnostic Applications. MPIF-1 is shown to play an important role in the regulation of the immune response and inflammation. In FIG. 19, it is shown that lipopolysaccharide induces the expression of MPIF-1 from human monocytes. Accordingly, in response to the presence of an endotoxin, MPIF-1 is expressed from monocytes and, therefore, administration of MPIF-1 may be employed to regulate the immune response of a host. MPIF-1 could be used as an anti-inflammatory agent.

Figure 10A:
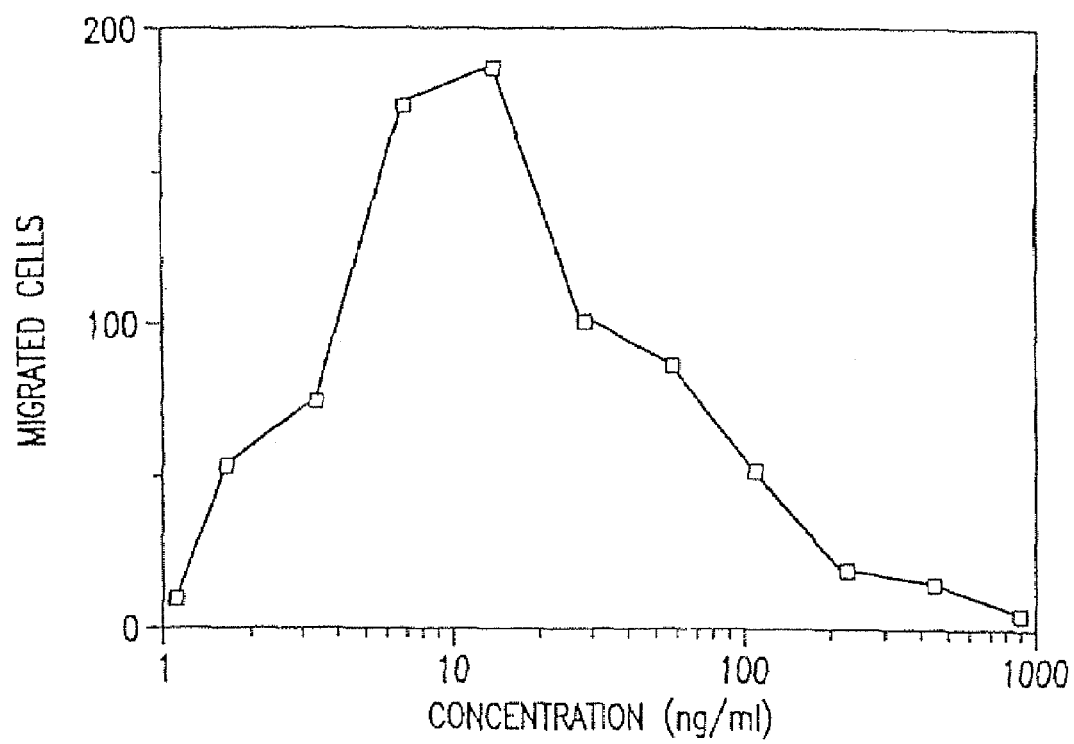
FIG. 10. The chemoattractant activity of MPIF-1 was determined with chemotaxis assays using a 48-well microchamber device (Neuro Probe, Inc.). The experimental procedure was as described in the manufacturers manual. For each concentration of MPIF-1 tested, migration in 5 high-power fields was examined. The results presented represent the average values obtained from two independent experiments. The chemoattractant activity on THP-1 (A) cells and human PBMCs (B) is shown.
Figure 10B:
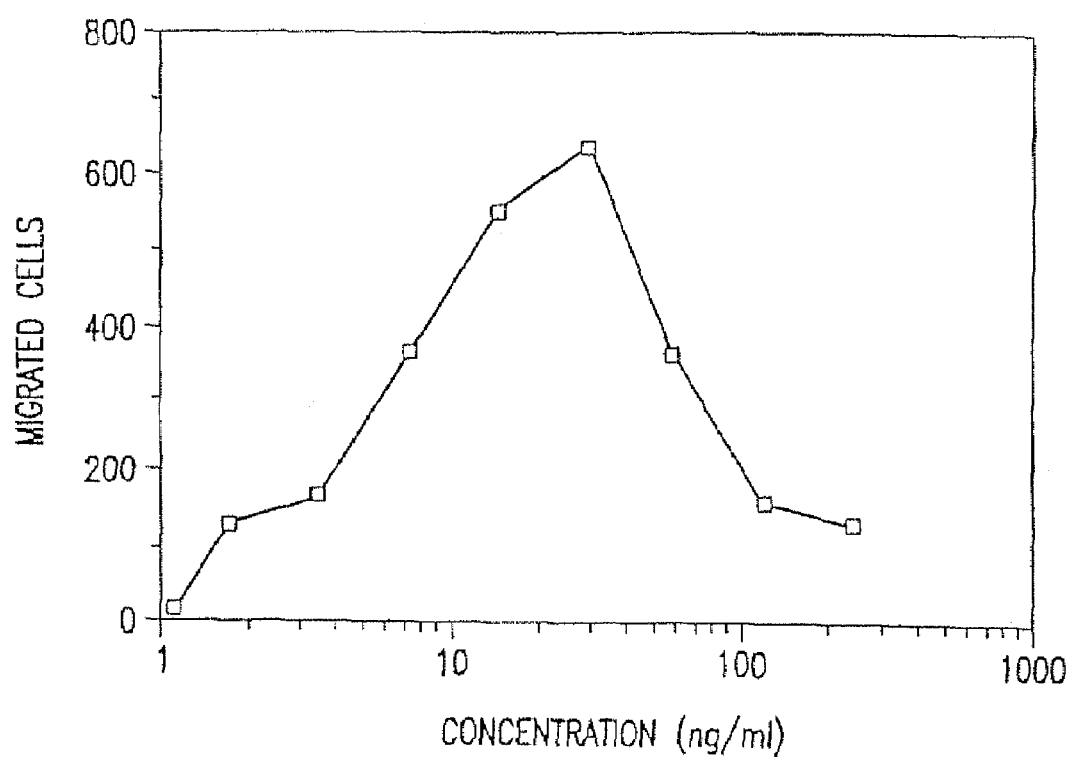

As illustrated in FIG. 10, the chemoattractant activity of MPIF-1 on THP-1 cells (A) and PBMCs (B) is significant. MPIF-1 also induces significant calcium mobilization in THP-1 cells (FIG. 11) showing that MPIF-1 has a biological effect on monocytes. Further, MPIF-1 produces a dose dependent chemotactic and calcium mobilization response in human monocytes.

Further, the polypeptides of the present invention can be useful in anti-tumor therapy since there is evidence that chemokine expressing cells injected into tumors have caused regression of the tumor, for example, in the treatment of Kaposi's sarcoma. MPIF-1 may induce cells to secrete TNF-α, which is a known agent for regressing tumors, in which case this protein could he used to induce tumor regression. MPIF-1 may also induce human monocytes to secrete other tumor and cancer inhibiting agents such as IL-6, IL-1 and G-CSF. Also, MPIF-1, MIP-4 and M-CIF stimulate the invasion and activation of host defense (tumoricidal) cells, e.g., cytotoxic T-cells and macrophages via their chemotactic activity, and in this way can also be used to treat solid tumors.

Figure 12:
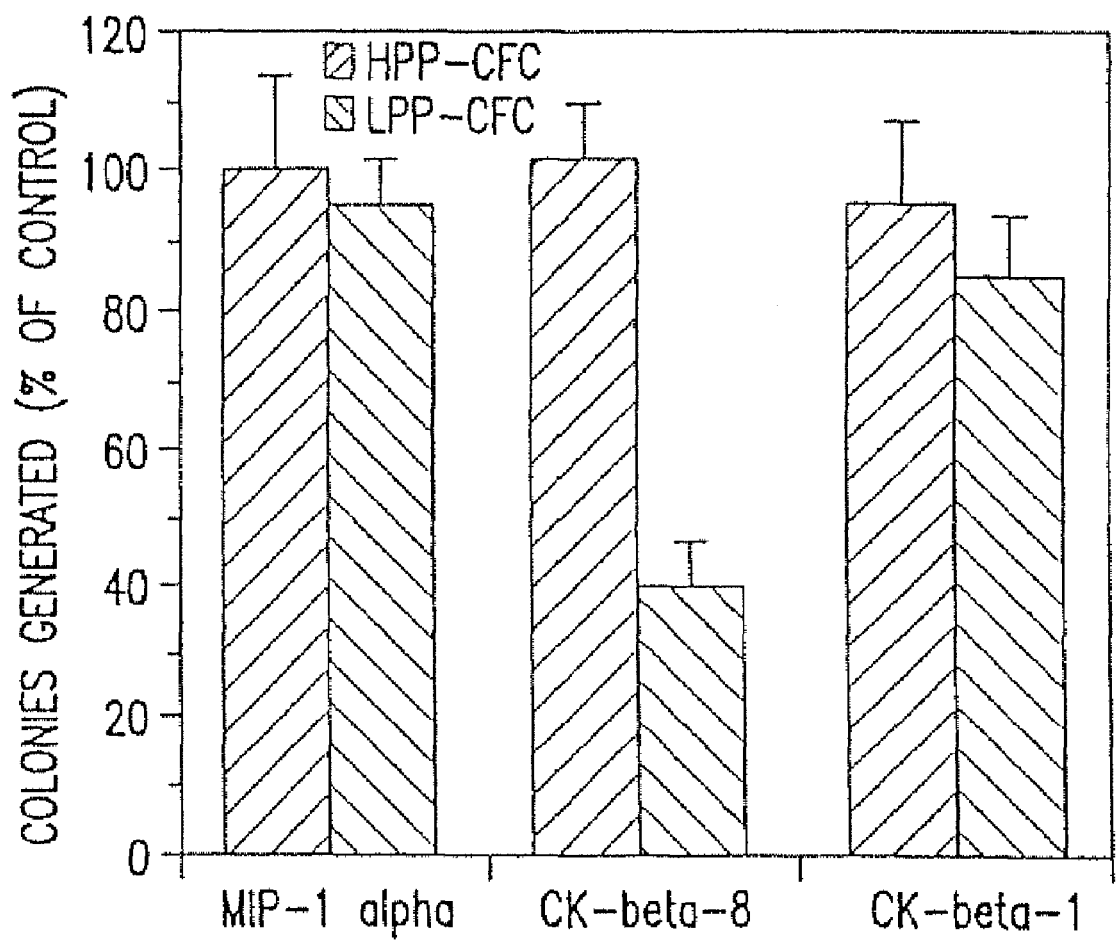
FIG. 12. A low density population of mouse bone marrow cells was plated (1,500 cells/dish) in agar containing-medium with or without the indicated chemokines (100 ng/ml), but in the presence of IL-3 (5 ng/ml), SCF (100 ng/ml), IL-1α (10 ng/ml), and M-CSF (5 ng/ml). The data shown represents the average obtained from two independent experiments (each performed in duplicate). Colonies were counted 14 days after plating. The number of colonies generated in the presence of chemokines is expressed as a mean percentage of those produced in the absence of any added chemokines.
Figure 13A:
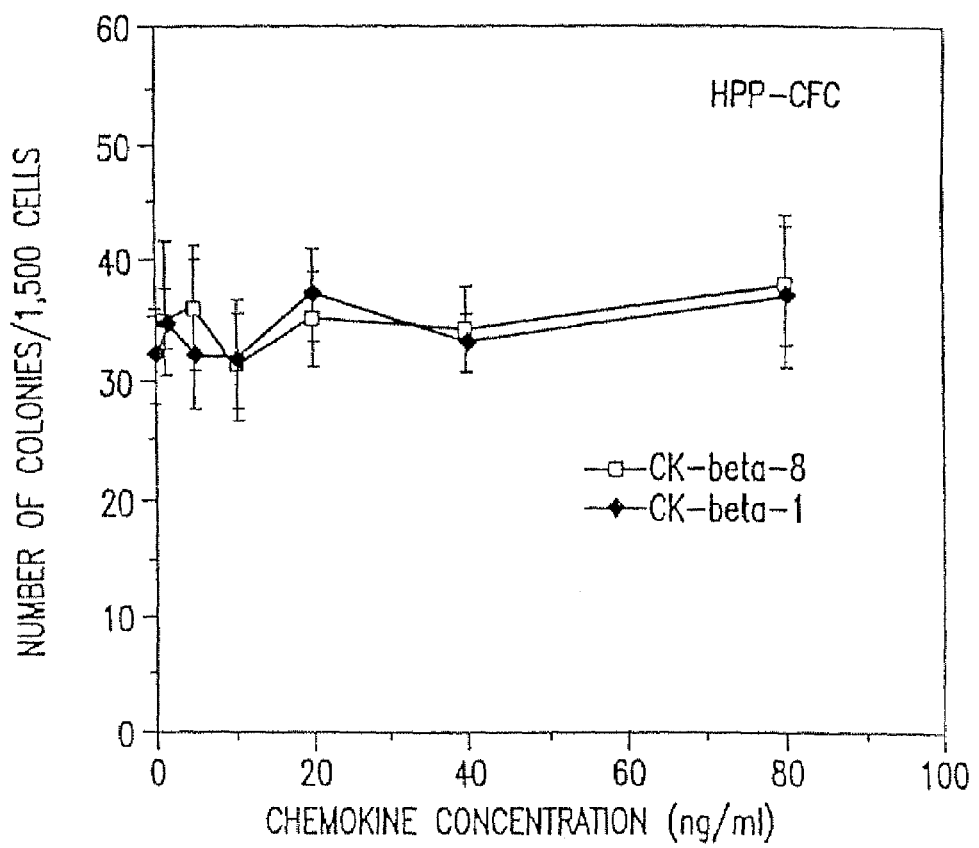
FIG. 13 illustrates the effect of MPIF-1 and M-CIF on mouse bone marrow colony formation by HPP-CFC (A) and LPP-CFC (B).
Figure 13B:
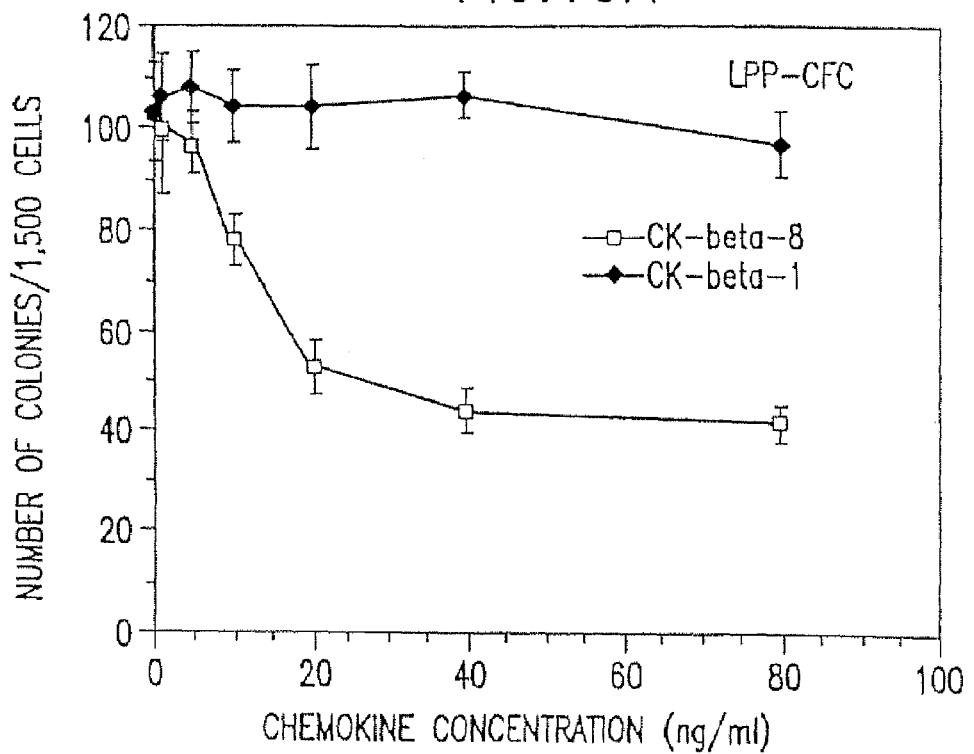
Figure 14:
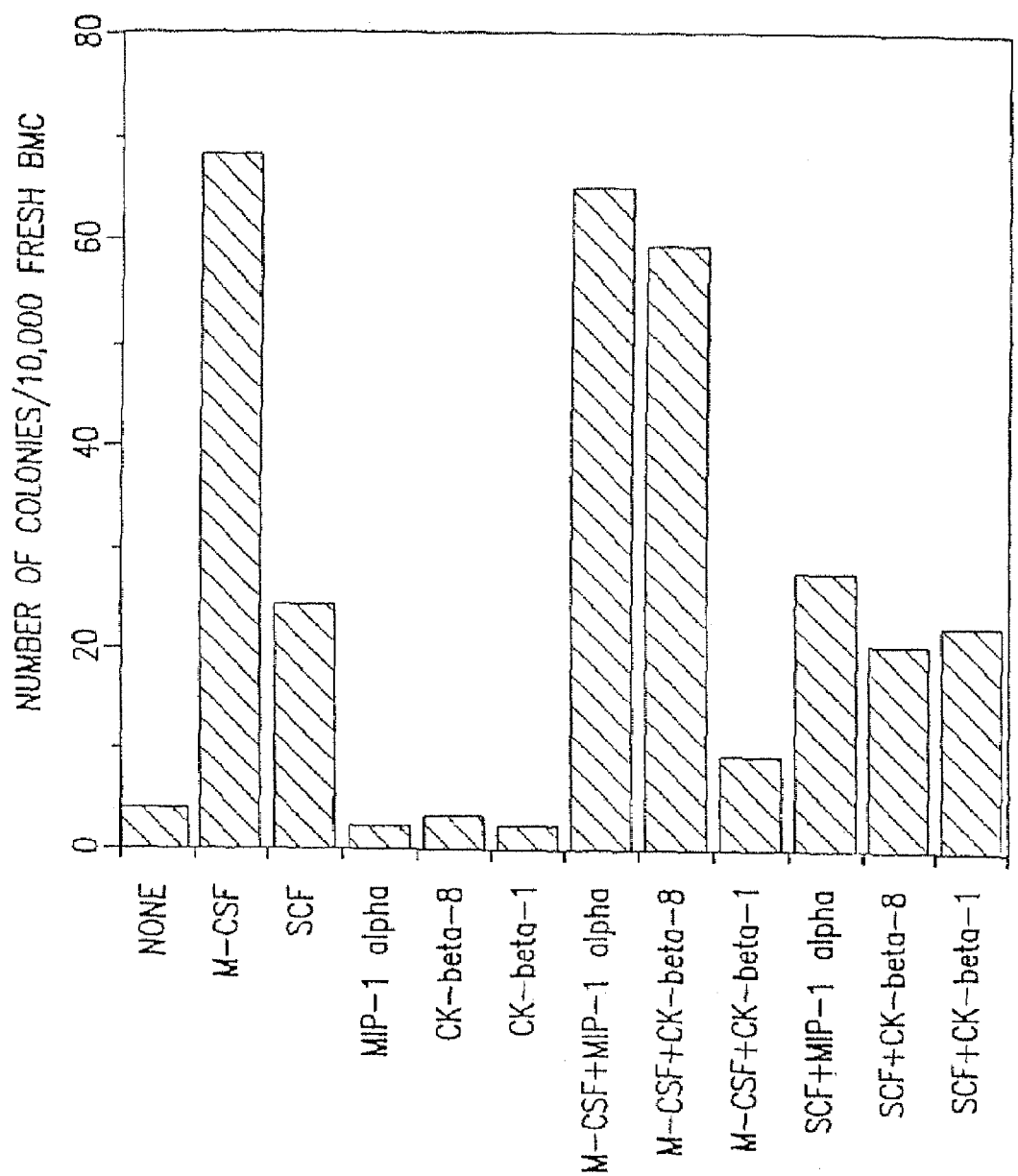
FIG. 14 illustrates the effect of baculovirus-expressed M-CIF and MPIF-1 on M-CFS and SCF-stimulated colony formation of freshly isolated bone marrow cells.

The polypeptides can also be employed to inhibit the proliferation and differentiation of hematopoietic cells and therefore may be employed to protect bone marrow stem cells from chemotherapeutic agents during chemotherapy. FIGS. 12 and 13 illustrate that MPIF-1 inhibits colony formation by low proliferative potential colony forming cells (LPP-CFC). FIG. 14 illustrates that M-CIF specifically inhibits M-CSF-stimulated colony formation, while MPIF-1 does not. Since, both MPIF-1 and M-CIF significantly inhibit growth and/or differentiation of bone marrow cells, this antiproliferative effect may allow administration of higher doses of chemotherapeutic agents and, therefore, more effective chemotherapeutic treatment.

The inhibitory effect of the M-CIF and MPIF-1 polypeptides on the subpopulation of committed progenitor cells, (for example granulocyte, and macrophage/monocyte cells) may be employed therapeutically to inhibit proliferation of leukemic cells.

Further, the inventors have found that MPIF-1, and variants thereof (e.g., MPIF-1Δ23), inhibit in vitro proliferation and differentiation of human myeloid and granulocyte precursors. Similarly, animal studies have shown that MPIF-1Δ23, for example, specifically inhibits the development of low proliferative potential-colony forming cells (LPP-CFCs) and granulocyte/monocyte committed progenitors both in vitro and in vivo. These findings indicate that MPIF-1 has therapeutic application as a chemoprotective agent that may spare early myeloid progenitors from the cytotoxic effects of commonly used chemotherapeutic drugs.

Because MPIF-1, and variants thereof, has the ability to selectively inhibit mycloid progenitor cells, MPIF-1 can be used to treat myeloproliferative disorders such as essential thrombocytosis (ET), polycythemia vera (PV), or agnogenic myeloid metaplasia (AMM), which are clinically closely related. Each disorder results from an acquired mutation of a single hematopoietic stem cell that gives the progeny of that stem cell a growth advantage. The pathophysiology of these disorders is distinct in that there is an overproduction of different cell types. In PV, there is an overproduction of erythrocytes, granulocytes, and megakaryocyte. In ET, there is, by definition, overproduction of platelets as well as leukocytes. AMM also shows thrombocytosis or leukocytosis in addition to bone marrow fibrosis.

Stabilization of PV patients can be addressed by removal of red cells by phlebotomy, However, there is no comparable therapy for elevated platelet levels in ET patients. Several myelosuppressive therapies have been studied for lowering the risk of thrombocytosis. Treatment with radioactive phosphorus, hydroxyurea, alkylating agents (busulfan and chlorambucil), interferons, or anagrelide have all shown significant side effects. In particular, there is an increased risk of acute leukemia with each myelosuppressive therapy except anagrelide. Anagrelide is a promising therapy. However, adverse reactions to anagrelide are a concern and its chronic toxicity potential has not been established. Interferons are, at present, considered second-line therapy because of expense, side effects, and the inconvenience of parenteral administration. These findings indicate that there is still a substantial need for therapy in these diseases.

In vivo studies in mice pretreated with MPIF-1Δ23 and then treated with 5-FU demonstrate an inhibition of platelet progenitor cell proliferation.

The present invention further encompasses the use of MPIF-1, and variants thereof, in combination with other myelosuppressive therapies and agents.

Figure 15:
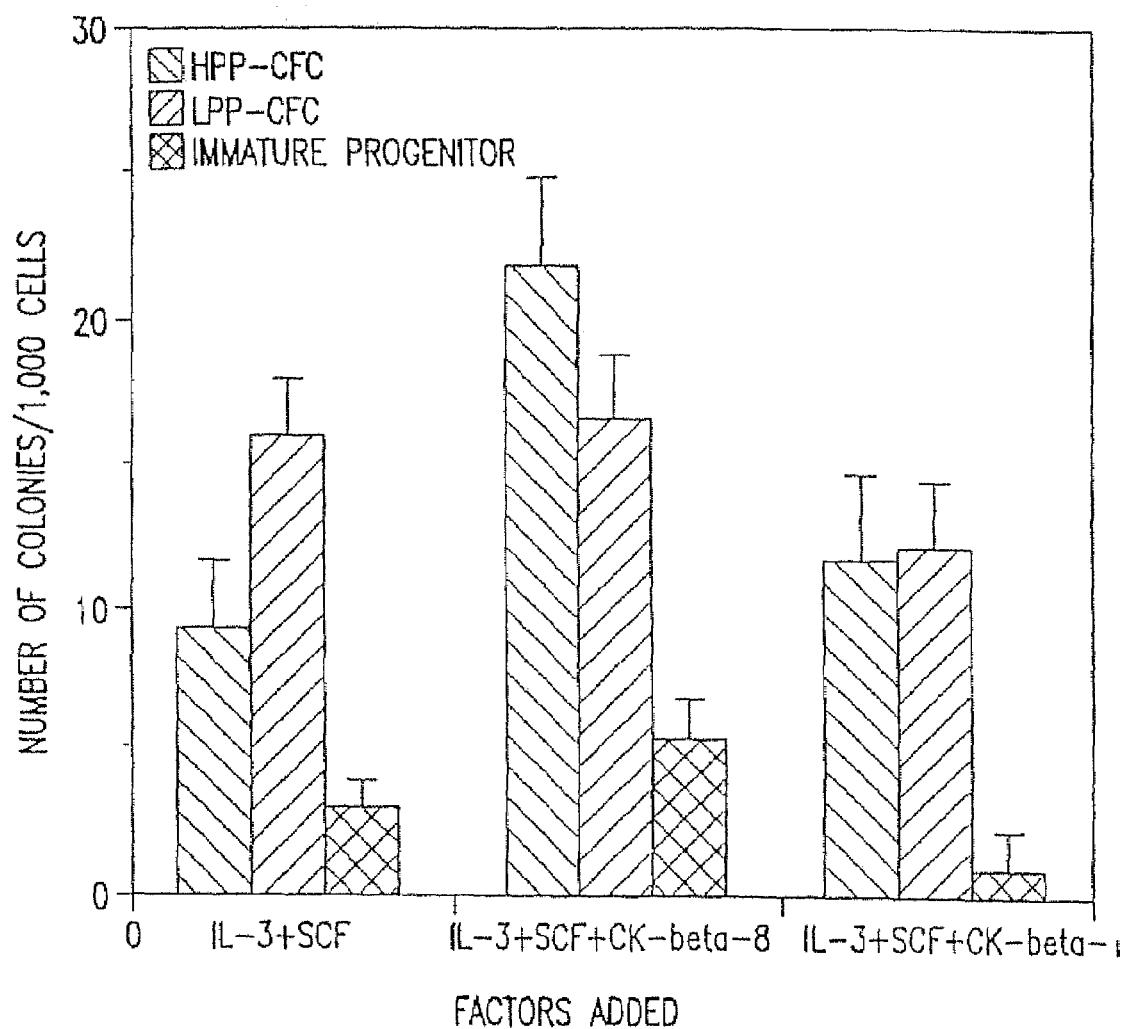
FIG. 15 illustrates the effect of MPIF-1 and M-CIF on IL3 and SCF-stimulated proliferation and differentiation of the lin population of bone marrow cells.
Figure 16A:
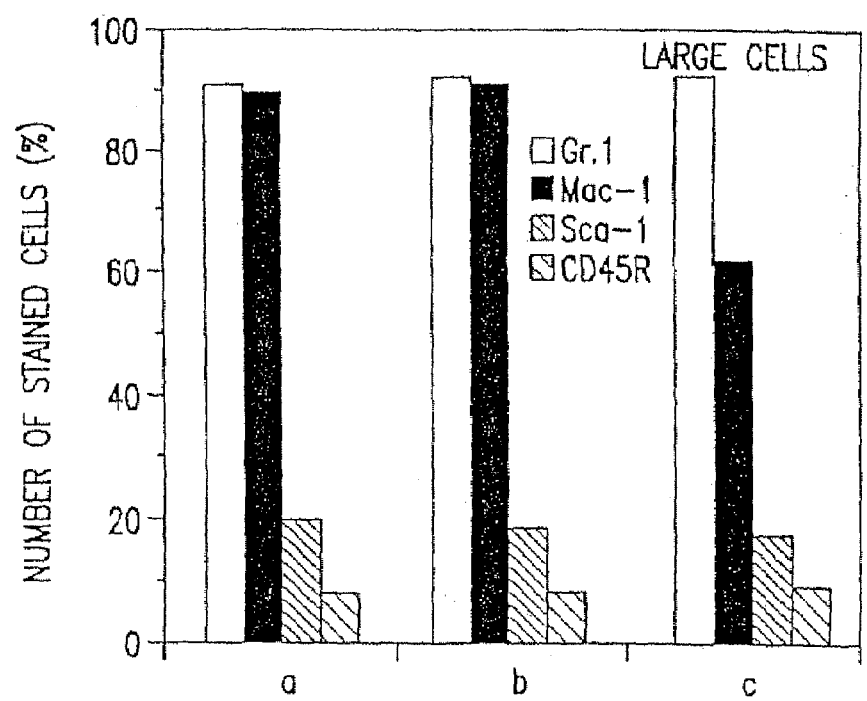
FIG. 16A-B.
Figure 16B:
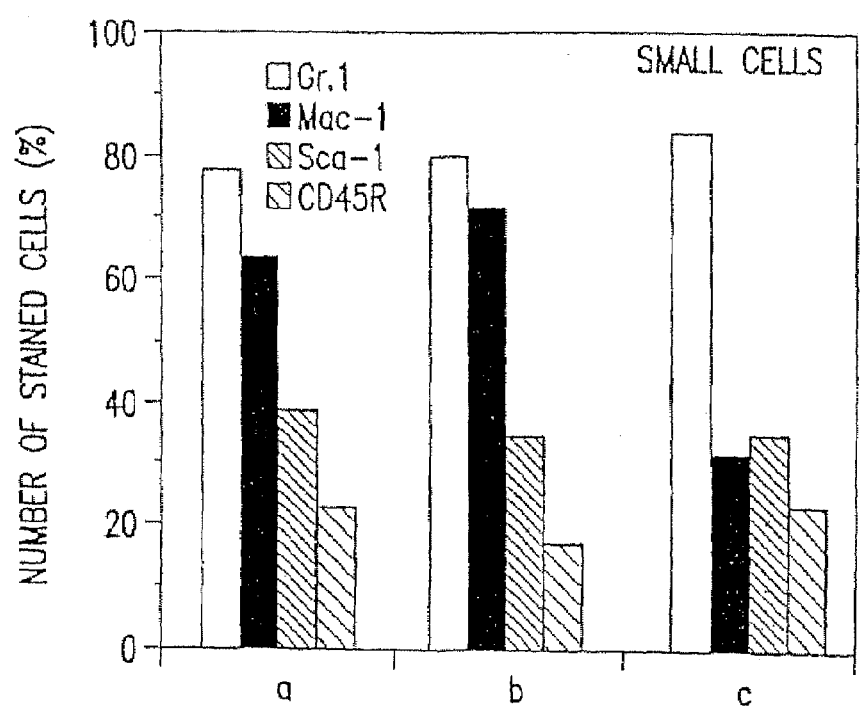
Figure 17:
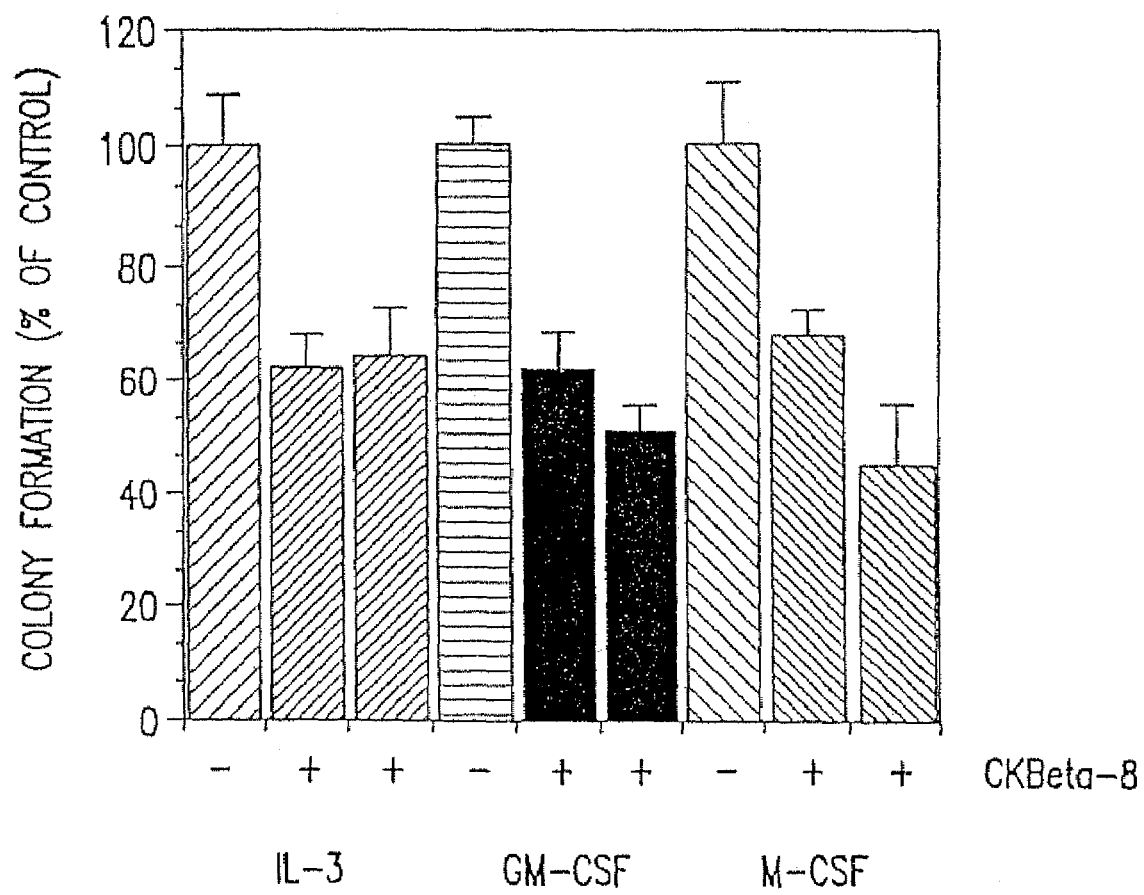
FIG. 17 illustrates that the presence of MPIF-1 protein inhibits bone marrow cell colony formation in response to IL3, M-CSF and GM-CSF.
Figure 18:
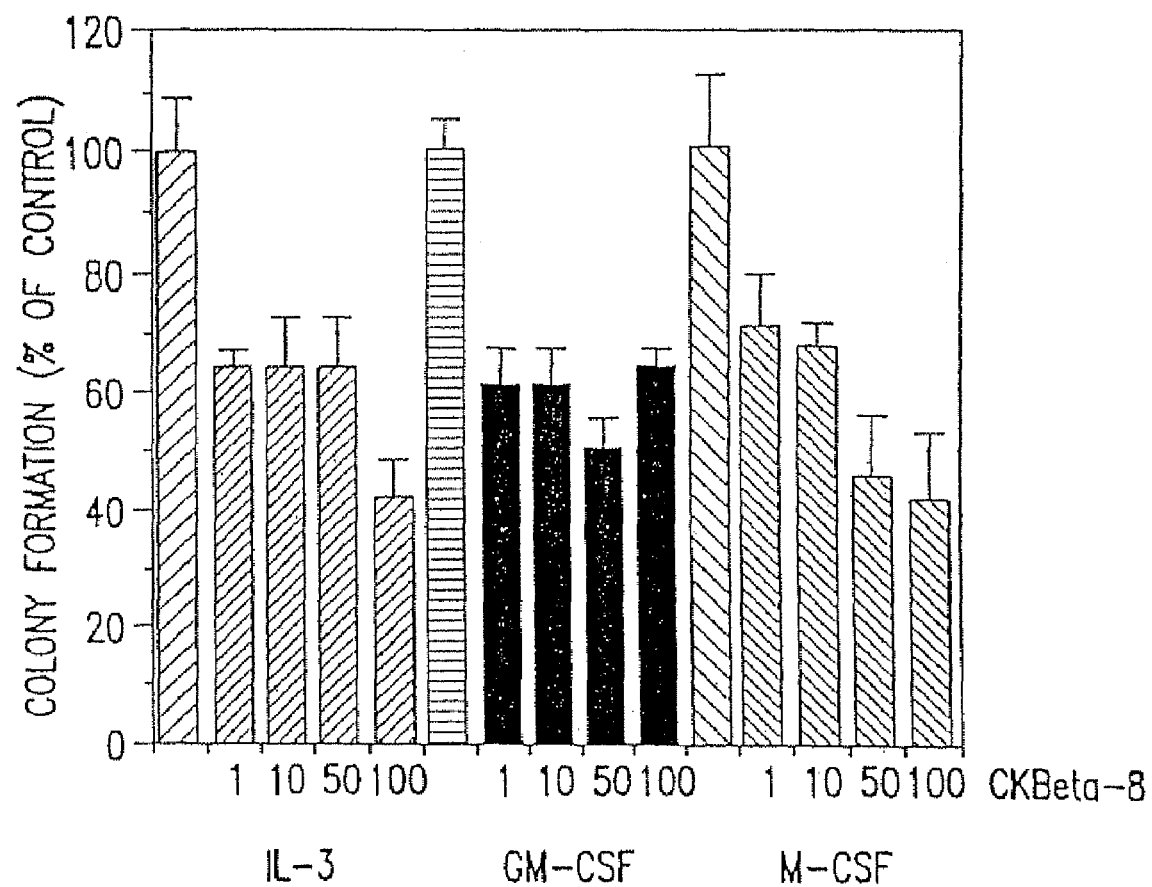
FIG. 18. Dose response of MPIF-1 inhibits bone marrow cell colony formation. Cells were isolated and treated as in FIG. 19. The treated cells were plated at a density of 1,000 cells/dish in agar-based colony formation assays in the presence of IL3, GM-CSF or M-CSF (5 ng/ml) with or without MPIF-1 at 1, 10, 50 and 100 ng/ml. The data is presented as colony formation as a percentage of the number of colonies formed with the specific factor alone. The data is depicted as the average of duplicate dishes with error bars indicating the standard deviation.

In FIGS. 15, 16 and 17 the committed cells of the cell lineages utilized were removed and the resulting population of cells were contacted with M-CIF and MPIF-1 causes a decrease in the Mac-1 positive population of cells by nearly 50%, which is consistent with the results of FIG. 14 which shows M-CIF induces inhibition of M-CSF responsive colony-forming cells. MPIF-1, as shown in FIG. 17, inhibits the ability of committed progenitor cells to form colonies in response to IL-3, GM-CSF and M-CSF. Further, as shown in FIG. 18, a dose response of MPIF-1 is shown to inhibit colony formation. This inhibition could be due to a specific blockage of the differentiative signal mediated by these factors or to a cytotoxic effect on the progenitor cells. In addition, Examples 15 and 16 demonstrate that MPF-1 has in vitro and in vivo myeloprotection activity against cytotoxicity of chemotherapeutic drugs. Thus, MPIF-1 can be useful as a myeloprotectant for patients undergoing chemotherapy.

As noted above, one major complication resulting from chemotherapy and radiation therapy is the destruction of non-pathological cell-types. The present invention provides methods for myeloprotection from radiation and chemotherapeutic agents by suppressing myeloid cell proliferation in an individual, These methods involve administering a myelosuppressive amount of MPIF-1 either alone or together with one or more chemokines selected from the group consisting of Macrophage Inflammatory Protein-1α (MIP-1α), Macrophage Inflammatory Protein-2α (MIP-2α), Platelet Factor 4 (PF4), Interleukin-8 (IL-8), Macrophage Chemotactic and Activating Factor (MCAF), and Macrophage Inflammatory Protein-Related Protein-2 (MRP-2) to an individual as part of a radiation treatment or chemotherapeutic regimen. The myelosuppressive compositions of the present invention thus provide myeloprotective effects and are useful in conjunction with therapies that have an adverse affect on myeloid cells. This is because the myelosuppressive compositions of the present invention place myeloid cells in a slow-cycling state thereby providing protection against cell damage caused by, for example, radiation therapy or chemotherapy using cell-cycle active drugs, such as cytosine arabinoside, hydroxyurea, 5-Fu and Ara-C. Once the chemotherapeutic drug has cleared the individual's system, it would be desirable to stimulate rapid amplification and differentiation of progenitor cells that were protected by MPIF-1 using, for example, myelostimulators, such as Interleukin-11 (IL-11), erythropoietin (EPO), GM-CSF, G-CSF, stem cell factor (SCF), and thrombopoietin (Tpo).

The ability of MPIF-1 to confer in vivo myeloprotection in the presence of a chemotherapeutic agent is demonstrated in Example 28. Example 28 shows that the administration of MPIF-1 to an individual prior to the administration of a chemotherapeutic agent accelerates the recovery of platelets in the blood even after multiple cycles of 5-Fu treatment, The experiments set forth in Example 28 also demonstrate that MPIF-1 treatment during multiple cycles of 5-Fu treatment results in the faster recovery of granulocytes. In addition, the results of Experiment 28 also suggest that MPIF-1 and G-CSF exert additive effects when co-administered.

As indicated, the inventors have found that MPIF-1, and variants thereof, exhibit potent in vitro suppression of low proliferation potential-colony forming cells (LPP-CFCs) from bone marrow. LPP-CFCs are bipotential hematopoietic progenitors that give rise to granulocyte and monocyte lineages. MPIF-1 also reversibly inhibits colony formation by human CD34$^+$ stem cell derived granulocyte and monocyte colony forming cells. The inventors' in vitro chemoprotection experiments have shown protection of these hematopoietic progenitors by MPIF-1Δ23 from the cytotoxic effects of the drugs 5-fluorouracil (5-Fu), cytosine arabinoside, and Taxol®.

The use of a MPIF-1 variant (Δ23) in an in vivo chemotherapeutic model has shown that it produces a more rapid recovery of both bone marrow progenitor cells and peripheral cell populations of neutrophils and platelets. Further, as shown in Examples 16 and 28, the administration of MPIF-1 results in the accelerated recovery from neutropenia and thrombocytopenia in experimental animals treated with 5-Fu. Thus, MPIF-1, and variants thereof, shorten the period of bone marrow aplasia, granulopenia, and thrombocytopenia associated with the chemotherapeutic agents and thereby reducing the likelihood of infection in patients undergoing treatment with such agents.

Thus, the invention relates to methods for protecting myeloid progenitor cells and to accelerating recovery of platelets and granulocytes which comprise the administration of MPIF-1 to an individual undergoing therapy which preferentially kills dividing cells (e.g., radiation therapy or treatment with a cell-cycle active drug). MPIF-1 is administered in sufficient quantity to provide in vivo myeloprotection against treatments and agents which preferentially kill dividing cells. By "MPIF-1 is administered" is meant that MPIF-1, an analog of MPIF-1, or combination thereof is administered in a therapeutically effective amount. Modes of administration of MIPF-1 are discussed in detail below.

MPIF-1 may be administered prior to, after, or during the therapy in which dividing cells are preferentially killed. In a preferred embodiment MPIF-1 is administered prior to radiation therapy or administration of a cell-cycle active drug and sufficient time is allowed for MPIF-1 to suppress the proliferation of myeloid cells. Further contemplated by the present invention is the use of MPIF-1 to protect myeloid cells during multiple rounds of therapy in which dividing cells are preferentially killed. In such a case, MPIF-1 may be administered in either a single dose or multiple doses at different time points in the therapy or treatment regimen.

As indicated above, MPIF-1 may be used alone or in conjunction with one or more myelostimulators. Myelostimulators are currently used in the art to stimulate the proliferation of mycloid cells after their depletion in an individual undergoing radiation therapy or treatment with a cell-cycle active drug. See, e.g., Kannan, V. et al., *Int. J. Radiat. Oncol. Biol. Phys.* 37:1005-1010 (1997); Engelhardt, M. et al., *Bone Marrow Transplant* 19:529-537 (1997); Vadhan-Raj, S. et al., *Ann Intern Med* 126:673-681 (1997); Harker, L. et al., *Blood* 89:155-165 (1997); Basser, R, et al., *Lancet* 348:1279-1281 (1996); Grossman, A. et al., *Blood* 88:3363-3370 (1996); Gordon, M. et al., *Blood* 87:3615-3624 (1996). MPIF-1 may, for example, be administered prior to therapy which kills dividing cells and one or more myelostimulators administered after or during the course of such therapy. In such a case, MWIF-1 will protect myeloid cells from the therapy and administration of the myelostimulator(s) will then result in expansion of the protected myeloid cell population.

Myelostimulators are typically administered to patients undergoing treatment with a chemotherapeutic agent in therapeutically effective amounts. Dosage formulation and mode of administration may vary with a number of factors including the individual being treated, the condition of the cells being stimulated, the stage of treatment in the chemotherapeutic regimen, and the myelostimulator(s) being used. GM-GSF and G-CSF, for examples, are therapeutically effective at dosages of about 1 μg/kilogram and 5 to 10 μg/kilogram of body weight, respectively, and may be administered daily by subcutaneous injection. See, e.g. Kannan, V. et al., *Int. J. Radiat. Oncol. Biol. Phys.* 37:1005-1010 (1997); Engelhardt, M. et al., *Bone Marrow Transplant* 19:529-537 (1997); Sniecinski, I. et al., *Blood* 89:1521-1528 (1997). IL-11 may be administered by daily subcutaneous injection at a dosage range of up to 100 μg/kilogram of body weight. Gordon, M. et al., supra. Doses of IL-11 below 10

μg/kilogram, however, are believed to be effective in reducing chemotherapy-induced thrombocytopenia. Tpo may be administered by intravenous injection at a dosage range of 0.3 to 2.5 μg/kilogram of body weight. See, e.g., Vadhan-Raj, S. et al., *Ann. Intern. Med* 126:673-681 (1997); Harker, L. et al., *Blood* 89:155-165 (1997). As one skilled in the art would recognize, the optimal dosage formulation and mode of administration will vary with a number of factors including those noted above. Dosage formulation and mode of administration for additional myelostimulators are known in the art.

The timing of administration of myelostimulators as part of a treatment protocol involving therapy which preferentially kill dividing cells may also vary with the factors described above for dosage formulation and mode of administration. A number of reports have been published which disclose the administration of myelostimulators to individuals as part of treatment protocols involving radiation therapy or cell-cycle active drugs. Vadhan-Raj, S. et al., supra, for example, report the use of a single intravenous dose of Tpo three weeks prior to the administration of a chemotherapeutic agent. Papadimitrou, C. et al., *Cancer* 79:2391-2395 (1997) and Whitehead, R. et al., *J. Clin. Oncol.* 15:2414-2419 (1997) report chemotherapeutic treatment methods which involve the administration of chemotherapeutic agents over the course of several weeks. In each of these cases, doses of G-CSF are administered at multiple time points after the first day and before the last day of treatment with the chemotherapeutic agent. Similar usage of both IL-11 and GM-CSF are reported in Gordon, M. et al., supra, and Michael, M., et al., *Am. J. Clin. Oncol.* 20:259-262 (1997). One skilled in the art would recognize, however, that optimal timing of administration of myelostimulators will vary with the particular myelostimulators used and the conditions under which they are administered.

Thus, the administration of myelostimulators to alleviate cytotoxic effects that therapies which preferentially kill dividing cells have on myeloid cells is known in the art. The myelostimulators may be administered by several routes, including intravenous and subcutaneous injection. The concentrations of myelostimulators administered vary widely with numerous factors but generally range between 0.1 to 100 μg/kilogram of body weight and may be administered in a single dose or in multiple doses at various time points in the chemotherapeutic or radiological treatment regimen. Myelostimulators are generally administered, however, prior to or after administration of the chemotherapeutic agent or radiological treatment. As one skilled in the art would understand, the conditions under which myelostimulators are used will vary with both the particular myelostimulator and the treatment regimen.

As the skilled artisan will appreciate, MPIF-1 can be used as described above to enhance the effectiveness of hematopoietic growth factors generally. Such hematopoietic growth factors include erythropoietin, which stimulates production of erythrocytes, and IL-3, a multilineage growth factor that stimulates more primitive stem cells, thus increasing the number of all blood cell types. Others include stem cell factor; GM-CSF; and hybrid molecules of G-CSF and erythropoietin; IL-3 and SCF; and GM-CSF and G-CSF.

The myelosuppressive pharmaceutical compositions of the present invention are also useful in the treatment of leukemia, which causes a hyperproliferative myeloid cell state. Thus, the invention further provides methods for treating leukemia, which involve administering to a leukemia patient a myelosuppressive amount of MPIF-1 either alone or together with one or more chemokines selected from the group consisting of MIP-1α, MIP-2α, PF4, IL-8, MCAF, and MRP-2.

By "suppressing myeloid cell proliferation" is intended decreasing the cell proliferation of myeloid cells and/or increasing the percentage of myeloid cells in the slow-cycling phase. As above, by "individual" is intended mammalian animals, preferably humans. Preincubation of the myelosuppressive compositions of the present invention with acetonitrile (ACN) significantly enhances the specific activity of these chemokines for suppression of myeloid progenitor cells. Thus, preferably, prior to administration, the myelosuppresive compositions of the present invention are pretreated with ACN as described in Broxmeyer H. E., et al., *Ann-Hematol.* 71(5):235-46(1995) and PCT Publication WO 94/13321, the entire disclosures of which are hereby incorporated herein by reference.

The myelosuppressive compositions of the present invention may be used in combination with a variety of chemotherapeutic agents including alkylating agents such as nitrogen mustards, ethylenimines, methylmelamines, alkyl sulfonates, nitrosuoureas, and triazenes; antimetabolites such as folic acid analogs, pyrimidine analogs, in particular fluorouracil and cytosine arabinoside, arid purine analogs; natural products such as vinca alkaloids, epipodophyliotoxins, antibiotics, enzymes and biological response modifiers; and miscellaneous products such as platinum coordination complexes, anthracenedione, substituted urea such as hydroxyurea, methyl hydrazine derivatives, and adrenocorticoid suppressant.

Chemotherapeutic agents can be administered at known concentrations according to known techniques. The myelosuppressive compositions of the present invention can be co-administered with a chemotherapeutic agent, or administered separately, either before or after chemotherapeutic administration.

Certain chemokines, such as MIP-1β, MIP-2β and GRO-α, inhibit (at least partially block) the myeloid suppressive affects of the myelosuppresive compositions of the present invention. Thus, in a further embodiment, the invention provides methods for inhibiting myelosuppression, which involves administering an effective amount of a myelosuppressive inhibitor selected from the group consisting of MIP-1β, MIP-2β and GRO-α to a mammal previously exposed to the myelosuppresive agent MPIF-1 either alone or together with one or more of MIP-1α, MIP-2α, PF4, IL-8, MCAF, and MRP-2.

One of ordinary skill will appreciate that effective amounts of the MPIF-1 polypeptides for treating an individual in need of an increased level of MPIF-1 activity (including amounts of MPIF-1 polypeptides effective for myelosuppression with or without myelosuppressive agents or myelosuppressive inhibitors) can be determined empirically for each condition where administration of MPIF-1 is indicated. The polypeptide having MPIF-1 activity my be administered in pharmaceutical compositions in combination with one or more pharmaceutically acceptable excipients.

MPIF-1 may also be employed to treat leukemia and abnormally proliferating cells, for example tumor cells, by inducing apoptosis. MPIF-1 induces apoptosis in a population of hematopoietic progenitor cells.

MPIF-1 may be employed for the expansion of immature hematopoietic progenitor cells, for example, granulocytes, macrophages or monocytes, by temporarily preventing their differentiation. These bone marrow cells may be cultured in vitro. Thus, MPIF-1 can also be, useful as a modulator of hematopoietic stem cells in vitro for the purpose of bone marrow transplantation and/or gene therapy. Since stem cells are rare and are most useful for introducing genes into for gene therapy, MPIF can be used to isolate enriched populations of stem cells. Stem cells can be enriched by culturing cells in the presence of cytotoxins, such as 5-Fu, which kills rapidly dividing cells, where as the stem cells will be protected by MPIF-1. These stem cells can be returned to a bone marrow transplant patient or can then be used for transfection of the desired gene for gene therapy. In addition, MPIF-1 can be injected into individuals which results in the release of stem cells from the bone marrow of the individual into the peripheral blood. These stem cells can be isolated for the purpose of autologous bone marrow transplantation or manipulation for gene therapy. After the patient has finished chemotherapy or radiation treatment, the isolated stem cells can be returned to the patient.

In addition, since MPIF-1 has effects on T-lymphocytes as well as macrophages, MPIF-1 may enhance the capacity of antigen presenting cells (APCs) to take up virus, bacteria or other foreign substances, process them and present them to the lymphocytes responsible for immune responses. MPIF-1 may also modulate the interaction of APCs with T-lymphocytes and B-lymphocytes. MPIF-1 may provide a costimulatory signal during antigen presentation which directs the responding cell to survive, proliferate, differentiate, secrete additional cytokines or soluble mediators, or selectively removes the responding cell by inducing apoptosis or other mechanisms of cell death. Since APCs have been shown to facilitate the transfer of HIV to CD4+ T-lymphocytes, MPIF-1 may also influence this ability and prevent infection of lymphocytes by HIV or other viruses mediated through APCs. This is also true for the initial infection of APCs, T-lymphocytes or other cell types by HIV, EBV, or any other such viruses.

In addition, recent demonstration that the MIP-1α receptor serves as a cofactor in facilitating the entry of HIV into human monocytes and T-lymphocytes raises an interesting possibility that MPIF-1 or its variants might interfere with the process of HIV entry into the cells. (See, Example 17). Thus, MPIF-1 can be useful as an antiviral agent for viruses and retroviruses whose entry is facilitated by the MIP-1α receptor.

MPIF-1 may act as an immune enhancement factor by stimulating the intrinsic activity of T-lymphocytes to fight bacterial and viral infection as well as other foreign bodies. Such activities are useful for the normal response to foreign antigens such as infection of allergies as well as immunoresponses to neoplastic or benign growth including both solid tumors and leukemias.

For these reasons the present invention is useful for diagnosis or treatment of various immune system-related disorders in mammals, preferably humans. Such disorders include tumors, cancers, and any disregulation of immune cell function including, but not limited to, autoimmunity, arthritis, leukemias, lymphomas, immonosuppression, sepsis, wound healing, acute and chronic infection, cell mediated immunity, humoral immunity, inflammatory bowel disease, myelosuppression, and the like.

M-CIF Therapeutic/Diagnostic Applications. M-CIF activity is useful for immune enhancement or suppression, myeloprotection, stem cell mobilization, acute and chronic inflammatory control and treatment of leukemia. In addition, since M-CIF has effects on T-lymphocytes as well as macrophages, M-CIF enhances the capacity of antigen presenting cells (APCs) to take up virus, bacteria or other foreign substances, process them and present them to the lymphocytes responsible for immune responses. In addition, M-CIF also modulates the interaction of APCs with T-lymphocytes and B-lymphocytes. For instance, M-CIF provides a costimulation signal during antigen presentation which directs the responding cell to survive, proliferate, differentiate, secrete additional cytokines or soluble mediatiors, or selectively removes the responding cell by inducing apoptosis or other mechanisms of cell death. Since APCs have been shown to facilitate the transfer of HIV to CD4+ T-lymphocytes, M-CIF also influences this ability and prevents infection of lymphocytes by HIV or other viruses mediated through APCs. This is also true for the initial infection of APCs, T-lymphocytes or other cell types by HIV, EBV, or any other such viruses.

M-CIF suppresses the immune system. As one mechanism, it is believed that M-CIF down regulates the activity of T-lymphocytes via CTLA-4. The activation and subsequent differentiation of T-cells requires two types of signals from APCs. One of these two signals is an antigen-independent signal mediated by engagement of the T cell surface molecule CD28 with members of the B7 family on the APC. Allison, Curr. Opin. Immunol. 6:414 (1994); June et al., Immunol. Today 15: 321 (1994): In contrast to CD28, CTLA-4 is critical for the negative regulation of T cell responses. Waterhouse et al., Science 270: 985 (1995). Recent studies suggest that the outcome of T cell activation is determined by a delicately balanced interplay between positive signals from CD28 and negative signals from CTLA-4. Waterhouse el al., Science 270: 985 (1995). The cumulative results of a number studies suggest that the blockade of CTLA-4 removed, whereas aggregation of CTLA-4 provided, inhibitory signals that down regulate T cell responses. Allison et al., Science 270: 932-933 (1995). In addition, the phenotype of CTLA-4 knock-out mice supports an inhibitory signaling role for CTLA-4 in the regulation of T cell responses. Allison et al., Science 270: 932-933 (1995). M-CIF appears to induce CTLA-4 cells which, as discussed above, is a known down regulator of T cells. In addition, M-CIF directly inhibits CD8+ T cells which is also a known down regulator of T cells.

The ability of M-CIF to down regulate T cells is useful for modulating the immune response to foreign antigens from infection by bacteria or viruses and allergies as well as immunoresponses to neoplastic or benign growth including both solid tumors and leukemias.

For these reasons the present invention is useful for diagnosis or treatment of various immune system-related disorders in mammals, preferably humans. Such disorders include tumors, cancers, and any disregulation of immune cell function including, but not limited to, autoimmunity, arthritis, asthma, leukemias, lymphomas, immunosuppression, sepsis, wound healing, acute and chronic infection, cell mediated immunity, humoral immunity, inflammatory bowel disease, myelosuppression, and the like.

M-CIF, as an antiinflammatory, can be used to treat such disorders as, but not limited to, those involving abnormal production of TNFα. Such disorders include, but are not limited to, sepsis syndrome, including cachexia, circulatory collapse and shock resulting from acute or chronic bacterial infection, acute and chronic parasitic or infectious processes, including bacterial, viral and fungal infections, acute and chronic immune and autoimmune pathologies, such as systemic lupus erythematosus (SLE) and rheumatoid arthritis, alcohol-induced hepatitis, chronic inflammatory pathologies such as sarcoidosis and Crohn's pathology, vascular inflammatory pathologies such as disseminated intravascular coagulation, graft-versus-host pathology, Kawasaki's pathology; malignant pathologies involving TNF-secreting tumors and neurodegenerative diseases, Neurodegenerative diseases include, but are not limited to, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors: hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multisystem disorder); demyelinating core disorders, such as multiple sclerosis, acute transverse myelitis; and disorders of the motor unit such as neurogenic muscular atrophies (anterior horn cell degeneration, such as amyotrophic lateral sclerosis, infantile spinal muscular atrophy and juvenile spinal muscular atrophy); Alzheimer's disease,; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis Hallerrorden-Spatz disease; and Dementia pugilistica. One preferred neurodegenerative disease is multiple sclerosis.

See, e.g., Berkow et al, eds., The Merck Manual, 16th edition, Merck and Co., Rahway, N. J., 1992, which reference, and references cited therein, are entirely incorporated herein by reference.

As noted above, M-CIF may also be used to treat SLE and other disease-states involving immune responses and inflammation. SLE is an autoimmune disease which results in the formation of complement-fixing immune aggregates capable of inducing glomerulonephritis and vasculitis. Steinberg, A. D. and Klinman, D. M., *Rheum. Dis. Clinics of No. Amer.* 14:25 (1988). A number of agents are currently in use, or are proposed for use, in treating SLE and both lupus associated glomerulonephritis and vasculitis. Among these agents are antibodies with specificity for cell surface receptors required for the induction of immune responses. Anti-CD11a and anti-CD-54 monoclonal antibodies, for example, have been shown to be effective in the treatment of experimental lupus nephritis. Koostra, C. J. et al., *Clin. Exp. Immunol.* 108:324-332 (1997). Blocking the interaction between CD28/CTLA-4 and their ligands (e.g., CD80 and CD86) has also been proposed as a means for suppressing immune responses associated with lupus, and the administration of CD80 and CD86 specific monoclonal antibodies has been shown to prevent the development and progression of lupus in an experimental animal model. Nakajima, A. et al., *Eur. J. Immunol.* 25:3060-3069 (1995). Chemical agents have also been shown to have therapeutic effect in the treatment of SLE and both lupus associated glomerulonephritis and vasculitis. These agents include antifolate compounds (e.g., methotrexate and MX-68) and immunosuppressants (e.g. corticosteroids, cyclophosphamide, mycophenolate mofetil, azathioprine). Coma, D. et al., *Kidney Int.* 51:1583-1589 (1997); Mihara, M. et al., *Int. Arch. Allergy Immunol.* 113:454-459 (1997); (Gansauge, S. et al., *Ann. Rheum. Dis.* 56:382-385 (1997). Additional agents have therapeutic effect for the treatment of afflictions associated with non-lupus associated immune complexes. Two classes of such compounds are free radical scavengers (e.g., OPC-15161) and angiotensin-converting enzyme inhibitors (e.g., quinapril). Sanaka, T. et al., *Nephrol.* 76:315-322 (1997); Ruiz-Ortega, M. et al., *J. Am. Soc. Nephrol.* 8:756-768 (1997).

As shown in Examples 19 and 29, M-CIF suppresses renal inflammation associated with cell mediated immunity and ameliorates the progression of lupus associated nephritis. The present invention thus provides a method for treating SLE, as well as other diseases involving immune responses (e.g., those resulting from cell mediated immunity and the formation of immune complexes), comprising the administration of M-CIF to a patient in need thereof. M-CIF may be administered as the sole immune response modulator or may be administered in conjunction with one or more additional agents which modulate immune responses.

Accordingly, MPIF-1, MIP-4 and M-CIF can be used to facilitate wound healing by controlling infiltration of target immune cells to the wound area. In a similar fashion, the polypeptides of the present invention can enhance host defenses against chronic infections, e.g. mycobacterial, via the attraction and activation of microbicidal leukocytes.

The polypeptides of the present invention, and polynucleotides encoding such polypeptides, may be employed as research reagents for in vitro purposes related to scientific research, synthesis of DNA and manufacture of DNA vectors, and for the purpose of developing therapeutics and diagnostics for the treatment of human disease. For example, M-CIF and MPIF-1 may be employed for the expansion of immature hematopoietic progenitor cells, for example, granulocytes, macrophages or monocytes, by temporarily preventing their differentiation. These bone marrow cells may be cultured in vitro.

Another use of the polypeptides is the inhibition of T-cell proliferation via inhibition of IL-2 biosynthesis, for example, in auto-immune diseases and lymphocytic leukemia.

MPIF-1, MIP-4 and M-CIF can also be useful for inhibiting epidermal keratinocyte proliferation which has utility in psoriasis (keratinocyte hyper-proliferation) since Langerhans cells in skin have been found to produce MIP-1α.

MPIF-1, MIP-4 and M-CIF can be used to prevent scarring during wound healing both via the recruitment of debris-cleaning and connective tissue-promoting inflammatory cells and by its control of excessive TGFβ-mediated fibrosis, in addition these polypeptides can be used to treat stroke, thrombocytosis, pulmonary emboli and myeloproliferative disorders, since MPIF-1, MIP-4 and M-CIF increase vascular permeability.

Pharmaceutical Compositions. The MPIF-1, M-CIF or MIP-4 polypeptide pharmaceutical composition comprises an effective amount of an isolated MPIF-1, M-CIF or MIP-4 polypeptide of the invention, particularly a mature form of the MPIF-1, M-CIF or MIP-4, effective to increase the MPIF-1, M-CIF or MIP-4 activity level in such an individual. Such compositions can be formulated and dosed in a fashion consistent with good medical practice, taking into account the clinical condition of the individual patient (especially the side effects of treatment with MPIF-1, M-CIF or MIP-4 polypeptide alone), the site of delivery of the MPIF-1, M-CIF or MIP-4 polypeptide composition, the method of administration, the scheduling of administration, and other factors known to practitioners. The "effective amount" of MPIF-1, M-CIF or MIP-4 polypeptide for purposes herein is thus determined by such considerations, Polypeptides, antagonists or agonists of the present invention can be employed in combination with a suitable pharmaceutical carrier. Such compositions comprise a therapeutically effective amount of the protein, and a pharmaceutically acceptable carrier or excipient. Such a carrier includes but is not limited to saline, buffered saline, dextrose, water, glycerol, ethanol, and combinations thereof. The formulation should suit the mode of administration.

By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The MPIF-1, M-CIF or MIP-4 polypeptide is also suitably administered by sustained-release systems. Suitable examples of sustained-release compositions include semi-permeable polymer matrices in the form of shaped articles, e.g. films, or microcapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547-556 (1983)), poly(2-hydroxyethyl methacrylate) (R. Langer et al., *J. Biomed. Mater. Res.* 15:167-277 (1981), and R. Langer, *Chem. Tech.* 12:98-105 (1982)), ethylene vinyl acetate (R. Langer et al., Id.) or poly-D-(−)-3-hydroxybutyric acid (EP 133,988). Sustained-release MPIF-1, M-CIF or MIP-4 polypeptide compositions also include liposomally entrapped MPIF-1, M-CIF or MIP-4 polypeptide. Liposomes containing MPIF-1, M-CIF or MIP-4 polypeptide are prepared by methods known per se: DE 3,218,121; Epstein et al., *Proc. Natl. Acad. Sci.* (*USA*) 82:3688-3692 (1985); Hwang et al., *Proc. Natl. Acad. Sci.* (*USA*) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal MPIF-1, M-CIF or MIP-4 polypeptide therapy.

For parenteral administration, in one embodiment, the MPIF-1, M-CIF or MIP-4 polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the MPIF-1, M-CIF or MIP-4 polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g. polyarginine or tripeptides; proteins, such as serum albumin, gelatin, or immunoglobulins, hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The MPIF-1, M-CIF or MIP-4 polypeptide is typically formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of MPIF-1, M-CIF or MIP-4 polypeptide salts.

When MPIF-1, and/or variants thereof, is administered as a myeloprotectant as part of a chemotherapeutic regimen for the treatment of hyperproliferative disorders in humans, a suitable dosage range for intravenous administration is 0.01 µg/kg to 10 µg/kg of body weight. Further, MPIF-1 may be administered intravenously at doses of 0.1, 1.0, 10, and 100 µg/kg of body weight. Extrapolation of data from animal studies indicates that a dosage of MPIF-1 suitable for myeloprotection in humans is 0.016 µg/kg of body weight.

Further, MPIF-1, and/or a variant thereof, may be administered once daily for a specified number of days (e.g., three days). In addition, when used in a chemotherapeutic regimen, MPIF-1 may be administered to a human prior to the administration of the chemotherapeutic agent(s). For example, MPIF-1 may be administered two days before, one day before and the day of administration of a chemotherapeutic agent(s).

When MPIF-1, and/or a variant thereof, is administered to a human for the treatment of myeloproliferative disorders the dosages administered may be the same as when MPIF-1 is used as a myeloprotectant. When administered to a human for the treatment of myeloproliferative disorders, MPIF-1 may be administered subcutaneously.

MPIF-1, M-CIF or MIP-4 polypeptide to be used for therapeutic administration must be sterile. Sterility is readily accomplished by filtration through sterile filtration membranes (e.g., 0.2 micron membranes). Therapeutic MPIF-1, M-CIF or MIP-4 polypeptide compositions generally are placed into a container having a sterile access port, for example, an intravenous solution bag or vial having a stopper pierceable by a hypodermic injection needle.

MPIF-1, M-CIF or MIP-4 polypeptide ordinarily will be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous MPIF-1, M-CIF or MIP-4 polypeptide solution, and the resulting mixture is lyophilized. The infusion solution is prepared by reconstituting the lyophilized MPIF-1, M-CIF or MIP-4 polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Modes of administration. It will be appreciated that conditions caused by a decrease in the standard or normal level of MPIF-1, M-CIF or MIP-4 activity in an individual, can be treated by administration of MPIF-1, M-CIF or MIP-4 protein. Thus, the invention further provides a method of treating an individual in need of an increased level of MPIF-1, M-CIF or MIP-4 activity comprising administering to such an individual a pharmaceutical composition comprising an effective amount of an isolated MPIF-1, M-CIF or MIP-4 polypeptide of the invention, particularly a mature form of the MPIF-1, M-CIF or MIP-4, effective to increase the MPIF-1, M-CIF or MIP-4 activity level in such an individual.

The amounts and dosage regimens of MPIF-1, MIP-4 and M-CIF administered to a subject will depend on a number of factors such as the mode of administration, the nature of the condition being treated and the judgment of the prescribing physician. The pharmaceutical compositions are administered in an amount which is effective for treating and/or prophylaxis of the specific indication. In general, the polypeptides will be administered in an amount of at least about 10 µg/kg body weight and in most cases they will be administered in an amount not in excess of about 10 mg/kg body weight per day and preferably the dosage is from about 10 µg/kg body weight daily, taking into account the routes of administration, symptoms, etc.

As a general proposition, the total pharmaceutically effective amount of MPIF-1, M-CIF or MIP-4 polypeptide administered parenterally per dose will more preferably be in the range of about 1 µg/kg/day to 10 mg/kg/day of patient body weight, although, as noted above, this will be subject to therapeutic discretion. Even more preferably, this dose is at least 0.01 mg/kg/day, and most preferably for humans between about 0.01 and 1 mg/kg/day. If given continuously, the MPIF-1, M-CIF or MIP-4 polypeptide is typically administered at a dose rate of about 1 µg/kg/hour to about 50 µg/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the MPIF-1, M-CIF or MIP-4 of the invention may be administered orally, rectally, parenterally, intracisternally, intravaginally, intraperitoneally, topically (as by powders, ointments, drops or transdermal patch), bucally, or as an oral or nasal spray.

Gene Therapy. The chemokine polypeptides, and agonists or antagonists which are polypeptides, may be employed in accordance with the present invention by expression of such polypeptides in vivo, which is often referred to as "gene therapy."

Thus, for example, cells from a patient can be engineered with a polynucleotide (DNA or RNA) encoding a polypeptide ex vivo, with the engineered cells then being provided to a patient to be treated with the polypeptides. Such methods are well-known in the art. For example, cells can be engineered by procedures known in the art by use of a retroviral particle containing RNA encoding the polypeptides of the present invention.

Similarly, cells can be engineered in vivo for expression of a polypeptides in vivo by, for example, procedures known in the art. As known in the art, a producer cell for producing a retroviral particle containing RNA encoding the polypeptides of the present invention can be administered to a patient for engineering the cells in vivo and expression of the polypeptides in vivo. These and other methods for administering polypeptides of the present invention by such method should be apparent to those skilled in the art from the teachings of the present invention. For example, the expression vehicle for engineering cells can be other than a retrovirus, for example, an adenovirus which can be used to engineer cells in vivo after combination with a suitable delivery vehicle.

The retroviral plasmid vectors may be derived from retroviruses which include, but are not limited to, Moloney Murine Sarcoma Virus, Moloney Murine leukemia Virus, spleen necrosis virus, Rous Sarcoma Virus and Harvey Sarcoma Virus.

In a preferred embodiment the retroviral expression vector, pMV-7, is flanked by the long terminal repeats (LTRs) of the Moloney marine sarcoma virus and contains the selectable drug resistance gene neo under the regulation of the herpes simplex virus (HSV) thymidine kinase (tk) promoter. Unique EcoRI and HindIII sites facilitate the introduction of coding sequence (Kirschmeier, P. T. et al., *DNA* 7:219-25 (1988)).

The vectors include one or more suitable promoters which include, but are not limited to, the retroviral LTR; the SV40 promoter; and the human cytomegalovirus (CMV) promoter described in Miller, et al., *Biotechniques*, Vol. 7, No. 9:980-990 (1989), or any other promoter (e.g. cellular promoters such as eukaryotic cellular promoters including, but not limited to, the histone, pol III, and β-actin promoters). The selection of a suitable promoter will be apparent to those skilled in the art from the teachings contained herein.

The nucleic acid sequence encoding the polypeptide of the present invention is under the control of a suitable promoter which includes, but is not limited to, viral thymidine kinase promoters, such as the Herpes Simplex thyinidine kinase promoter; retroviral LTRs, the β-actin promoter, and the native promoter which controls the gene encoding the polypeptide.

The retroviral plasmid vector is employed to transduce packaging cell lines to form producer cell lines. Examples of packaging cells which may be transfected include, but are not limited to, the PE501, PA317 and GP+aml2. The vector may transduce the packaging cells through any means known in the art. Such means include, but are not limited to, electroporation, the use of liposomes, and $CaPO_4$ precipitation.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced, include but are not limited to, fibroblasts and endothelial cells.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but can vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which can be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation can be accomplished using known buffers and conditions with 10 units to T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456-457 (1973).

Having now generally described the invention, the same will be more readily understood through reference to the following example which is provided by way of illustration, and is not intended to be limiting of the present invention.

EXAMPLE 1

Bacterial Expression and Purification of MPIF-1

The DNA sequence encoding for MPIF-1, ATCC®#75676 is initially amplified using PCR oligonucleotide primers corresponding to the 5' and sequences of the processed MPIF-1 protein (minus the signal peptide sequence) and the vector sequences 3' to the MPIF-1 gene. Additional nucleotides corresponding to Bam HI and XbaI were added to the 5' and 3' sequences respectively. The 5' oligonucleotide primer has the sequence 5'-TCAGGATC-CGTCACAAAAGATGCAGA-3' (SEQ ID NO:12) contains a BamHI restriction enzyme site followed by 18 nucleotides of MPIF-1 coding sequence starting from the presumed terminal amino acid of the processed protein codon. The 3' sequence 5'-CGCTCTAGAGTAAAACGACGGCCAGT-3' (SEQ ID NO:13) contains complementary sequences to an XbaI site.

The restriction enzyme sites correspond to the restriction enzyme sites on the bacterial expression vector pQE-9 (Qiagen, Inc. Chatsworth, Calif.). pQE-9 encodes antibiotic resistance (Amp'), a bacterial origin of replication (ori), an IPTG-regulatable promoter operator (P/O), a ribosome binding site (RBS), a 6-His tag and restriction enzyme sites. pQE-9 is then digested with BamHI and XbaI. The amplified sequences are ligated into pQE-9 and are inserted in frame with the sequence encoding for the histidine tag and the RBS. The ligation mixture is then used to transform E. coli strain M15/rep4 available from Qiagen. M15/rep4 contains multiple copies of the plasmid pREP4, which expresses the lact repressor and also confers kanamycin resistance (Kan'). Transformants are identified by their ability to grow on LB plates and ampicillin/kanamycin resistant colonies are selected. Plasmid DNA is isolated and confirmed by restriction analysis overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6, IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 M Guanidine HCl. After clarification, solubilized MPIF-1 is purified from this solution by chromatography on a Nickel-Chelate column under conditions that allow for tight binding by proteins containing the 6-His tag. Hochuli, E. et al., J. Chromatography 411: 177-184(1984). MPIF-1 (95% pure) is eluted from the column in 6 M guanidine HCl pH 5.0 and for the purpose of renaturation adjusted to 3 M guanidine HCl, 100 mM sodium phosphate, 10 mM glutathione (reduced) and 2 mM glutathione (oxidized). After incubation in this solution for 12 hours the protein is dialyzed to 10 mM sodium phosphate.

Alternatively, the following non-tagged primers were used to clone the gene into plasmid pQE70:

```
5' primer:
                                              (SEQ ID NO:14)
5' CCC GCA TGC GGG TCA CAA AAG ATG CAG 3'
        SphI 3' primer:
                                              (SEQ ID NO:15)
5' AAA GGA TCCTCA ATT CTT CCT GGT CTT 3'
        BamHI       Stop
```

Construction of E. coli Optimized MPIF-1

In order to increase expression levels of MPIF-1 in an E. coli expression system, the codons of the gene were optimized to highly used E. coli codons. For the synthesis of the optimized region of MPIF-1, a series of 4 oligonucleotides were made: mpif-1 oligo numbers 1-4 (set forth below). These overlapping oligos were used in a PCR reaction for seven rounds at the following conditions:

| | |
|---|---|
| Denaturation | 95 degrees 20 seconds |
| Annealing | 58 degrees 20 seconds |
| Extension | 72 degrees 60 seconds |

Following the seven rounds of synthesis, a 5' primer to this region, (ACA TGC ATG CGU GUU ACC AAA GAC GCU GAA ACC GAA UUC AUG AUG UCC (SEQ ID NO:16)) and a 3' primer to this entire region, (GCC CAA GCT TTC AGT TTT TAC GGG TTT TGA TAC GGG (SEQ ID NO:17)), were added to a PCR reaction, containing 1 microliter from the initial reaction of the six oligonucleotides. This product was amplified for 30 rounds using the following conditions:

| Denaturation | 95 degrees 20 seconds |
|---|---|
| Annealing | 55 degrees 20 seconds |
| Extension | 72 degrees 60 seconds |

The product produced by this final reaction was restricted with Sph I and HindIII, and cloned into pQE70, which was also cut with Sph I and HindIII. These clones were expressed and found to have superior expression levels that without the above mutations.

mpif Oligo Number 1:

```
5' GCA TGC GUG UUA CCA AAG ACG CUG    (SEQ ID NO:18)
AAA CCG AAU UCA UGA UGU CCA AAC UGC
CGC UGG AAA ACC CGG UUC UGC UGG ACC
GUU UCC ACG C 3'
``` mpif-1 Oligo Number 2:

```
5' GCU GGA AUC CUA CUU CGA AAC CAA    (SEQ ID NO:19)
CUC CGA AUG CUC CAA ACC GGG UGU UAU
CUU CCU GAC CAA AAA AGG UCG UCG UUU
CUG CGC UAA CCC GUC CGA CAA
ACA GG 3'
``` mpif1 Oligo Number 3:

```
5' AAG CCT TCA GTT TTT ACG GGT TTT    (SEQ ID NO:20)
GAT ACG GGT GTC CAG TTT CAG CAT ACG
CAT ACA AAC CTG AAC CTG TTT GTC GGA
CGG GTT AGC GC 3'
``` mpif-1 Oligo Number 4:

```
5' GGT TTC GAA GTA GGA TTC CAG CAG    (SEQ ID NO:21)
GGA GCA CGG GAT GGA ACG CGG GGT GTA
GGA GAT GCA GCA GTC AGC GGA GGT AGC
GTG GAA ACG GTC CAG C 3'
```

Construction of MPIF-1 Deletion Mutants

Deletion mutants were constructed from the 5' terminus of the MPIF-1 gene using the E. coli optimized MPIF-1 construct set forth above. The primers used to construct the 5' deletions are set forth below. The PCR amplification was performed as set forth above for the E. coli optimized MPIF-1 construct. The products for the Delta 17-A qe6, Delta 23, Delta 28 were restricted with NcoI for the 5' site and HindIII for the 3' site and cloned into plasmid pQE60 that was digested with NcoI and HindIII. All other products were restricted with SphI for the 5' site and HindIII for the 3' site and cloned into plasmid pQE70 that was digested with SphI and HindIII.

The 5' primers used are as follows:

Delta 17-A qe6 (pQE60)

```
5' NcoI gc gca g ccatgg aa aac ccg    (SEQ ID NO:22)
gtt ctg ctg gac 3'
```

The resulting amino acid sequence of this deletion mutant:

```
MENPVLLDRFHATSADCCISYTPRSIPCSLLESYFE    (SEQ ID NO:23)
TNSECSKPGVIFLTKKGRRFCANPSDKQVQVCMRML
KLDTRIKTRKN
```

Delta 16-A qe7 (pQE70)

```
5' SphI gc cat g gcatgc tg gaa aac    (SEQ ID NO:24)
ccg gtt ctg ctg gac
```

The resulting amino acid sequence of this deletion mutant:

```
MLENPVLLDRFHATSADCCISYTPRSIPCSLLESYE    (SEQ ID NQ:25)
ETNSECSKPGVTELTKKGRRFCANPSDKQVQVCMRM
LKLDTRIKTRKN
```

Delta 23 (pQE60)

```
                                        (SEQ ID NO:26)
5' NcoI gc gca g ccatgg ac cgt ttc cac gct acc tcc
```

The resulting amino acid sequence of this deletion mutant:

```
MDRFHATSADCCISYTPRSIPCSLLESYFETNSECS    (SEQ ID NO:27)
KIPGVWLTKKGRRFCANPSDKQVQVCMRMLKLDT
RIKTRKN
```

Delta 24 (pQE70)

```
                                        (SEQ ID NO:28)
5' SphI ggc atg gcatgc gtt tcc acg cta cct cc
```

The resulting amino acid sequence of this deletion mutant:

```
MRFHATSADCCISYTPRSIPCSLLESYFETNSECSKP    (SEQ ID NO:8)
GVIFLTKKGRRFCANPSDKQVQVCMRMLKLDTR
IKTRKN
```

Delta 28 (pQE60)

5' NcoI gcg cag ccatgg cta cct ccg    (SEQ ID NO:29)

ctg act gct gc

The resulting amino acid sequence of this deletion mutant:

MATSADCCISYTPRSIPCSLLESYEETNSECSKPGV (SEQ ID NO:30)

WLTKKGRRFCANPSDKQVQVCMRMLKLDTRIKTRKN

S70 to A mutant (Ser at position 70 was mutated to Ala) (pQE70)

antisense (SEQ ID NO:31)
    ttc gaa gta ggc ttc cag cag sense (SEQ ID NO:32)
    ctg ctg gaa gcc tac ttc gaa 5' SphI full (SEQ ID NO:33)
    gcc atg gcatgc gtg tta cca aag acg ctg aaa cc The resulting amino acid sequence of this deletion mutant:

MRVTKDAETEFMMSKLPLENPVLLDRYHATSADCCI (SEQ ID NO:34)

SYTPRSIPCSLLEaYFETNSECSKPGVIELTKKGRR

FCANPSDKQVQVCMRMLKLDTRIKTRKN

The 3' primer used for all constructs:

3' Hind III (SEQ ID NO:35)
gcc c aagctt tca gt ttt tac ggg ttt tga tac ggg

The full length MPIF-1 sequence (from *E. coli* biased nt's)

MRVTKDAETEFMMSKLPLENPVLLDREHATSADCCIS (SEQ ID NO:7)

YTERSIPCSLLESYFETNSECSKPGVIFLTKKGRRFC

ANFSDKQVQVCMRMLKLDTRIKTRKN

EXAMPLE 2

Bacterial Expression and Purification of MIP-4

The DNA sequence encoding for MIP-4 ATCC® # 75675 was initially amplified using PCR oligonucleotide primers corresponding to the 5' sequences of the processed MIP-4 protein (minus the signal peptide sequence). Additional nucleotides corresponding to Bam HI and XbaI were added to the 5' and 3' sequences respectively. The 5' oligonucleotide primer has the sequence 5'-TCAGGATCCTGTGCA-CAAGTT GGTACC-3' (SEQ ID NO:36) contains a BamHI restriction enzyme site followed by 18 nucleotides of MIP-4 coding sequence starting from the presumed terminal amino acid of the processed protein codon; The 3' sequence 5'-CGCTCTAGAGTAAAACGACGGC CAGT-3' (SEQ ID NO:13) contains complementary sequences to an XbaI site.

The restriction enzyme sites correspond to the restriction enzyme sites on the bacterial expression vector pQE-9 (Qiagen, Inc., Chatsworth, Calif.). pQE-9 encodes antibiotic resistance ($Amp^r$), a bacterial origin of replication (ori), an IPTG-regulatable promoter operator (P/O), a ribosome binding site (RBS), a 6-His tag and restriction enzyme sites. pQE-9 was then digested with BamHI and XbaI The amplified sequences were ligated into pQE-9 and were inserted in frame with the sequence encoding for the histidine tag and the RBS. The ligation mixture was then used to transform *E. coli* strain 15/rep4 available from Qiagen. M15/rep4 contains multiple copies of the plasmid pREP4, which expresses the lad repressor and also confers kanamycin resistance ($Kan^r$). Transformants are identified by their ability to grow on LB plates and ampicillin/kanamycin resistant colonies were selected. Plasmid DNA was isolated and confirmed by restriction analysis. Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 ($O.D.^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 M Guanidine HCl. After clarification, solubilized MIP-4 was purified from this solution by chromatography on a Nickel-Chelate column under conditions that allow for tight binding by proteins containing the 6-His tag. Hochuli, E. et al., J. Chromatography 411:177-184 (1984). MIP-4 (95% pure) was eluted from the column in 6 M guanidine HCl pH 5.0 and for the purpose of renaturation adjusted to 3 Mr guanidine HCl, 100 mM sodium phosphate, 10 mM glutathione (reduced) and 2 mM glutathione (oxidized). After incubation in this solution for 12 hours the protein was dialyzed to 10 mM sodium phosphate.

Alternatively, the following non-tagged primers were used to clone the gene into plasmid pQE60:

```
5' AAA AAG CTT TCA CCC ATT CAC CTT CAG 3'  (SEQ ID NO:37)     pQE60
        HindIII                                                          (3' primer)

5' AAA CCA TGG CAC AAG TTG GTA CCA AC 3'   (SEQ ID NO:38)     pQE60
        NcoI                                                             (5' primer)
```

EXAMPLE 3

Bacterial Expression and Purification of M-CIF

The DNA sequence encoding for M-CIF (ATCC® # 75572) is initially amplified using PCR oligonucleotide primers corresponding to the 5' and 3' sequences of the processed M-CIF protein (minus the signal peptide sequence) and additional nucleotides corresponding to Bam HI and XbaI were added to the 5' and 3' sequences respectively. The 5' oligonucleotide primer has the sequence 5'-GCCCGCGGATCCTCCTCACGGGG ACCTTAC-3' (SEQ ID NO:39) contains a BamHI restriction enzyme site followed by 15 nucleotides of M-CIF coding sequence starting from the presumed terminal amino acid of the processed protein codon; The 3' sequence 5'-GCCTGCTCTAGATCAAAGCAGGGAAGCTCCAG-3' (SEQ ID NO:40) contains complementary sequences to XbaI site a translation stop codon and the last 20 nucleotides of M-CIF coding sequence.

Figure 7:
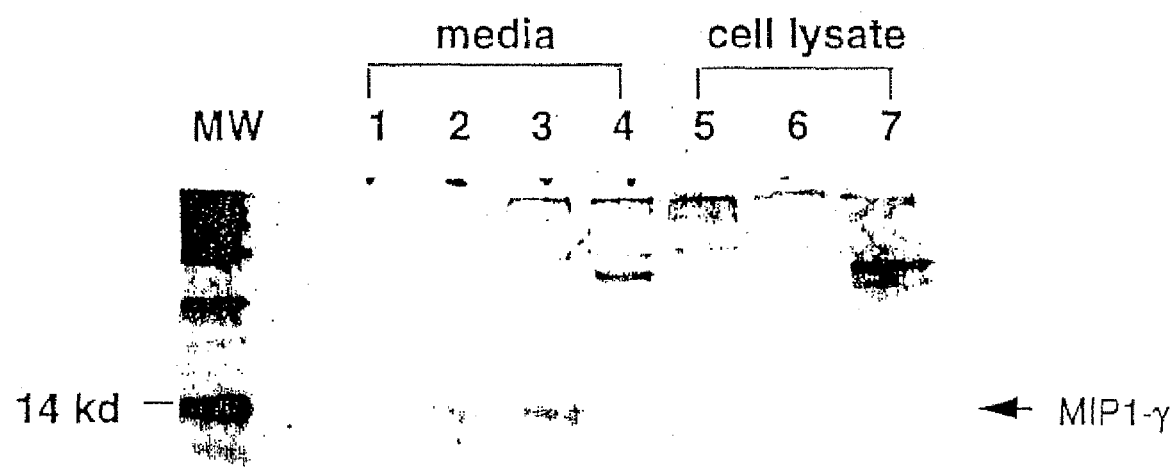
FIG. 7 is a photograph of a gel in which M-CIF has been electrophoresed after the expression of HA-tagged M-CIF in COS cells.
Figure 8:
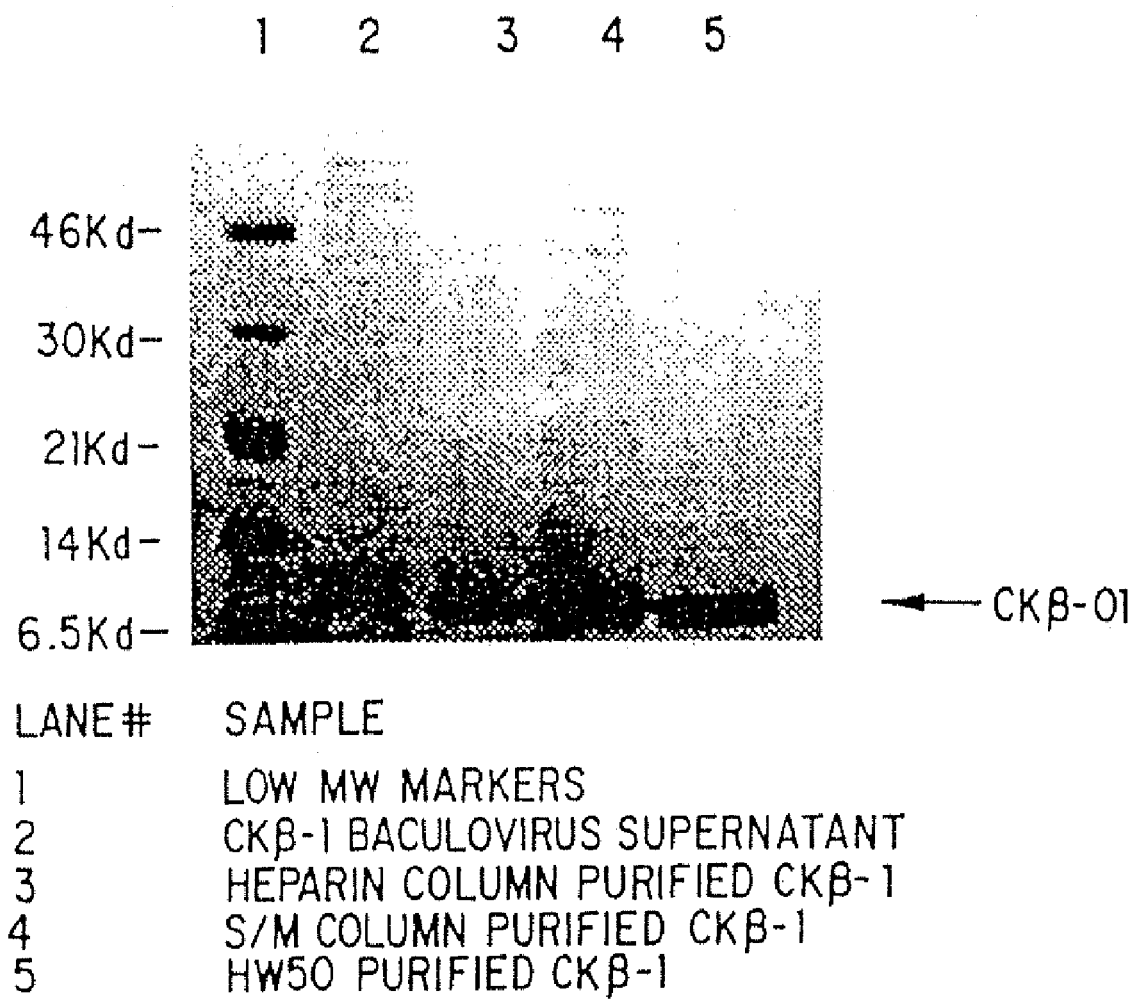
FIG. 8 is a photograph of a SDS-PAGE gel after expression and purification of M-CIF in a baculovirus expression system.

The restriction enzyme sites correspond to the restriction enzyme sites on the bacterial expression vector pQE-9. (Qiagen, Inc. 9259 Eton Avenue, Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 was then digested with BamHI and XbaI. The amplified sequences were ligated into pQE-9 and were inserted in frame with the sequence encoding for the histidine tag and the RBS. FIG. 6 shows a schematic representation of this arrangement. The ligation mixture was then used to transform E. coli strain available from Qiagen under the trademark M15/rep4. M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized M-CIF was purified from this solution by chromatography on a Nickel-Chelate column under conditions that allow for tight binding by proteins containing the 6-His tag Hochuli, E. et al., J. Chromatography 411:177-184 (1984). M-CIF (95% pure) was eluted from the column in 6 M guanidine HCl pH 5.0 and for the purpose of renaturation adjusted to 3 M guanidine HCl, 100 mM sodium phosphate, 10 mM glutathione (reduced) and 2 mM glutathione (oxidized). After incubation in this solution for 12 hours the protein was dialyzed to 10 mM sodium phosphate. The presence of a new protein corresponding to 14 kDa following induction demonstrated expression of the M-CIF (FIG. 7).

Alternatively, the following non-tagged primers were used to insert the gene into plasmid pQE60:

```
5' primer:
                                              (SEQ ID NO:41)
  5' AAA TCA TGA CCA AGA CTG AAT CCT CCT 3'
          BspHI 3' primer:
                                              (SEQ ID NO:42)
  5' AAA AAG CTT TCA GTT CTC CTT CAT GTC 3'
          HindIII
```

EXAMPLE 4

Most of the vectors used for the transient expression of the MPIF-1, M-CIF or MIP-4 protein gene sequence in mammalian cells should carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLV1, HIV1 and the early promoter of the cytomegalovirus (CMV). However, cellular signals can also be used (e.g., human actin promoter). Suitable expression vectors for use in practicing the present invention include, for example, vectors such as pSVL and pMSG (Pharmacia, Uppsala, Sweden), pRSVcat (ATCC® 37152), pSV2dhfr (ATCC® 37146) and pBC12MI (ATCC® 67109). Mammalian host cells that could be used include, human HeLa, 283, H9 and Jurkat cells, mouse NIH3T3 and C127 cells, Cos 1, Cos 7 and CV1, African green monkey cells, quail QC1-3 cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) (Murphy et al., Biochem. J. 227:277-279 (1991); Bebbington et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., Molecular and Cellular Biology, 438-447 (March, 1985)) plus a fragment of the CMV-enhancer (Boshart et al., Cell 41:521-530 (1985)). Multiple cloning sites, e.g., with the restriction enzyme cleavage sites BamHI, XbaI and Asp718, facilitate the cloning of the gene of interest. The vectors contain in addition the 3□ intron, the polyadenylation and termination signal of the rat preproinsulin gene.

A. Expression of Recombinant MPIF-1 in COS Cells

The expression of plasmid, CMV-MPIF-1 HA is derived from a vector pcDNAI/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire MPIF-1 precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (Wilson, H., et al., Cell 37:767 (1991)). The infusion of HA tag to our target protein allows easy detection of the recombinant protein with an antibody that recognizes the HA epitope.

The plasmid construction strategy is described as follows:

The DNA sequence, ATCC® # 75676, encoding for MPIF-1 is constructed by PCR on the original EST cloned using two primers: the 5' primer 5'-GGAAAGCTT ATGAAGGTCTCCGTGGCT-3' (SEQ ID NO:43) contains a HindRIII site followed by 18 nucleotides of MPIF-1 coding sequence starting from the initiation codon; the 3' sequence 5'-CGCTCTAGATCAAGCGTAGTCTGG-GACGTCGTATGGGTAATTCTTCCTGG TCTTGATCC-3' (SEQ ID NO:44) contains complementary sequences to Xba I site, translation stop codon, HA tag and the last 20 nucleotides of the MPIF-1 coding sequence (not including the stop codon). Therefore, the PCR product contains a HindIII site, MPIF-1 coding sequence followed by HA tag fused in frame, a translation termination stop codon next to the HA tag, and an XbaI site. The PCR amplified DNA fragment and the vector, pcDNA1/Amp, are digested with HindIII and XbaI restriction enzyme and ligated. The ligation mixture is transformed into E. coli strain SURE (available from Stratagene Cloning Systems, 11099 North Torrey Pines Road, La Jolla, Calif. 92037) the transformed culture is plated on ampicillin media plates and resistant colonies are selected. Plasmid DNA is isolated from transformants and examined by restriction analysis for the presence of the correct fragment. For expression of the recombinant MPIF-1, COS cells are transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the MPIF-1-HA protein is detected by radiolabeling and immunoprecipitation method. (E. Harlow, D. Lane, Antibodies: A Laboratory Manual, Cold Spring Harbor Laboratory Press, (1988)). Cells are labeled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media are precipitated with a HA specific monoclonal antibody. Proteins precipitated are analyzed on 15% SDS-PAGE gels.

B. Cloning and Expression in CHO Cells

The vector pC1 is used for the expression of MPIF-1 protein. Plasmid pC1 is a derivative of the plasmid pSV2-dhfr (ATCC® Accession No. 37146). Both plasmids contain the mouse DHFR gene under control of the SV40 early promoter Chinese hamster ovary- or other cells lacking dihydrofolate activity that are transfected with these Plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357-1370, Hamlin, J. L. and Ma, C. 1990, Biochem. et Biophys. Acta, 1097:107-143, Page, M. J. and Sydenham, M. A. 1991, Biotechnology Vol. 9:64-68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the an to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., Molecular and Cellular Biology, March 1985:438-4470) plus a fragment isolated from the enhancer of the immediate early gene of human cytomegalovirus (CMV) Boshart et al., Cell 41:521-530, 1985). Downstream of the promoter are the following single restriction enzyme cleavage sites that allow the integration of the genes: BamHI, followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, eg., G418 plus methotrexate.

The plasmid pC1 is digested with the restriction enzyme BamHI and then dephosphorylated using calf intestinal phosphates by procedures known in the art. The vector is then isolated from a 1% agarose gel.

The DNA sequence encoding MPIF-1, ATCC® No. 75676, is amplified using PCR oligonucleotide primers corresponding to the 5' and 3' sequences of the gene:

The 5' primer has the sequence:

(SEQ ID NO:45)
5' AAA <u>GGA TTC GCC ACC</u> ATG AAG GTC TCC GTG GTC 3'
        BamHI  KOZAK containing the underlined BamHI restriction enzyme site and a portion of the sequence encoding the MPIF-1 protein of FIG. 1 (SEQ ID NO:3). Inserted into an expression vector, as described below, the 5' end of the amplified fragment encoding human MPIF-1 provides an efficient signal peptide. An efficient signal for initiation of translation in eukaryotic cells, as described by Kozak, M., J. Mol. Biol. 196: 947-950 (1987) is appropriately located in the vector portion of the construct.

The 3' primer has the sequence:

(SEQ ID NO:46)
5' AAA <u>GGA TCC TCA</u> ATT CTT CCA GGT CTT 3'
       BamHI  Stop containing the Asp718 restriction site and a portion of nucleotides complementary to the MPIF-1 coding sequence set out in FIG. 1 (SEQ ID NO:3), including the stop codon.

The amplified fragments are isolated from a 1% agarose gel as described above and then digested with the endonucleases BamHI and Asp718 and then purified again on a 1% agarose gel.

The isolated fragment and the dephosphorylated vector are then ligated with T4 DNA ligase. E. coli HB101 cells are then transformed and bacteria identified that contained the plasmid pC1 inserted in the correct orientation using the restriction enzyme BamHI. The sequence of the inserted gene is confirmed by DNA sequencing.

Transfection of CHO-DHFR-Cells

Chinese hamster ovary cells lacking an active DHFR enzyme are used for transfection. 5 μg of the expression plasmid C1 are cotransfected with 0.5 μg of the plasmid pSVneo using the lipofecting method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greitter, Germany) and cultivated from 10-14 days. After this period, single clones are trypsinized and then seeded in 6-well petri dishes using different concentrations of methotrexate (25 nM, 50 nM, 100 nM, 200 nM, 400 nM). Clones growing at the highest concentrations of methotrexate are then transferred to new 6-well plates containing even higher concentrations of methotrexate (500 nM, 1 μM, 2 μM, 5 μM). The same procedure is repeated until clones grow at a concentration of 100 μM.

The expression of the desired gene product is analyzed by Western blot analysis and SDS-PAGE.

EXAMPLE 5

A. Expression of Recombinant MIP-4 in COS Cells

The expression of plasmid, CMV-MIP-4 HA is derived from a vector pcDNAI/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire MIP-4 precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (Wilson, H., et al., Cell 37:767 (1984)). The infusion of HA tag to the target protein allows easy detection of the recombinant protein with an antibody that recognizes the HA epitope.

The plasmid construction strategy is described as follows:

The DNA sequence ATCC® No. 75675 encoding for MIP-4 is constructed by PCR using two primers: the 5' primer 5'-GGAAAGCTTATGAAGGGCCTTGCA GCTGCC-3' (SEQ ID NO:47) contains a HindIII site followed by 20 nucleotides of MIP-4 coding sequence starting from the initiation codon; the 3' sequence 5'-CGCTCTAGA TCAAB-CGTAGTCTGGGACGTCGTATGGGTAG-GCATTCAGCTTCAGGTC-3' (SEQ ID NO:48) contains complementary sequences to Xba I site, translation stop codon, HA tag and the last 19 nucleotides of the MIP-4 coding sequence (not including the stop codon). Therefore, the PCR product contains a HindIII site, MIP-4 coding sequence followed by HA tag fused in frame, a translation termination stop codon next to the HA tag, and an XbaI site. The PCR amplified DNA fragment and the vector, pcDNAI/Amp, are digested with HindIII and XbaI restriction enzyme and ligated. The ligation mixture is transformed into E. coli strain SURE (available from Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant MIP-4, COS cells are transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the MIP-4-HA protein is detected by radiolabeling and immunoprecipitation method. (E. Harlow, D. Lane, Antibodies: A Laboratory Manual, Cold Spring Harbor Laboratory Press, (1988)). Cells are labeled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5). (Wilson, H., et al., Cell 37:767 (1984)). Both cell lysate and culture media are precipitated with a HA specific monoclonal antibody. Proteins precipitated are analyzed on 15% SDS-PAGE gels.

B. Cloning and Expression in CHO Cells

The vector pC1 is used for the expression of MIP-4 protein. Plasmid pC1 is a derivative of the plasmid pSV2-dhfr (ATCC® Accession No. 37146). Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g. Alt, F. W., Kellems, R. M., Bertino, J. R., and Schimke, R. T., 1978, J. Biol. Chem. 253:1357-1370, Hamlin, J. L. and Ma, C. 1990, Biochem. et Biophys. Acta, 1097:107-143, Page, M. J. and Sydenham, M. A. 1991, Biotechnology Vol. 9:64-68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., Molecular and Cellular Biology, March 1985:438-4470) plus a fragment isolated from the enhancer of the immediate early gene of human cytomegalovirus (CMV) (Bushart et al., Cell 41:521-530, 1985). Downstream of the promoter are the following single restriction enzyme cleavage sites that allow the integration of the genes: BamHI, followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphates by procedures known in the art. The vector is then isolated from a 1% agarose gel.

The DNA sequence encoding MIP-4, ATCC® No. 75675, is amplified using PCR oligonucleotide primers corresponding to the 5' and 3' sequences of the gene:

The 5' primer has the sequence:

(SEQ D NO:49)
5' AAA GGA TCC GCC ACC ATG AAG GGC CTT GCA AGC 3'
        BamHI   KOZAK containing the underlined BamHI restriction enzyme site and a portion of the sequence encoding the MIP-4 protein of FIG. 3 (SEQ ID NO:5). Inserted into an expression vector, as described below, the 5' end of the amplified fragment encoding human MIP-4 provides an efficient signal peptide. An efficient signal for initiation of translation in eukaryotic cells, as described by Kozak, M., J. Mol. Biol. 196:947-950 (1987) is appropriately located in the vector portion of the construct.

The 3' primer has the sequence:

(SEQ ID NO:50)
5' AAA GGA TTC TCA GGC ATT CAG CTT CAG 3'
        BamHI   Stop containing the Asp718 restriction site followed by nucleotides complementary to a portion of the MIP-4 coding sequence set out in FIG. 3 (SEQ ID NO:5), including the stop codon.

The amplified fragments are isolated from a 1% agarose gel as described above and then digested with the endonucleases BamHI and Asp718 and then purified again on a 1% agarose gel.

The isolated fragment and the dephosphorylated vector are then ligated with T4 DNA ligase. E. coli HB101 cells are then transformed and bacteria identified that contained the plasmid pC1 inserted in the correct orientation using the restriction enzyme BamHI. The sequence of the inserted gene is confirmed by DNA sequencing.

Transfection of CHO-DHFR-Cells

Chinese hamster ovary cells lacking an active DHFR enzyme are used for transfection. Five µg of the expression plasmid C1 are cotransfected with 0.5 µg of the plasmid pSVneo using the lipofecting method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10-14 days. After this period, single clones are trypsinized and then seeded in 6-well petri dishes using different concentrations of methotrexate (25 nM, 50 nM, 100 nM, 200 nM, 400 nM). Clones growing at the highest concentrations of methotrexate are then transferred to new 6-well plates containing even higher concentrations of methotrexate (500 nM, 1 µM, 2 µM, 5 µM). The same procedure is repeated until clones grow at a concentration of 100 µM.

The expression of the desired gene product is analyzed by Western blot analysis and SDS-PAGE.

EXAMPLE 6

A. Expression of Recombinant M-CIF in COS Cells

The expression of plasmid, CMV-M-CIF HA is derived from a vector pcDNA1/Amp (Invitrogen) containing 1) SV40 origin of replication, 2) ampicillin resistance gene, 3) E. coli replication origin, 4) CMV promoter followed by a polylinker region, a SV40 intron and polyadenylation site. A DNA fragment encoding the entire M-CIF precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (Wilson, H., et al., Cell 37:767 (1984)). The infusion of HA tag to our target protein allows easy detection of the recombinant protein with an antibody that recognizes the HA epitope.

The plasmid construction strategy is described as follows: The DNA sequence encoding for M-CIF, ATCC® # 75572, was constructed by PCR using two primers: the 5' primer 5'-GGAAAGCTTATGAAGATTCCGTGGCTGC-3' (SEQ ID NO:51) contains a HindIII site followed by 20 nucleotides of M-CIF coding sequence starting from the initiation codon; the 3' sequence 5'-CGCTCTAGATCA AGCGTAGTCTGGGACGTCGTATGGG-TAGTTCTCCTTCATGTCCTTG-3' (SEQ ID NO:52) contains complementary sequences to Xba I site, translation stop codon, HA tag and the last 19 nucleotides of the M-CIF coding sequence (not including the stop codon). Therefore, the PCR product contains a HindIII site, M-CIF coding sequence followed by HA tag fused in frame, a translation termination stop codon next to the HA tag, and an XbaI site. The PCR amplified DNA fragment and the vector, pcDNAI/Amp, were digested with HindIII and XbaI restriction enzyme and ligated. The ligation mixture was transformed into E. coli strain SURE (Stratagene Cloning Systems, La Jolla, Calif.) the transformed culture was plated on ampicillin media plates and resistant colonies were selected. Plasmid DNA was isolated from transformants and examined by restriction analysis for the presence of the correct fragment. For expression of the recombinant M-CIF, COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the M-CIF-HA protein was detected by radiolabeling and immunoprecipitation method. (E. Harlow, D. Lane, Antibodies: A Laboratory Manual, Cold Spring Harbor Laboratory Press, (1988)). Cells were labeled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson, H., et al., Cell 37:767 (1984)). Both cell lysate and culture media were precipitated with a HA specific monoclonal antibody. Proteins precipitated were analyzed on 15% SDS-PAGE gels.

B. Cloning and Expression in CHO Cells

The vector pC1 is used for the expression of M-CIF protein. Plasmid pC1 is a derivative of the plasmid pSV2-dhfr (ATCC® Accession No. 37146). Both plasmids contain the mouse DHFR gene under control of the SV40 early promoter Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357-1370, Hamlin, J. L. and Ma, C. 1990, Biochem. et Biophys. Acta, 1097:107-143, Page, M. J. and Sydenham, M. A. 1991, Biotechnology Vol. 9:64-68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., Molecular and Cellular Biology, March 1985:438-4470) plus a fragment isolated from the enhancer of the immediate early gene of human cytomegalovirus (CMV) (Boshart et al., *Cell* 41:521-530, 1985). Downstream of the promoter are the following single restriction enzyme cleavage sites that allow the integration of the genes: BamHI, followed by the 3☐ intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well, Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphates by procedures known in the art. The vector is then isolated from a 1% agarose gel.

The DNA sequence encoding M-CIF, ATCC® No. 75572, is amplified using PCR oligonucleotide primers corresponding to the 5' and 3' sequences of the gene:

The 5' primer has the sequence:

```
                                    (SEQ ID NO:53)
5' AAA GGA TCC GCC ACC ATG AAG ATC TCC GTG GCT 3'
        BamHI   KOZAK
``` containing the underlined BamH1 restriction enzyme site and the sequence of M-CIF of FIG. 2 (SEQ ID NO:1). Inserted into an expression vector, as described below, the 5' end of the amplified fragment encoding human M-CIF provides an efficient signal peptide. An efficient signal for initiation of translation in eukaryotic cells, as described by Kozak, M., *J. Mol. Biol.* 196:947-950 (1987) is appropriately located in the vector portion of the construct.

The 3' primer has the sequence:

```
                                    (SEQ ID NO:54)
5' AAA GGA TCC TCA GTT CTC CTT CAT GTC CTT 3'
        BamHI Stop
``` containing the Asp718 restriction site and a portion of the M-CIF coding sequence set out in FIG. 2 (SEQ ID NO:1), including the stop codon.

The amplified fragments are isolated from a 1% agarose gel as described above and then digested with the endonucleases BamHI and Asp718 and then purified again on a 1% agarose gel.

The isolated fragment and the dephosphorylated vector are then ligated with T4 DNA ligase. *E. coli* HB101 cells are then transformed and bacteria identified that contained the plasmid pC1 inserted in the correct orientation using the restriction enzyme BamHI. The sequence of the inserted gene is confirmed by DNA sequencing.

Transfection of CHO-DHFR-Cells

Chinese hamster ovary cells lacking an active DHFR enzyme are used for transfection. Five µg of the expression plasmid C1 are cotransfected with 0.5 µg of the plasmid pSVneo using the lipofecting method (Felgner et al. supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10-14 days. After this period, single clones are trypsinized and then seeded in 6-well petri dishes using different concentrations of methotrexate (25 nM, 50 nM, 100 nM, 200 nM, 400 nM). Clones growing at the highest concentrations of methotrexate are then transferred to new 6-well plates containing even higher concentrations of methotrexate (500 nM, 1 µM, 2 µM, 5 µM). The same procedure is repeated until clones grow at a concentration of 100 µM.

The expression of the desired gene product is analyzed by Western blot analysis and SDS-PAGE.

EXAMPLE 7

Expression Pattern of M-CIF in Human Tissue

Northern blot analysis was carried out to examine the levels of expression of M-CIF in human tissues. Total cellular RNA samples were isolated with RNAzol™ B system (Biotecx Laboratories, Inc. Houston, Tex.). About 10 ug of total RNA isolated from each human tissue specified was separated on 1% agarose gel and blotted onto a nylon filter. (Sambrook, Fritsch, and Maniatis, *Molecular Cloning, A Laboratory Manual*, Cold Spring Harbor Press, (1989)). The labeling reaction was done according to the Stratagene Prime-It kit with 50 ng DNA fragment. The labeled DNA was purified with a Select-G-50 column. (5 Prime-3 Prime, Inc., Boulder, Colo.). The filter was then hybridized with radioactive labeled full length M-CIF gene at 1,000,000 cpm/ml in 0.5 M NaPO$_4$, pH 7.4 and 7% SDS overnight at 65° C. After wash twice at room temperature and twice at 60° C. with 0.5×SSC, 0.1% SDS, the filter was then exposed at −70° C. overnight with an intensifying screen.

EXAMPLE 8

Expression Pattern of MPIF-1 in Human Tissue

Northern blot analysis was carried out to examine the levels of expression of MPIF-1 in human tissues. Total cellular RNA samples were isolated with RNAzol™ B system (Biotecx Laboratories, Inc. 6023 South Loop East, Houston, Tex. 77033). About 10 ug of total RNA isolated from each human tissue specified is separated on 1% agarose get and blotted onto a nylon filter. (Sambrook, Fritsch, and Maniatis, Molecular Cloning, Cold Spring Harbor Press, (1989)). The labeling reaction is done according to the Stratagene Prime-It kit with 50 ng DNA fragment. The labeled DNA is purified with a Select-G-50 column. (5 Prime-3 Prime, Inc. 5603 Arapahoe Road, Boulder, Colo. 80303). The filter is then hybridized with radioactive labeled full length MPIF-4 gene at 1,000,000 cpm/ml in 0.5 M $NaPO_4$, pH 7.4 and 7% SDS overnight at 65° C. After wash twice at room temperature and twice at 60° C. with 0.5× SSC, 0.1% SDS, the filter is then exposed at −70° C. overnight with an intensifying screen.

EXAMPLE 9

Expression Pattern of MIP-4 in Human Cells

Northern blot analysis was carried out to examine the levels of expression of MIP in human cells. Total cellular RNA samples were isolated with RNAzol™ B system (Biotecx Laboratories, Inc. 6023 South Loop East, Houston, Tex. 77033). About 10 ug of total RNA isolated from each human tissue specified was separated on 1% agarose gel and blotted onto a nylon filter. (Sambrook, Fritsch, and Maniatis, Molecular Cloning, Cold Spring Harbor Press, (1989)). The labeling reaction was done according to the Stratagene Prime-It kit with 50 ng DNA fragment. The labeled DNA was purified with a Select-G-50 column. (5 Prime-3 Prime, Inc. 5603 Arapahoe Road, Boulder, Colo. 80303). The filter was then hybridized with radioactive labeled full length MIP-4 gene at 1,000,000 cpm/ml in 0.5 M $NaPO_4$, pH 7.4 and 7% SDS overnigIt at 65° C. After wash twice at room temperature and twice at 60° C. with 0.5×SSC, 0.1% SDS, the filter was then exposed at −70° C. overnight with an intensifying screen. See FIG. 6.

EXAMPLE 10

Expression and Purification of Chemokine MPIF-1 using a Baculovirus Expression System SF9 cells were infected with a recombinant baculovirus designed to express the MPIF-1 cDNA. Cells were infected at an MOI of 2 and cultured at 28° C. for 72-96 hours. Cellular debris from the infected culture was removed by low speed centrifugation. Protease inhibitor cocktail was added to the supernatant at a final concentration of 20 µg/ml Pefabloc SC, 1 µg/ml leupeptin, 1 µg/ml E-64 and 1 mM EDTA. The level of MPIF-1 in the supernatant was monitored by loading 20-30 µl of supernatant only 15% SDS-PAGE gels. MPIF-1 was detected as a visible 9 Kd band, corresponding to an expression level of several mg per liter. MPIF-1 was further purified through a three-step purification procedure; Heparin binding affinity chromatography. Supernatant of baculovirus culture was-mixed with ⅓ volume of buffer containing 100 mM HEPES/MES/NaOAc pH 6 and filtered through 0.22 µm membrane. The sample was then applied to a heparin binding column (HEI poros 20, Bi-Perceptive System Inc.). MPIF-1 was eluted at approximately 300 mM NaCl in a linear gradient of 50 to 500 mM NaCl in 50 mM HEPES/MES/NaOAc at pH 6; Cation exchange chromatography. The MPIF-1-enriched from heparin chromatography was subjected to a 5-fold dilution with a buffer containing 50 mM HEPES/MES/NaOAc pH 6. The resultant mixture was then applied to a cation exchange column (S/M poros 20, Sio-Perceptive System Inc.). MPIF-1 was eluted at 250 mM NaCl in a linear gradient of 25 to 300 mM NaCl it 50 mM HEPES/MES/NaOAc at pH 6; Size exclusion chromatography. Following the cation exchange chromatography, MPIF-1 was further purified by applying to a size exclusion column (HW50, TOSO HAAS, 1.4×45 cm). MPIF-1 fractionated at a position close to a 13.7 Kd molecular weight standard (RNase A), corresponding to the dimeric form of the protein.

Figure 9A:
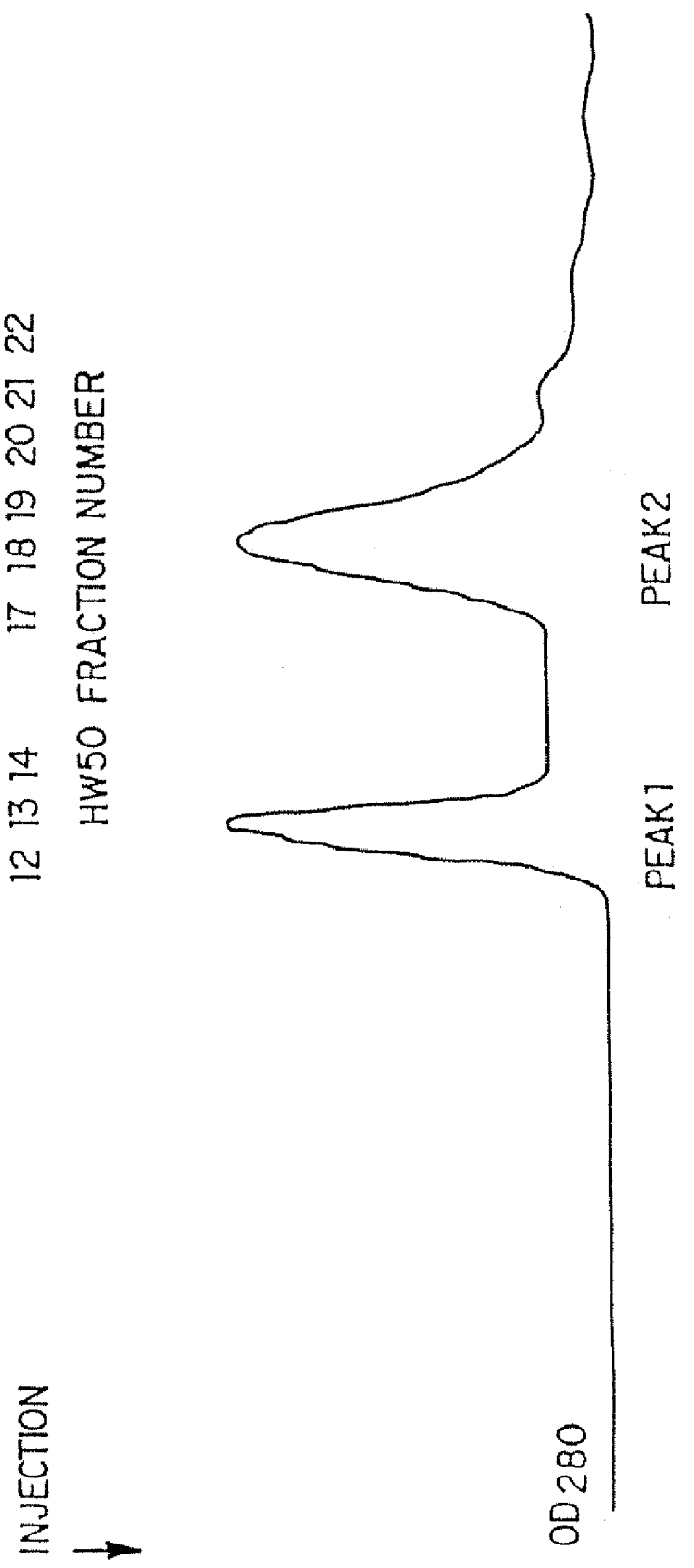
Figure 9B:
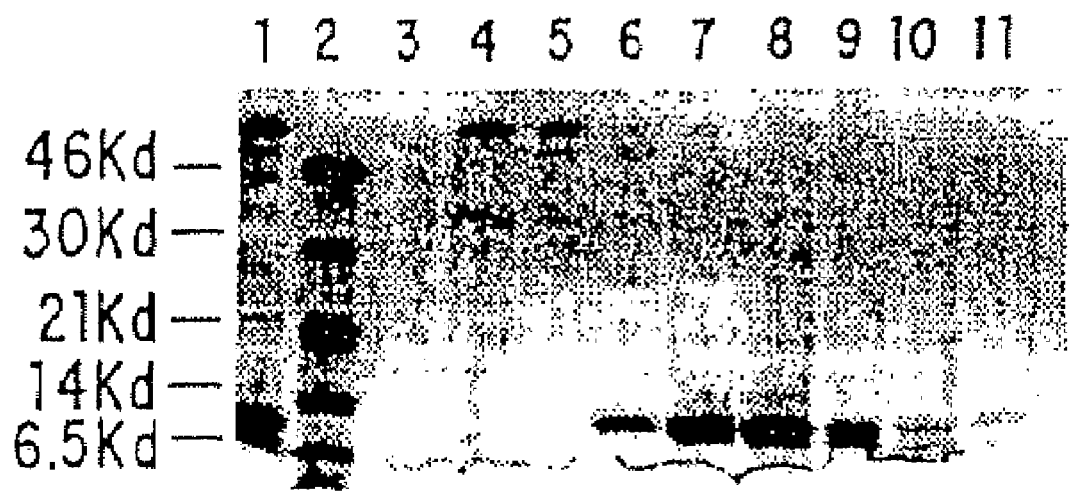
FIG. 9B is a photograph of an SDS-PAGE gel of such purified MPIF-1.

Following the three-step purification described above, the resultant MPIF-1 was judged to be greater than 90% pure as determined from commassie blue staining of an SDS-PAGE gel (FIG. 9B).

The purified MPIF-1 was also tested for endotoxin/LPS contamination. The LPS content was less than 0.1 ng/ml according to LAL assays (Bio Whittaker).

EXAMPLE 11

Effect of Baculovirus-Expressed M-CIF and MPIF-1 on M-CSF and SCF-Stimulated Colony Formation of Freshly Isolated Bone Marrow Cells A low density population of mouse bone marrow cells were incubated in a treated tissue culture dish for one hour at 37° C. to remove monocytes, macrophages, and other cells that adhere to the plastic surface. The non-adherent population of cells were then plated (10,000 cells/dish) in agar containing growth medium in the presence or absence of the factors shown in FIG. 14. Cultures were incubated for 10 days at 37° C. (88% $N_2$, 5% $CO_2$, and 7% $O_2$) and colonies were score expressed as mean number of colonies and was obtained from assays performed in triplicate.

EXAMPLE 12

Effect of MPIF-1 and M-CIF on IL-3 and SCF Stimulated Proliferation and Differentiation of Lin-Population of Bone Marrow Cells A population of mouse bone marrow cells enriched in primitive hematopoietic progenitors was obtained using a negative selection procedure, where the committed cells of most of the lineages were removed using a panel of monoclonal antibodies (anti cdIIb, CD4, CD8, CD45R, and Gr-1 antigens) and magnetic beads. The resulting population of cells (lineage depleted cells) were plated ($5 \times 10^4$ cells/ml) in the presence or absence of the indicated chemokine (50 ng/ml) in a growth medium supplement ng/ml) plus stem cell factor (SCF) (100 ng/ml). After seven days of incubation at 37° C. in a humidified incubator (5% $CO_2$, 7% $O_2$, and 88% $N_2$ environment), cells were harvested and assayed for the HPP-CFC, and immature progenitors. In addition, cells were analyzed for the expression of certain differentiation antigens by FACScan. Colony data are expressed as mean number of colonies ±SD) and were obtained from assays performed in six dishes for each population of cells (FIG. 15).

EXAMPLE 13

MPIF-1 Inhibits Colony Formation in Response to IL-3, M-CSF, and GM-CSF

Mouse bone marrow cells wore flushed from both the femur and tibia, separated on a ficoll density gradient and monocytes removed by plastic adherence. The resulting population of cells were incubated overnight in an MEM-based medium supplemented with IL-3 (5 ng/ml), GIM-CSF (5 ng/ml), M-CSF (10 ng/ml) and G-CSF (10 ng/ml). These cells were plated at 1,000 cells/dish in agar-based colony formation assays in the presence of IL-3 (5 ng/ml), GM-CSF (5 ng/ml) or M-CSF (5 ng/ml) with or without M-CIF at 50 ng/ml. The data is presented as colony formation as a percentage of the number of colonies formed with the specific factor alone. Two experiments are shown with the data depicted as the average of duplicate dishes with error bars indicating the standard deviation for each experiment (FIG. 17).

EXAMPLE 14

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted and the chunks of tissue remain fixed to the bottom of the flask and fresh media (e.g. Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, *DNA* 77219-25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer having contains a HindIII site. Equal quantities of the Moloney murine sarcoma virus linear backbone and the EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+aml2 packaging cells are grown in tissue culture to confluent density in Dulbeccol's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

EXAMPLE 15

In Vitro Myeloprotection

Figure 21A:
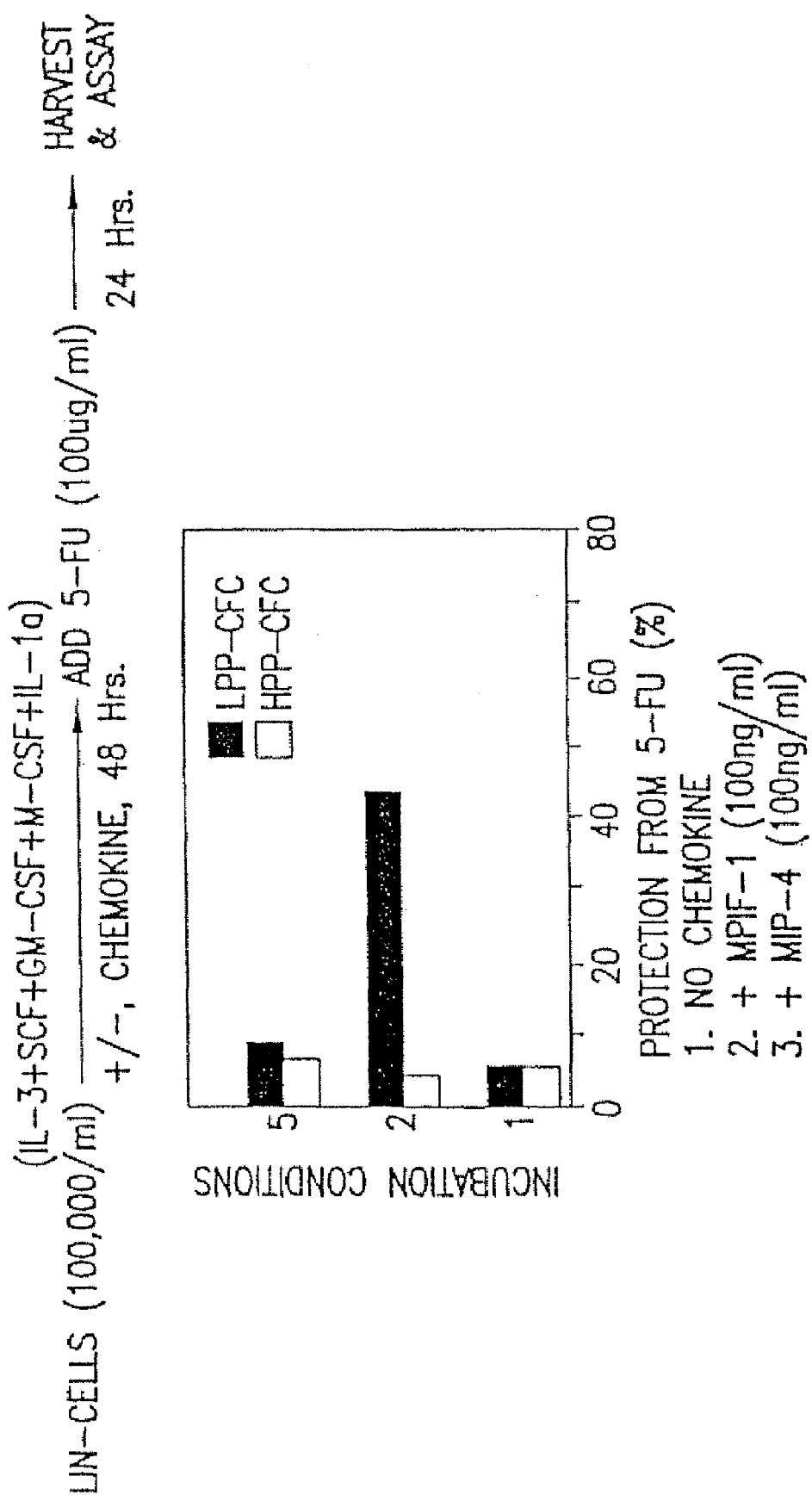
FIG. 21A-B.

As demonstrated above, MPIF-1 is a potent inhibitor of the Low Proliferative Potential Colony-Forming Cell (LPP-CFC), a myeloid progenitor that gives rise to granulocyte and monocyte lineages. To demonstrate that MPIF-1 provides protection for LPP-CFC from the cytotoxicity of the cell cycle acting chemotherapeutic drug, lineage-depleted populations of cells (Lin-cells) were isolated from mouse bone marrow and incubated in the presence of multiple cytokines with or without MPIF-1. After 48 hours, one set of each culture received 5-Fu and the incubation was then continued for additional 24 hours, at which point the numbers of surviving LLP-CFC were determined by a clonogenic assay. As shown in FIG. 21A, ~40% of LPP-CFC were protected from the 5-Fu-induced cytotoxicity in the presence of MPIF-1, whereas little protection (<5%) of LPP-CFC was observed in the absence of MPIF-1 or in the presence of an unrelated protein. High Proliferative Potential Colony-Forming Cells (HPP-CFC) were not protected by MPIF-1 under the same culture conditions, demonstrating specificity of the MPIF-1 protective effect.

Figure 21B:
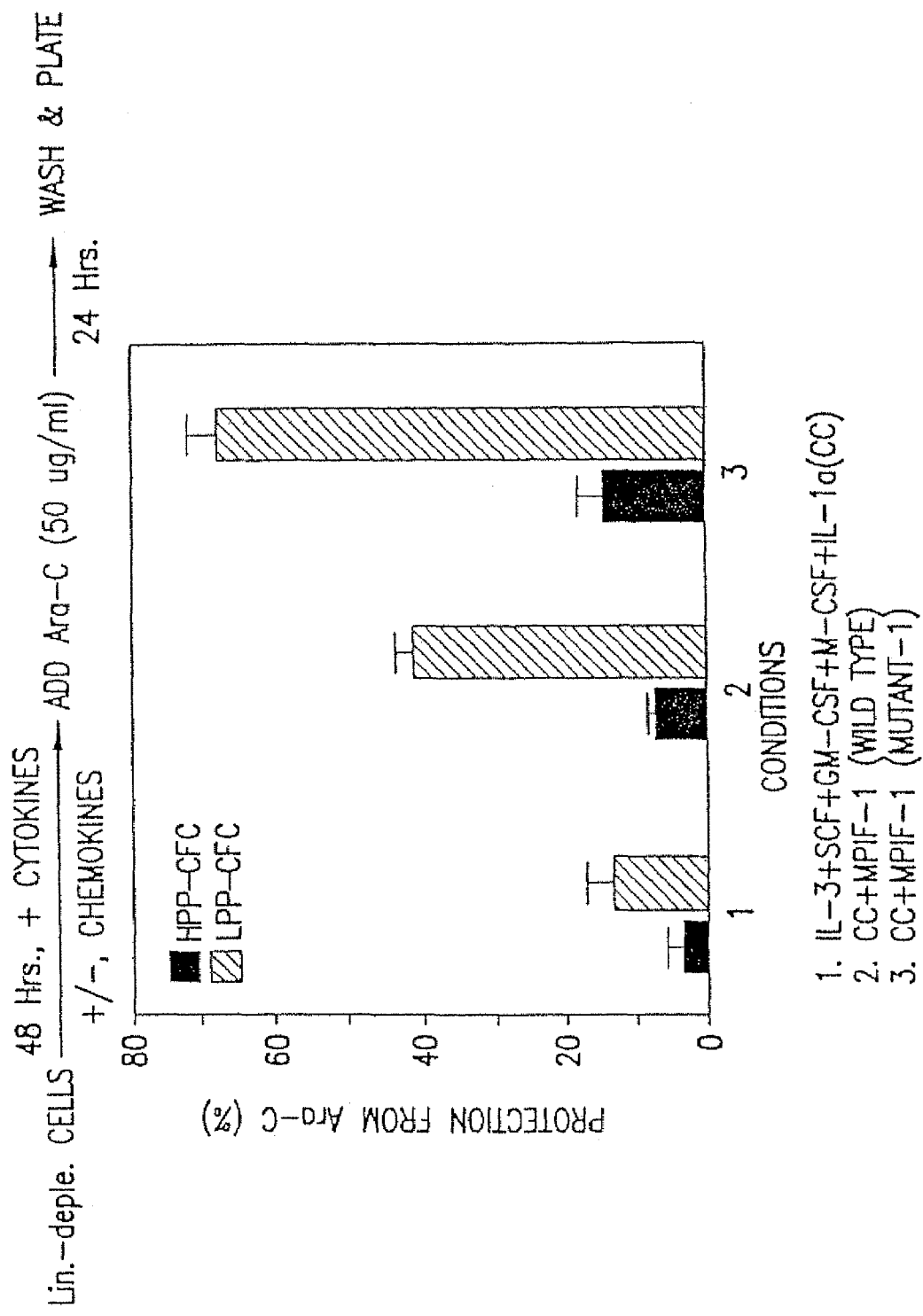

Similar experiments were performed using the chemotherapeutic agent, Ara-C instead of 5-Fu. As shown in FIG. 21B, dramatic protection of LPP-CFC by both from wild type MPIF-1 and a mutant MPIF-1 (i.e., mutant-1, see Example 17 below for description of this mutant). Thus, MPIF-1 is able to protect LPP-CFC from the cytotoxicity induced by both chemotherapeutic drugs, 5-Fu and Ara-C.

EXAMPLE 16

In Vivo Myeloprotection

The in vitro myeloprotection results suggest that myclotoxicity elicited by the cytotoxic drugs, a severe side effect observed in cancer patients undergoing chemotherapy, might be ameliorated if the critical cell types within the bone marrow could be protected by MPIF-1 during the period of action of the chemotherapeutic drugs. To demonstrate in vivo myeloprotection, two types of experiments were performed in mice. In one experiment, a group of mice (Group-4) were injected (I.P.) daily for three days, at 24 hour intervals, with 1.0 mg/Kg MPIF-1, and on the third day these mice were also injected (I.P.) with 5-Fu at 150 mg/Kg. Animals injected with either saline (Group-1), MPIF-1 alone (Group-2), or 5-Fu alone (Group-3) served as controls. Then, four animals from each of the groups were sacrificed at 3, 6, and 10 days post 5-Fu administration to determine White Blood Cell (WBC) counts in the peripheral blood. As shown in the FIG. 22, injection of MPIF-1 alone had little effect on the WBC counts. As expected, 5-Fu treatment resulted in a dramatic reduction in the circulating WBC counts on day 6 post 5-Fu. Significantly, animals treated with MPIF-1 prior to 5-Fu administration exhibited about two fold higher WBC counts in the blood compared to animals treated with 5-Fu alone. Thus, treatment of mice with MPIF-1 prior to 5-Fu results in the accelerated recovery from neutropenia.

Hematopoietic stem and multipotential progenitor cells in the bone marrow are responsible for restoring all the hematopoietic lineages following chemotherapy. In normal individuals, these cells divide less frequently, and are, therefore, spared from a single dose of the chemotherapeutic drug. However, these cells are killed if a second dose of the drug is administered within three days after the first dose because the critical progenitor cell types in the marrow are rapidly dividing during this period.

Figure 23:
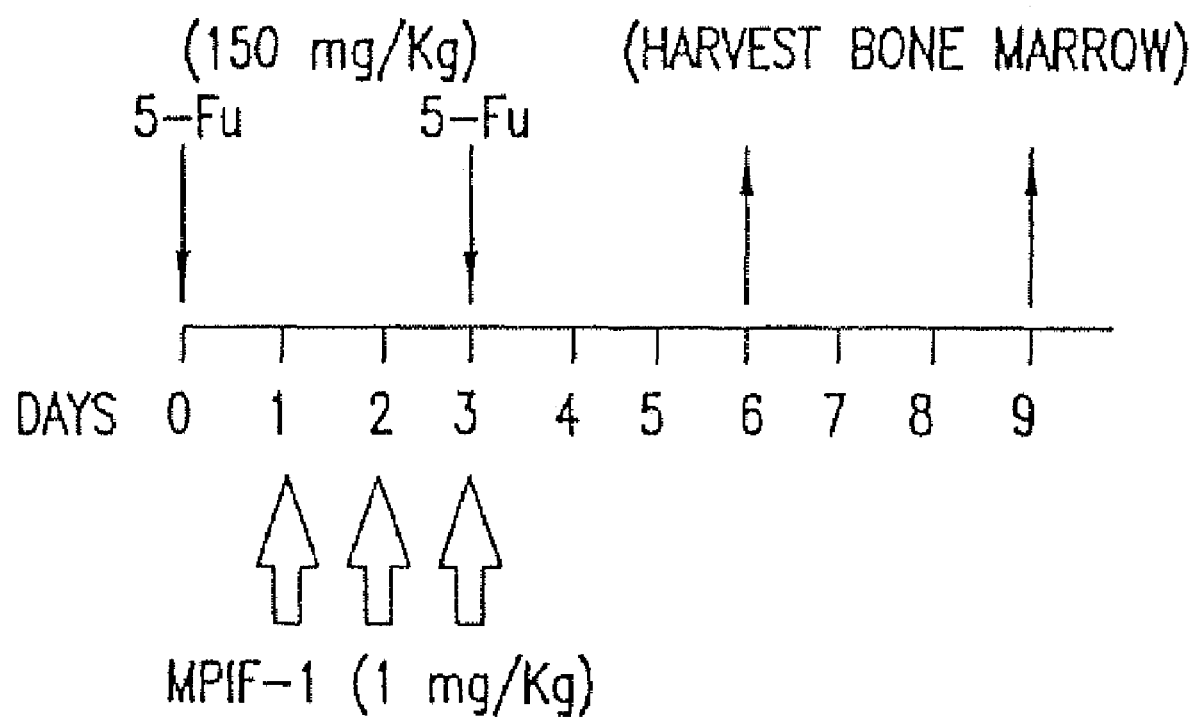
FIG. 23 shows the experimental design involving three groups of mice (6 animals per group) that were treated as follows: Group-1, injected with saline on days 1, 2, and 3; Group-2, injected with 5-Fu on days 0 and 3; Group-3, injected with 5-Fu on days 0 and 3 and MPIF-1 on days 1, 2, and 3. Bone marrow was harvested on days 6 and 9 to determine LPP-CFC frequencies using a clonogenic assay.

To demonstrate that MPIF-1 is able to protect these cell types in the bone marrow, the following experiment was performed. The experimental was performed using three groups of mice (6 animals per group) that were treated as follows: Group-1, injected with saline on days 1, 2, and 3; Group-2, injected with 5-Fu on days 0 and 3; and Group-3, injected with 5-Fu on days 0 and 3 and MPIF-1 on days 1, 2, and 3. (See FIG. 23.) Bone marrow was harvested on days 6 and 9 to determine HPP-CFC and LPP-CFC frequencies using a clonogenic assay well known to those of skill in the art. The results demonstrate that administration of MPIF-1 prior to the second dose of 5-Fu results in a rapid recovery of the HPP-CFC and LPP-CFC frequencies by day 9 compared to animals treated with 5-Fu alone. (See, FIG. 24.)

EXAMPLE 17

Studies with the MPIF-1 Mutants

A number of MPIF-1 variants that are truncated from the N-terminus have been identified and characterized. The amino terminal sequences of these variants as determined by Edman degradation are presented in the FIG. 25. For example, Mutants-2, -3, -7, and -8 arose spontaneously during the purification of the mature form of MPIF-1 and this preparation is called Preparation K0871. Similarly, Mutants-2, -3, -4, and -5 were discovered in another batch of the purified MPF-1 preparation (Preparation HG00300-B7). Since it was not possible to purify these variants from one another, Preparations K0871 and H1100300-B7 were used as is in the experiments described below. Mutant-6, which is identical to Mutant-3 with respect to the amino terminal sequence except for the N-terminal methionine, was generated by in vitro mutagenesis. Mutant-1, which is identical to the wild type except for the N-terminal methionine, was also generated by mutagenesis. In addition, an alternatively spliced form of MPIF-1 (Mutant-9), the cDNA clone of which encodes for a protein of 137 amino acids (FIG. 26A) (SEQ ID NO.11) was discovered (See, FIG. 25). Comparison of the amino acid sequence for Mutant-9's with that of MPIF-1 reveals an insertion of 18 amino acids between residues 45 and 46 in the MPIF-1 sequence and a loss of arginine 46 of MPIF-1 (FIG. 26B). The following summarizes the biological activities of these MPIF-1 mutant proteins.

Intracellular Calcium mobilization. In the foregoing Examples, MPIF-1 protein has been shown to mobilize calcium in monocytes. The wild type and mutant MPIF-1 proteins were tested for their ability to induce mobilization of intracellular calcium in human monocytes using human MIP-1α as a positive control. The experiment was performed as follows: Human monocytes were isolated by elutriation and loaded with Indo-1/acetoxymethylester by incubating $1\times10^6$ cells in 1 ml of in HBSS containing 1 mM $CaCl_2$, 2 mM $MgSO_4$, 5 mM glucose and 10 mM HEPES, pH 7.4 plus 2.5 mM Indo-1/acetoxymethylester for 30 min at 37° C. Cells were then washed with HBSS and resuspended in the same buffer at $5\times10^5$ cells/ml and stimulated with various concentrations of the indicated proteins at 37° C. The fluorescent signal induced in response to changes in intracellular calcium $((Ca^{++})i)$ was measured on a Hatachi F-2000 fluorescence spectrophotometer by monitoring Indo-1 excitation at 330 nm and emission at 405 and 485 nm. The results are shown in FIG. 27.

The results demonstrate that preparations K0871, H000300-B7, and Mutant-9 are ten-fold more active than the wild type, whereas Mutants-6 is indistinguishable from the wild type and Mutant-1 is about two-fold more active than the wild type. (See, FIG. 27). Since MIP-1α and MPIF-1 are 45% identical with respect to the primary amino acid sequence, it was of interest to determine whether they interacted with the same receptor. To explore this possibility, the ability of MFIP-1 to desensitize MIP-1α-induced calcium mobilization was studied. FIGS. 28A and 28B show that MIP-1α and the MPIF-1 wild type protein can desensitize each others ability to mobilize calcium in monocytes, but not MCP-4 (another beta-chemokitie).

In similar experiments, preparations K0871, H000300-B7, and Mutants-1, -6, and -9 were able to block MIP-1α induced calcium mobilization. This experiment was performed as follows: Calcium mobilization response of human monocytes to the indicated proteins at 100 ng/ml was measured as indicated above for the experiment disclosed in FIG. 27. For desensitization studies, monocytes were first exposed to one factor and when the response to the first treatment returned to baseline a second factor was added to the same cells. No response to the second factor is indicated by the (−) sign and a stimulatory response to the first factor by a (+) sign. (See, FIG. 29).

Thus, MPIF-1 and its mutant variants appear to interact with or share a component of the cell surface receptor for MIP-1α. Recent demonstration that the MIP-1α receptor serves as a cofactor in facilitating the entry of HIV into human monocytes and T-lymphocytes raises an interesting possibility that MPIF-1 or its variants might interfere with the process of HIV entry into the cells.

Chemotaxis. Chemotaxis of human peripheral blood mononuclear cell (PBMC) fraction (consisting mainly of lymphocytes and monocytes) was measured in response to various concentrations of MPIF-1 and its variants in a 96-well neuroprobe chemotaxis chambers. The experiment was performed as follows: cells were washed three times in HBSS with 0.1% BSA (HBSS/BSA) and resuspended at $2\times10^6$/ml for labeling. Calcein-AM (Molecular Probes) was added to a final concentration of 1 mM and the cells were incubated at 37° C. for 30 minutes. Following this incubation, the cells were washed three times in HBSS/BSA. Labeled cells were then resuspended to $8\times10^6$/ml and 25 ml of this suspension ($2\times10^5$ cells) dispensed into each upper chamber of a 96 well chemotaxis plate. The chemotactic agent was distributed at various concentrations in the bottom chamber of each well. The upper and the bottom chambers are separated by a polycarbonate filter (3-5 mm pore size; PVP free; NeuroProbe, Inc.). Cells were allowed to migrate for 45-90 minutes and then the number of migrated cells (both attached to the bottom surface of the filter as well as in the bottom chamber) were quantitated using a Cytofluor 11 fluorescence plate reader (PerSeptive Biosystems). Values represent concentrations at which peak activity was observed with the relative fold induction over background indicated in parentheses.

The results, shown in FIG. 30, demonstrate that preparations K0871 and H000300-B7 are more potent inducers of chemotaxis than the wild type, whereas Mutants-1 and -6 were indistinguishable from the wild type.

Effects on colony formation by LPP-CFC. To determine the impact of MPIF-1 variants on colony formation by LPP-CFC, a limiting number of mouse bone marrow cells were plated in soft agar containing medium supplemented with multiple cytokines with or without various concentrations of MPIF-1 variants. The experiment was performed as follows: a low density population of mouse bone marrow cells were plated (1,500 cells/3.5 cm diam. dish) in agar containing medium with or without the indicated MPIF-1 variants at various concentrations, but in the presence of the following recombinant murine cytokines IL-3 (5 ng/ml), SCF (100 ng/ml), IL-1 alpha (10 ng/ml), and M-CSF (5 ng/ml). Dishes were then incubated in a tissue culture incubator for 14 days at which point LPP-CFC colonies were scored under an inverted microscope. Data presented in FIG. 31 are pooled from several different experiments where each condition was assayed in duplicates.

The results demonstrate that the effective concentration required for 50% of maximal ind)ibition in the case of preparations K0871 and HG000300-B7 were 20- to 100-fold lower than that of the wild type and for Mutant-6 it was 2- to 10-fold lower. (See, FIG. 31). Thus, deletion of the N-terminal amino acids of MPIF-1 protein results in an increased potency of the molecule.

EXAMPLE 18

M-CIF Protection of Lipopolysaccharide-Induced Lethal Sepsis

Septic shock, a disease with significant morbidity and mortality in humans, results from uncontrollable release of cytokines in response to blood-borne bacterial infection. Bacterial endotoxins are recognized as a major factor in the pathogenesis of Gram-negative septic shock (Morrison & Ryan, *Annu. Rev. Med.* 38:417 (1987); Wolff & Benett, *N. Engl. J. Med.* 291:733 (1974)), which appears to be mediated by macrophages in response to endotoxins for the production of TNF-α and other cytokines (Freudenberg et al., *Infect. Immun.* 51:891 (1986), Tracey et al., *Nature (Lond).* 330:662 (1987)).

M-CIF is a new member of the beta-chemokine family with no in vitro chemotactic activity to monocytes/macrophages and some degree of chemotactic activity to T lymphocytes. It is inactive on most leukocytes except that it induces monocyte/macrophages for intracellular $Ca^{++}$ change via receptors shared with MIP-1α and RANTES (Schulz-Knappe et al., *J. Exp. Med*, 183:295 (1996)). In addition, M-CIF has been shown to have a strong inhibitory effect on M-CSF-induced promonocytic colony formation (Kreider et al., *Abstract for The International Society for Interferon and Cytokine Research.* Geneva, Switzerland, 1996).

In the present study, we examine the effect of M-CIF on endotoxin-induced septic shock in animal models. In some experiments, to bypass the known natural resistance of mice to the effect of bacterial toxins (Peavy et al., *J. Immunol.* 105:1453 (1970)), we increased their sensitivity by pretreatment with D-galactosamine (Galanos et al., *Proc. Natl. Acad. Sci. USA*. 76:5939 (1979); Lehmann et al., *J. Exp. Med.* 165:657 (1987)). We show that systemic treatment of potentially septic mice with M-CIF significantly prevented LPS-induced lethal shock.

Materials and Methods

Chemicals and reagents. The endotoxins LPS (derived from *E. coli* 0127:B8) and D-galactosamine were purchased from Sigina Chemical Co. (St Louis, Mo.). Recombinant human M-CIF was produced utilizing three different vector systems: baculovirus, *E. coli* and CHO cells, for protein expression and purification. Final protein preparations for in vivo usage contained more than 90% M-CWF as determined by SDS-PAGE analysis and had an endotoxin level less than 4.0 EU/mg.

TABLE 2

Batches and vectors of M-CIF used in experiments

| M-CIF | Vector | Batch No. | % Purity (SDS-PAGE) | Endo-toxin level (EU/mg) | Buffer content (NaOAc; NaCl) |
|---|---|---|---|---|---|
| 1. | Baculovirus | B8 | >95 | 4.0 | 40 mM; pH 5.5; 500 mM |
| 2. | Baculovirus | B9 | >95 | 0.2 | 40 mM; pH 5.5; 150 mM |
| 3. | Baculovirus | B11 | >90 | 2.4 | 40 mM; pH 5.5; 150 mM |
| 4. | *E. coli* | E1 | 95 | 0.04 | 40 mM; pH 6.0; 400 mM |
| 5. | CHO | C1 | >95 | 0.75 | 50 mM; pH 6.5; 500 mM |

Animals. These experiments were conducted with Balb/c and CF-1 mice purchased from Harlan Sprague Dawley (Indianapolis, Ind.) and Balb/c scid/scid (SCID) mice purchased from the Animal Production Facility at National Cancer Institute/Charles River (Frederick, Md.). All mice were used at 8-12 weeks of age and were maintained on a standard lab diet with free access to tap water. Animals were housed under controlled conditions in plastic microisolator cages with filter tops in a room with a 12 hour light cycle (6 am to 6 pm, light) and monitored 22° C. temperature and 65% humidity for at least one week before use in experiments. SCID mice had all bedding and water autoclaved and food irradiated before use.

Experimental design. Lethal sepsis was induced in mice with i.p. injection of LPS at various doses dissolved in normal saline on day 0 with or without prior (1 hour before LPS) D-gal sensitization. M-CIF from various vectors/batches at different doses was given i.p. daily for 3 consecutive days on day −1, day 0 (1 hour before LPS) and day 1. Mice receiving buffer (40 mM sodium acetate, pH 5.5; 150 mM NaCl) serve as the disease control. Animals were monitored for morbundity and morbidity 3 times/day after LPS challenge for as long as 120 hours after LPS challenge, Percent surviving mice is calculated as: number of living mice/total mice×100%.

Results

Effect of M-CIF in two animal models of septic shock in SBal/c mice The first model of lethal shock was induced in mice with LPS (25 mg/kg, i.p.). In this model, 85% of the animals died 52 hours atr LPS injection. M-CIF (3 mg/kg, i.p.) daily treatment for 3 days prevented lethality as much as 40% compared with the buffer control (FIG. 32). The second model of lethal sepsis was induced by injecting mice with LPS (1 ug/mouse, i,p,) one hour after D-gal (20 mg/mouse, i.p.) sensitization and all animals died within 8 hours after LPS administration. Pretreatment of mice with M-CIF (1 mg/kg, i.p.) for 3 days in a similar dosing regiment prevented 50% lethality in comparison with saline control, and single dosing treatment only prevented lethality in 25% of the mice. In addition, the combination treatment of M-CIF with either LPS (1 ug/mouse) or D-gal (20 mg/mouse) caused no sign of morbidity and moribundity in animals suggesting that the endotoxin level in M-CIF preparation is negligible (Table 3).

TABLE 3

| Group | Strain | M-CIF ip 1 mg/kg | D-gal ip 20 mg | LPS ip 1 ug | NaCl ip 0.1 ml | Survival within (living/total) | | |
|---|---|---|---|---|---|---|---|---|
| | | | | | | 8 hr | 11 hr | 22 hr |
| 1 | BALB/c | – | + | + | –1, 0, +1 | 0/4 | 0/4 | ND |
| 2 | BALB/c | 0 | + | + | – | 2/4 | 1/4 | ND |
| 3 | BALB/c | –1, 0, +1 | + | + | – | 2/4 | 2/4 | ND |
| 4 | BALB/c | –1, 0, +1 | – | + | – | 4/4 | 4/4 | ND |
| 5 | BALB/c | –1, 0, +1 | + | – | – | 4/4 | 4/4 | ND |

Mice were injected for 3 consecutive days 1 day prior to LPS on day –1, 1 hr prior to LPS on day 0 and 1 day post LPS on day 1 (–1,0,+1) or 1 hr prior to LPS on day 0 only (0). ND=not done.

Preventitve effect of M-CIF on sepsis is independent of animal strains. CF-1 mice were also used in the D-gal-sensitized LPS-induced lethal shock model. Unlike Balb/c mice, only 50% of the CF-1 mice suffered from lethality by 11 hours post LPS in the saline control group and additional M-CIF daily dosing for 3 consecutive days prevented all of the mice from dying (Table 4). These results suggest that human M-CIF may be very close to the murine homologue and the protective effect M-CIF on sepsis is a broad phenomenon rather than animal strain-selective.

TABLE 4

| Group | Strain | M-CIF ip 1 mg/kg | D-gal ip 20 mg | LPS ip 1 ug | NaCl ip 0.1 ml | Survival within (living/total) | | |
|---|---|---|---|---|---|---|---|---|
| | | | | | | 8 hr | 11 hr | 22 hr |
| 1 | CF-1 | – | + | + | –2, –1, 0 | 4/4 | 2/4 | 2/4 |
| 2 | CF-1 | –2, –1, 0 | + | + | – | 4/4 | 4/4 | 4/4 |
| 3 | CF-1 | –2, –1, 0 | – | + | – | 5/5 | 5/5 | 5/5 |

Mice were injected for 3 consecutive days 2 days prior to LPS on day –2, 1 day prior to LPS on day –1 and 1 hr prior to LPS on day 0 (–2,–1,0).

Preventive effect of M-CIF on septic shock is dependent on LPS dose. In a large scale experiment, Balb/c mice were challenged i.p. one dose of LPS (25 mg/kg), and the degrees of lethality in this group was 90% (FIG. 33). Pretreatment of M-CIF daily at 10 mg/kg for 3 consecutive days protected as much as 70% (FIG. 36).

Dose-dependent effect of M-CIF on lethal sepsis. This large scale experiment was based on 25 mg/kg of LPS in Balb/c mice. 100% lethality was induced in the buffer control group within 48 hours after LPS injection. In contrast, there was still 40% survival in the mice treated with 1 mg/kg of M-CIF in the same period of time and by day 5 all mice died in this group. Moreover, M-CIF at 3 and 10 mg/kg doses prevented 50% and 65% of mice from lethal shock, respectively (FIG. 34).

M-CIF is capable of preventing sepsis in Balb/c SCID mice. SCID mice, which have a deficiency in B and T lymphocytes, were injected i.p. with 20, 30, 40 or 50 mg/kg of LPS to determine the optimal degree of lethality. Unlike the normal Balb/c mice, no deaths occurred in the mice injected with 20 mg/kg LPS with or without M-CIF treatment (n=8). Only 30% lethality was observed in the 30 mg/kg LPS group and additional treatment with 3 mg/kg of M-CIF protected all of the SCID mice from shock. As the LPS dose was further increased to 40 mg/kg, 80% mortality was induced in the buffer control group of the immunodeficient mice and additional treatment of M-CIF at 3 mg/kg for three consecutive days protected 40% of the mice from lethality (FIGS. 35A and 35B). Once the LPS dose was given at 50 mg/kg, just like normal Balb/c mice, all of the SCID mice died in the buffer control group within 24 hours; and none of the 5 animals could be protected by additional M-CIF treatment.

Consistent protective effect of M-CIF from different vector preparations on sepsis. M-CIF proteins, prepared from *E. coli* and CHO expression vectors were tested in LPS-induced lethal sepsis in Balb/c mice. Compared with the buffer control which showed 100% lethality within 48 hours after 25 mg/kg LPS challenge, M-CIF (1 mg/kpg) derived from the CHO vector saved as much as 60% of the mice from death during the same time period and 50% 3 days after LPS injection. Moreover, the same dose of the protein from the *E. coli* vector also prevented 25% of the mice from lethal shock. However, this preparation of M-CIF seems less potent than the materials derived from the other two vectors, suggesting that there may be a significant change during the protein expression and purification process (FIG. 36).

EXAMPLE 19

M-CIF Modulation in Renal Injury

TNF-α has been shown to be involved in the pathogenesis of several types of glomerular injury (Martin, et al., *Clin. Exp. Immunol.* 2:283-288 (1995); Ortiz, et al., *Adv. Nephrol. Necker. Hosp.* 24:53-77(1995); Karkar, et al., *Kidney Int.* 44:967-973 (1993); Nikolic-Paterson, et al., *Kidney Int.* 45:S79-S82 (1994); Egido, et al., *Kidney Int.* 43:S59-S64 (1993)) and may play a role in tubulointerstitial nephritis, fibrosis, and renal allograft rejection (Baud, el al., *Miner. Electrolyte Metab.* 21:336-341 (1995); Tang, et al., *Lab. Invest* 70:631-638 (1994); Wilson, in *The Kidney*, Brenner, ed, Philadelphia, W.B. Saunders Company, p. 1253 (1996); Perkins, et al., in *The Kidney*, Brenner, ed, Philadelphia, W.B. Saunders Company, p. 2576 (1996)). To investigate the efficacy of M-CIF in modifying the onset and progression of renal diseases, animal models are utilized for crescentic glomerulonephritis, focal and segmental glomerulosclerosis (FSGS), and drug induced interstitial nephritis.

A model of anti-GBM disease is induced in a strain of rats (WKY) particularly prone to the development of glomerular crescents (Huang et al., *Kidney Int* 46:69-78 (1994); Bolton el al., *Kidney Int.* 44:294-306, (1993). The antibody used in this study is produced in female New Zealand White rabbits. The rabbits are immunized repeatedly with the basement membrane-rich sediment of kidney (Schreiner, et al., *J. Exp. Med.*/47:369-384 (1978)). The immune serum are heat-inactivated at 56° C. for 30 min and absorbed with rat red blood cells and the resultant serum called nephrotoxic serum (NTS). Normal male WKY rats (125-150 g) receive a single intravenous injection of a subnephritogenic dose of NTS. The dose is chosen such that immediate glomerular injury is not caused in Lewis rats.

According to known methods, administration of NTS to WKY rats causes macrophages to infiltrate the glomeruli within 30 minutes and to increase in number over a 10 day period. Glomerular hypercellularity is apparent within 48 hours and by day 6 there is necrosis and the presence of early crescent formation. Ten days after administration of NTS the majority of the glomeruli will exhibit a diffuse and proliferative glomerulonephritis.

To test the efficacy of M-CIF to alter disease progression, rats receive NTS and then are treated daily with an intraperitoneal injection of M-CIF daily or placebo. The disease progression is monitored by daily collection of urine and serum for assessment of proteinuria and TNF-α levels, respectively. At various time points ranging from 30 minutes to 10 days after NTS administration, rats are sacrificed and the identity of the infiltrating cells is assessed by immunohistological examination of frozen sections using commercially available monoclonal antibodies specific for macrophages and T cells.

A model of chronic aminonucleoside nephrosis is used as a prototype of progressive focal and segmental glomerulosclerosis. In this model, macrophages infiltrate the renal cortex in which are found increased levels of TNF-α and elevated expression of the endothelin receptor gene (Diamond, et al., *Am. J. Pathol* 141:887-894 (1992); Diamond et al., *Lab. Invest* 64:21-28 (1991); Nakamura, et al., *J. Am. Soc. Nephrol.* 5:1585-1590 (1995)). Male Sprague-Dawley rats weighing 125-150 g are used for these studies. These rats receive a single intravenous injection of puromycin aminonucleoside (50 mg/kg; Sigma Chemical Co, St. Louis, Mo.) through the right jugular vein over a period of 3 minutes. Within 2 weeks the animals develop proteinuria, severe tubulointerstitia abnormalities, and exhibit an influx of macrophages. This period of proteinuria will abate and then reappear by 18 weeks at which time 44% of the glomeruli will exhibit focal and segmental glomerulosclerosis (Diamond, et al., *Kidney Int.* 32:671-677 (1987)).

To test the ability of M-CIF to prevent this progressive renal injury, rats are injected intravenously with puromycin aminonucleoside and then treated with a daily intraperitoneal injection of either M-CIF or placebo. Proteinuria and serum levels of TNF-α are monitored at selected intervals over the 18 week study. At various time points rats are sacrificed and the renal cortical infiltrate examined on sections of kidneys using commercially available monoclonal antibodies to macrophages and T cells. The degree of morphologic abnormalities are assessed on standard paraffin sections stained with hematoxylin and eosin by two individuals in a blinded fashion and by using a computerized morphometric unit.

A model of cell-mediated immune injury to the renal tubules leading to granuloma formation is used to evaluate the efficacy of M-CIF to ameliorate drug-induced interstitial nephritis. Male Brown Norway rats weighing 140-180 g are used in this model as previously reported (Rennke, et al., *Kidney Int.* 45:1044-1056 (1994)). A haptenic molecule (ABA) is used as the target antigen. To produce the immunogen (ABA-KLH), 31.4 mg of p-Arsanilic acid (Eastman Kodak Co., Rochester, N.Y.) are dissolved in 2.5 ml of 1N HCl and then diazotized by the slow addition of sodium nitrite, resulting in activated ABA. A solution of keyhole limpet hemocyanin (KLH) (Calbiochem Corp, La Jolla, Calif.) is prepared by dissolving 500 mg in 20 ml of borate buffered saline and the pH is adjusted to 9.2. The diazotized arsanilic acid is added slowly and after 60 minutes the mixture dialyzed against phosphate buffered saline. The resultant ABA-KLH is frozen in aliquots at −20° C. until use.

Rats are immunized subcutaneously at the base of tail with 1 mg of ABA-KLH emulsified in complete Freund's adjuvant containing 5 mg/ml of H37Ra mycobacterium tuberculosis (Difco laboratories, Detroit, Md.). Ten days after this immunization the left kidney is perfused through the renal artery successively with 1-2 ml of phosphate buffered saline, containing 0.05 mg/ml verapamil, 2 ml of activated ABA (4 mM solution in borate buffered saline solution at pH 8.1), and 1 ml of phosphate buffered saline containing 0.05 mg/ml of verapamil.

To accomplish this, rats are anesthetized, placed on a heated operating table, and a laparotomy performed. The left renal vessels are isolated and loose snares placed around the left renal vein and the abdominal aorta. The left renal artery is cannulated with a 30 gauge needle and the snares around the aorta and renal vein closed. Ex viva perfusion of the left kidney then occurs at a rate of 1.1 ml/min and the effluent is then drained through a puncture of the temporarily ligated left renal vein. After hemostasis is restored and the ligatures released, re-perfusion of the kidney occurs within 1-2 min. Within 24 hours a mild but diffuse inflammatory cell infiltrate is produced that is composed of polymorphonuclear leukocytes and mononuclear cells. By day 5 monocytes and macrophages predominate. At this time (day 5), 75% of the renal cortex is involved by a granulomatous inflammation.

To test the efficacy of M-CIF in this model, M-CIF or placebo is administered intraperitoneally daily. Rats are sacrificed at various time points, their serum levels of TNF-α quantitated, and the amount of renal cortex involved in the inflammatory process estimated on standard paraffin sections stained with hematoxylin and eosin using a computerized morphometric unit. The identity of the infiltrating inflammatory cells are identified on histological sections using commercially available monoclonal antibodies to monocytes/macrophages and T cells. M-CIF is expected to provide reduced inflammation in renal injuries.

EXAMPLE 20

Protection of Chronic Joint Inflammation in Adjuvant Arthritis in Rats by M-CIF

In rheumatoid arthritis, pain and swelling can generally be controlled by currently available drugs, but it has been difficult to halt the progressive joint destruction associated with this disease. Therefore, much effort has been directed at more specific inhibition of the cellular and molecular mechanisms underlying bone and cartilage destruction. The Freund's adjuvant-induced arthritis model in rats shares a number of features with the arthritis patient, from the presence of a proliferative synovitis and swelling of the extremities ultimately leading to cartilage and bone erosion (Pearson & Wood, Arthritis Rheum. 2:440 (1959); Jones & Ward, *Arthritis Rheum.* 6:23 (1963)). As in rheumatoid arthritis in humans, macrophages are abundantly present in the inflamed synovial membrane of rats with adjuvant arthritis (Johnson et al., *Arthritis Rheum.* 29:1122 (1986)). Macrophages are thought to play a major role in arthritis, either as effector cells of tissue destruction, by secreting tissue-degrading enzymes or pro-inflammatory cytokines (Lopex-Bote et al., *Arthritis Rheum.* 31:769 (1988)), or by virtue of their immunoregulatory functions in the course of antigen-driven responses (Unanue & Allen, *Science* 236:551 (1987). This animal model has been used for the detection of anti-inflammatory and immunosuppressive drugs by quantitating hind-paw swelling (as a measure of acute inflammation), and histopathological alterations in cartilage and bone for chronic joint damage. In this study, we have tested the effect of M-CIF on both acute and chronic inflammatory arthritis in the adjuvant arthritis rat model.

On day 0 adult male Lewis rats (120-150 g) were injected intradermally at the base of the tail with Freund's complete adjuvant, which was prepared by adding Mycobacterium butyricum (Difco Lab, Detroit, Mich.) into mineral oil at a concentration of 5 mg/ml. M-CIF or its buffer were injected intraperitoneally to rats daily from day 0 to day 16 or from day 0 to day 40 as described below. Indomethacin at a dose of 1 mg/kg or its methylcellulose vehicle were orally administered daily in other groups of rats. Swelling of the hindpaws were measured using a plethysmometer chamber (Baxco Electronics, Troy, N.Y.). The hindpaw volume was expressed as the mean of the volumes of both hindpaws and as a percent change in paw volume.

At the end of experiment, the ankle and tarsal joints were excised and processed for histological evaluation. Two investigators evaluated the pathological changes and alterations of bone and cartilage in a blinded fashion using the following parameters: blood vessel dilation, fibrosis/fibroplasia, hyperplasia/hypertrophy, perivascular lymphoid aggregates, pannus formation, cartilage destruction, and bone destruction. A subjective semiquantitive scoring system, used to differentiate the degree and distribution of the changes, was defined as follows: 0=normal; 0.5=slight; 1=moderate; 2=severe; and 3=very severe.

In the first experiment, the animals were treated from day 0 to day 16. Their ankles were swollen by day 14 (the first time period tested) and reached their maximal severity between day 16 and 20. After this time the acute inflammation gradually subsided. The effect of M-CIF on ankle swelling is shown in FIG. 37. Both doses of M-CIF showed moderate reduction in paw swelling, however indomethacin was much more effective in reducing the edema. In a pilot study the limbs from two animals from each group were processed for histopathological scoring and the results are shown in FIG. 38. Taking both the acute and chronic features into account, animals treated with M-CIF from day 0 to day 16 showed a significant reduction in total joint inflammation compared with the buffer control group.

Based on these results, a second experimental protocol was utilized in which the rats were treated daily throughout the experiment (day 0 to day 40). At the end of the study, limbs from five animals per groups were processed for histological evaluation. When M-CIF was given daily at a dose of 3 mg/kg, there was significant reduction in the chronic synovitis (FIG. 39) and the bone and cartilage erosion (FIG. 40) when compared with its buffer controls. Indomethacin failed to show any efficacy in the histopathology of chronic arthritis. Therefore, M-CIF showed a significant protective effect on the chronic features of arthritis, most importantly the bone and cartilage erosion, although only a mild effect on acute edema.

M-CIF treatment prevents developing type II Collagen-induced arthritis in DBA/1 mice. An emulsion was prepared using equal volumes of a 2 mg/ml solution of bovine type II collagen and complete Freund's adjuvant Female DBA/ILacJ mice, 5-6 weeks old were immunized intradermally at the base of the tail with 100 µl of the emulsion. Eighteen days later, the mice were divided into 3 groups of 10 mice and injected intraperitoneally with 3 mg/ml of indomethacin, M-CIF, or a control buffer. This injection was repeated for 14 days. Two days after the start of this treatment (which is 20 days after the start of the experiment), the mice were challenged with a sac. injection of 60 µg of LPS in a total volume of 100 µl. The animals were examined and their clinical presentation semiquantified for development of the arthritis by the following scoring system:

$$\text{Incidence} = \frac{\text{number of mice with at least one affected paw}}{\text{total number of mice}} \times 100$$

| Clinical severity score | Description |
| --- | --- |
| 0.5 | One or more swollen digits. |
| 1.0 | Entire paw swollen |
| 2.0 | Deformity observed after inflammation subsides. |
| 3.0 | Ankylosis: total loss of joint function in the paw. |

As shown in FIG. 41, about 70% mice developed acute paw edema by 4-10 days post LPS challenge in both M-CIF and its buffer treated groups. However, the severity of this acute inflammation is less pronounced it M-CIF treated mice than that in the buffer group (FIG. 42). Over time, the buffer treated group's incidence and severity increased while M-CIF treated animals improved. Indomethacin, used as positive control, was also effective in reducing both the incidence and severity as expected.

Discussion. Adjuvant and collagen induced arthritis are widely used experimental models of rheumatoid arthritis with common clinical and histological features. In rheumatoid arthritis, pain and swelling can generally be controlled by currently available drugs, but it has been difficult to halt the progressive joint destruction associated with this disease. Therefore, much effort has been directed at more specific inhibition of the cellular and molecular mechanisms underlying bone and cartilage destruction. The protective effect of M-CIF on chronic features of arthritis, most importantly the bone and cartilage erosion which leads to joint deformity and destruction strongly suggests that M-CIF has good potential as a therapeutic agent for chronic inflammatory arthritis such as rheumatoid arthritis in human. Although M-CIF only has a mild effect on acute edema, combinational treatment of M-CIF and NSAID may be beneficial for both acute phase arthritis such as pain and swelling and the progressive joint destruction. Thus, M-CIF is shown to provide protection against the chronic features of arthritis, such as inflammation and pain.

EXAMPLE 21

Suppressive Effect of M-CIF on Systemic TNF-α Production

Septic shock is a disease with significant morbidity and mortality in humans, which results from uncontrollable release of cytokines in response to blood-borne bacterial infection. Bacterial endotoxins are recognized as a major factor in the pathogenesis of Gram-negative septic shock (Morrison & Ryan, *Annu. Rev. Med* 38:417 1987; Wolff & Benett, *N. Engl. J. Med*, 291:733 (1974). It appears to be mediated by macrophages in response to endotoxins for the production of TNF-n and other cytokines (Freudenberg et al, *Infect. Immun.* 51:891 (1986); Tracey et al., *Nature (Lond)*. 330:662 (1987)).

Earlier work showed that systemic treatment of mice with M-CIF significantly prevented LPS-induced lethal shock in two animal models. Since TNF-α production is central in causing septic shock we asked whether M-CIF interferes with the production of TNF-α and thereby protects against TNF-mediated endotoxic shock in vivo.

In Vivo. Female Balb/c mice, 7-8 weeks old, were challenged with 25 mg/kg of lipopolysaccharide (LPS) from *E. coli* serotype 0127:B8 (Sigma Chemical Co., St. Louis, Mo.) in saline on Day 0. M-CIF or its buffer were administered intraperitoneally 1 day before and 1 hour before the LPS injection. Groups of 4 mice were sacrificed at 1, 2, and 4 hours after LPS administration. Sera was obtained from the retrobital plexus and the TNF-α levels determined using an ELISA kit purchased from Geuzyme Corp., Cambridge, Mass. The assay was performed as described by the manufacturer. Each sample was diluted 1:4 and assayed in duplicate wells and the results analyzed with an unpaired T test. Data are expressed as mean values +SEM.

As shown in FIG. 43, serum TNF-α levels in the buffer control group is highest at one hour post LPS injection and then quickly declines afterwards. In contrast, mice given 3 mg/kg of M-CIF had significantly less TNF-α in their serum at one hour post LPS than the buffer control group. Animals treated with 1 mg/kg of M-CIF had reduced levels but this did not attain statistical significance.

The inhibitory effect of M-CIF on systemic TNF-α production is expected to be one aspect of the mechanism by which M-CIF protects mice from LPS-induced septic shock, and this effect would be beneficial for treating autoimmune inflammatory diseases such as rheumatoid arthritis and osteoarthritis.

In vitro. Female Balb/c mice, 4-6 weeks old were put into 2 groups of ten animals per group. The groups were either injected intraperitonealy with vehicle control or injected with M-CIF at 3 mg/kg for 2 consecutive days. One hour after the second injection, the mice were sacrificed and peritoneal cavity lavage performed to collect the resident cells. The cells were then washed and resuspended at a density of $1 \times 10^6$ cells/ml in culture medium (RPMI 1640/20% FBS). The cells were then plated in 48 well plates and incubated overnight in the presence or absence of LPS (1 and 10 ng/ml). After 18 hours, the supernatants from each well were collected and stored frozen until use. The ELISA for the determination of TNF-α content in the supernatants was performed as specified by the manufacturer (Genzyme Diagnostics, Cambridge, Mass.). As seen in FIG. 44, cells isolated from M-CIF treated animals and then treated with LPS in vitro secrete statistically significant lower amounts of TNF-α than do cells isolated from control mice.

M-CIF thus has the capacity to inhibit TNF-α production in vivo. This activity would be beneficial for both acute and chronic inflammation. Taken together with the data on the circulating TNF-α levels presented above, this can explain one aspect of the mechanism by which M-CIF protects from LPS induced sepsis. Since increased levels of TNF-α have been correlated with a wide variety of immune cell diseases or reactions, M-CIF treatment could be used on such disease states, as described herein.

Recent studies have shown the efficacy of inhibiting TNF-α activity with the use of antibodies to TNF-α or soluble TNF-α receptors. These diseases include acute pancreatitis, allograft rejection, non-insulin dependent diabetes mellitus (NIDDM), asthma, delayed hypersensitivity reactions in the skin, pulmonary fibrosis, and ischemia/reperfusion injury. In contrast, TNF-α plays a paracrine role in liver regeneration and in some circumstances suppresses skin and cardiac allograft rejection. Thus, M-CIF or its agonists are expected to be beneficial in such disease situations.

EXAMPLE 22

M-CIF as a Chemoattractant for T-Lymphocytes in Vivo.

Female Balb/c mice, 4-6 weeks old were put into 4 groups often animals per group. The groups were either untreated, injected intraperitoneally with vehicle control or injected with M-CIF at 1 mg/kg or 3 mg/kg for 6 consecutive days. On day seven, mice were sacrificed and peritoneal cavity lavage performed to collect the resident cells. Total cell numbers were calculated and the cells subjected to cell surface staining using the following panel of monoclonal antibodies. CD3, CD4, CDS, Mac1, GR1, B220, MHC class II, CD14, CD45, and CD5 (Pharmingen, San Diego, Calif.).

As shown in FIG. 45, the total cell numbers within the peritoneal cavity increased 2-3 fold over untreated or vehicle treated controls. This appears to be due to an influx of T-lymphocytes as determined by cell surface staining for CD4, CD5, and CD8. There is a dramatic increase in CD4 positive cells (FIG. 46) as well as CD5 and CD8 cells resulting in a net increase in the relative number of T-lymphocytes (FIG. 47 (2)). In addition, there is a significant increase in MacI positive, MHC class II negative, subpopulation of cells within the peritoneal cavity with a corresponding decrease in the percentage of MHC class II positive, Mac1 positive subpopulation of cells (FIG. 48). This is also reflected in the total number of MHC class II negative, Mac1 positive cells within the peritoneal cavity (FIG. 49).

M-CIF is thus shown to be a chemoattractant for T-lymphocytes in vivo. This could be for CD4, CD8 or both subpopulations of T-cells. Based on this, M-CIF may be beneficial for disease states which would benefit from the attraction and/or activation of this population of immune cells. This would include bacterial or viral infection, cancer, and the like. Also, if M-CIF has a specific effect on the Th1 or Th2 subclass of CD4 lymphocytes, it could bias the normal production of cytokines from these cells and dramatically influence other immune cells such as monocytes, macrophages, eosinophils, and other immune cells.

The fact that the MHC class II negative subpopulation of MacI positive cells increases in the M-CIP treated animals suggests that the monocyte population within these animals consists of a higher percentage of non-activated cells, This is consistent with the data showing that the peritoneal cells from the M-CIF treated animals produce less TNF-α in response to LPS.

EXAMPLE 23

In Vivo Stem Cell Mobilization Induced by MPIF-1

To demonstrate that MPIF-1 stimulates stem cell mobilization in vivo, the following experiment was performed. Six mice were used for each treatment group (C57Black 6/J, female, about 6 weeks old). The mice were injected (I.P,) with either (vehicle control) or MPIF-1 at 5 µg/mouse. After 30 minutes, mice were bled and analyzed for WBC by Coulter counter. Then, blood from all six animals of each group was pooled and analyzed for the Gr.1+ cells and CD34.Sca-1+ double positive cells by FACScan. WBC counts are expressed as Mean+S.D. and FACScan data as % of total cells. Since CD34.Sca-1+ double positive cells are thought to exhibit properties expected of the hematopoietic stem cells, the results shown in FIG. 50 illustrate that MPIF-1 can be used as stem cell mobilizer.

EXAMPLE 24

Purification of M-CIF

Purification from CHO Expression System

Following expression of M-CIF in Chinese hamster ovary cells, the protein was purified using the following procedure.

All of the purification procedures were performed at 5-10° C., unless otherwise specified. The transfected CHO cells were grown in HGS-CHO-3 medium using the microcarrier culture system (cytodex I, Pharmacia) for 4 days. The conditioned media were harvested using low speed centrifugation to remove cells and cell debris. After pH was adjusted to 7.0 with acetic acid, the conditioned media was loaded onto a strong cation exchange column (Poros HS-50, Perseptive Biosystems Inc.) pre-equilibrated with phosphate buffered saline (PBS), pH 7.0. The column was then washed with same buffer until the absorbance at 280 nm was less than 0.01 O.D. (10 CV). The desired protein was eluted by washing the column with 1M NaCl in phosphate buffered saline, pH 7.0. Fractions were then analyzed by SDS-PAGE through 4-20% gradient gels to confirm the presence of the desired polypeptide.

Those fractions containing M-CIF were then pooled and loaded onto a gel filtration column of Superdex-75 resin (Pharmacia) equilibrated in "sizing buffer" comprising 50 mM sodium acetate and 150 mM NaCl, pH 6.0. The sample loaded was less than 10% (V/V) of the column volume. After allowing the sample to run into the column, the protein was eluted from the gel filtration matrix using the same buffer. Fractions were collected and the absorbance at 280 nm of the effluent was continuously monitored. Fractions identified by A280 as containing eluted material were then analyzed by SDS-PAGE. Fractions containing M-CIF was eluted in a peak centered at 0.62 column volumes and pooled.

The pooled fractions from gel filtration chromatography was applied onto a set of strong anion (Poros HQ-50, Perseptive Biosystems) and weak anion (Poros CM-20) exchange columns in a tandem mode. Both columns were pre-equilibrated and washed with 50 mM sodium acetate buffer, pH 6.0 after sample loading. The cation exchange column (CM-20) was then washed with 0.3M NaCl followed by a 0.3M to 0.8M NaCl gradient elution in the same buffer system. The eluted fractions were analyzed through SDS-PAGE and fractions containing protein of interest were combined.

Following the purification steps described above, the resultant M-CIF was of greater than 95% purity as determined from Commassie blue staining of a SDS-PAGE gel The purified protein was also tested for endotoxin/LPS contamination. The LPS content was less than 0.1 ng/mg of purified protein according to LAL assays.

An alternative purification procedure was also used to purify M-CIF. The procedure involves the following steps, and unless otherwise specified, all procedures were conducted at 5-10° C.

Upon completion of the production phase of a CHO culture, the conditioned media were obtained after cells/cell debris removal using low speed centrifugation. Following pH of the media being adjusted to pH 7.0 by adding acetic acid, the media were loaded onto a strong cation exchange column (Poros HS-50, Perspective Biosystems, Inc.) pre-equilibrated with phosphate buffered saline (PBS), pH 7.0. The column was then washed with same buffer until the absorbance at 280 nm was less than 0.01 O.D. (10 CV). The desired protein was eluted by washing the column with 1M NaCl in phosphate buffered saline, pH 7.0. Fractions were then analyzed by SDS-PAGE through 4-20% gradient gels to confirm the presence of the M-CIF.

Those fractions containing M-CIF were then pooled, followed by the addition of 4 volumes of 10 mM sodium acetate, pH 6.5. The diluted sample was then loaded onto a previously prepared set of tandem columns of strong anion (Poros HQ-50, Perseptive Biosystems) and weak anion (Poros CM-20, Perceptive Biosystems) exchange resin. The columns were equilibrated with 50 mM sodium acetate pH 6.5. The CM-20 column was washed with 5 column volumes of 0.2 M NaCl, 50 mM sodium acetate, pH 6.5 and eluted using a 10 column volume linear gradient ranging from 0.2M NaCl, 50 mM sodium acetate, pH 6.5 to 1.0M NaCl 50 mM sodium acetate, pH 6.5. Fractions were collected under constant A280 monitoring of the effluent. Those fractions containing the protein of interest determined by a 4-20% SDS-PAGE) were then pooled.

The combined fractions containing M-CIF were then loaded (V/V, 5% of the column volume) onto a sizing exclusion column (Superdex-75, Pharmacia) equilibrated with 100 mM NaCl, 50 mM sodium acetate, pH 6.5. After allowing the sample the column, the protein was elated from the gel filtration matrix using 100 mM NaCl, 50 mM sodium acetate, pH 6.5. Fractions were collected and the absorbance at 280 nm of the effluent was continuously monitored. Fractions identified to $A_{280}$ as containing the eluted material were then analyzed by SDS-PAGE. Fractions containing M-CIF was then pooled.

Following the three step purification procedure described above, the resultant M-CIF was of greater than 95% purity as determined from Commassie blue staining of a SOS-PAGE gel. The purified protein was also tested for endotoxin/LPS contamination. The LPS content was less than 0.1 ng/mg of purified protein according to LAL assays.

Purification of M-CIF from *E. coli*

The purification involves the following steps, and unless otherwise specified, all procedures were conducted at 4-10° C.

Upon completion of the production phase of the *E. coli* fermentation, the cell culture was cooled to 4-10° C. and were harvested by continuous centrifugation at 15,000 rpm (Heraeus Sepatech). On the basis of the expected yield of protein per unit weight of cell paste and the amount of purified protein required, an appropriate amount of cell paste, by weight, was suspended in a buffer solution containing 100 mM Tris, 50 mM EDTA, pH 7.4. The cells were dispersed to a homogeneous solution using a high shear mixer.

The cells were then lysed by passing the solution through microfluidizer (Microfluidics, Corp. or APV Gaulin, Inc.) twice at 4000-6000 psi. The homogenate was then mixed with NaCl solution to a final concentration of 0.5 M NaCl, followed by centrifugation at 7000 g for 15 min. The resulted pellet was washed again using 0.5M NaCl, 100 mM Tris, 50 mM EDTA, pH 7.4.

The washed inclusion body was solubilized with 1.5 M Guanidine hydrochloride (GuHCl) for 24 hours. After 7000 g centrifugation for 15 min., pellet was discarded and the M-CIF-containing supernatant was placed at 4° C. overnight for further GuHCl extraction.

Following high speed centrifugation (30000 g) to remove the insoluble particles, the GuHCl solubilized proteins were refolded by quickly mixing the GuHCl extraction with 20 volumes of buffer containing 50 mM sodium, pH 4.5, 150 mM NaCl, 2 mM EDTA by vigorous stirring. The refolded diluted protein solution was set kept at 4° C. without mixing for 12 hours prior to further purification steps.

To clarify the refolded M-CIF solution, a previously prepared tangential filtration unit equipped with 0.16 um membrane filter with appropriate surface area (Filtron), equilibrated with 40 mM sodium acetate, pH 6.0 was employed. The filtered sample was loaded onto a cation exchange of poros HS-50 resin (Perseptive Biosystems). The column was washed with 40 mM sodium acetate, pH 6.0 and eluted with 250 mM, 500 mM, 1000 mM, and 1500 mM NaCl in the same buffer, in a stepwise manner. The absorbance at 280 mm of the effluent was continuously monitored. Fractions were collected and further analyzed by SDS-PAGE.

Those fractions contained desired protein was then pooled and mixed with 4 volumes of water. The diluted sample was then loaded onto a previously prepared set of tandem columns of strong anion (Poros HQ-50, Perseptive Biosystems) and weak anion (Poros CM-20, Perseptive Biosystems) exchange resin. The columns were equilibrated with 40 mM sodium acetate, pH 6.0. Both columns were washed with 40 mM sodium acetate, pH 6.0, 200 mM NaCl. The CM-20 column was then eluted using a 10 column volume linear gradient ranging from 0.2 M NaCl, 50 mM sodium acetate, pH 6.0 to 1.0M NaCl, 50 mM sodium acetate, pH 6.5. Fractions were collected under constant A280 monitoring of the effluent. Those fractions containing the protein of interest (determined by 16% SDS-PAGE) were then pooled.

The resultant M-CIF was of greater than 95% purity after the above refolding and purification steps. No major contaminant bands was observed from the Commassie blue stained 16% SDS-PAGE gel when 5 ug of purified protein was loaded. The purified protein was also tested for endotoxin/LPS contamination. The LPS content was less than 0.1 ng/ml according to LAL assays.

EXAMPLE 25

M-CIF Inhibits M-CSF-Stimulated Colony Formation of Human and Mouse Cells in a Dose Dependent Manner Progenitor cells are isolated and processed as described herein. Murine bone marrow cells are isolated from the femur and tibia, ficoll separated and depleted of plastic adherent cells. Both cell populations are plated in agar containing medium in the presence of M-CSF (5 ng/ml) with or without M-CIF at the concentrations indicated. Data is expressed as mean number of colonies+/−S.D. from samples done in duplicate.

Clonogenic assays on mouse bone marrow cells. CFU-M colony formation assays is performed in a two-layered agar culture system. The bottom layer is prepared in 3.5 cm diameter tissue culture dishes with 1 ml of MEM medium supplemented with 20% FBS (Sigma Tissue Culture Products, St. Louis, Mo.), 0.5% Difco agar and 15 ng/ml of M-CSF in the presence or absence of the indicated concentrations of M-CIF or a control beta-family chemokine. This layer is then overlayed with 0.5 ml of murine bone marrow cell suspension ($10^4$ cells/dish) prepared in the agar medium described above except that it contained 0.3% agar and no cytokiltes. The dishes are then incubated for seven days in a tissue culture incubator (37° C., 88% $N_2$, 5% $CO_2$, and 7% $O_2$) and CFU-M colonies are scored under an inverted microscope.

Clonogenic assays on human CD34' derived cells. Freshly purified CD34' cells ($5 \times 10^4$ cells/ml) are cultured for four days in Myclocult H5100 growth medium (Stem Cell Technologies Inc., Vancouver, Canada) supplemented with human IL-3 (10 ng/ml) and human SCF (50 ng/ml). The resulting populations of committed hematopoietic progenitors are counted and 1,000 cells in 1 ml of MethoCult medium (Stem Cell Technologies Inc., Vancouver, BC, Canada are plated in 3.5 cm diameter tissue culture dishes with supplemented M-CSF (10 ng/ml) in the presence or absence of the indicated concentrations of M-CIF or a control beta-family chemokine. After fourteen days in incubator (37° C., 88% $N_2$, 5% $CO_2$, and 7% $O_2$), the colonies are scored under an inverted microscope.

EXAMPLE 26

Evaluation of M-CIF in a Surgically-Induced Model Osteoarthritis in Guinea Pigs

To demonstrate that M-CIF slows the onset and progression of osteoarthritis (OA), a surgically-induced model of OA in Hartley guinea pig is used. The use of the guinea pig in experimental OA is a well-characterized, relevant and reproducible model of OA. This strain has been shown to develop spontaneous osteoarthritis with age. Surgically-induced joint instability creates altered biomechanical loads in the knee joint, leading to OA. Pathologic changes observed in this model are similar to those observed in human OA (Meacock, S. C. et al., *J. Exp. Pathol.* 71(2): 279-93 (1990), Bendele, A. M. et al., *Vet Pathol.* 28:207-215 (1991), Jimenez, P. A. et al., *Inflam. Res.* 44(2):129-130 (1995)).

Surgery is performed on eight week old male Hartley guinea pigs (n=5) anesthetized subcutaneously with ketamine (40 mg/kg), xylazine (5 mg/kg), fentanyl (0.06 mg/kg) and post-operative buprenorphine (0.05 mg/kg). Prior to surgery, guinea pigs are fasted for 12 hours. Animals are kept on a heating pad during skin disinfection, surgery and post-surgery. An incision is made with a #10 blade trough the joint capsule of the right knee. The fascia over the medial meniscus is dissected, and the medial collateral ligament and medial incision retracted. The anterior medial meniscus is isolated with a Tyrel micro-dissecting hook and the anterior portion excised with a #15 blade. The joint capsule is sutured with continuous 5-0 Vicrylt. Two wound clips are used to close the skin and are then removed at 4 days post-surgery. The weights of the animals are determined at the beginning of the experiment and every two weeks thereafter.

M-CIF and placebo are administered daily (i.p) for six weeks commencing on the day of surgery. Used are: an untreated control, a placebo group and M-CIF treated groups. Radiographs are taken at the end of the study prior to euthanasia. At the end of the experiment, all animals are euthanized with an overdose of sodium pentobarbital (300 mg/kg). The knee joints are harvested, fixed in 10% fonnalin for 4 days and decalcified in 20% formic acid in PBS (pH 7.2) for 4 days. Sections are cut at 5 intervals and stained with Safranin 0, Fast Green and Hematoxylin.

Histopathologic evaluation is performed using the Mankin scoring system (Mankin H. J., *Orth. Clin. North America* 2:19-30 (1971).

EXAMPLE 27

Evaluation of M-CIF in a Peptidoglycan-Polysaccharide Polymer Model of Granulomatous Enterocolitis in Rats To demonstrate that M-CIF would slow the onset and progression of granulomatous enterocolitis in a surgically-induced model of colitis in Lewis rats is used. The use of the Lewis rat in experimental colitis is a well characterized, relevant and reproducible model of enterocolitis. The Lewis stain of rats has been shown to be susceptible to the enterocolitis following surgical implantation of peptidoglycanpolysaccharide (PG-PS) in various areas of the distal ileum, peyer's patches, cecum and distal colon. Surgically-implanted PG-PS creates an acute enterocolitis which peaks at 1-2 days, remains quiescent for 7-9 days, and spontaneously reactivates by 12-17 days with an active inflammation which can persist for up to four months. (Elson et al., *Gastroenterol.* 109:1344-1367 (1995)). Development of chronic inflammation is dependent on a T-cell mediated immune response, poorly degradable PG-PS, and genetic host susceptibility (Sartor et al., *Methods: A Companion to Methods in Enzymology* 9:233-247 (1996)). Immune responses observed in this model are similar to those observed in human enterocolitis.

Surgery is performed on 130-170 g Lewis rats (n=10) anesthetized subcutaneously with ketamine (40 mg/kg), xylazine (5 mg/kg), fentanyl (0.06 mg/kg) and post-operative buprenorphine (0.05 mg/kg). Animals are kept on a heating pad during skin disinfection, surgery and post-surgery. A 6-8 cm incision is made with a #10 blade through the abdomen to expose the ileum, cecum and colon. Rats are injected intramurally (subserosally) with PG-APS (45 mg dry weight and 15 mg rhamnose/g body wt). At each site 0.05 ml (¹⁄₁₀ of the total dose) is injected 2 and 4 cm proximal to the ileocecal valve, two distal peyers patches, four midoecal sites, lymphoid aggregate at the cecal tip, and removed at 4 days post-surgery. The weights of the animals are determined at the beginning of the experiment and every five days thereafter. The extent of inflammation is assessed by morphological scoring of the extent of swelling of the ankle joint. Size of the ankle joint has been shown to be a reliable indicator of the presence of inflammation in the intestines.

M-CIF and placebo will be administered (i.p.) daily for four weeks commencing on the day of surgery. There will be an untreated control, a placebo group and M-CIF groups.

Two hours prior to euthanasia, rats are injected with BrdU (100 mg/kg i.p.). At the end of the experiment, all animals are killed using $CO_2$ asphyxiation. Samples taken from distal ileum, cecum and distal colon are fixed in 10% formalin. Sections are cut and stained with H & E, mucicarmine, trichrome, and anti-BrdU antibodies, Histopathologic evaluation is performed using the Sartor scoring system. (Sartor, et al., *Methods: A Companion to Methods in Enzymology* 9:233-247 (1996).

EXAMPLE 28

MPIF-1 Treatment During 5-Fu Treatment Results in Faster Recovery of Platelets and Granulocytes Two of the major complications resulting from chemotherapy are neutropenia (reduced blood neutrophil counts) and thrombocytopenia (reduced platelet counts). Granulocyte-Colony Simulating Factor (G-CSF) is currently used in the clinic to mitigate neutropenia. G-CSF is known to stimulate colony formation by the Colony Forming Unit-Granulocyte (CFU-G) in vitro and stimulate granulocyte production in animal models. Thrombopoietin (Tpo) is in clinical trials for the purpose of alleviating thrombocytopenia. Tpo is known to stimulate colony formation by Colony Forming Unit-Megakaryocyte (CFU-Meg) in vitro and stimulate platelet production in experimentally induced thrombocytopenia in animals. One of the major limitations of G-CSF in the clinic is that it is not effective in alleviating neutropenia in patients that are subjected to multiple cycles of chemotherapy. This is likely due to the depletion of CFU-G in the bone marrow, a target cell upon which G-CSF acts. Tpo might also suffer from the same fate as indicated by the initial clinical trial results. Any agent that can prevent the depletion of G-CSF and Tpo target cells during chemotherapy would be of great clinical value. The data shown below suggests that MPIF-1 could meet this clinical need.

In the previous Examples, MPIF-1 has been shown to inhibit colony formation by bipotential, granulocyte/monocyte myeloid progenitors in vitro. In particular, Examples 15-16 provide data demonstrating that MPIF-1 protects primitive, multipotential myeloid progenitors from 5-Fu induced cytotoxicity in vitro and in vivo. These multipotential progenitors are expected to give rise to more committed progenitors of all the myeloid lineages including CFU-G and CFU-Meg. The following experiment was performed to demonstrate that MPIF-1 treatment during two or three cycles of 5-Fu treatment results in faster recovery of platelets and granulocytes.

Materials and Methods: C57BL6 female mice (7-10 weeks old) with a mean body weight 19.4 g (±1.1 S.D., n=150) were used. All mice were housed under standard diet and housing conditions of dark/light cycle and temperature throughout the course of the experiment. MPIF-1 preparation (H100304-E6) was made in *E. coli* and represents the truncated form of MPIF-1 lacking 23 N-terminal amino acids of the mature protein (i.e., MPIF-1 Mutant-3 in FIG. 25 with an N-terminal Met added thereto). Clinical grade of G-CSF (Neupogen®) was purchased from the Shady Grove Pharmacy, Rockville, Md. 20850 (Neupogen® is manufactured by Amgen Inc., Amgen Center, Thousand Oaks, Calif. 91370). 5-Fluorouracil (5-Fu) was purchased from Sigma Chemicals and it was freshly prepared by dissolving in warm water just prior to use. MPIF-1 solution was freshly prepared by dilution in normal saline. Likewise, G-CSF was diluted in a buffer consisting of 10 mM sodium acetate, 5% (wt/v) mannitol, 0.004% (v/v) Tween 80, pH 4.0. Appropriate fluorochrome conjugated rat monoclonal antibodies against mouse CD41a, Gra.1, and Mac.1 antigens were purchased from Pharmingen.

Five groups of mice (30 mice per group) were treated as follows:

Group 1 was injected I.P. with 0.1 ml of normal saline on −2, −1, 0, 6, 7, and 8 days to serve as normal control.

Group 2 was injected with I.P. with 0.2 ml of 5-Fu solution (at 100 mg/kg body weight) on days 0 and 8.

Group 3 was injected with 5-Fu as in Group 2 and in addition 0.1 ml of MPIF-1 solution (at 1.0 mg/Kg body weight) was injected I.P. on −2, −1, 0, 6, 7, and 8 days.

Group 4 was injected with 5-Fu as in Group 2 and in addition 0.1 ml of G-CSF solution (at 0.5 mg/Kg body weight) was injected I.P. on 1, 2, 3, 9, 10, and 11 days.

Group 5 was injected with 5-Fu as in Group 2, MPIF-1 as in Group 3, and G-CSF as in Group 4.

Six animals from each of the groups were then analyzed on the indicated days for monitoring platelet and granulocyte recovery at the level of the peripheral blood and the bone marrow. It should be noted that the mice analyzed on 6 and 8 days post first 5-Fu did not receive second treatment with MPIF-1 or 5-Fu.

Peripheral blood was collected from the retroorbital sinus in EDTA-coated tubes and was immediately analyzed by FACS Vantage to determine platelet (CD41a positive events) and granulocyte (Gra.1 and Mac.1 double positive cells) counts. It should be noted that the method of analysis and the species of animal employed here does not permit obtaining absolute counts. Instead, granulocytes are expressed as percentage of total white blood cells and platelets were estimated as CD41a positive events per 15 seconds on the sorter. Mice were then sacrificed to obtain bone marrow cells using standard methods. Bone marrow cells were also analyzed by FACS to monitor percentage of Gra.1 and Mac. 1 double positive populations of cells in the bone marrow. Since the stage at which these antigens begin to be expressed in the granulocyte lineage is not precisely known, Gra.1 and Mac.1 double positive cells in the bone marrow are expected to be heterogenous with regards to tile stage of their development and maturation potential.

Bone marrow was also analyzed to determine the frequency of clonogenic progenitors using an in vitro clonogenic assay. Briefly, High Proliferative Potential Colony forming Cell (HPP-CFC) and Low Proliferative Potential Colony Forming Cell (LLP-CFC) assay was performed in a two-layered agar culture system. The bottom layer was prepared in 3.5 cm diameter dishes with 1 ml of MEM supplemented with 20% FBS, 0.5% Difco agar, 7.5 ng/ml mIL-3, 75 ng/ml mSCF, 7.5 ng/ml hM-CSF and 15 ng/ml mIL-1α. This layer was then overlayed with 0.5 ml of murine bone marrow cell suspension to have 2,000 cells/dish in MEM with 20% FBS and 0.3% agar. The top agar was allowed to solidify at room temperature for about 15 minutes. The dishes were then incubated for 14 days in a tissue culture incubator (37° C., 88% $N_2$, 5% $CO_2$, and 7% $O_2$) and colonies were scored under an inverted microscope. In this experiment total colony counts are reported.

FACS data were generated by analyzing material obtained from three animals of each of the groups per time point, whereas the clonogenic assay was performed with cells obtained from six animals of each of the groups per time point. Finally, data points for the day 1 group of the experiment represents values obtained from the saline injected normal mice (Group 1).

Results: To monitor the recovery of platelets in the peripheral blood, the steady state levels of CD41a positive cells was determined by FACS Vantage. As shown in FIG. 51, MPIF-1 treatment prior to 5-Fu (Group 3) resulted in a much faster and stronger recovery of platelets than that observed in mice treated with 5-Fu+saline (Group 2). As expected the kinetics of platelet recovery in mice treated with G-CSF (Group 4) was indistinguishable from that observed in mice treated 5-Fu+saline. Also, administering G-CSF plus MPIF-1 to 5-Fu treated mice (Group 5) had little effect on the overall steady state levels of platelets when compared to that observed in mice treated with MPIF-1 alone (Group 3). Thus, MPIF pre-treatment of mice prior to the 5-Fu treatment resulted in a rapid recovery of platelets in the peripheral blood.

The recovery of granulocytes in the peripheral blood was monitored by quantitating the steady state levels of Gra.1 and Mac.1 double positive cells in the blood. As illustrated in the FIG. 52, 5-Fu treatment of mice resulted in a sharp decrease in the steady state levels of Gra.1 and Mac.1 double positive cells in the blood at six days after the first as well as the second 5-Fu treatments, MPIF-1 pre-treatment had two beneficial effects; the degree of neutropenia (the extent of depletion of Gra.1 and Mac.1 double positive cells) was much smaller and the rate of recovery was much faster compared to that observed in mice treated with 5-Fu +saline (Group 2). As expected, the administration of G-CSF after 5-Fu treatment (Group 4) resulted in a rapid recovery of Gra.1 and Mac.1 double positive cells in the blood. However, the extent of the recovery from neutropenia in the G-CSF treated mice was notably smaller than that observed in the MPIF-1 treated mice on day 8 (Group 3). The effect of administering MPIF-1 plus G-CSF (Group 5) on the granulocyte depletion and recovery was quite dramatic in that these mice displayed much higher steady state levels of Gra.1 and Mac.1 double positive cells in the blood than that observed in mice treated with either MPIF-1 or G-CSF alone. Thus, as indicated in FIG. 52, it appears that MPIF-1 and G-CSF may exert additive effects when they are co-administered.

As indicated above, recovery at the level of the bone marrow was monitored by FACS Vantage method and clonogenic assay. Results obtained with FACS are illustrated in FIG. 53. As expected, the level of Gra.1 and Mac.1 double positive population of cells in the 5-Fu treated marrows (Group 2) remained remarkably depressed from days 6 through 14 and then recovered to normal level by day 16. This effect of 5-Fu mediated depletion of Gra.1 and Mac.1 double positive cells was completely abrogated when mice were treated with MPIF-1 prior to 5-Fu (Group 3). Surprisingly, G-CSF (Group 4) was able to prevent the depletion of the Gra.1 and Mac.1 double positive cells in response to the first 5-Fu dose, but not the second. This is likely due to the availability of G-CSF target cell and the timing of G-CSF administration. A similar response was evident in mice that were treated with MPIF-1 plus G-CSF (Group 5), although the extent of recovery on day 8 post first 5-Fu was much higher than that observed in mice treated with either MPIF-1 or G-CSF alone.

Data from the clonogenic assay are presented in FIG. 54. The frequency of progenitors in the bone marrow remained depressed in response to 5-Fu throughout the fourteen days of the experiment period with a hint of recovery on day 16. This reduction in the frequency of the progenitors was abrogated in mice that were treated with MPIF-1 prior to 5-Fu. In contrast, G-CSF treatment of mice was not effective in sustaining the frequency of progenitors found either in normal or MPIF-1 treated marrows. The effect of administering G-CSF plus MPIF-1 on the progenitor frequency in the bone marrow appears to be complex.

EXAMPLE 29

Amelioration of Lupus Nephritis in MRL lpr/lpr Mice by rhM-CIF Treatment

Systemic lupus erythematosus (SLE) is a multi-organ-associated autoimmune disease characterized by the over-production of pathogenic autoantibodies, and the formation of complement-fixing immune aggregates capable of inducing life-threatening glomerulonephritis and vasculitis (Steinberg, A. D. and Klinman, D. M., *Rheum. Dis. Clinics of No. Amer.* 14:25 (1988)).

MRL lpr/lpr mice, due to a mutation in the apoptotic fas receptor (Watanabe-Fukunaga, R., et al., *Nature* 356:314-317 (1992)), spontaneously develop an autoimmune disease with important similarities serologically and immunopathologically to human SLE (Andrews, B. S., et al, *J. Exp. Med.* 148:1198 (1978)). Extensive characterization of this murine model has provided many insights into the pathology of human lupus, including high autoantibody titers to a variety of autoantigens, glomerulonephritis, arthritis, vasculitis and premature death (Theofilopoulos, A. N. and Dixon, F. J., *Immunol. Rev.* 55:179 (1981); Tarkowski, A. et al., *Clin Exp. Immunol.* 72:91 (1988)).

Abnormnal macrophages and other cellular and molecular defects in MRL lpr/lpr mice are implicated in the pathogenesis of autoimmune disease (Cohen, P. L. and Eisenberg, R. A., *Annu. Rev. Immunol.* 9:243-269 (1991)). MRL lpr/lpr mice have an increased number of peritoneal macrophages, which are in a more activated stage than the macrophages from normal mice (Kelly, V. E. and Roths, J. B., *J. Immunol.* 129:923 (1982); Dang-Vu, A. P., et al., *J. Immunol.* 138: 1757 (1987)). In addition, MRL lpr/lpr macrophages produce higher levels of the proinflammatory cytokines such as IL-1 and TNF-α. Macrophages are rarely present in normal renal glomeruli, but can be found in MRL lpr/lpr glomeruli before proteinuria and are more prominent as the glomerulonephritis progresses (Boswell, J. M., et al., *J. Immunol.* 141:3050(1988)).

rhM-CIF, a new beta-Clemokine, has weak chemotactic activity and is inactive on most leukocytes except that it induces monocyte intracellular $Ca^{++}$ flux via receptors shared with MIP-1α and RANTES (Schulz-Knappe, P., el al., *J. Exp. Med.* 183:295 (1996)). In addition, rhM-CIF has a strong selective inhibitory effect on M-CSF-induced promonocytic colony formation (Kreider, B. L., et al., "A beta-family chemokine which specifically inhibits M-CSF mediated colony formation." Oral presentation at First Joint Meeting of the International Cytokine Society and the International Society for Interferon and Cytokine Research (1996)). Our early in vivo work demonstrated that rhM-CIF has a significant protective effect on LPS- or live *E. coli* bacteria-induced macrophage-mediated lethal sepsis, which is at least in part due to its reduction of TNFα and increase of IL-10 serum levels in mice (Zhang, J., el al., "Selective modulation of TNF-α and IL-10 by rhM-CIF (HCC-1) correlated with its protective effect on LPS-mediated lethal sepsis in SCID mice. Oral and poster presentations at Keystone Symposia, The Role of Chemokines in Leukocyte Trafficking and Disease (1997)). A significant ameliorative effect of rhM-CIF on moderate and progressive joint damage has also been observed in both murine collagen-induced arthritis and rat adjuvant arthritis models (Zhang, J., et al., "Protection of Progressive Joint Destruction by rhM-CIF (HCC-1) in a Rat Model of Adjuvant Arthritis." Poster presentation at ILAR Congress of Rhoumatology (1997); Storm, B., et al., "Ameliorative effect of rhM-CIF (HCC-1) on collagen-induced arthritis in mice." Abstract submitted for 61st National Meeting of American College of Rheumatology (1997)).

In the present study, we examined the possible effect of rhM-CIF on this spontaneous lupus model in MRL lpr/lpr mice. Preventive treatment with rhM-CIF for the entire course of lupus nephritis development significantly ameliorated the glomerular lesions and nephrosclerosis, and may have protected kidney function by reducing protein cast formation. Neither rhM-CIF nor methotrexate had any significant effect on premature death, probably as a consequence of the severity of disease in other organs beside kidney.

Materials and Methods

Animals

Female MRL lpr/lpr mice were purchased from The Jackson Laboratory (Bar Harbor, Me.) and maintained according to recommended standards at the HGS animal facility for at least one week before being employed in experiments.

Chemicals

Amethopterin (methotrexate) was purchased from Sigma Chemicals (St. Louis, Mo.). Saline solution was obtained from Abbott Labs (North Chicago, Ill.). Recombinant human M-CIF (batch B9) was expressed in baculovirus vector and purified by SDS-PAGE with a molecular weight of 8.677 Kd. The protein was then dissolved in a buffer consisting of 40 mM NaOAc, 150 mM NaCl, pH 5.5 with an endotoxin level less than 0.2 EU/mg.

Experimental Design

Fifty MRL lpr/lpr mice, 8-9 per group, were administered rhM-CIF in buffer or methotrexate in saline (1 or 5 mg/kg, i.p.) daily, Monday-Friday, each week for 14 weeks beginning at 8 weeks of age when there is no sign of disease. Mice receiving buffer or saline served as the disease control. Animals were monitored for clinical symptoms and morbidity weekly or biweekly until the lethality rate reached 50% in the buffer treated group. All of the remaining animals were sacrificed at the end of the experiment for the histopathological evaluation of kidneys.

Histopathology Analysis

Both kidneys were removed and immediately placed in 10% neutral buffered formalin for the procedure of paraffin embedding and sectioning. Tissue sections were stained with hematoxylin and eosin, PAS and trichrome for comprehensive examination. The pathological evaluation of the kidney lesions were conducted with a multi-blinded procedure. According to the general impression after viewing all the slides, a subjective scoring system was employed that allowed differentiation of degree and distribution of the changes by giving 0, ±, +, ++, +++, ++++ to the following histopathological features:

1) glomerular lesions such as irregular hypercellularity and enlargement, the basement membrane thickening, karyorrhexis, fibrosis and hyalinization, crescent formation and fibrosis of the Bowman capsule;

2) tubular lesions including the formation of protein casts in the lumens of the tubules (for the convenience of assessment of the lesion severity, protein cast formation was classified here, even though it also contributed to the increased permeability of the basement membrane of glomerular capillary tufts) and substantial atrophy and compensatory hypertrophy and dialation of the tubules;

3) the interstitial lesions including inflammatory infiltration, lymphocytic perivasculitis, interstitial fibrosis;

4) gross appearance such as granular nephrosclerosis.

The semiquantification analysis was done by using the following scoring systems: 0=0; +/−=1; +=2; ++=4; +++=6; and ++++=8.

Upon completion of individual histopathological evaluation, the slides were decoded and matched to each group for interpretation of the pathological changes with respect to the regimen of treatment.

Macrophage Immunohistochemical Analysis

Paraffin sections from MRL lpr/lpr kidneys were stained for macrophages using a specific rat monoclonal antibody against mouse (F4/80) macrophage antigen (Caltag Labs, San Francisco, Calif.) followed by a standard immunohistochemisty technique. The criteria for evaluating the degree of macrophages infiltration in the kidney were similar to those mentioned above (0 to ++++).

Statistical Analysis

Percentage of surviving mice was calculated as number of living mice/total mice×100%. Analysis of the histopathology data was performed only for the groups with no less than 4 surviving mice at the end of the experiment. Mean scores, SEM and P values for different pathological features were calculated individually or in combination by InStat statistical software.

Results

Effect of rhM-CIF on the Survival of MRL lpr/lpr Mice

Spontaneous autoimmune MRL lpr/lpr mice were treated with buffer or methotrexate in saline (1 or 5 mg/kg, i.p.)

daily Monday-Friday each week for 14 weeks when the B11 batch of rhM-CIF was exhausted. Compared with the buffer treated group, which served as a disease development control, rhM-CIF treatment showed a similar rate during the 16-week-experiment period, except that at the end of the experiment when the buffer treated group reach 56% lethality, there was a 63% survival rate in the rhM-CIF 1 mg/kg treated group (FIG. 55). Similar to rhM-CIF treatment, the group treated with the low dose of methotrexate (1 mg/kg) showed a parallel pattern to the saline control group until the last week of the experiment when there was about 20% protection. However, the group treated with the high dose of methotrexate (5 mg/kg) showed an accelerated death rate, which may be due to its accumulated toxicity (FIG. 56).

Reduction of Protein Casts in MRL lpr/lpr Kidney by rhM-CIF Treatment

Protein cast information as measured by histopathological evaluation was selected as an alternative measure for proteinuria to assess renal function. Only three groups (buffer, 1 mg/kg of rhM-CIF and methotrexate) had 4 mice surviving at the end of this pilot experiment, which qualified for their subsequent histology analysis. As shown in FIG. 57, the buffer control group revealed a great amount of the protein and cellular casts in Henle's loops, die distal convoluted tubules, the collecting tubules and the tubular lumens of MRL lpr/lpr kidneys. In contrast, only a small amount of protein casts was found in the rhM-CIF (1 mg/kg) treated mice; and one mouse in the methotrexate (1 mg/kg) group showed a severe protein cast formation while the other three mice remained totally free of this pathological feature. The reduction in the formation of protein casts by rhM-CIF is statistically significant ($p=0.02$) when compared with the buffer group.

Ameliorative Effect of rhM-CIF on the Glomerular Lesions

The glomerular lesions, especially the lesions of capillary tufts and the basement membrane of the glomeruli, are the essential features seen in this lupus model. Half of the surviving animals (two mice) in the buffer control group showed extremely severe damage in almost all of the visible glomeruli, which were represented by hyper-proliferation of macrophages in the Bowman's capsule and extensive formation of crescents; mesangial cell proliferation in the tufts demonstrated by PAS staining, karyorrhexis due to nuclear breakdown, thickening of the basement membrane resulting in "wire-loop lesion", leakage of red blood cells to the Bowman's capsule, and fibrosis and/or hyalinization. In addition, complete or partially dysfunctional glomeruli extensively spread in the cortex region. Crescent formation, adhesion of the parietal and visceral layers, and fibrosis of the Bowman's capsule were as severe as the glomerular lesions in terms of percentage. The other two mice in this group showed much less severe lesions. In contrast, most of the surviving mice (⅗) treated with rhM-CIF (1 mg/kg) showed about 50% severity of the buffer controls, and the others (⅖) showed only very mild damage or were without obvious glomerular lesions. Similar mild lesions were also seen in most of the surviving mice (¾) with methotrexate treatment, except that only one animal showed relatively severe glomerular lesions. The reduced glomerular lesions in rhM-CIF treated mice are statistically significant ($p=0.01$) in comparison with the buffer control (FIG. 58).

rhM-CIF Retarded the Development of Nephrosclerosis

The progressive and long standing process of lupus glomerulonephritis eventually leads to nephrosclerosis due to focal atrophy and compensated hypermophy of glomeruli and tubules. This late stage feature was severe in two of the four mice treated with buffer control, and the surface of their kidneys showed punctate scarring resembling grained leather. The other two mice did not show such advanced changes. Comparatively, none of the mice in rhM-CIF treated group showed obvious nephrosclerosis, except that milder atrophy of tubules was observed occasionally. Furthermore, only one mouse in the methotrexate group (n=4) developed an advanced state of the sclerotic feature with the other three mice remaining free of nephrosclerosis. Statistical analysis indicates that the severity of nephrosclerosis in the buffer control was significantly higher than that of rhM-CIF and methotrexate treated groups (FIG. 59).

rhM-CIF Moderately Inhibited Fire Macrophage Infiltration in MRL lpr/lpr Kidney

The presence of macrophages in MRL lpr/lpr kidneys is an important sign of progressive glomerulonephritis. Immunohistochemical analysis showed that macrophages extensively infiltrated the kidney of the buffer treated mice. The severity was parallel to the other pathological features as described above. The two mice with significant kidney lesions showed most severe macrophage infiltration. They appeared in the glomerular crescents mixed with the proliferating epithelial cells of Bowman's capsule, in the periglomerular area, interstitium of the nephrons and the areas of perivascular infiltrates. The other three mice in this group showed moderate or mild macrophage infiltration which was also parallel to their lesion severity. However, two mice with mild histopathological lesions from the methotrexate treated group revealed relatively higher scores of macrophage infiltration. The most severe mouse in this group also showed the most severe infiltration of macrophages. In the rhM-CIF group, the appearance of the macrophage seems moderately suppressed compared to the buffer group, even though the p value was 0.08, marginally significant statistically.

Lack of Effect of rhM-CIF an Lymphocyte Infiltration and Perivasculitis in MRL lpr/lpr Kidney Massive and diffuse infiltration of lymphoid cells in the interstitial tissue of the kidney is another prominent pathological feature in this MRL lpr/lpr model. These infiltrates were seen mainly in the perivascular (larger arteries such as interlobular arteries or even the arteries) area, the periglomular area, and the interstitium. The lymphoid cell infiltrates in the interstitium seem to be more severe in the buffer control because of massive atrophic tubules. However, a large amount of infiltrate was found in the periglomerular areas of rhM-CIF and methotrexate treated mice, although their glomerular lesions were very mild. The cell types of the infiltrates vary. In the perivascular area (especially around the larger arteries), most cells were lymphoblasta and mononuclearblasts. The whole picture of the infiltrates showed multiple cellular types of lymphoid cells, which were similar to the cellular classifications seen in the enlarged lymph nodes (data not shown). Semiquantification and comparison among buffer, rhM-CIF and methotrexate treated groups showed no obvious difference of perivasculitis and perigiomerulitis (FIG. 61).

Discussion

In this pilot experiment, protein cast formation evaluated by renal histopathology at the end of experiment was selected as an alternative feature to proteinuria to assess renal function. The preliminary results showed that preventive treatment of rhM-CIF for 14 weeks during the course of lupus nephritis development, resulted in significant reduction of protein cast formation, and amelioration of the glomemlar lesions and nephrosclerosis in the 5-6 month old MRL lpr/lpr kidney. However, rhM-CIF showed little or no effect on nephritis and/or vasculitis-induced premature death.

The presence of abnormal activated macrophages in the MRL lpr/lpr renal glomeruli has been implicated in the pathogenesis of lupus nephritis; and increased level of M-CSF mRNA transcripts in the kidney and M-CSF protein in the circulation of MRL lpr/lpr mice may be responsible for macrophage infiltration and activation (Yui, M. A., et al., *Amer. J. Path.* 139:255 (1991)). Although rhM-CIF treatment showed a moderate inhibition on macrophage infiltration in MRL lpr/lpr kidney, the possible effect of rhM-CIF on M-CSF-mediated renal macrophage function which causes tissue destruction remains unclear. However, previous studies indicated that rhM-CIF is effective in (1) inhibiting M-CSF-induced promonocytic colony formation, (2) protecting LPS-induced macrophage mediated lethal sepsis, and (3) down-regulating TNF-α and up-regulating IL-10 systematically in vivo. All these consequences may provide supporting evidence for the ameliorative effect of rhM-CIF on lupus nephritis.

Massive infiltration of lymphocytes in the interstitial tissue of the kidney is a unique pathological feature of MRL lpr/lpr mice from human SLE, which is caused by fas receptor deficiency in the clonal deletion of lymphocytes during any immune or autoimmune responses. Lack of effect of rhM-CIF on lymphocyte infiltration in the MRL lpr/lpr kidney suggests that rhM-CIF has no inhibiting effect on the migration, activation and clonal expansion of MRL lpr/lpr lymphocytes. Indeed, rhM-CIF has been shown to be chemotactic for activated T lymphocytes in vitro.

SUMMARY

Preliminary study showed that prolonged treatment of rhM-CIF, like methotrexate, during the development of spontaneous autoimmune disease, significantly ameliorated the progression of lupus nephritis by reducing protein cast formation, the glomerular lesions and eventually nephrosclerosis in MRL lpr/lpr kidney. However, rhM-CIF, like methotrexate, showed little or no effect on nephritis and/or vasculitis-induced premature death.

Summary Preclinical Pharmacology Tables

The following tables (Tables 5, 6, and 7) summarize the in vitro and in vivo primary and secondary pharmacology studies.

Table Key for Batches Referenced in Tables 6, 7, and 9. MPIF-1 batches are designated by a multi-component code which indicates the organism the protein was expressed in and the form of the expressed product (e.g., mature, full-length, or a variant). Letters after a hyphen at the end of the designation indicate either the organism the protein was expressed in or the vector used for expression (i.e., B=baculovirus, C=CHO cells, E=*E. coli*). The last three digits preceding the hyphen indicate the form or variant of the protein expressed (i.e., 300=full-length MPIF-1, 301=the MPIF-1Δ17 variant, 302=mature MPIF-1 with a methionine residue added to the amine terminus of the mature amino acid sequence, 304=the MPIF-1Δ23 variant, 311=full-length MPIF-1). Thus, the batch designation indicates the form of the expressed MPIF-1 protein, whether the protein will be secreted from the host cell, and the form of the secreted protein, if any. For example, HG00300-B5 indicates that the full-length MPIF-1 protein was expressed using a baculovirus vector. Further, since MPIF-1 expressed using this system is processed by the insect host cells, the secreted form of this protein is mature MPIF-1. One exception to the above noted nomenclature occurs with batch HG00300-B7. This batch contains a mixture of four different MPIF-1 polypeptides. The inventors believe that these polypeptides were produced as a result of proteolytic cleavage of MPIF-1 which occurred during the purification process. The MPIF-1 variants present in batch HG00300-B7 are discussed in Example 17.

TABLE 5

Primary Pharmacology-In Vitro

| Experimental Design | Cell Type | MPIF-1Δ23 Dose | Chemical Agent | Results |
|---|---|---|---|---|
| Effect of MPIF-1 or MPIF-1Δ23 on colony formation using mouse bone marrow | HPP-CFC LPP-CFC | 0.01-100 ng/mL | NA | Both of MPIF-1 and MPIF-1Δ23 caused a dose dependent reduction of the frequency of LPP-CFCs. MPIF-1Δ23 was significantly more effective than MPIF-1 at all concentrations tested. Neither isoform had a significant effect on the frequency of HPP-CFCs. |
| Effect of MPIF-1Δ23 on the proliferation of human hematopoietic progenitor cells | CD34+, human cord blood | 1-1000 ng/mL | NA | MPIF-1Δ23 treatment resulted in 20% to 40% inhibition of cell survival. The results suggest that MPIF-1Δ23 is a myeloid progenitor inhibitory factor. |
| Determination of the specific progenitor cell types targeted by MPIF-1Δ23 | CD34+, human | 50 ng/mL | NA | MPIF-1Δ23 inhibits (50% to 64%) the formation of CFU-GM and CFU-Mix. Formation of BFU-E, CFU-G, CFU-M, and CFU-Meg were not inhibited. The results define MPIF-1Δ23 as an inhibitor of human granulocyte/monocyte precursor cells. |
| Characterization of the inhibitory effects of MPIF-1Δ23 on mouse bone marrow | Mouse bone marrow | 50 ng/mL | NA | MPIF-1Δ23 reduced the frequency of myeloid CFU-GM colonies to 30% of control. The frequency of LPP-CFC colonies was reduced to 24% of control. MPIF-1Δ23 did not inhibit the formation of CFU-E, BFU-E and HPP-CFC colonies. |
| Determined the ability of MPIF-1Δ23 to protect lineage-depleted populations of bone marrow cells from the cytotoxic effects of 5-FU | Mouse bone marrow | NA | 5-FU | MPIF-1Δ23 protects 40% to 50% of LPP-CFC from cytotoxicity induced by 5-FU. MPIF-1Δ23 did not protect HPP-CFC. |

TABLE 6

Primary Pharmacology-In Vivo

| Experimental Design | Species | MPIF-1 Batch | MPIF-1 Dose, Schedule, Route | Chemical Agent | Dose, Schedule, Route | Endpoint |
|---|---|---|---|---|---|---|
| In vivo effects of MPIF-1 or MPIF-1Δ23 on the frequency of HPP-CFC and LPP-CFC in peripheral blood and bone marrow | Mouse | HG00300-B5 HG00304-E2 | 0.5 mg/kg/injection twice a day at 8 hour intervals for 2 days, i.p. | NA | NA | MPIF-1Δ23 significantly reduced the frequency of LPP-CFC in bone marrow. The effects of MPIF-1Δ23 on the frequency of LPP-CFC in blood were variable. MPIF-1Δ23 had no effect on the frequency of HPP-CFC. |
| Determination of the optimal MPIF-1Δ23 dosing schedule for protection against the cytotoxic effects of 5-FU | Mouse | HG00304-E2 | 1 mg/kg, variable between Days −3 and 0, i.p. | 5-FU | 150 mg/kg, Day 0, i.p. | MPIF-1Δ23 given on Days −2, −1, and 0 was most effective in protecting bone marrow against the cytotoxic effects of 5-FU. |
| Determination of dose dependency of MPIF-1Δ23 on bone marrow recovery after 5-FU | Mouse | HG00304-E6 | to 10 mg/kg, i.p. on Days −2, −1, 0 | 5-FU | 150 mg/kg, i.p. | A dose-dependent response was observed on Day 4, with the best recovery occurring at the lowest dose tested (0.01 mg/kg). No dose response was observed on Day 6. A bell shaped dose-response curve was obtained on Day 8, with optimal activity observed at 0.1 mg/kg. |
| Determination of the ability of MPIF-1Δ23 to protect myeloid progenitors in vivo from cytotoxic therapy | Mouse | HG00304-E6 | mg/kg; Days −2, −1, 0, i.p. | 5-FU | 150 mg/kg, Day 0, i.p. | Colony formation from bone marrow of mice treated with MPIF-1Δ23 returned to normal 7 days after treatment with 5-FU. Bone marrow colony formation from mice treated with 5-FU alone showed no recovery at this time. |
| Determination of the protective effect of MPIF-1Δ23 against multiple cycles of chemotherapy | Mouse | HG00304-E6 | mg/kg, Days −2, −1, 0, 6, 7, 8 | 5-FU | 100 mg/kg, Days 0 and 8, i.p. | MPIF-1Δ23 protected progenitor cells after two cycles of 5-FU. The most dramatic protection was seen after the second cycle of 5-FU. The chemoprotective effect of MPIF-1Δ23 was manifest in the periphery by increased numbers of hematopoietic-derived CD45+cells in blood. |
| Determination of the ability of MPIF-1Δ23 to accelerate recovery of bone marrow colonies, neutrophils and platelets after multiple cycles of chemotherapy Determination of the activity of MPIF-1Δ23 in combination with G-CSF | Mouse | HG00304-E6 | mg/kg; Days −2, −1, 0, 6, 7, 8, i.p. | 5-FU G-CSF | 100 mg/kg, Days 0 and 8, i.p. 0.5 mg/kg, Days 1, 2, 3, 9, 10, and 11 | The degree of neutropenia as measured by the depletion of Gr-1 and Mac-1 double positive cells was significantly less and the rate of recovery more rapid in mice treated with MPIF-1 and 5-FU compared with that in mice treated with 5-FU alone. Treatment with G-CSF after 5-FU resulted in a rapid recovery of double positive cells in the blood. The extent of recovery in G-CSF treated mice was markedly less than that observed in MPIF-1 treated mice on Day 8. Mice treated with MPIF-1 and G-CSF had higher steady state levels of positive cells in the blood than those treated with either MPIF-1 or G-CSF alone. There was a marked decrease in colony formation from the bone marrow of mice treated with 5-FU. MPIF-1 treatment prior to 5-FU abrogated the effect of 5-FU on colony formation. There was a more rapid and stronger recovery of platelets in mice treated with MPIF-1 and 5-FU relative to that seen in mice |

TABLE 6-continued

Primary Pharmacology-In Vivo

| Experimental Design | Species | MPIF-1 Batch | MPIF-1 Dose, Schedule, Route | Chemical Agent | Dose, Schedule, Route | Endpoint |
|---|---|---|---|---|---|---|
| | | | | | | treated with 5-FU alone. Addition of G-CSF had no further effect. |

TABLE 7

Secondary Pharmacology-In Vitro

| Experimental Design | Cell Type | MPIF-1 Batch | MPIF-1 Dose Range | Results |
|---|---|---|---|---|
| Determination of calcium mobilization by MPIF-1 or MPIF-1Δ23 | T cells, B cells, monocytes, neutrophils, basophils, dendritic cells, NK cells THP-1 cells | HG00300-B7 HG00302-E2 HG00302-E3 HG00304-E2 HG00304-E3 HG00304-E6 HG00304-E7 HG00301-C1 HG00311-C1 | 1 to 1000 ng/mL | Detectable responses were observed in monocytes and dendritic cells at 100 ng/mL. The monocytic cell line THP-1 responded to MPIF-1Δ23 with a maximal effect at 100 ng/mL. |
| Determination of the chemotactic activity of MPIF-1Δ23. | T cells, monocytes, neutrophils, lymphocytes, eosinophils, basophils, NK cells, platelets | HG00300-B5 HG00300-B7 HG00302-E1 HG00302-E2 HG00303-E1 HG00304-E2 HG00304-E6 HG00304-E7 | 0.1 to 1000 ng/mL | MPIF-1Δ23 stimulated chemotaxis in resting T cells with a maximal response at 10 ng/mL. MPIF-1Δ23 was chemotactic for freshly isolated monocytes with a maximal effect at 100 ng/mL. A weak chemotactic response was observed in neutrophils. There was no response in the other cells tested. |
| Effect of MPIF-1 or MPIF-1Δ23 on monocytes | Monocytes | HG00300-B7 HG00302-E1 HG00302-E2 HG00302-E3 HG00304-E3 HG00304-E6 HG00301-C1 HG00311-C1 | 0.5 to 1000 ng/mL | MPIF-1Δ23 induced a low but variable release of lysosomal N-acetyl-β-D-glucosidase from freshly isolated monocytes. MPIF-1Δ23 had no effect on the release of the lysosonal enzymes elastase, glucuromidase, and myleperoxidase. MPIF-1Δ23 does not induce monocytes to secrete IL-1β, TNF-α, IL-10, or IL-12. MPIF-1Δ23 had no effect on oxidative burst or cytotoxic activity of activated macrophages. |
| Effect of MPIF-1 or MPIF-1Δ23 on histamine release | Basophils, human | HG00300-B5 HG00300-B7 HG00302-E2 HG00304-E6 | 1 to 1000 ng/mL | MPIF-1 and MPIF-1Δ23 did not induce histamine release from basophils. |
| Effect of MPIF-1 or MPIF-1Δ23 on NK cell-mediated killing | NK cells, human | HG00302-E1 HG00300-B7 | 1 to 100 ng/mL | MPIF-1 and MPIF-1Δ23 had no effect on IL-2 stimulated NK cell-mediated killing of K562 cells. |
| Effect of MPIF-1 or MPIF-1Δ23 on platelet aggregation | Platelets, human | HG00302-E1 HG00300-B7 | 0.1 to 100 ng/mL | MPIF-1Δ23 did not induce or modulate platelet aggregation. |
| Effect of MPIF-1Δ23 on the growth of non-transformed human cells | Fibroblasts, astrocytes, Schwann cells, smooth muscle cells, epithelial cells, vein and microvascular endothelial cells, bone marrow, B cells, T cells, monocytes, neutrophils, keratinocytes | HG00300-B5 HG00302-E1 | 0.1 to 1000 ng/mL | MPIF-1Δ23 did not induce, enhance, or inhibit the proliferation of the cells listed studied. |
| Effect of MPIF-1 or MPIF-1Δ23 on the release of IL-6 and prostaglandins | Human primary endothelial cells, lung fibroblasts, and aortic smooth muscle cells | HG00300-B5 HG00300-B7 HG00302-E1 HG00300-E2 HG00304-E2 HG00301-C1 | 0.1 to 1000 ng/mL | MPIF-1 and MPIF-1Δ23 had no effect on release of IL-6 or prostaglandins. |
| Effect of MPIF-1Δ23 on formation of capillaries | Primary microvascular endothelial cells | HG00304-E2 | 0.1 to 100 ng/mL | MPIF-1Δ23 did not induce the formation of capillaries in vitro. |
| Effect of MPIF-1 on ability of tumor cells to infiltrate through a confluent monolayer of endothelial cells | Primary endothelial cells | HG00300-B7 | 0.1 to 10 ng/mL | No effect. |

TABLE 7-continued

Secondary Pharmacology-In Vitro

| Experimental Design | Cell Type | MPIF-1 Batch | MPIF-1 Dose Range | Results |
|---|---|---|---|---|
| Effect of MPIF-1 or MPIF-1Δ23 on adhesion of peripheral blood mononuclear cells or granulocytes to IL-1 activated endothelium | Primary endothelial cells | HG00300-B5 HG00300-B5 HG00304-E6 HG00304-E7 HG00301-C1 | 0.1 to 100 mg/mL | No effect. |

EXAMPLE 30

Production, Recovery, and Purification of MPIF-1Δ23 Using the pHE4-5 Expression Vector MPIF-1 is a novel human β-chemokine. The mature form of MPIF-1 is secreted as a 99 amino acid peptide, with a molecular mass of 11.2 kDa. A truncated from (MPIF-1Δ23) 76 amino acids in length was also identified during initial expression studies of MPIF-1. In a baculovirus expression system, MPIF-1Δ23 was subsequently isolated and subcloned. Biological assays indicate that the truncated form is more active than the full length counterpart.

Clotting and Expression

The MPIF-1Δ23 gene originally isolated from an aortic endothelial complementary deoxyribonucleic acid library has been subcloned into the expression vector pHE4 at the single restriction enzyme cleavage sites NdeI and Asp 718 (FIG. 62) and has been transformed into the K12 derived $E.$ $coli$ strain SG 13009 (available from Susan Gortesman, National Institutes of Health, Bethesda, Md.). Additional strains of $E.$ $coli$ which may serve as suitable hosts for protein expression using pHE4 include strains DH5α and W3110 (ATTC® Accession No. 27325). The pHE4 vector contains a strong synthetic promoter with two lac operators. Expression from this promoter is regulated by tile presence of a lac repressor, and is induced using isopropyl B-D-thiogalactopyranoside (IPTO) or lactose. The plasmid also contains an efficient ribosomal binding site and a synthetic transcriptional terminator downstream of the MPIF-1Δ23 gene. The vector also contains the replication region of pUC plasmids and the neomycinphosphotransferase gene resulting in kanamycin resistance in transformed bacteria.

Method of Manufacture

Overview of Fermentation Process

The fermentation process for MPIF-1Δ23 is outlined in following stages and is illustrated in FIG. 63.

Master Seed Bank

A master cell bank (MCB) of $E.$ $coli$ transformed with the plasmid expressing MPIF-1Δ23 was prepared under current Good Manufacturing Practices. The bank was prepared in media containing glycerol as a cryopreservative, and frozen at −80° C. After preparation, the MCB was tested to assure the absence of phage or contamination with other microorganisms.

First Seed Stage

First seed stage culture is prepared in a baffled shake flask containing inoculum preparation medium. The shake flask is inoculated at a 1:2000 dilution with thawed seed stock and is placed in a shaker maintained at 225 rpm and 37° C. for 12 hours.

Production Phase

Production Phase culture is prepared in a 100 liter Fed-Batch fermenter equipped with $DO_2$, pH, temperature and nutrient feed control. The production medium (37° C.) is inoculated with first seed stage culture to provide an optical density (OD) of 0.20 units per milliliter at 600 nm. When the culture reaches an OD of 10 plus or minus 2 units per milliliter at 600 nm, protein expression is induced with the addition of IPTG (final concentration 20 mM). Cells are harvested 4 hours after induction.

Cell Harvest Phase

Bacteria are recovered by centrifugation at 18,000 g using a continuous flow centrifuge. The resulting cell paste is stored at −80° C.

Recovery of MPIF-1Δ23

The recovery of MPIF-1Δ23 is outlined in FIG. 64.

Cell Lysis

The $E.$ $coli$ cell paste is thawed and resuspended in ten volumes of resuspension buffer. Cells are then disrupted following their passage (twice) through a homogenizer at 7000 psi.

Inclusion Body Wash

NaCl is added to the cell lysate to a final concentration of 0.5 M and then concentrated two-fold by tangential flow filtration using a 0.45-μm membrane. The remaining retentate is diafiltered against three volumes wash-2 buffer (100 mM Tris-HCl, 500 mM NaCl, and 25 mM FDTA-$Na_2$), followed by one volume wash-1 (100 mM Tris-HCl, 25 mM EDTA-$Na_2$). The retentate is diluted two-fold with wash-1 buffer, and the insoluble fraction is collected by continuous centrifugation. Alternatively, inclusion bodies can be washed by centrifugation.

Inclusion Body Solubilization

The resulting pellet obtained following centrifugation is suspended in an equivalent of nine packed inclusion body volumes of solubilization buffer (100 mM Tris-HCl, 1.75 M Guanidine-HCl, and 25 mM EtDTA-$Na_2$). The suspension is stirred initially for 2 to 4 hours at room temperature, and then for 12 to 18 hours at 2° to 10° C.

Refold

The suspension is centrifuged, and the supernatant is collected and mixed with nine volumes of refold buffer (100 mM Sodium Acetate, 125 mM NaCl, and 2 mM EDTA-$Na_2$). The diluted material is kept for about two hours (2° to 10° C.) to allow the precipitate to settle. The material is filtered and then may be processed immediately or stored for up to 72 hours and then processed.

Purification

HS-50 Cation Exchange Chromatography

The purification of MPIF-1Δ23 is outlined in FIG. 65. The filtrate is loaded onto a POROS HS-50 column equilibriated with 50 mM NaOAc, 150 mM NaCl, pH 5.8 to 6.2. The protein is eluted in a stepwise manner with NaCl (300 to 1500 mM). Fractions are eluted with 500 mM NaCl are pooled and are diluted two-fold with water for injection.

HQ-50/CM-20 Anion/Cation Exchange Chromatography

Pooled fractions obtained following HS-50 chromatography are loaded onto a tandem set of columns (HQ-50 column followed by CM-20 column) equilibrated with CM-1 buffer. MPIF-1Δ23 is eluted from the CM-20 column with NaCl (100 to 900 mM). Eluted fractions are analyzed by sodium dodecyl sulfate-polyacrylamide gel electrophoresis (SDS-PAGE) and reverse-phase high-performance liquid chromatography (HPLC), those fractions containing MPIF-1Δ23 are pooled and concentrated by ultrafiltration or passage through an additional HS-50 column.

Size Exclusion Chromatography

The CM-20 eluate is loaded onto a Sephacryl-100 HR equilibrated with S-100 buffer. Fractions are collected and analyzed by SDS-PAGE and reverse-phase HPLC. Fractions containing MPIF-1Δ23 are pooled, sterile-filtered using a 0.2 μm filter and stored at 2° to 10° C.

Specifications for Bulk Substance

The following specifications, listed in Table 8, have been established for bulk MPIF-1Δ23.

TABLE 8

Tests and Tentative Specifications for Release of Bulk MPIF-1Δ23

| Description | Specification |
| --- | --- |
| Appearance | Clear, colorless solution |
| pH | 5.8 ± 0.2 |
| Protein concentration by BCA | 1-5 mg/mL |
| Purity* | |
| Reverse-phase HPLC | ≧90% |
| Size-exclusion HPLC | ≧90% |
| SDS-PAGE (Coomassie blue staining) | |
| Reducing conditions | ≧90% |
| Non-reducing conditions | ≧90% |
| Residual DNA | ≦100 pg per mg protein |
| Endotoxin | ≦10 EU per mg protein |
| Limulus amoebocyte lysate gel clot | |
| Bioassay (Assessed by $Ca^{2+}$ mobilization assay) | Report results |

The purity of MPIF-1Δ23 preparations will be compared to a standard reference, the specifications for which are currently being defined.

Specifications for Drug Product

The finished drug product meets all of the specifications as described for the bulk substance in Table 8, and is also tested for sterility (21CRF610.12).

MPIF-1Δ23 Mediated Inhibition of Colony Formation Correlates With the Ability of MPIF-1 to Mobilize Intracellular $Ca^{2+}$ in Monocytes MPIF-1Δ23 inhibits LPP-CFC colony formation in in vitro soft agar assays and induces mobilization of intracellular calcium in monocytes including THP-1 cells (human myelomonocytic cell line). Both assays have been used to assess biological activity of MPIF-1Δ23 in purification and stability studies. In the LPP-CFC assay, freshly isolated murine bone marrow cells are plated in soft agar in the presence of multiple cytokines (5 ng/mL IL-3, 50 ng/mL SCF, 5 ng/mL M-CSF, and 10 ng/mL IL-1α). Cultures are incubated for 14 days, after which time, colonies are scored using an inverted microscope.

Calcium mobilization assays use freshly isolated human monocytes or THP-1 cells loaded with Fura-2 (0.2 nM per million). When cells are stimulated with MPIF-1Δ23, $Ca^{2+}$ mobilization is assessed by a fluorimeter. The $Ca^{2+}$ mobilization assay provides a rapid indicator regarding the activity of the MPIF-1Δ23 preparation (Table 9).

TABLE 9

MPIF-1Δ23 Mediated Inhibition of Colony Formation Correlates With the Ability of MPIF-1 to Mobilize Intracellular $Ca^{2+}$ in Monocytes

| MPIF-1 Construct/Batch/Condition | Ca2+ mobilization (ng/mL)* | LPP-CFC inhibition (ng/mL)[†] |
| --- | --- | --- |
| MPIF-1/HG00300-B5 | 1000 | 20-40 |
| MPIF-1Δ23/HG00304-E2, stored at 4° C. for 3 months | 100 | 5-10 |
| MPIF-1Δ23/HG00304, stored for 1 week | 100 | 5-10 |
| MPIF-1Δ23/HG00304, stored for 4 weeks | 100 | 5-10 |
| MPIF-1HG00302-E2, stored at 4° C. for 3 months | 1000 | >100 |
| MPIF-1Δ23/HG00304-E3, first peak from CM column | 100 | 5-10 |
| MPIF-1Δ23/HG00304-E4, second peak from CM column | 100 | 5-10 |
| MPIF-1Δ23/HG00304-E3, third peak from CM column | >1000 | >1000 |

*Minimum concentration required to mobilize calcium in human monocytes and/or THP-1 cells.
[†]Concentration producing 50% inhibition of LPP-CFC colony formation compared to the control.

Formulation and Storage

Bulk MPIF-1Δ23 is manufactured aseptically, and the liquid formulation is a sterile, single-use, product. The protein is buffered in 50 mM sodium acetate, 125 mM NaCl, pH 5.8, filled into a 5-mL Wheaton Type 1 glass vials and stored at 2° to 8° C.

Stability

The stability study was performed using a protein concentration of 1.0 mg/mL buffered with sodium acetate at pH 5, 6, and 7 at temperatures of −80° C., 2° to 8° C., 20° to 25° C., and 2° to 8° C. MPIF-1Δ23 has been found to be stable for at least six months when stored at or below 2° to 8° C. in a solution of 10 mM sodium acetate, 125 mM NaCl at pH 5 to 7. In currently ongoing studies, samples will be assayed for appearance, protein concentration, purity (SIDS-PAGE (reduced and nonreduced), reverse-phase and size-exclusion HPLC), and activity ($Ca^{2+}$ mobilization bioassay) to meet the specifications previously outlined.

A stability study for the MPIF-1Δ23 batch (H000304-E10) used in the preclinical toxicology studies was initiated. The MPIF-1Δ23 batch used in these studies was formulated at a protein concentration of 4.0 mg/mL in 50 mM NaOAc, 125 mM NaCl, pH 5.9. The storage conditions are −80° C., 2° to 8° C., 25° C., and 37° C., at a relative humidity of 75%. The stability study duration is 12 months for temperatures up to 25° C., 6 mnonths at 37° C., and 1 month at 45° C. The stability will be assayed for appearance, pH, protein concentration, purity (SDS-PAGE (reduced and non-reduced);

reverse-phase and size-exclusion HPLC), and activity ($Ca^{2+}$ mobilization bioassay). Endotoxin assay and bioburden tests will be performed at selected time points.

It will be clear that the invention may be practiced otherwise than as particularly described in the foregoing description and examples.

Numerous modifications and variations of the present invention are possible in light of the above teachings and, therefore, are within the scope of the appended claims.

The disclosures of all patents, patent applications, and publications referred to herein are hereby incorporated by reference.

---

What is claimed is:

1. An isolated antibody or fragment thereof that specifically binds to a protein selected from the group consisting of:
   (a) a protein whose amino acid sequence consists of amino acid residues 1 to 120 of SEQ ID NO:4;
   (b) a protein whose amino acid sequence consists of amino acid residues 22 to 120 of SEQ ID NO:4;
   (c) a protein whose amino acid sequence consists of amino acid residues 45 to 120 of SEQ ID NO:4;
   (d) a protein whose amino acid sequence consists of a portion of SEQ ID NO:4, wherein said portion is at least 30 contiguous amino acid residues in length; and
   (e) a protein whose amino acid sequence consists of a portion of SEQ ID NO:4, wherein said portion is at least 50 contiguous amino acid residues in length.

2. The antibody or fragment thereof of claim 1 that specifically binds protein (a).

3. The antibody or fragment thereof of claim 1 that specifically binds protein (b).

4. The antibody or fragment thereof of claim 1 that specifically binds protein (c).

5. The antibody or fragment thereof of claim 1 that specifically binds protein (d).

6. The antibody or fragment thereof of claim 1 that specifically binds protein (e).

7. The antibody or fragment thereof of claim 2 that specifically binds protein (b).

8. The antibody or fragment thereof of claim 4 wherein said protein bound by said antibody or fragment thereof is glycosylated.

9. The antibody or fragment thereof of claim 4 wherein said antibody or fragment thereof is human.

10. The antibody or fragment thereof of claim 4 wherein said antibody or fragment thereof is polyclonal.

11. The antibody or fragment thereof of claim 4 wherein said antibody or fragment thereof is monoclonal.

12. The antibody or fragment thereof of claim 4 which is selected from the group consisting of:
   a) a chimeric antibody or fragment thereof
   b) a humanized antibody or fragment thereof
   c) a single chain antibody; and
   d) a Fab fragment.

13. The antibody or fragment thereof of claim 4 which is labeled.

14. The antibody or fragment thereof of claim 4 wherein said antibody or fragment thereof specifically binds to said protein in a Western blot or an ELISA.

15. An isolated cell that produces the antibody or fragment thereof of claim 4.

16. A hybridoma that produces the antibody or fragment thereof of claim 4.

17. A method of detecting MPIF-1 protein in a biological sample comprising:
   a) contacting the biological sample with the antibody or fragment thereof of claim 4 ; and
   b) detecting the MPIF-1 protein in the biological sample.

18. The method of claim 17, wherein the biological sample comprises a bodily fluid selected from the group consisting of: serum, plasma, urine, synovial fluid, and spinal fluid.

19. An isolated antibody or fragment thereof that specifically binds a MPIF-1 protein, wherein said MPIF-1 protein is purified from a cell culture, and wherein said MPIF-1 protein is encoded by a polynucleotide encoding amino acids 1 to 120 of SEQ ID NO:4.

20. The antibody or fragment thereof of claim 19 wherein said antibody or fragment thereof is monoclonal.

21. The antibody or fragment thereof of claim 19 wherein said antibody or fragment thereof is polyclonal.

22. The antibody or fragment thereof of claim 19 wherein said antibody or fragment thereof is human.

23. The antibody or fragment thereof of claim 19 which is selected from the group consisting of:
   c) a chimeric antibody or fragment thereof;
   d) a humanized antibody or fragment thereof;
   e) a single chain antibody; and
   f) a Fab fragment.

24. The antibody or fragment thereof of claim 19 wherein said antibody or fragment thereof specifically binds to said protein in a Western blot or an ELISA.

25. The antibody or fragment thereof of claim 19 wherein the amino acid sequence of said MPIF-1 protein consists of amino acid residues 22 to 120 of SEQ ID NO:4.

26. A method of detecting MPIF-1 protein in a biological sample comprising:
   contacting the biological sample with an antibody or fragment thereof selected from the group consisting of:
   a) an antibody or fragment thereof that specifically binds to a protein whose amino acid sequence consists of amino acid residues 1 to 120 of SEQ ID NO:4;
   b) an antibody or fragment thereof that specifically binds to a protein whose amino acid sequence consists of amino acid residues 22 to 120 of SEQ ID NO:4; and
   c) an antibody or fragment thereof that specifically binds to a protein whose amino acid sequence consists of amino acid residues 45 to 120 of SEQ ID NO:4; and
   detecting the MPIF-1 protein in the biological sample.

27. The method of claim 26, wherein the biological sample comprises a bodily fluid selected from the group consisting of: serum, plasma, urine, synovial fluid, and spinal fluid.

28. The method of claim 27, wherein the bodily fluid is serum.

29. The method of claim 27, wherein the bodily fluid is plasma.

30. The method of claim 26, wherein the biological sample is derived from a bodily fluid selected from the group consisting of: serum, plasma, urine, synovial fluid, and spinal fluid.

31. The method of claim 30, wherein the bodily fluid is serum.

32. The method of claim 30, wherein the bodily fluid is plasma.

33. The method of claim 26, wherein the biological sample consists of a bodily fluid selected from the group consisting of: serum, plasma, urine, synovial fluid, and spinal fluid.

34. The method of claim 33, wherein the bodily fluid is serum.

35. The method of claim 33, wherein the bodily fluid is plasma.

* * * * *

SEQUENCE LISTING

<160> NUMBER OF SEQ ID NOS: 60

<210> SEQ ID NO 1
<211> LENGTH: 282
<212> TYPE: DNA
<213> ORGANISM: Homo sapiens
<220> FEATURE:
<221> NAME/KEY: CDS
<222> LOCATION: (1)..(282)

<400> SEQUENCE: 1

```
atg aag atc tcc gtg gct gca att ccc ttc ttc ctc ctc atc acc atc      48
Met Lys Ile Ser Val Ala Ala Ile Pro Phe Phe Leu Leu Ile Thr Ile
1               5                   10                  15 gcc cta ggg acc aag act gaa tcc tcc tca cgg gga cct tac cac ccc      96
Ala Leu Gly Thr Lys Thr Glu Ser Ser Ser Arg Gly Pro Tyr His Pro
                20                  25                  30 tca gag tgc tgc ttc acc tac act acc tac aag atc ccg cgt cag cgg     144
Ser Glu Cys Cys Phe Thr Tyr Thr Thr Tyr Lys Ile Pro Arg Gln Arg
            35                  40                  45 att atg gat tac tat gag acc aac agc cag tgc tcc aag ccc gga att     192
Ile Met Asp Tyr Tyr Glu Thr Asn Ser Gln Cys Ser Lys Pro Gly Ile
        50                  55                  60 gtc ttc atc acc aaa agg ggc cat tcc gtc tgt acc aac ccc agt gac     240
Val Phe Ile Thr Lys Arg Gly His Ser Val Cys Thr Asn Pro Ser Asp
65                  70                  75                  80 aag tgg gtc cag gac tat atc aag gac atg aag gag aac tga             282
Lys Trp Val Gln Asp Tyr Ile Lys Asp Met Lys Glu Asn
                85                  90
```

<210> SEQ ID NO 2
<211> LENGTH: 93
<212> TYPE: PRT
<213> ORGANISM: Homo sapiens

<400> SEQUENCE: 2

```
Met Lys Ile Ser Val Ala Ala Ile Pro Phe Phe Leu Leu Ile Thr Ile
1               5                   10                  15

Ala Leu Gly Thr Lys Thr Glu Ser Ser Ser Arg Gly Pro Tyr His Pro
                20                  25                  30

Ser Glu Cys Cys Phe Thr Tyr Thr Thr Tyr Lys Ile Pro Arg Gln Arg
            35                  40                  45

Ile Met Asp Tyr Tyr Glu Thr Asn Ser Gln Cys Ser Lys Pro Gly Ile
        50                  55                  60

Val Phe Ile Thr Lys Arg Gly His Ser Val Cys Thr Asn Pro Ser Asp
65                  70                  75                  80

Lys Trp Val Gln Asp Tyr Ile Lys Asp Met Lys Glu Asn
                85                  90
```

<210> SEQ ID NO 3
<211> LENGTH: 363
<212> TYPE: DNA
<213> ORGANISM: Homo sapiens

```
<220> FEATURE:
<221> NAME/KEY: CDS
<222> LOCATION: (1)..(363)

<400> SEQUENCE: 3 atg aag gtc tcc gtg gct gcc ctc tcc tgc ctc atg ctt gtt act gcc        48
Met Lys Val Ser Val Ala Ala Leu Ser Cys Leu Met Leu Val Thr Ala
1               5                   10                  15 ctt gga tcc cag gcc cgg gtc aca aaa gat gca gag aca gag ttc atg        96
Leu Gly Ser Gln Ala Arg Val Thr Lys Asp Ala Glu Thr Glu Phe Met
            20                  25                  30 atg tca aag ctt cca ttg gaa aat cca gta ctt ctg gac aga ttc cat        144
Met Ser Lys Leu Pro Leu Glu Asn Pro Val Leu Leu Asp Arg Phe His
        35                  40                  45 gct act agt gct gac tgc tgc atc tcc tac acc cca cga agc atc ccg        192
Ala Thr Ser Ala Asp Cys Cys Ile Ser Tyr Thr Pro Arg Ser Ile Pro
    50                  55                  60 tgt tca ctc ctg gag agt tac ttt gaa acg aac agc gag tgt tcc aag        240
Cys Ser Leu Leu Glu Ser Tyr Phe Glu Thr Asn Ser Glu Cys Ser Lys
65                  70                  75                  80 ccg ggt gtc atc ttc ctc acc aag aag ggg cga cgt ttc tgt gcc aac        288
Pro Gly Val Ile Phe Leu Thr Lys Lys Gly Arg Arg Phe Cys Ala Asn
                85                  90                  95 ccc agt gat aag caa gtt cag gtt tgc atg aga atg ctg aag ctg gac        336
Pro Ser Asp Lys Gln Val Gln Val Cys Met Arg Met Leu Lys Leu Asp
            100                 105                 110 aca cgg atc aag acc agg aag aat tga                                    363
Thr Arg Ile Lys Thr Arg Lys Asn
        115                 120

<210> SEQ ID NO 4
<211> LENGTH: 120
<212> TYPE: PRT
<213> ORGANISM: Homo sapiens

<400> SEQUENCE: 4

Met Lys Val Ser Val Ala Ala Leu Ser Cys Leu Met Leu Val Thr Ala
1               5                   10                  15

Leu Gly Ser Gln Ala Arg Val Thr Lys Asp Ala Glu Thr Glu Phe Met
            20                  25                  30

Met Ser Lys Leu Pro Leu Glu Asn Pro Val Leu Leu Asp Arg Phe His
        35                  40                  45

Ala Thr Ser Ala Asp Cys Cys Ile Ser Tyr Thr Pro Arg Ser Ile Pro
    50                  55                  60

Cys Ser Leu Leu Glu Ser Tyr Phe Glu Thr Asn Ser Glu Cys Ser Lys
65                  70                  75                  80

Pro Gly Val Ile Phe Leu Thr Lys Lys Gly Arg Arg Phe Cys Ala Asn
                85                  90                  95

Pro Ser Asp Lys Gln Val Gln Val Cys Met Arg Met Leu Lys Leu Asp
            100                 105                 110

Thr Arg Ile Lys Thr Arg Lys Asn
        115                 120

<210> SEQ ID NO 5
<211> LENGTH: 270
<212> TYPE: DNA
<213> ORGANISM: Homo sapiens
<220> FEATURE:
<221> NAME/KEY: CDS
<222> LOCATION: (1)..(270)
```

```
<400> SEQUENCE: 5 atg aag ggc ctt gca gct gcc ctc ctt gtc ctc gtc tgc acc atg gcc      48
Met Lys Gly Leu Ala Ala Ala Leu Leu Val Leu Val Cys Thr Met Ala
1               5                   10                  15 ctc tgc tcc tgt gca caa gtt ggt acc aac aaa gag ctc tgc tgc ctc      96
Leu Cys Ser Cys Ala Gln Val Gly Thr Asn Lys Glu Leu Cys Cys Leu
            20                  25                  30 gtc tat acc tcc tgg cag att cca caa aag ttc ata gtt gac tat tct     144
Val Tyr Thr Ser Trp Gln Ile Pro Gln Lys Phe Ile Val Asp Tyr Ser
        35                  40                  45 gaa acc agc ccc cag tgc ccc aag cca ggt gtc atc ctc cta acc aag     192
Glu Thr Ser Pro Gln Cys Pro Lys Pro Gly Val Ile Leu Leu Thr Lys
    50                  55                  60 aga ggc cgg cag atc tgt gct gac ccc aat aag aag tgg gtc cag aaa     240
Arg Gly Arg Gln Ile Cys Ala Asp Pro Asn Lys Lys Trp Val Gln Lys
65                  70                  75                  80 tac atc agc gac ctg aag ctg aat gcc tga                             270
Tyr Ile Ser Asp Leu Lys Leu Asn Ala
                85

<210> SEQ ID NO 6
<211> LENGTH: 89
<212> TYPE: PRT
<213> ORGANISM: Homo sapiens

<400> SEQUENCE: 6

Met Lys Gly Leu Ala Ala Ala Leu Leu Val Leu Val Cys Thr Met Ala
1               5                   10                  15

Leu Cys Ser Cys Ala Gln Val Gly Thr Asn Lys Glu Leu Cys Cys Leu
            20                  25                  30

Val Tyr Thr Ser Trp Gln Ile Pro Gln Lys Phe Ile Val Asp Tyr Ser
        35                  40                  45

Glu Thr Ser Pro Gln Cys Pro Lys Pro Gly Val Ile Leu Leu Thr Lys
    50                  55                  60

Arg Gly Arg Gln Ile Cys Ala Asp Pro Asn Lys Lys Trp Val Gln Lys
65                  70                  75                  80

Tyr Ile Ser Asp Leu Lys Leu Asn Ala
                85

<210> SEQ ID NO 7
<211> LENGTH: 100
<212> TYPE: PRT
<213> ORGANISM: Homo sapiens

<400> SEQUENCE: 7

Met Arg Val Thr Lys Asp Ala Glu Thr Glu Phe Met Met Ser Lys Leu
1               5                   10                  15

Pro Leu Glu Asn Pro Val Leu Leu Asp Arg Phe His Ala Thr Ser Ala
            20                  25                  30

Asp Cys Cys Ile Ser Tyr Thr Pro Arg Ser Ile Pro Cys Ser Leu Leu
        35                  40                  45

Glu Ser Tyr Phe Glu Thr Asn Ser Glu Cys Ser Lys Pro Gly Val Ile
    50                  55                  60

Phe Leu Thr Lys Lys Gly Arg Arg Phe Cys Ala Asn Pro Ser Asp Lys
65                  70                  75                  80

Gln Val Gln Val Cys Met Arg Met Leu Lys Leu Asp Thr Arg Ile Lys
                85                  90                  95

Thr Arg Lys Asn
```

<210> SEQ ID NO 8
<211> LENGTH: 76
<212> TYPE: PRT
<213> ORGANISM: Homo sapiens

<400> SEQUENCE: 8

```
Met Arg Phe His Ala Thr Ser Ala Asp Cys Cys Ile Ser Tyr Thr Pro
1               5                   10                  15

Arg Ser Ile Pro Cys Ser Leu Leu Glu Ser Tyr Phe Glu Thr Asn Ser
            20                  25                  30

Glu Cys Ser Lys Pro Gly Val Ile Phe Leu Thr Lys Lys Gly Arg Arg
        35                  40                  45

Phe Cys Ala Asn Pro Ser Asp Lys Gln Val Gln Val Cys Met Arg Met
    50                  55                  60

Leu Lys Leu Asp Thr Arg Ile Lys Thr Arg Lys Asn
65                  70                  75
```

<210> SEQ ID NO 9
<211> LENGTH: 78
<212> TYPE: PRT
<213> ORGANISM: Homo sapiens

<400> SEQUENCE: 9

```
His Ala Ala Gly Phe His Ala Thr Ser Ala Asp Cys Cys Ile Ser Tyr
1               5                   10                  15

Thr Pro Arg Ser Ile Pro Cys Ser Leu Leu Glu Ser Tyr Phe Glu Thr
            20                  25                  30

Asn Ser Glu Cys Ser Lys Pro Gly Val Ile Phe Leu Thr Lys Lys Gly
        35                  40                  45

Arg Arg Phe Cys Ala Asn Pro Ser Asp Lys Gln Val Gln Val Cys Met
    50                  55                  60

Arg Met Leu Lys Leu Asp Thr Arg Ile Lys Thr Arg Lys Asn
65                  70                  75
```

<210> SEQ ID NO 10
<211> LENGTH: 599
<212> TYPE: DNA
<213> ORGANISM: Homo sapiens
<220> FEATURE:
<221> NAME/KEY: CDS
<222> LOCATION: (35)..(448)

<400> SEQUENCE: 10

```
gtcctccggc cagccctgcc tgcccaccag gagg atg aag gtc tcc gtg gct gcc        55
                                    Met Lys Val Ser Val Ala Ala
                                    1               5 ctc tcc tgc ctc atg ctt gtt act gcc ctt ggc tcc cag gcc cgg gtc        103
Leu Ser Cys Leu Met Leu Val Thr Ala Leu Gly Ser Gln Ala Arg Val
        10                  15                  20 aca aaa gat gca gag aca gag ttg acg atg tca aag ctt cca ttg gaa        151
Thr Lys Asp Ala Glu Thr Glu Leu Thr Met Ser Lys Leu Pro Leu Glu
    25                  30                  35 aat cca gta ctt ctg gac atg ctc tgg agg aga aag att ggt cct cag        199
Asn Pro Val Leu Leu Asp Met Leu Trp Arg Arg Lys Ile Gly Pro Gln
40                  45                  50                  55 atg acc ctt tct cat gcc gca gga ttc cat gct act agt gct gac tgc        247
Met Thr Leu Ser His Ala Ala Gly Phe His Ala Thr Ser Ala Asp Cys
                60                  65                  70
```

-continued

```
tgc atg tcc tac acc cca cga agc atc ccg tgt tca ctc ctg gag agt    295
Cys Met Ser Tyr Thr Pro Arg Ser Ile Pro Cys Ser Leu Leu Glu Ser
         75                  80                  85 tac ttt gaa acg aac agc gag tgc tcc aag ccg ggt gtc atc ttc ctc    343
Tyr Phe Glu Thr Asn Ser Glu Cys Ser Lys Pro Gly Val Ile Phe Leu
         90                  95                 100 acc aag aag ggg cga cgt ttc tgt gcc aac ccc agt gat aag caa gtt    391
Thr Lys Lys Gly Arg Arg Phe Cys Ala Asn Pro Ser Asp Lys Gln Val
        105                 110                 115 cag gtt tgc atg aga atg ctg aag ctg gac aca cgg atc aag acc agg    439
Gln Val Cys Met Arg Met Leu Lys Leu Asp Thr Arg Ile Lys Thr Arg
120                 125                 130                 135 aag aat tga acttgtcaag gtgaagggga cacaagttgc cagccaccaa            488
Lys Asn ctttcttgcc tcaactaact tcctgaattc ttttttaag aagcatttat tcttgtgttc   548
tggatttaga gcaattcatc ttttctcacc tttaaaaaaa aaaaaaaaaa a           599

<210> SEQ ID NO 11
<211> LENGTH: 137
<212> TYPE: PRT
<213> ORGANISM: Homo sapiens

<400> SEQUENCE: 11

Met Lys Val Ser Val Ala Ala Leu Ser Cys Leu Met Leu Val Thr Ala
1               5                   10                  15

Leu Gly Ser Gln Ala Arg Val Thr Lys Asp Ala Glu Thr Glu Leu Thr
            20                  25                  30

Met Ser Lys Leu Pro Leu Glu Asn Pro Val Leu Leu Asp Met Leu Trp
        35                  40                  45

Arg Arg Lys Ile Gly Pro Gln Met Thr Leu Ser His Ala Ala Gly Phe
    50                  55                  60

His Ala Thr Ser Ala Asp Cys Cys Met Ser Tyr Thr Pro Arg Ser Ile
65                  70                  75                  80

Pro Cys Ser Leu Leu Glu Ser Tyr Phe Glu Thr Asn Ser Glu Cys Ser
                85                  90                  95

Lys Pro Gly Val Ile Phe Leu Thr Lys Lys Gly Arg Arg Phe Cys Ala
            100                 105                 110

Asn Pro Ser Asp Lys Gln Val Gln Val Cys Met Arg Met Leu Lys Leu
        115                 120                 125

Asp Thr Arg Ile Lys Thr Arg Lys Asn
    130                 135

<210> SEQ ID NO 12
<211> LENGTH: 26
<212> TYPE: DNA
<213> ORGANISM: Artificial sequence
<220> FEATURE:
<223> OTHER INFORMATION: Primer

<400> SEQUENCE: 12
tcaggatccg tcacaaaaga tgcaga                                        26

<210> SEQ ID NO 13
<211> LENGTH: 26
<212> TYPE: DNA
<213> ORGANISM: Artificial sequence
<220> FEATURE:
<223> OTHER INFORMATION: Primer

<400> SEQUENCE: 13
```
cgctctagag taaaacgacg gccagt 26

<210> SEQ ID NO 14
<211> LENGTH: 27
<212> TYPE: DNA
<213> ORGANISM: Artificial sequence
<220> FEATURE:
<223> OTHER INFORMATION: Primer

<400> SEQUENCE: 14
cccgcatgcg ggtcacaaaa gatgcag 27

<210> SEQ ID NO 15
<211> LENGTH: 27
<212> TYPE: DNA
<213> ORGANISM: Artificial sequence
<220> FEATURE:
<223> OTHER INFORMATION: Primer

<400> SEQUENCE: 15
aaaggatcct caattcttcc tggtctt 27

<210> SEQ ID NO 16
<211> LENGTH: 48
<212> TYPE: DNA
<213> ORGANISM: Artificial sequence
<220> FEATURE:
<223> OTHER INFORMATION: Primer

<400> SEQUENCE: 16
acatgcatgc guguuaccaa agacgcugaa accgaauuca ugaugucc 48

<210> SEQ ID NO 17
<211> LENGTH: 36
<212> TYPE: DNA
<213> ORGANISM: Artificial sequence
<220> FEATURE:
<223> OTHER INFORMATION: Primer

<400> SEQUENCE: 17
gccgaagctt tcagtttttta cgggttttga tacggg 36

<210> SEQ ID NO 18
<211> LENGTH: 88
<212> TYPE: DNA
<213> ORGANISM: Artificial sequence
<220> FEATURE:
<223> OTHER INFORMATION: Oligo

<400> SEQUENCE: 18
gcatgcgugu uaccaaagac gcugaaaccg aauucaugau guccaaacug ccgcuggaaa 60
acccgguucu gcuggaccgu uuccacgc 88

<210> SEQ ID NO 19
<211> LENGTH: 104
<212> TYPE: DNA
<213> ORGANISM: Artificial sequence
<220> FEATURE:
<223> OTHER INFORMATION: Oligo

<400> SEQUENCE: 19
gcuggaaucc uacuucgaaa ccaacuccga augcuccaaa ccgggguguua ucuuccugac 60 caaaaaaggu cgucguuucu cgcuaaaccc guccgacaaa cagg 104

```
<210> SEQ ID NO 20
<211> LENGTH: 89
<212> TYPE: DNA
<213> ORGANISM: Artificial sequence
<220> FEATURE:
<223> OTHER INFORMATION: Oligo

<400> SEQUENCE: 20
aagctttcag tttttacggg tgggcagacg ggtgtccagt ttcagcatac gcatacaaac        60
ctgaacctgt tgtcggacg gcttagcgc                                          89

<210> SEQ ID NO 21
<211> LENGTH: 94
<212> TYPE: DNA
<213> ORGANISM: Artificial sequence
<220> FEATURE:
<223> OTHER INFORMATION: Oligo

<400> SEQUENCE: 21
ggtttcgaag taggattcca gcagggagca cgggatggaa cgcggggtgt aggagatgca        60
gcagtcagcg gaggtagcgt ggaaacggtc cagc                                   94

<210> SEQ ID NO 22
<211> LENGTH: 32
<212> TYPE: DNA
<213> ORGANISM: Artificial sequence
<220> FEATURE:
<223> OTHER INFORMATION: Primer

<400> SEQUENCE: 22
gcgcagccat ggaaaacccg gttctgctgg ac                                     32

<210> SEQ ID NO 23
<211> LENGTH: 83
<212> TYPE: PRT
<213> ORGANISM: Homo sapiens

<400> SEQUENCE: 23

Met Glu Asn Pro Val Leu Leu Asp Arg Phe His Ala Thr Ser Ala Asp
1               5                   10                  15

Cys Cys Ile Ser Tyr Thr Pro Arg Ser Ile Pro Cys Ser Leu Leu Glu
            20                  25                  30

Ser Tyr Phe Glu Thr Asn Ser Glu Cys Ser Lys Pro Gly Val Ile Phe
        35                  40                  45

Leu Thr Lys Lys Gly Arg Arg Phe Cys Ala Asn Pro Ser Asp Lys Gln
    50                  55                  60

Val Gln Val Cys Met Arg Met Leu Lys Leu Asp Thr Arg Ile Lys Thr
65                  70                  75                  80

Arg Lys Asn

<210> SEQ ID NO 24
<211> LENGTH: 35
<212> TYPE: DNA
<213> ORGANISM: Artificial sequence
<220> FEATURE:
<223> OTHER INFORMATION: Primer

<400> SEQUENCE: 24
gccatggcat gctggaaaac ccggttctgc tggac                                  35

<210> SEQ ID NO 25
```

```
<211> LENGTH: 84
<212> TYPE: PRT
<213> ORGANISM: Homo sapiens

<400> SEQUENCE: 25

Met Leu Glu Asn Pro Val Leu Leu Asp Arg Phe His Ala Thr Ser Ala
1               5                   10                  15

Asp Cys Cys Ile Ser Tyr Thr Pro Arg Ser Ile Pro Cys Ser Leu Leu
                20                  25                  30

Glu Ser Tyr Phe Glu Thr Asn Ser Glu Cys Ser Lys Pro Gly Val Ile
            35                  40                  45

Phe Leu Thr Lys Lys Gly Arg Arg Phe Cys Ala Asn Pro Ser Asp Lys
    50                  55                  60

Gln Val Gln Val Cys Met Arg Met Leu Lys Leu Asp Thr Arg Ile Lys
65                  70                  75                  80

Thr Arg Lys Asn

<210> SEQ ID NO 26
<211> LENGTH: 32
<212> TYPE: DNA
<213> ORGANISM: Artificial sequence
<220> FEATURE:
<223> OTHER INFORMATION: Primer

<400> SEQUENCE: 26
gcgcagccat ggaccgtttc cacgctacct cc                              32

<210> SEQ ID NO 27
<211> LENGTH: 77
<212> TYPE: PRT
<213> ORGANISM: Homo sapiens

<400> SEQUENCE: 27

Met Asp Arg Phe His Ala Thr Ser Ala Asp Cys Cys Ile Ser Tyr Thr
1               5                   10                  15

Pro Arg Ser Ile Pro Cys Ser Leu Leu Glu Ser Tyr Phe Glu Thr Asn
                20                  25                  30

Ser Glu Cys Ser Lys Pro Gly Val Ile Phe Leu Thr Lys Lys Gly Arg
            35                  40                  45

Arg Phe Cys Ala Asn Pro Ser Asp Lys Gln Val Gln Val Cys Met Arg
    50                  55                  60

Met Leu Lys Leu Asp Thr Arg Ile Lys Thr Arg Lys Asn
65                  70                  75

<210> SEQ ID NO 28
<211> LENGTH: 29
<212> TYPE: DNA
<213> ORGANISM: Artificial sequence
<220> FEATURE:
<223> OTHER INFORMATION: Primer

<400> SEQUENCE: 28
gccatggcat gcgtttccac gctacctcc                                  29

<210> SEQ ID NO 29
<211> LENGTH: 32
<212> TYPE: DNA
<213> ORGANISM: Artificial sequence
<220> FEATURE:
<223> OTHER INFORMATION: Primer

<400> SEQUENCE: 29
```

-continued gcgcagccat ggctacctcc gctgactgct gc                     32

<210> SEQ ID NO 30
<211> LENGTH: 73
<212> TYPE: PRT
<213> ORGANISM: Homo sapiens

<400> SEQUENCE: 30

Met Ala Thr Ser Ala Asp Cys Cys Ile Ser Tyr Thr Pro Arg Ser Ile
1               5                   10                  15

Pro Cys Ser Leu Leu Glu Ser Tyr Phe Glu Thr Asn Ser Glu Cys Ser
            20                  25                  30

Lys Pro Gly Val Ile Phe Leu Thr Lys Lys Gly Arg Arg Phe Cys Ala
        35                  40                  45

Asn Pro Ser Asp Lys Gln Val Gln Val Cys Met Arg Met Leu Lys Leu
    50                  55                  60

Asp Thr Arg Ile Lys Thr Arg Lys Asn
65                  70

<210> SEQ ID NO 31
<211> LENGTH: 21
<212> TYPE: DNA
<213> ORGANISM: Artificial sequence
<220> FEATURE:
<223> OTHER INFORMATION: Primer

<400> SEQUENCE: 31
ttcgaagtag gcttccagca g                                 21

<210> SEQ ID NO 32
<211> LENGTH: 21
<212> TYPE: DNA
<213> ORGANISM: Artificial sequence
<220> FEATURE:
<223> OTHER INFORMATION: Primer

<400> SEQUENCE: 32
ctgctggaag cctacttcga a                                 21

<210> SEQ ID NO 33
<211> LENGTH: 35
<212> TYPE: DNA
<213> ORGANISM: Artificial sequence
<220> FEATURE:
<223> OTHER INFORMATION: Primer

<400> SEQUENCE: 33
gccatggcat gcgtgttacc aaagacgctg aaacc                  35

<210> SEQ ID NO 34
<211> LENGTH: 100
<212> TYPE: PRT
<213> ORGANISM: Homo sapiens

<400> SEQUENCE: 34

Met Arg Val Thr Lys Asp Ala Glu Thr Glu Phe Met Met Ser Lys Leu
1               5                   10                  15

Pro Leu Glu Asn Pro Val Leu Leu Asp Arg Phe His Ala Thr Ser Ala
            20                  25                  30

Asp Cys Cys Ile Ser Tyr Thr Pro Arg Ser Ile Pro Cys Ser Leu Leu
        35                  40                  45

```
Glu Ala Tyr Phe Glu Thr Asn Ser Glu Cys Ser Lys Pro Gly Val Ile
 50                  55                  60

Phe Leu Thr Lys Lys Gly Arg Arg Phe Cys Ala Asn Pro Ser Asp Lys
 65                  70                  75                  80

Gln Val Gln Val Cys Met Arg Met Leu Lys Leu Asp Thr Arg Ile Lys
                 85                  90                  95

Thr Arg Lys Asn
            100

<210> SEQ ID NO 35
<211> LENGTH: 36
<212> TYPE: DNA
<213> ORGANISM: Artificial sequence
<220> FEATURE:
<223> OTHER INFORMATION: Primer

<400> SEQUENCE: 35
gcccaagctt tcagttttta cgggttttga tacggg                          36

<210> SEQ ID NO 36
<211> LENGTH: 27
<212> TYPE: DNA
<213> ORGANISM: Artificial sequence
<220> FEATURE:
<223> OTHER INFORMATION: Primer

<400> SEQUENCE: 36
tcaggatcct gtgcacaagt tggtacc                                    27

<210> SEQ ID NO 37
<211> LENGTH: 27
<212> TYPE: DNA
<213> ORGANISM: Artificial sequence
<220> FEATURE:
<223> OTHER INFORMATION: Primer

<400> SEQUENCE: 37
aaaaagcttt caggcattca gcttcag                                    27

<210> SEQ ID NO 38
<211> LENGTH: 26
<212> TYPE: DNA
<213> ORGANISM: Artificial sequence
<220> FEATURE:
<223> OTHER INFORMATION: Primer

<400> SEQUENCE: 38
aaaccatggc acaagttggt accaac                                     26

<210> SEQ ID NO 39
<211> LENGTH: 30
<212> TYPE: DNA
<213> ORGANISM: Artificial sequence
<220> FEATURE:
<223> OTHER INFORMATION: Primer

<400> SEQUENCE: 39
gcccgcggat cctcctcacg gggaccttac                                 30

<210> SEQ ID NO 40
<211> LENGTH: 32
<212> TYPE: DNA
<213> ORGANISM: Artificial sequence
<220> FEATURE:
<223> OTHER INFORMATION: Primer
```

<400> SEQUENCE: 40
gcctgctcta gatcaaagca gggaagctcc ag　　　　　　　　　　　　　　　　32

<210> SEQ ID NO 41
<211> LENGTH: 27
<212> TYPE: DNA
<213> ORGANISM: Artificial sequence
<220> FEATURE:
<223> OTHER INFORMATION: Primer

<400> SEQUENCE: 41
aaatcatgac caagactgaa tcctcct　　　　　　　　　　　　　　　　　　27

<210> SEQ ID NO 42
<211> LENGTH: 27
<212> TYPE: DNA
<213> ORGANISM: Artificial sequence
<220> FEATURE:
<223> OTHER INFORMATION: Primer

<400> SEQUENCE: 42
aaaaagcttt cagttctcct tcatgtc　　　　　　　　　　　　　　　　　　27

<210> SEQ ID NO 43
<211> LENGTH: 27
<212> TYPE: DNA
<213> ORGANISM: Artificial sequence
<220> FEATURE:
<223> OTHER INFORMATION: Primer

<400> SEQUENCE: 43
ggaaagctta tgaaggtctc cgtggct　　　　　　　　　　　　　　　　　　27

<210> SEQ ID NO 44
<211> LENGTH: 59
<212> TYPE: DNA
<213> ORGANISM: Artificial sequence
<220> FEATURE:
<223> OTHER INFORMATION: Primer

<400> SEQUENCE: 44
cgctctagat caagcgtagt ctgggacgtc gtatgggtaa ttcttcctgg tcttgatcc　　59

<210> SEQ ID NO 45
<211> LENGTH: 33
<212> TYPE: DNA
<213> ORGANISM: Artificial sequence
<220> FEATURE:
<223> OTHER INFORMATION: Primer

<400> SEQUENCE: 45
aaaggatccg ccaccatgaa ggtctccgtg gtc　　　　　　　　　　　　　　33

<210> SEQ ID NO 46
<211> LENGTH: 27
<212> TYPE: DNA
<213> ORGANISM: Artificial sequence
<220> FEATURE:
<223> OTHER INFORMATION: Primer

<400> SEQUENCE: 46
aaaggatcct caattcttcc aggtctt　　　　　　　　　　　　　　　　　　27

<210> SEQ ID NO 47

<210> SEQ ID NO 47
<211> LENGTH: 30
<212> TYPE: DNA
<213> ORGANISM: Artificial sequence
<220> FEATURE:
<223> OTHER INFORMATION: Primer

<400> SEQUENCE: 47
ggaaagctta tgaagggcct tgcagctgcc                             30

<210> SEQ ID NO 48
<211> LENGTH: 57
<212> TYPE: DNA
<213> ORGANISM: Artificial sequence
<220> FEATURE:
<223> OTHER INFORMATION: Primer

<400> SEQUENCE: 48
cgctctagat caabcgtagt ctgggacgtc gtatgggtag gcattcagct tcaggtc     57

<210> SEQ ID NO 49
<211> LENGTH: 33
<212> TYPE: DNA
<213> ORGANISM: Artificial sequence
<220> FEATURE:
<223> OTHER INFORMATION: Primer

<400> SEQUENCE: 49
aaaggatccg ccaccatgaa gggccttgca agc                         33

<210> SEQ ID NO 50
<211> LENGTH: 27
<212> TYPE: DNA
<213> ORGANISM: Artificial sequence
<220> FEATURE:
<223> OTHER INFORMATION: Primer

<400> SEQUENCE: 50
aaaggatcct caggcattca gcttcag                                27

<210> SEQ ID NO 51
<211> LENGTH: 28
<212> TYPE: DNA
<213> ORGANISM: Artificial sequence
<220> FEATURE:
<223> OTHER INFORMATION: Primer

<400> SEQUENCE: 51
ggaaagctta tgaagattcc gtggctgc                               28

<210> SEQ ID NO 52
<211> LENGTH: 58
<212> TYPE: DNA
<213> ORGANISM: Artificial sequence
<220> FEATURE:
<223> OTHER INFORMATION: Primer

<400> SEQUENCE: 52
cgctctagat caagcgtagt ctgggacgtc gtatgggtag ttctccttca tgtccttg    58

<210> SEQ ID NO 53
<211> LENGTH: 33
<212> TYPE: DNA
<213> ORGANISM: Artificial sequence
<220> FEATURE:
<223> OTHER INFORMATION: Primer

<400> SEQUENCE: 53

```
aaaggatccg ccaccatgaa gatctccgtg gct                              33
```

<210> SEQ ID NO 54
<211> LENGTH: 30
<212> TYPE: DNA
<213> ORGANISM: Artificial sequence
<220> FEATURE:
<223> OTHER INFORMATION: Primer

<400> SEQUENCE: 54

```
aaaggatcct cagttctcct tcatgtcctt                                  30
```

<210> SEQ ID NO 55
<211> LENGTH: 92
<212> TYPE: PRT
<213> ORGANISM: Homo sapiens

<400> SEQUENCE: 55

```
Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
            20                  25                  30

Cys Cys Phe Ser Tyr Thr Ser Arg Gln Ile Pro Gln Asn Phe Ile Ala
        35                  40                  45

Asp Tyr Phe Glu Thr Ser Ser Gln Cys Ser Lys Pro Gly Val Ile Phe
    50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
                85                  90
```

<210> SEQ ID NO 56
<211> LENGTH: 4208
<212> TYPE: DNA
<213> ORGANISM: Homo sapiens

<400> SEQUENCE: 56

```
aagcttaaaa aactgcaaaa aatagtttga cttgtgagcg gataacaatt aagatgtacc     60
caattgtgag cggataacaa tttcacacat taaagaggag aaattacata tggaccgttt    120
ccacgctacc tccgctgact gctgcatctc ctacaccccg cgttccatcc cgtgctcgct    180
gctggaatcc tacttcgaaa ccaactccga atgctccaaa ccgggtgtta tcttcctgac    240
caaaaaaggt cgtcgtttct cgctaaccc gtccgacaaa caggttcagg tttgtatgcg     300
tatgctgaaa ctggacaccc gtatcaaaac ccgtaaaaac tgataaggta cctaagtgag    360
tagggcgtcc gatcgacgga cgccttttt ttgaattcgt aatcatggtc atagctgttt     420
cctgtgtgaa attgttatcc gctcacaatt ccacacaaca tacgagccgg aagcataaag    480
tgtaaagcct ggggtgccta atgagtgagc taactcacat taattgcgtt gcgctcactg    540
cccgctttcc agtcgggaaa cctgtcgtgc cagctgcatt aatgaatcgg ccaacgcgcg    600
gggagaggcg gtttgcgtat tgggcgctct tccgcttcct cgctcactga ctcgctgcgc    660
tcggtcgttc ggctgcggcg agcggtatca gctcactcaa aggcggtaat acggttatcc    720
acagaatcag gggataacgc aggaaagaac atgtgagcaa aaggccagca aaaggccagg    780
aaccgtaaaa aggccgcgtt gctggcgttt ttccataggc tccgccccc tgacgagcat     840 cacaaaaatc gacgctcaag tcagaggtgg cgaaacccga caggactata aagataccag    900
```

```
gcgtttcccc ctggaagctc cctcgtgcgc tctcctgttc cgaccctgcc gcttaccgga    960
tacctgtccg cctttctccc ttcgggaagc gtggcgcttt ctcatagctc acgctgtagg   1020
tatctcagtt cggtgtaggt cgttcgctcc aagctgggct gtgtgcacga accccccgtt   1080
cagcccgacc gctgcgcctt atccggtaac tatcgtcttg agtccaaccc ggtaagacac   1140
gacttatcgc cactggcagc agccactggt aacaggatta gcagagcgag gtatgtaggc   1200
ggtgctacag agttcttgaa gtggtggcct aactacggct acactagaag aacagtattt   1260
ggtatctgcg ctctgctgaa gccagttacc ttcggaaaaa gagttggtag ctcttgatcc   1320
ggcaaacaaa ccaccgctgg tagcggtggt ttttttgttt gcaagcagca gattacgcgc   1380
agaaaaaaag gatctcaaga agatcctttg atcttttcta cggggtctga cgctcagtgg   1440
aacgaaaact cacgttaagg gattttggtc atgagattat cgtcgacaat cgcgcgcga   1500 aggcgaagcg gcatgcattt acgttgacac catcgaatgg tgcaaaacct ttcgcggtat   1560
ggcatgatag cgcccggaag agagtcaatt cagggtggtg aatgtgaaac cagtaacgtt   1620
atacgatgtc gcagagtatg ccggtgtctc ttatcagacc gtttcccgcg tggtgaacca   1680
ggccagccac gtttctgcga aaacgcggga aaaagtggaa gcggcgatgg cggagctgaa   1740
ttacattccc aaccgcgtgg cacaacaact ggcgggcaaa cagtcgttgc tgattggcgt   1800
tgccacctcc agtctggccc tgcacgcgcc gtcgcaaatt gtcgcggcga ttaaatctcg   1860
cgccgatcaa ctgggtgcca cgtggtggt gtcgatggta gaacgaagcg gcgtcgaagc   1920
ctgtaaagcg gcggtgcaca atcttctcgc gcaacgcgtc agtgggctga tcattaacta   1980
tccgctggat gaccaggatg ccattgctgt ggaagctgcc tgcactaatg ttccggcgtt   2040
atttcttgat gtctctgacc agacacccat caacagtatt attttctccc atgaagacgg   2100
tacgcgactg ggcgtggagc atctggtcgc attgggtcac cagcaaatcg cgctgttagc   2160
gggcccatta agttctgtct cggcgcgtct gcgtctggct ggctggcata aatatctcac   2220
tcgcaatcaa attcagccga tagcggaacg ggaaggcgac tggagtgcca tgtccggttt   2280
tcaacaaacc atgcaaatgc tgaatgaggg catcgttccc actgcgatgc tggttgccaa   2340
cgatcagatg gcgctgggcg caatgcgcgc cattaccgag tccgggctgc gcgttggtgc   2400
ggatatctcg gtagtgggat acgacgatac cgaagacagc tcatgttata tcccgccgtt   2460
aaccaccatc aaacaggatt ttcgcctgct ggggcaaacc agcgtggacc gcttgctgca   2520
actctctcag ggccaggcgg tgaagggcaa tcagctgttg cccgtctcac tggtgaaaag   2580
aaaaaccacc ctggcgccca atacgcaaac cgcctctccc cgcgcgttgg ccgattcatt   2640
aatgcagctg gcacgacagg tttcccgact ggaaagcggg cagtgagcgc aacgcaatta   2700
atgtaagtta gcgcgaattg tcgaccaaag cggccatcgt gcctcccac tcctgcagtt   2760 cggggggcatg gatgcgcgga tagccgctgc tggtttcctg gatgccgacg gatttgcact   2820
gccggtagaa ctccgcgagg tcgtccagcc tcaggcagca gctgaaccaa ctcgcgaggg   2880
gatcgagccc ggggtgggcg aagaactcca gcatgagatc cccgcgctgg aggatcatcc   2940
agccggcgtc ccggaaaacg attccgaagc ccaacctttc atagaaggcg gcggtggaat   3000
cgaaatctcg tgatggcagg ttgggcgtcg cttggtcggt catttcgaac cccagagtcc   3060
cgctcagaag aactcgtcaa gaaggcgata gaaggcgatg cgctgcgaat cgggagcggc   3120
gataccgtaa agcacgagga agcggtcagc ccattcgccg ccaagctctt cagcaatatc   3180
acgggtagcc aacgctatgt cctgatagcg gtccgccaca cccagccggc cacagtcgat   3240
gaatccagaa aagcggccat tttccaccat gatattcggc aagcaggcat cgccatgggt   3300
```

```
cacgacgaga tcctcgccgt cgggcatgcg cgccttgagc ctggcgaaca gttcggctgg      3360
cgcgagcccc tgatgctctt cgtccagatc atcctgatcg acaagaccgg cttccatccg      3420
agtacgtgct cgctcgatgc gatgtttcgc ttggtggtcg aatgggcagg tagccggatc      3480
aagcgtatgc agccgccgca ttgcatcagc catgatggat actttctcgg caggagcaag      3540
gtgagatgac aggagatcct gccccggcac ttcgcccaat agcagccagt cccttcccgc      3600
ttcagtgaca acgtcgagca cagctgcgca aggaacgccc gtcgtggcca gccacgatag      3660
ccgcgctgcc tcgtcctgca gttcattcag ggcaccggaa aggtcggtct tgacaaaaag      3720
aaccgggcgc ccctgcgctg acagccggaa cacggcggca tcagagcagc cgattgtctg      3780
ttgtgcccag tcatagccga atagcctctc cacccaagcg gccggagaac ctgcgtgcaa      3840
tccatcttgt tcaatcatgc gaaacgatcc tcatcctgtc tcttgatcag atcttgatcc      3900
cctgcgccat cagatccttg gcggcaagaa agccatccag tttactttgc agggcttccc      3960
aaccttacca gagggcgccc cagctggcaa ttccggttcg cttgctgtcc ataaaaccgc      4020
ccagtctagc tatcgccatg taagcccact gcaagctacc tgctttctct ttgcgcttgc      4080
gttttccctt gtccagatag cccagtagct gacattcatc cggggtcagc accgtttctg      4140
cggactggct ttctacgtgt tccgcttcct ttagcagccc ttgcgccctg agtgcttgcg      4200
gcagcgtg                                                              4208

<210> SEQ ID NO 57
<211> LENGTH: 112
<212> TYPE: DNA
<213> ORGANISM: Homo sapiens

<400> SEQUENCE: 57
aagcttaaaa aactgcaaaa aatagtttga cttgtgagcg gataacaatt aagatgtacc       60
caattgtgag cggataacaa tttcacacat taaagaggag aaattacata tg              112

<210> SEQ ID NO 58
<211> LENGTH: 74
<212> TYPE: PRT
<213> ORGANISM: Homo sapiens

<400> SEQUENCE: 58

Met His Ala Thr Ser Ala Asp Cys Cys Ile Ser Tyr Thr Pro Arg Ser
1               5                   10                  15

Ile Pro Cys Ser Leu Leu Glu Ser Tyr Phe Glu Thr Asn Ser Glu Cys
            20                  25                  30

Ser Lys Pro Gly Val Ile Phe Leu Thr Lys Lys Gly Arg Arg Phe Cys
        35                  40                  45

Ala Asn Pro Ser Asp Lys Gln Val Gln Val Cys Met Arg Met Leu Lys
    50                  55                  60

Leu Asp Thr Arg Ile Lys Thr Arg Lys Asn
65                  70

<210> SEQ ID NO 59
<211> LENGTH: 79
<212> TYPE: PRT
<213> ORGANISM: Homo sapiens

<400> SEQUENCE: 59

Met His Ala Ala Gly Phe His Ala Thr Ser Ala Asp Cys Cys Met Ser
1               5                   10                  15
```

-continued

```
Tyr Thr Pro Arg Ser Ile Pro Cys Ser Leu Leu Glu Ser Tyr Phe Glu
            20                  25                  30

Thr Asn Ser Glu Cys Ser Lys Pro Gly Val Ile Phe Leu Thr Lys Lys
            35                  40                  45

Gly Arg Arg Phe Cys Ala Asn Pro Ser Asp Lys Gln Val Gln Val Cys
            50                  55                  60

Met Arg Met Leu Lys Leu Asp Thr Arg Ile Lys Thr Arg Lys Asn
65                  70                  75

<210> SEQ ID NO 60
<211> LENGTH: 85
<212> TYPE: PRT
<213> ORGANISM: Homo sapiens

<400> SEQUENCE: 60

Met Pro Gln Met Thr Leu Ser His Ala Ala Gly Phe His Ala Thr Ser
1               5                   10                  15

Ala Asp Cys Cys Met Ser Tyr Thr Pro Arg Ser Ile Pro Cys Ser Leu
            20                  25                  30

Leu Glu Ser Tyr Phe Glu Thr Asn Ser Glu Cys Ser Lys Pro Gly Val
            35                  40                  45

Ile Phe Leu Thr Lys Lys Gly Arg Arg Phe Cys Ala Asn Pro Ser Asp
            50                  55                  60

Lys Gln Val Gln Val Cys Met Arg Met Leu Lys Leu Asp Thr Arg Ile
65                  70                  75                  80

Lys Thr Arg Lys Asn
            85
```